United States Patent
Stupi et al.

(10) Patent No.: US 9,399,798 B2
(45) Date of Patent: Jul. 26, 2016

(54) 3'-OH UNBLOCKED, FAST PHOTOCLEAVABLE TERMINATING NUCLEOTIDES AND METHODS FOR NUCLEIC ACID SEQUENCING

(71) Applicant: LASERGEN, INC., Houston, TX (US)

(72) Inventors: Brian P. Stupi, Cypress, TX (US); Hong Li, Milwaukee, WI (US); Weidong Wu, Houston, TX (US); Megan N. Hersh, Houston, TX (US); David Hertzog, Houston, TX (US); Sidney E. Morris, Houston, TX (US); Michael L. Metzker, Houston, TX (US)

(73) Assignee: LASERGEN, INC., Houston, TX (US)

( * ) Notice: Subject to any disclaimer, the term of this patent is extended or adjusted under 35 U.S.C. 154(b) by 0 days.

(21) Appl. No.: 14/504,093

(22) Filed: Oct. 1, 2014

(65) Prior Publication Data

US 2015/0176074 A1 Jun. 25, 2015

Related U.S. Application Data

(62) Division of application No. 13/615,284, filed on Sep. 13, 2012, now Pat. No. 8,889,860.

(60) Provisional application No. 61/627,211, filed on Oct. 7, 2011, provisional application No. 61/534,347, filed on Sep. 13, 2011.

(51) Int. Cl.
*C12Q 1/68* (2006.01)
*C07H 19/073* (2006.01)
(Continued)

(52) U.S. Cl.
CPC ............ *C12Q 1/6869* (2013.01); *C07H 19/073* (2013.01); *C07H 19/10* (2013.01);
(Continued)

(58) Field of Classification Search
CPC ................... C12Q 1/6869; C12Q 2525/117
USPC ............ 435/6.12; 536/22.1, 25.32, 26.1, 26.2
See application file for complete search history.

(56) References Cited

U.S. PATENT DOCUMENTS 3,822,996 A  7/1974  Lofquist
3,845,035 A  10/1974  Kampe et al.
(Continued)

FOREIGN PATENT DOCUMENTS

EP  0272007  6/1988
EP  0640146  3/1995
(Continued)

OTHER PUBLICATIONS

Adzamli et al., "Development of phosphonate derivatives of gadolinium chelates for NMR imaging of calcified soft tissues," *J. Med. Chem.*, 32(1):139-144, 1989.
(Continued)

*Primary Examiner* — Jezia Riley
(74) *Attorney, Agent, or Firm* — Parker Highlander PLLC

(57) ABSTRACT

The present invention relates generally to 3'-OH unblocked nucleotides and nucleosides labeled and unlabeled with 5-methoxy-substituted nitrobenzyl-based photocleavable terminating groups for use in methods and systems related to DNA and RNA sequencing and analysis. These compounds may be used as reversible terminators as they exhibit fast nucleotide incorporation kinetics, single-base termination, high nucleotide selectivity, and rapid terminating group cleavage that results in a naturally occurring nucleotide.

26 Claims, 13 Drawing Sheets

(51) Int. Cl.

| | |
|---|---|
| *C07H 19/10* | (2006.01) |
| *C07H 19/173* | (2006.01) |
| *C07H 19/20* | (2006.01) |
| *C07H 19/14* | (2006.01) |
| *C07H 21/00* | (2006.01) |

(52) U.S. Cl.
CPC ............ *C07H 19/14* (2013.01); *C07H 19/173* (2013.01); *C07H 19/20* (2013.01); *C12Q 1/6883* (2013.01); *C12Q 2525/117* (2013.01); *C12Q 2600/156* (2013.01); *C12Q 2600/16* (2013.01)

(56) References Cited

U.S. PATENT DOCUMENTS

| | | |
|---|---|---|
| 3,859,045 A | 1/1975 | Saunders et al. |
| 3,917,499 A | 11/1975 | Holden et al. |
| 4,304,568 A | 12/1981 | Johnson et al. |
| 4,439,356 A | 3/1984 | Colvin et al. |
| 4,631,066 A | 12/1986 | Minemura et al. |
| 4,737,155 A | 4/1988 | Kuczkowski |
| 5,151,507 A | 9/1992 | Hobbs, Jr. et al. |
| 5,188,934 A | 2/1993 | Menchen et al. |
| 5,302,509 A | 4/1994 | Cheeseman |
| 5,614,386 A | 3/1997 | Metzker |
| 5,684,142 A | 11/1997 | Mishra et al. |
| 5,728,529 A | 3/1998 | Metzker |
| 5,763,594 A | 6/1998 | Hiatt |
| 5,770,367 A | 6/1998 | Southern et al. |
| 5,773,423 A | 6/1998 | Jacobson et al. |
| 5,808,045 A | 9/1998 | Hiatt |
| 5,861,287 A | 1/1999 | Metzker |
| 5,872,244 A | 2/1999 | Hiatt |
| 5,994,063 A | 11/1999 | Metzker |
| 6,214,987 B1 | 4/2001 | Hiatt |
| 6,255,083 B1 | 7/2001 | Williams |
| 6,664,079 B2 | 12/2003 | Ju et al. |
| RE38,416 E | 2/2004 | Petrie et al. |
| 6,762,048 B2 | 7/2004 | Williams |
| 6,818,395 B1 | 11/2004 | Quake |
| 6,833,246 B2 | 12/2004 | Balasubramanian |
| 6,869,764 B2 | 3/2005 | Williams |
| 6,995,841 B2 | 2/2006 | Scott et al. |
| 7,057,026 B2 | 6/2006 | Barnes et al. |
| 7,125,660 B2 | 10/2006 | Stanton et al. |
| 7,329,492 B2 | 2/2008 | Briggs et al. |
| 7,345,159 B2 | 3/2008 | Edwards et al. |
| 7,355,036 B2 | 4/2008 | Guimil et al. |
| 7,414,116 B2 | 8/2008 | Milton et al. |
| 7,476,734 B2 | 1/2009 | Liu |
| 7,541,444 B2 | 6/2009 | Milton et al. |
| 7,592,435 B2 | 9/2009 | Milton |
| 7,635,578 B2 | 12/2009 | Ju et al. |
| 7,713,698 B2 | 5/2010 | Ju et al. |
| 7,771,973 B2 | 8/2010 | Milton et al. |
| 7,816,503 B2 | 10/2010 | Milton et al. |
| 7,893,227 B2 | 2/2011 | Wu et al. |
| 7,897,737 B2 | 3/2011 | Wu et al. |
| 7,964,352 B2 | 6/2011 | Wu et al. |
| 8,148,503 B2 | 4/2012 | Litosh et al. |
| 8,198,029 B2 | 6/2012 | Wu et al. |
| 8,212,015 B2 | 7/2012 | Milton et al. |
| 8,361,727 B2 | 1/2013 | Wu et al. |
| 8,497,360 B2 | 7/2013 | Litosh et al. |
| 8,877,905 B2 | 11/2014 | Litosh et al. |
| 8,889,860 B2 | 11/2014 | Stupi et al. |
| 8,969,535 B2 | 3/2015 | Wu et al. |
| 2002/0034750 A1 | 3/2002 | Short |
| 2003/0060400 A1 | 3/2003 | Lacolla et al. |
| 2003/0092668 A1 | 5/2003 | Liang et al. |
| 2003/0180769 A1 | 9/2003 | Metzker |
| 2004/0014096 A1 | 1/2004 | Anderson et al. |
| 2004/0110196 A1 | 6/2004 | Getts |
| 2005/0048601 A1 | 3/2005 | Dellinger et al. |
| 2005/0049407 A1 | 3/2005 | Dellinger et al. |
| 2005/0049411 A1 | 3/2005 | Dellinger et al. |
| 2006/0160081 A1 | 7/2006 | Milton et al. |
| 2008/0131952 A1 | 6/2008 | Wu et al. |
| 2008/0132692 A1 | 6/2008 | Wu et al. |
| 2009/0081686 A1 | 3/2009 | Wu et al. |
| 2010/0041041 A1 | 2/2010 | Litosh et al. |
| 2011/0200988 A1 | 8/2011 | Wu et al. |
| 2011/0287427 A1 | 11/2011 | Wu et al. |
| 2013/0035237 A1 | 2/2013 | Litosh et al. |
| 2013/0072388 A1 | 3/2013 | Wu et al. |
| 2013/0095471 A1 | 4/2013 | Wu et al. |
| 2013/0122489 A1 | 5/2013 | Stupi et al. |
| 2014/0051848 A1 | 2/2014 | Litosh et al. |

FOREIGN PATENT DOCUMENTS

| | | |
|---|---|---|
| WO | WO 91/05060 | 4/1991 |
| WO | WO 97/00967 | 1/1997 |
| WO | WO 98/50047 | 11/1998 |
| WO | WO 01/96353 | 12/2001 |
| WO | WO 02/083937 | 10/2002 |
| WO | WO 03/021212 | 3/2003 |
| WO | WO 03/048387 | 6/2003 |
| WO | WO 03/087302 | 10/2003 |
| WO | WO 2004/018493 | 3/2004 |
| WO | WO 2004/018497 | 3/2004 |
| WO | WO 2004/058791 | 7/2004 |
| WO | WO 2005/044836 | 5/2005 |
| WO | WO 2005/084367 | 9/2005 |
| WO | WO 2008/070749 | 6/2008 |
| WO | WO 2009/152353 | 12/2009 |
| WO | WO 2012/037394 | 3/2012 |

OTHER PUBLICATIONS

Agbanyo et al., "5'-S-(2-aminoethyl)-N6-(4-nitrobenzyl)-5'-thioadenosine (SAENTA), a novel ligand with high affinity for polypeptides associated with nucleoside transport. Partial purification of the nitrobenzylthioinosine-binding protein of pig erythrocytes by affinity chromatography," *Biochem. J.*, 270:605-614, 1990.

Aliotta et al., "Thermostable *Bst*DNA polymerase I lacks a 3'→5' proofreading exonuclease activity," *Genet Anal. Biomol Eng.*, 12:185-95, 1996.

Barltrop et al., "Photosensitive Protecting Groups," *Chem. Commun.*, 822-23, 1966.

Barone et al., "Novel Nucleoside Triphosphate Analogs for the Enzymatic Labeling of Nucleic Acids," *Nucleosides, Nucleotides, and Nucleic Acids*, 20:1141-45, 2001.

Barth et al., "Time-Resolved Infrared Spectroscopy of Intermediates and Products from Photolysis of 1-(2-Nitrophenyl)ethyl Phosphates: Reactions of the 2-Nitrosoacetophenone Byproduct with Thiols," *J. Amer. Chem. Soc.*, 119:4149-59, 1997.

Bartholomew and Broom, "One-step chemical synthesis of ribonucleosides bearing a photolabile ether protecting group," *J. Chem. Soc. Chem. Commun.*, 38, 1975.

Beadling et al., "Multiplex Mutation Screening by Mass Spectroscopy," *J. Mol. Diagn.*, 13:504-13, 2012.

Bentley et al., "Accurate Whole Human Genome Sequencing Using Reversible Terminator Chemistry," *Nature*, 456:53-59, 2008.

Berlier et al. "Quantitative comparison of long-wavelength alexa fluor dyes to cy dyes: fluorescence of the dyes and their bioconjugates," *The Journal of Histochemistry & Cytochemistry*, 51(12):1699-1712, 2003.

Berson & Brown, "Studies on Dihydropyridines. I. The Preparation of Unsymmetrical 4-Aryl-1,4-dihydropyridines by the Hantzsch-Beyer Synthesis," *J. Amer. Chem. Soc.*, 77:447-50, 1955.

Bodepudi et al., "Synthesis of 2'-deoxy-7,8-dihydro-8-oxoguanosine and 2'-deoxy-7,8-dihydro-8-oxoadenosine and their incorporation into oligomeric DNA," *Chem. Res. Toxicol.*, 5:608-617, 1992.

Bowers et al., "Virtual Terminator Nucleotides for Next-Generation DNA sequencing," *Nature Methods*, 6:593-95, 2009.

Brandis, "Dye structure affects *Taq* DNA polymerase terminator selectivity," *Nucleic Acids Research*, 27(8):1912-1918, 1999.

(56) References Cited

OTHER PUBLICATIONS

Bressi et al., "Adenosine analogues as inhibitors of *Trypanosoma brucei* phosphoglycerate kinase: Elucidation of a novel binding mode for a 2-amino-$N^6$ substituted andenosine," *J. Med. Chem.*, 43;4135-4250, 2000.

Cameron and Frechet, "Photogeneration of Organic Bases from O-nitrobenzyl-derived Carbamates," *J. Am. Chem. Soc.*, 113:4303-13, 1991.

Canard & Sarfati, "DNA Polymerase Fluorescent Substrates with Reversible 3'-tags," *Gene*, 148:1-6, 1994.

Carrasco & Vázquez, "Molecular Bases for the Action and Selectivity of Nucleoside Antibiotics," *Med. Res. Rev.*, 4:471-512, 1984.

Chaulk and MacMillan, "Caged RNA: photo-control of a ribozyme reaction," *Nucleic Acids Res.*, 26:3173-3178, 1998.

Chaves des Neves and Pais, "Identification of a spathe regreening factor in *Zantedeschia aethiopicia*," *Biochemical and Biophysical Research Communications*, 95(4):1387-1392, 1980.

Cho et al., "$^{15}$N nuclear magnetic resonance studies on the tautomerism of 8-hydroxy-2'-deoxyguanosine, 8-hydroxyguanosine, and other C8-substituted guanine nucleosides," *Chem. Res. Toxicol.*, 3:445-452, 1990.

Cho et al., "Correlation between NMR spectral parameters of nucleosides and its implication to the conformation about the glycosyl bond," *Biochemical and Biophysical Research Communications*, 180(1):273-278, 1991.

Cleland, "Dithiothreitol, a New Protective Reagent for SH groups," *Biochemistry*, 3:480-82, 1964.

Corrie et al., "Synthesis and Absolute Stereochemistry of the two Diastereoisomers of $P^3$-1-(2-nitrophenyl)ethyl adenosine triphosphate ('Caged' ATP)," *J. Chem. Soc., Perkin Trans. 1*, 1015-19, 1992.

Corrie, in *Dynamics studies in biology*, Goeldner and Givens (Eds.), Wiley-VCH Verlag GmbH & Co. KGaA, Weinheim, pp. 1-28, 2005.

Corrigenda in: Welch et al., "Synthesis of nucleosides designed for combinatorial DNA sequencing," *Chem. Eur. J.*, 11:7145, 2005.

De Mayo, in *Advances in Organic Chemistry*, Raphael et al. (Eds.), Interscience, NY, 2:367-425, 1960.

Dewey et al., "New uridine derivatives for systematic evolution of RNA ligands by exponential enrichment," *J. Am. Chem. Soc.*, 117:8474-8475, 1995.

Dressman et al., "Transforming single DNA molecules into fluorescent magnetic particles for detection and enumeration of genetic variations," *Proc. Natl. Acad. Sci. USA*, 100:8817-8822, 2003.

Dutta et al., "Synthesis and biological activities of some N6-(nitro- and - aminobenzyl)adenosines," *Journal of Medicinal Chemistry*, 18(8):780-783, 1975.

Eid et al., "Real-Time DNA Sequencing from Single Polymerase Molecules," *Science*, 323:133-138, 2009.

Erlich, et al., "Alta-Cyclic: a Self-optimizing Base Caller for Next-Generation Sequencing," *Nat. Meth.*, 5:679-682, 2008.

Erratum in: Welch and Burgess, "Synthesis of fluorescent, photolabile 3'-O-protected nucleoside triphosphates for the base addition sequencing scheme," *Nucleosides, Nucleotides, and Nucleic Acids*, 25:119, 2006.

Fare et al., "Effects of Atmospheric Ozone on Microarray Data Quality," *Anal. Chem.*, 75:4672-4675, 2003.

Fedurco, et al., "BTA, a Novel Reagent for DNA Attachment on Glass and Effective Generation of Solid-Phase Amplified DNA Colonies," *Nucleic Acids Rev.*, 34:e22, 2006.

Friest et al., "Valyl-tRNA, Isoleucyl-tRNA and Tyrosyl-tRNA synthetase from Baker's Yeast," *Eur. J. Biochem.*, 66:493-497, 1976.

Futreal et al., "A Census of Human Cancer Genes," *Nature Rev. Cancer*, 4:177-83, 2004.

Gao et al., "Structural determinants of A3 adenosine receptor activation: Nucleoside ligands at the agonist/antagonist boundary," *J. Med. Chem.*, 45:4471-4484, 2002.

Gardner and Jack, "Acyclic and dideoxy terminator preferences denote divergent sugar recognition by archaaeon and *Taq* DNA polymerases," *Nucleic Acids Research*, 30(2):605-613, 2002.

Gardner and Jack, "Determinants of nucleotide sugar recognition in an archaeon DNA polymerase," *Nucleic Acids Research*, 27(12):2545-2553, 1999.

Gardner et al., "Rapid Incorporation Kinetics and Improved Fidelity of a Novel Class of 3'-OH Unblocked Reversible Terminators," *Nucleic Acids Res.*, 40(15):7404-15, 2012.

Gebeyehu et al., "Novel biotinylated nucleotide—analogs for labeling and colorimetric detection of DNA," *Nucleic Acids Research*, 15(11):4513-4534, 1987.

Gershon, "Microarrays Go Mainstream," *Nature Methods*, 1:263-270, 2004.

Gibbs, "Identification of mutations leading to the Lesch-Nyhan syndrome by automated direct DNA sequencing of in vitro amplified cDNA," *Proc. Natl. Acad. Sci. USA*, 86:1919-1923, 1989.

Giegrich et al., "New Photolabile Protecting Groups in Nucleoside and Nucleotide Chemistry-Synthesis, Cleavage Mechanisms, and Applications," *Nucleosides Nucleotides*, 17:1987-1996, 1998.

Golisade et al., "Anti-malarial activity of $N^6$-substituted Adenosine derivatives. Part I.," *Bioorganic & Medicinal Chemistry*, 10:769-777, 2002.

Gommers-Ampt and Borst, "Hypermodified bases in DNA," *FASEB J.*, 9(11):1034-1042, 1995.

Guo et al., "Four-color DNA sequencing with 3'-O-modified Nucleotide Reversible Terminators and Chemically Cleavable Fluorescent Dideoxynucleotides," *Proc. Natl. Acad. Sci. USA*, 105:9145-50, 2008.

Hampton et al., "Species- or isozyme-specific enzyme inhibitors. 4. Design of a two-site inhibitor of adenylate kinase with isozyme selectivity," *J. Med. Chem.*, 25:638-644, 1982.

Hardwick et al., "Photochromotropic Behavior of 2-(2',4'-dinitrobenzyl)-pyridine," *Trans. Farad. Soc.*, 56:44-50, 1960.

Harris et al., "Single-molecule DNA sequencing of a viral genome," *Science*, 320:106-109, 2008.

Hasan et al., "Photolabile Protecting Groups for Nucleosides: Synthesis and Photodeprotection Rates," *Tetrahedron*, 53:4247-64, 1997.

Hashizume et al., "Synthesis and cytokinin activity of alpha-anomeric $N^6$-benzyladenosine," *Agric. Biol. Chem.*, 49(1):225-227, 1985.

Henderson et al., "4,4'-Dimethoxytrityl and 4,4',4"-trimethoxytrityl as protecting tropus for amino functions; selectivity for primary amino groups and application in $^{15}$N-labeling," *J. Chem. Soc. Perkin Trans.*, 1:3407-3413, 1997.

Hermanns et al., "Synthesis of 8-[18O]hydroxy-2'-deoxyguanosine," *Journal of Labelled Compounds and Radiopharmaceuticals*, 36(2):191-197, 1993.

Hobarnter and Silverman, "Modulation of RNA tertiary folding by incorporation of caged nucleotides," *Angew. Chem. Int. Ed.*, 44:7305-7309, 2005.

Holmes and Robins, "Purine nucleosides. IX. The synthesis of 9-beta-D-Ribofuranysyl uric acid and other related 8-substituted purine ribonucleosides," *Journal of the American Chemical Society*, 87:8:1772-176, 1965.

Honda et al., "New type of prefabricated fully protected ribonucleotide monomer unites as useful synthetic intermediates in rapid oligoribonucleotide synthesis," *Chemistry Letters*, pp. 15-18, 1982.

Hsia et al., "Structural and Functional Insight into Sugar-Nonspecific Nucleases in Host Defense," *Current Opinion in Structural Biology*, 15:126-134, 2005.

Iafrate et al., "Detection of Large-scale Variation in the Human Genome," *Nature Genet.*, 36:949-51, 2004.

International Human Genome Sequencing Consortium., "Initial sequencing and analysis of the human genome," *Nature*, 409:860-921, 2001.

Ito et al., "Role of Tet proteins in 5mC to 5hmC conversion, ES-cell Self-renewal and Inner Cell Mass Specification," *Nature*, 466:1129-33, 2010.

Jacobson et al., "A novel pharmacological approach to treading cardiac ischemia,"*J. Biol. Chem.*, 275(39): 30272-30279, 2000.

Jacobson et al., "Methancarba analogues of purine nucleosides as potent and selective adenosine receptor agonists," *J. Med. Chem.*, 43:2196-2203, 2000.

Ju et al., "Four-color DNA sequencing by synthesis using cleavable fluorescent nucleotide reversible terminators," *Proc. Natl. Acad. Sci. USA*, 103:19635-40, 2006.

(56) References Cited

OTHER PUBLICATIONS

Ju, et al., "Fluorescence energy transfer dye-labeled primers for DNA sequencing and analysis," *Proc. Natl. Acad. Sci. USA*, 92:4347-4351, 1995.

Juillerat et al., "Directed evolution of O6-Alkylguanine-DNA alkyltransferase for efficient labeling of fusion proteins with small molecules in vivo," *Chem Biol.*, 10:313-317, 2003.

Kahl et al., "Introducing structural diversity in oligonucleotides via photolabile, concertible C5-substituted nucleotides," *K. Am. Chem. Soc.*, 121(4):597-604, 1999.

Kaiser et al., "A Comparison of Eubacterial and Archaeal Structure-specific 5'-Exonucleases," *J. Biol. Chem.*, 274:21387-394, 1999.

Kaplan, et al., "Rapid Photolytic Release of Adenosine 5'-triphosphate from a Protected Analog: Utilization by the Sodium:Potassium Pump of Human Red Blood Cell Ghosts," *Biochemistry*, 17(10):1929-1935, 1978.

Kim et al., "2-Substitution of N6-benzyladenosine-5'-uronamides enhances selectivity for A3 adenosine receptors," *J. Med. Chem.*, 37:3614-3621, 1994.

Kim, et al., "Polony Multiplex Analysis of Gene Expression (PMAGE) in Mouse Hypertrophic Cardiomyopathy," *Science*, 316:1481-1484, 2007.

Kobayashi et al., "A microfluidic device for conducting. gas-liquid-solid hydrogenation reactions," *Science*, 304:1305-1308, 2004.

Kong et al., "Characterization of a DNA polymerase from the hyperthermophile archaea *Thermococcus litoralis*," *The Journal of Biological Chemistry*, 268(3):1965-1975, 1993.

Kornher and Livak, "Mutation detection using nucleotide analogs that alter electrophoretic mobility," *Nucleic Acids Research*, 17(19):7779-7784, 1989.

Kriaucionis & Heintz, "The Nuclear DNA Base, 5-Hydromethylcytosine is Present in Purkinje Neurons," *Science*, 324:929-30, 2009.

Kulikowski et al., "Structure-activity relationships and conformational features of antiherpetic pyrimidine and purine analogues. A review," *Pharmacy World & Science*, 16(2):127-138, 1994.

Lee et al., "New energy transfer dyes for DNA sequencing," *Nucleic Acids Research*, 25(14):2816-2822, 1997.

Levy et al., "The diploid genome sequence of an individual human," *PLoS Biol.*, 5:e254, 2007.

Lewis et al., "Color-blind fluorescence detection for four-color DNA sequencing," *PNAS*, 102(15):5346-5351, 2005.

Li et al., "A photocleavable fluorescent nucleotide for DNA sequencing and analysis," *PNAS*, 100(2):414-419, 2003.

Limbach, et al., "Summary: the Modified Nucleosides of RNA," *Nucleic Acids Res.*, 22:2183-2196, 1994.

Lin, et al., "8-Substituted guanosine and 2'-Deoxyguanosine derivatives as potential inducers of the differentiation of friend erythroleukemia cells," *J. Med. Chem.*, 28:1194-1198, 1985.

Litosh et al., "Improved Nucleotide Selectivity and Termination of 3'-OH Unblocked Reversible Terminators by Molecular Tuning of 2-Nitrobenzyl Alkylated HOMedU Triphosphates," *Nucleic Acid Res.*, 39:e39, 2011.

Liu et al., "A molecular gate which controls unnatural ATP analogue recognition by the tyrosine kinase v-Src," *Bioorganic & Medicinal Chemistry*, 6:1219-1226, 1998.

Lyamichev et al., "Polymorphism Identification and Quantitative Detection of Genomic DNA by Invasive Cleavage of Oligonucleotide Probes," *Nature Biotechnol.*, 17:292-296, 1999.

Malecki et al., "Mutations in NEUROD1 are associated with the development of type 2 diabetes mellitus," *Nature Genetics*, 23:323-328, 1999.

Margulies et al, "Genome Sequencing in Microfabricated High-density Picolitre Reactors," *Nature*, 437:376-80, 2005.

McCray et al., "A New Approach to Time-Resolved Studies of ATP-requiring Biological Systems; Laser Flash Photolysis of Caged ATP," *Proc. Natl. Acad. Sci. USA*, 77:7237-41, 1980.

McDougall et al., "Analogs of Guanine Nucleoside Triphosphates for Sequencing Applications," *Nucleosides, Nucleotides & Nucleic Acids*, 20:501-6, 2001.

McGall et al., "The Efficiency of Light-Directed Synthesis of DNA Arrays on Glass Substrates," *J. Amer. Chem. Soc.*, 119:5081-90, 1997.

McMinn et al., Novel solid phase synthesis supports for the preparation of oligonucleotides containing 3'- Alykl Amines, *Tetrahedron*, 52:3827-3840, 1996.

Meldrum et al., "Next-Generation Sequenching for Cancer Diagnostics: A Practical Perspective," *Clin. Biochem. Rev.*, 32:177-95, 2011.

Metzker et al., "Electrophoretically uniform fluorescent dyes for automated DNA sequencing," *Science*, 271:1420-1422, 1996.

Metzker et al., "Elimination of residual natural nucleotides from 3'-O-modified-dNTP syntheses by enzymatic mop-up," *BioTechniques*, 25:814-817, 1998.

Metzker et al., "Emerging technologies in DNA sequencing," *Genome Research*, 15:1767-1776, 2005.

Metzker et al., "Termination of DNA Synthesis by Novel 3'-modifieddeoxyribonucleoside 5'-phosphates," *Nucleic Acids Res.*, 22:4259-67, 1994.

Metzker, "Sequencing Technologies—The Next Generation," *Nature Rev. Genet.*, 11:31-46, 2010.

Mitra et al., "Fluorescent In Situ Sequencing on Polymerase Colonies," *Anal. Biochem.*, 320:55-65, 2003.

Molecular Probes™ invitrogen detection technologies, "Alexa Fluor® Dyes—Simply the Best and Brightest, Fluorescent dyes and conjugates," 2005.

Moore and Koreeda, "Application of the change in partition coefficient with pH to the structure determination of alkyl substituted guanosines," *Biochemical and Biophysical Research Communications*, 73(2):459-464, 1976.

Morrison, In: *The chemistry of nitro and nitroso groups*, Feuer (Ed.), Interscience publishers, NY, 165-213, 1969.

Mosher et al., "Photochromotropism of gamma-(2,4-dinitrobenzyl)-Pyridine in Solution," *J. Chem. Phys.* 32:1888-89, 1960.

Mounetou et al., "O6-(alkyl/aralkyl)guanosine and 2'-deoxyguanosine derivatives: synthesis and ability to enhance chloroethylnitrosourea antitumor action," *J. Med. Chem.*, 40:2902-2909, 1997.

Mounteou et al., "Synthesis of three no-carrier-added $O^6$-4-[$^{125}$I] iodobenzylguanosine derivatives, new reagents for the assay of O6-alkylguanine-DNA alkyltransferase activity," *Journal of Labelled Compounds and Radiopharmaceuticals*, 36(12):1216-1225, 1995.

Nampalli et al., "Efficient synthesis of 8-Oxo-dGTP: A mutagnic nucleotide," *Bioorganic & Medicinal Chemistry Letters*, 10:1677-1679, 2000.

Office Communication issued in U.S. Appl. No. 13/615,284, dated Mar. 17, 2014.

Office Communication issued in U.S. Appl. No. 13/615,284, dated Jan. 27, 2014.

Ohtsuka et al., "Studies on transfer ribonucleic acids and related compounds. IX. Ribooligonucleotide synthesis using a photosensitive o-nitrobenzyl protection at the 2'-hydroxyl group," *Nucleic Acids Res.*, 1:1351-1357, 1974.

Panchuk-Voloshina et al., "Alexa dyes, a series of new fluorescent dyes that yield exceptionally bright, photostable conjugates," *The Journal of Histochemistry & Cytochemistry*, 47(9):1179-1188, 1999.

Patchornik et al., "Photosensitive Protecting Groups," *J. Am. Chem. Soc.*, 92:6333-35, 1970.

Patchornik, In: *Pharmacology of hormonal polypeptides and proteins* (Back et al. (Eds.), Plenum Press, NY, 11-16, 1968.

PCT International Search Report and Written Opinion issued in International Patent Application No. PCT/US2012/055231, dated Nov. 14, 2012.

Pease et al., "Light-generated oligonucleotide arrays for rapid DNA sequence analysis," *Proc. Natl. Acad. Sci. USA*, 91:5022-5026, 1994.

Perler et al., "Intervening sequences in an Archaea DNA polymerase gene," *Proc. Natl. Acad. Sci. USA*, 89:5577-5581, 1992.

Perler et al., "Thermostable DNA polymerases," *Adv. Protein Chem.*, 48:377-435, 1996.

Pillai et al., "Photoremovable protecting groups in organic synthesis," *Synthesis*, 1-26, 1980.

Pop & Salzberg, "Bioinformatics Challenges of New Sequencing Technology," *Trends Genet.*, 24:142-149, 2008.

Prober et al., "A system for rapid DNA sequencing with fluorescent chain-terminating dideoxynucleotides," *Science*, 4825:336-341, 1987.

Ramanathan et al., "An Integrative Approach for the Optical Sequencing of Single DNA Molecules," *Anal. Biochem.*, 330:227-241, 2004.

(56) References Cited

OTHER PUBLICATIONS

Redon et al., "Global variation in copy number in the human genome," *Nature*, 444:444-454, 2006.
Reeve and Fuller, "A novel thermostable polymerase for DNA sequencing," *Nature*, 376:796-797, 1995.
Reichmanis et al., "O-nitrobenzyl Photochemistry: Solutions vs. Solid-State Behavior," *J. Polymer Sci.*, 23:1-8, 1985.
Robbins and Trip, "Sugar-modified $N^6$-(3-methyl-2-butenyl)adenosine derivatives, $N^6$-benzyl analogs, and cytokinin-related nucleosides," *Biochemistry*, 12(12):2179-2187, 1973.
Rockhill et al., "2'-Deoxy-7-(hydroxymethyl)-7-deazaadenosine: A New Analogue to Model Structural Water in the Major Groove of DNA," *J. Am. Chem. Soc.*, 118:10065-68, 1996.
Ronaghi et al., "A Sequencing Method Based on Real-Time Pyrophosphate," *Science*, 281:363-365, 1998.
Sanger, et al., "DNA sequencing with chain-terminating inhibitors," *Proc. Natl. Acad. Sci. USA*, 74(12):5463-5467, 1977.
Schold et al., "Treatment of human brain tumor xenografts with O6-benzyl-2'-deoxyguanosine and BCNU," *Cancer Research*, 56:2076-2081, 1996.
Sebat et al., "Large-Scale Copy Number Polymorphism in the Human Genone," *Science*, 305:525-528, 2004.
Seela and Peng, In: *Current Protocols in Nucleic Acid Chemistry*, Beaucage et al. (Eds.), John Wiley & Sons, Inc., 1.10.1, 2005.
Seio et al., "Synthesis and properties of new nucleotide analogues processing squaramide moieties as new phosphate isosters," *Eur. J. Org. Chem.*, 5163-5170, 2005.
Seo et al., "Four-color DNA sequencing by synthesis on a chip using photocleavable fluorescent nucleotides," *PNAS*, 102(17):5926-5931, 2005.
Seo et al., "Photocleavable fluorescent nucleotides for DNA sequencing on a chip constructed by site-specific coupling chemistry," *PNAS*, 101(15):5488-5493, 2004.
Service, "Chemical Accessories Give DNA New Talents," *Science*, 282:1020-1021, 1998.
Shankar et al., "O6-3-[125I]iodobenzyl-2'-deoxyguanosine ([125I]IBdG): synthesis and evaluation of its usefulness as an agent for quantification of alkylguanine-DNA alkyltransferase (AGT)," *Bioorganic & Medicinal Chemistry*, 13:3889-3898, 2005.
Shapiro and Shiuey, "Reactions of cytidine with 7-bromomethylbenz[a]anthracene, benzyl bromide, and p-methoxybenzyl bromide. Ratio of Amino to 3 substitution," *J. Org. Chem.*, 41(9): 1597-1600, 1976.
Shendure, et al., "Accurate Multiplex Polony Sequencing of an Evolved Bacterial Genome," *Science*, 309:1728-1732, 2005.
Sierzchala et al., "Solid-phase oligodeoxynucleotide synthesis: A two-step cycle using peroxy anion deprotection," *J. Am. Chem. Soc.*, 125:13427-13441, 2003.
Šilhár, et al., "Synthesis, cytostatic and anti-HCV activity of 6-(N-substituted aminomethyl)-, 6-(O-substituted hydroxymethyl)- and 6(S-substituted sulfanylmethyl)purine nucleosides," *Bioorg. & Med. Chem.*, 16:2329-2366, 2008.
Soengas et al., "Helix-destabilizing Activity of φ29 Single-stranded DNA Binding Protein: Effect on the Elongation Rate During Strand Displacement DNA Replication," *J. Mol. Biol.*, 253:517-29, 1995.
Sousa & Weinstein, "Photoisomerization of 2-(2,4-dinitrobenzyl)pyridine and 2-(2-nitro-4-cyanobenzyl)pyridine," *J. Org. Chem.*, 27:3155-59, 1962.
Southworth et al., "Cloning of thermostable DNA polymerases from hyperthermophilic marine Archaea with emphasis on *Thermococcus* sp. 9°N-7 and mutations affecting 3'-5' exonuclease activity," *Proc. Natl. Acad. Sci. USA*, 93:5281-5285, 1996.
Stranger et al., "Relative impact of nucleotide and copy number variation on gene expression phenotypes," *Science*, 315:848-853, 2007.
Stupi et al., "Stereochemistry of Benzylic Carbon Substitution Coupled with Ring Modification of 2-Nitrobenzyl Groups as Key Determinants for Fast-Cleaving Reversible Terminators," *Angew. Chem. Int. Ed.*, 51:1724-1727, 2012.
Su et al., "A Platform for Rapid Detection of Multiple Oncogenic Mutations with Relevance to Targeted Therapy in Non-Small-Cell Lung Cancer," *J. Mol Diagn.*, 13:74-84, 2011.
Supplemental Information for Ju et al., "Four-color DNA sequencing by synthesis using cleavable fluorescent nucleotide reversible terminators," *Proc. Natl. Acad. Sci. USA*, 103:19635-40, 2006.
Tabor and Richardson, "A single residue in DNA polymerases of the *Escherichia coli* DNA polymerase I family is critical for distinguishing between deoxy- and dideoxyribonucleotides," *Proc. Natl. Acad. Sci. USA*, 92:6339-6343, 1995.
Tahiliani et al., "Conversion of 5-Methylcytosine to 5-Hydroxymethylcytosine in Mammalian DNA by MLL Partner TET1," *Science*, 324:930-35, 2009.
Terrashima et al., "Substrate specificity of human $O^6$-methylguanine-DNA methyltransferase for $O^6$-benzylguanine derivatives in oligodeoxynucleotides," *Chem. Res. Toxicol.*, 10:1234-1239, 1997.
The International SNP Map Working Group, "A map of human genome sequence variation containing 1.42 million single nucleotide polymorphisms," *Nature*, 409:928-933, 2001.
Turcatti et al., "A New Class of Cleavable Fluorescent Nucleotides: Synthesis and Optimization as Reversible Terminators for DNA sequencing by Synthesis," *Nucleic Acids Res.*, 36:e25, 2008.
Tuzun et al., "Fine-scale Structural Variation of the Human Genome," *Nature Genet.*, 37:727-32, 2005.
Valouev, et al., "A High-resolution, Nucleosome Position Map of *C. elegans* Reveals a Lack of Universal Sequence-dictated Positioning," *Genome Res.*, 18:1051-1063, 2008.
van Tilburg et al., "$N^6$,5'-disubstituted adenosine derivatives as partial agonists for the human adenosine $A_3$ receptor," *J. Med. Chem.*, 42:1393-1400, 1999.
Vander Horn et al., "Thermo Sequenase™ DNA polymerase and *T. acidophilum* pyrophosphatase: new thermo-stable enzymes for DNA sequencing," *BioTechniques*, 22:758-765, 1997.
Walker et al., "Photolabile Protecting Groups for an Acetylcholine Receptor Ligand. Synthesis and Photochemistry of a New Class of O-nitrobenzyl Derivatives and Their Effects on Receptor Function," *Biochemistry*, 25:1799-1805, 1986.
Wang, et al., "RNA-Seq: a Revolutionary Tool for Transcriptomics," *Nature Rev. Genet.*, 10:57-63, 2009.
Weinstein et al., "Substituent Effects in Photochromic Nitrobenzylpyridines," *J. Org. Chem.*, 31:1983-1985, 1966.
Welch and Burgess, "Synthesis of fluorescent, photolabile 3'-O-protected nucleoside triphosphates for the base addition sequencing scheme," *Nucleosides & Nucleotides*, 18(2):197-201, 1999.
Welch et al., "Synthesis of nucleosides designed for combinatorial DNA sequencing," *Chem. Eur. J.*, 5(3):951-960, 1999.
Wettermark, "Photochromism of O-nitrotoluenes," *Nature*, 194:677, 1962.
Wootton & Trentham, In: *Photochemical probes in biochemistry* (*NATO Science Series C*), Nielsen (Ed)., Kluwer Academic Publishers, Ann Arbor, 272:277-296, 1989.
Wu et al., "Somatic Histone H3 Alterations in Pediatric Diffuse Intrinsic Pontine Gliomas and Non-brainstem Glioblastomas," *Nature Genet.*, 44:251-253, 2012.
Wu et al., "Termination of DNA synthesis by $N^6$-alkylated, not 3'-O-alkylated, photocleavable 2'-deoxyadenosine triphosphates," *Nucleic Acids Research*, 35(19):6339-6349, 2007.
Wyatt & Cohen, "The Bases of the Nucleic Acids of Some Bacterial and Animal Viruses: the Occurrence of 5-Hydromethylcytosine," *Biochem. J.*, 55:774-782, 1953.
Yamashita et al., "Studies on antitumor agents. IX. Synthesis of 3'-O-benzyl-2'-deoxy-5-trifluoromethyluridine," *Chem Pharm. Bull.*, 37(9):2287-2292, 1989.
Yu et al., "Synthesis of 3,7,8-$^{15}N_3$-$N^1$-(beta-D-*erythro*-pentofuranosyl)-5-guanidinohydantoin," *Journal of Labelled Compounds and Radiopharmaceuticals*, 46:1269-1277, 2003.

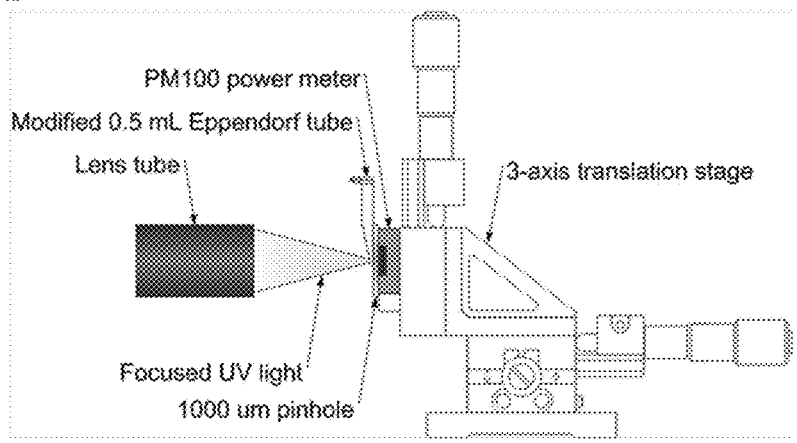
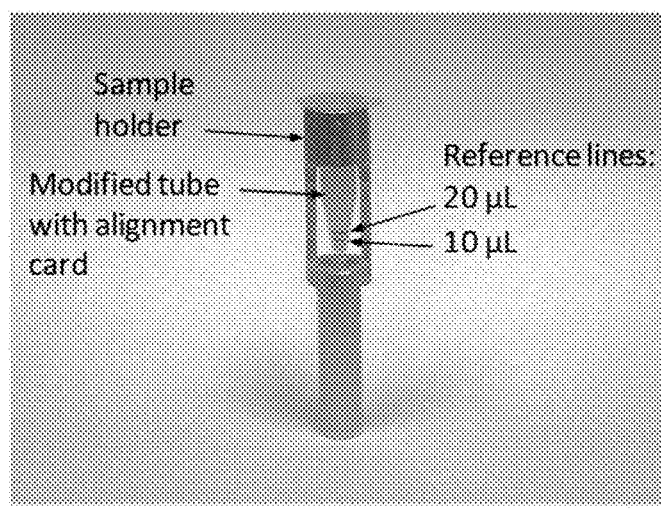
FIGS. 5A & B

3'-OH UNBLOCKED, FAST PHOTOCLEAVABLE TERMINATING NUCLEOTIDES AND METHODS FOR NUCLEIC ACID SEQUENCING

The present application is a divisional patent application of co-pending U.S. patent application Ser. No. 13/615,284, filed Sep. 13, 2012, which claims the benefit of priority to U.S. Provisional Application No. 61/627,211, filed Oct. 7, 2011, and U.S. Provisional Application No. 61/534,347, filed Sep. 13, 2011. The contents of each of the above-referenced applications are incorporated herein by reference.

BACKGROUND OF THE INVENTION

I. Field of the Invention

The present invention relates generally to compositions and methods for DNA sequencing and other types of DNA analysis. More particularly, the invention relates in part to fast 3'-OH unblocked nucleotides and nucleosides with photochemically cleavable groups and methods for their use in a number of DNA sequencing methods, including applications in biomedical research.

II. Description of Related Art

Methods for rapidly sequencing DNA are needed for analyzing diseases and mutations in the population and developing therapies (Metzker, 2010, which is incorporated herein by reference). Commonly observed forms of human sequence variation are single nucleotide polymorphisms (SNPs), which occur in approximately 1-in-300 to 1-in-1000 base pairs of genomic sequence and structural variants (SVs) including block substitutions, insertion/deletions, inversions, segmental duplications, and copy number variants. Structural variants can account for 22% of all variable events and more variant bases than those contributed by SNPs (Levy et al., 2007, which is incorporated herein by reference). This finding is consistent with that of Scherer, Hurles, and colleagues who analyzed 270 individuals using microarray based methods (Redon et al., 2006, which is incorporated herein by reference). Building upon the complete sequence of the human genome, efforts are underway to identify the underlying genetic link to common diseases and cancer by SNP and SV mapping or direct association. Technology developments focused on rapid, high-throughput, and low cost DNA sequencing would facilitate the understanding and use of genetic information, such as SNPs and SVs, in applied medicine.

In general, 10%-to-15% of SNPs will affect protein function by altering specific amino acid residues, will affect the proper processing of genes by changing splicing mechanisms, or will affect the normal level of expression of the gene or protein by varying regulatory mechanisms. SVs may also play an important role in human biology and disease (Iafrate et al., 2004; Sebat et al., 2004; Tuzun et al., 2005; Stranger et al., 2007, which are incorporated herein by reference). It is envisioned that the identification of informative SNPs and SVs will lead to more accurate diagnosis of inherited disease, better prognosis of risk susceptibilities, or identity of sporadic mutations in tissue. One application of an individual's SNP and SV profile would be to significantly delay the onset or progression of disease with prophylactic drug therapies. Moreover, an SNP and SV profile of drug metabolizing genes could be used to prescribe a specific drug regimen to provide safer and more efficacious results. To accomplish these ambitious goals, genome sequencing will move into the resequencing phase with the potential of partial sequencing of a large majority of the population, which would involve sequencing specific regions in parallel, which are distributed throughout the human genome to obtain the SNP and SV profile for a given complex disease.

Sequence variations underlying most common diseases are likely to involve multiple SNPs, SVs, and a number of combinations thereof, which are dispersed throughout associated genes and exist in low frequency. Thus, DNA sequencing technologies that employ strategies for de novo sequencing are more likely to detect and/or discover these rare, widely dispersed variants than technologies targeting only known SNPs.

One example how NGS technologies can be applied in the detection of SNPs, SVs, single nucleotide variants (SNVs) and a number of combinations thereof is cancer diagnostics. These assays have traditionally been a single-marker, single-assay approach that has recently progressed to assaying multiple markers with a single experimental approach. However, each cancer is genetically complex often with many mutations occurring simultaneously in numerous genes. Therefore, traditional methods lead to expensive and time-consuming testing, while providing information only on a select few of known sequence variants. Recent advances in NGS technologies have allowed targeted approaches that center on many medically actionable gene targets associated with various cancer types (See Su et al., 2011; Beadling et al. 2012). Due to recent successes of sequencing efforts, such as The Cancer Genome Atlas (TCGA) project, the International Cancer Genome Consortium (ICGC) project, and the Catalogue of Somatic Mutations in Cancer (COSMIC) database, there is a large compendium of knowledge regarding these gene targets in many cancer types and the result of therapeutics on cancers containing those mutations (See Futreal et al., 2004). Additional work, in part as a result of the Pediatric Cancer Genome Project, has shown that pediatric cancers have distinct genetic profiles marked by a fewer number of mutations and a prevalence of mutations in alternative molecular pathways (See, Wu et al., 2012; Meldrum et al. 2011). The largest current unmet need in cancer diagnostics is a fast, high-throughput technology with the needed accuracy and sensitivity for early-stage detection to identify rare sequence variants that belong to a limited subpopulation of cells undergoing a cancerous transformation.

Traditionally, DNA sequencing has been accomplished by the "Sanger" or "dideoxy" method, which involves the chain termination of DNA synthesis by the incorporation of 2',3'-dideoxynucleotides (ddNTPs) using DNA polymerase (Metzker et al., 2005, which is incorporated herein by reference). Since 2005, there has been a fundamental shift away from the application of automated Sanger sequencing for genome analysis. Advantages of next-generation sequencing (NGS) technologies include the ability to produce an enormous volume of data cheaply, in some cases in excess of a hundred million short sequence reads per instrument run. Many of these approaches are commonly referred to as sequencing-by-synthesis (SBS), which does not clearly delineate the different mechanics of sequencing DNA (Metzker, 2010; Metzker 2005, which are incorporated herein by reference). DNA polymerase-dependent strategies have been classified as cyclic reversible termination (CRT), single nucleotide addition (SNA, e.g., pyrosequencing), and real-time sequencing. An approach whereby DNA polymerase is replaced by DNA ligase is referred to as sequencing-by-ligation (SBL). These approaches have been described in Metzker (2010), which is incorporated herein by reference.

Sequencing technologies include a number of methods that are grouped broadly as (a) template preparation, (b) sequencing and imaging, and (c) data analysis. The unique combination of specific protocols distinguishes one technology from another and determines the type of data produced from each platform. These differences in data output present challenges when comparing platforms based on data quality and cost. Although quality scores and accuracy estimates are provided by each manufacturer, there is no consensus that a 'quality base' from one platform is equivalent to that from another platform.

Two methods used in preparing templates for NGS reactions include: clonally amplified templates originating from single DNA molecules and single DNA molecule templates. Sequencing methods that use DNA polymerases are classified as cyclic reversible termination (CRT), single-nucleotide addition (SNA) and real-time sequencing, (See Metzker 2010). Sequencing by ligation (SBL), an approach in which DNA polymerase is replaced by DNA ligase, has also been used in the NGS technologies, (see, e.g., Shendure et al., 2005; Valouev et al., 2008). Imaging methods coupled with these sequencing strategies range from measuring bioluminescent signals to four-color imaging of single molecular events. The voluminous data produced by these NGS platforms place substantial demands on information technology in terms of data storage, tracking and quality control (see Pop & Salzberg, 2008).

The need for robust methods that produce a representative, non-biased source of nucleic acid material from the genome under investigation remains an important goal. Current methods generally involve randomly breaking genomic DNA into smaller sizes from which either fragment templates or mate-pair templates are created. A common theme among NGS technologies is that the template is attached or immobilized to a solid surface or support. The immobilization of spatially separated template sites allows thousands to billions of sequencing reactions to be performed simultaneously.

Although clonally amplified methods offer certain advantages over bacterial cloning, some of the protocols are typically cumbersome to implement and require a large amount of genomic DNA material (3-20 µg). The preparation of single-molecule templates is more straightforward and requires less starting material (<1 µg). Moreover, these methods do not require PCR, which creates mutations in clonally amplified templates that masquerade as sequence variants. AT-rich and GC-rich target sequences may also show amplification bias in product yield, which results in their underrepresentation in genome alignments and assemblies. Quantitative applications, such as RNA-seq (See Wang et al., 2009), perform more effectively with non-amplified template sources, which do not alter the representational abundance of mRNA molecules.

An important aspect of the CRT method is the reversible terminator, of which there are two main types: 3'-O-blocked and 3'-OH unblocked (Metzker, 2010). The use of a ddNTP, which acts as a chain terminator in Sanger sequencing, provided the basis for the initial development of reversible blocking groups attached to the 3'-end of nucleotides (Metzker et al. 1994; Canard & Sarfati, 1994). Blocking groups such as 3'-O-allyl-dNTPs (Metzker et al., 1994; U.S. Pat. No. 6,664,079; Ju et al., 2006; U.S. Pat. No. 7,057,026; U.S. Pat. No. 7,345,159; U.S. Pat. No. 7,635,578; U.S. Pat. No. 7,713,698) and 3'-O-azidomethyl-dNTPs (U.S. Pat. No. 7,057,026; Guo et al., 2008; Bentley et al., 2008; U.S. Pat. No. 7,414,116; U.S. Pat. No. 7,541,444; U.S. Pat. No. 7,592,435; U.S. Pat. No. 7,556,537; U.S. Pat. No. 7,771,973) have been used in CRT. 3'-O-Blocked terminators require the cleavage of two chemical bonds to remove the fluorophore from the nucleobase and restore the 3'-OH group. A drawback in using these reversible terminators is that the blocking group attached to the 3'-end typically causes a bias against incorporation with DNA polymerase. Mutagenesis of DNA polymerase is often required to facilitate incorporation of 3'-O-blocked terminators. Large numbers of genetically engineered DNA polymerases have to be created by either site-directed or random mutagenesis containing one or more amino acid substitutions, insertions, and/or deletions and then identified by high-throughput screening with the goal of incorporating 3'-blocked nucleotides more efficiently.

The difficulty in identifying a modified enzyme that efficiently incorporates 3'-O-blocked terminators by screening large libraries of mutant DNA polymerases has led to the development of 3'-unblocked reversible terminators. It was demonstrated that a small photocleavable group attached to the base of a 3'-OH unblocked nucleotide can act as an effective reversible terminator and be efficiently incorporated by wild-type DNA polymerases (Wu et al., 2007; Metzker, 2010; Litosh et al., 2011, Gardner et al., 2012; U.S. Pat. Nos. 7,897,737, 7,964,352; and 8,148,503, U.S. Patent Appl. Publication 2011/0287427). For example, 5-hydroxymethyl-2'-deoxyuridine (HOMedU) is found naturally in the genomes of numerous bacteriophages and lower eukaryotes (Gommers-Ampt, 1995, which is incorporated herein by reference). Its hydroxymethyl group can serve as molecular handle to attach a small photocleavable terminating group. Other naturally occurring hypermodified bases that can be further modified to function as reversible terminators include 5-hydroxymethyl-2'-deoxycytidine (HOMedC), which is found naturally in the genomes of T2, T4, and T6 bacteriophages (Wyatt & Cohen, 1953; Gommers-Ampt, 1995) and of mammals (Kriaucionis & Heintz, 2009; Tahiliani et al., 2009; Ito et al., 2010). The pyrrolopyrimidine ring structure (7-deazapurine) is also found naturally in nucleoside antibiotics (Carrasco & Vázquez, 1984, which is incorporated herein by reference) and tRNA bases (Limbach, et al., 1994, which is incorporated herein by reference), and the compounds 7-deaza-7-hydroxymethyl-2'-deoxyadenosine ($C^7$-HOMedA) (Rockhill et al., 1997) and 7-deaza-7-hydroxymethyl-2'-deoxyguanosine ($C^7$-HOMedG) (McDougall et al., 2001) have been reported.

One aspect of the present invention is the use of a modified 2-nitrobenzyl group attached to the nucleobase of hydroxymethyl nucleoside and nucleotides. Described over a half century ago, solutions of 2-nitrotoluene (Wettermark, 1962) and its derivatives (Wettermark, 1962; Hardwick et al., 1960; Mosher et al., 1960; Sousa & Weinstein, 1962; Weinstein et al., 1966) were reported to exhibit the property of photochromism, a phenomenon considered to be the result of transient formation of an aci-nitro anion intermediate (Weinstein et al., 1966; Morrison, 1969). Without being bound by theory, it is generally accepted that absorption of a photon by the nitro group results in hydrogen abstraction from the α-carbon (Mosher et al., 1960; Berson & Brown, 1955; De Mayo, 1960), formation of the aci-nitro anion intermediate, and then release of the 'caged' effector molecule and creation of a nitrosocarbonyl by-product (Corrie, 2005). These early studies suggested that α-substitution of the benzylic carbon (Wettermark, 1962) or substitution of the 4-position of the benzene ring with an electron-donating group (Sousa & Weinstein, 1962; Weinstein et al, 1966) increased the rate of the photochromic effect. These findings led to the development of photosensitive 2-nitrobenzyl protecting groups (Barltrop et al., 1966; Patchornik, 1968; Patchornik et al., 1970). The degree to which the rate of photochemical cleavage is altered, however, typically depends on numerous factors that are reported to include substitution of the benzylic carbon (Walker et al., 1986; Hasan et al., 1997; Giegrich et al., 1998), functional group(s) attached to the benzyl ring (Wootton & Trentham, 1989; Hasan et al., 1997; Giegrich et al., 1998), and the leaving group (Walker et al., 1986) as well as pH (McCray et al., 1980; Walker et al., 1986; Wootton & Trentham, 1989), solvent (Sousa & Weinstein, 1962; McGall et al., 1997; Giegrich et al., 1998), and light intensity (McCray et al., 1980; McGall et al., 1997). One property, however, that has not been studied is stereochemistry, whereby, substitution of 2-nitrobenzyl's benzylic or α-carbon results in a chiral center. For the case of nucleotide synthesis, coupling of a racemic α-substituted 2-nitrobenzyl alcohol would result in two diastereomers, which differ only by the absolute configuration (R or S) at the benzylic carbon.

Another class of 3'-OH unblocked nucleotides has been described by Mitra et al. (2003) and Turcatti et al. (2008), which rely on steric hindrance of the bulky dye group to stop incorporation after the addition of the first nucleotide. It is noted that the substituted 2-nitrobenzyl nucleotide analogs described by Wu et al. (2007), Litosh et al. (2011), and Gardner et al., 2012 cause termination of DNA synthesis without the requirement of bulky substituents such as fluorescent dyes. A further class of 3'-unblocked nucleotides has been described by Helicos Biosciences. These nucleotides use a second nucleoside or nucleotide analog that acts as an inhibitor of DNA synthesis (Bowers et al., 2009; U.S. Pat. No. 7,476,734). A significant difference in termination properties is observed when comparing compounds of the present invention with those described by Bowers. For example, Bowers et al. described pre-steady-state kinetics employing two-base homopolymer templates, for which $k_{pol(+2)}$ rates were measured for all of their 3'-OH unblocked 'virtual' terminators. Bowers et al. conducted their termination experiments at submicromolar nucleotide concentrations (i.e., from 100 to 250 nM), termination assays. In contrast, several compounds of the present invention were performed at 10 μM over the time course of 0.5 to 20 min. Both compounds dU.V and dU.VI were rapidly incorporated at the first base position (100% by 2 min) and then terminated DNA synthesis at that position. No appreciable signal could be detected at the expected second-base position up to incubation times of 20 min. See Gardner et al., 2012 for more details.

3'-OH unblocked reversible terminators typically have several advantages over 3'-O-blocked nucleotides. For example, for many 3'-OH unblocked reversible terminators the cleavage of only a single bond removes both the terminating and fluorophore groups from the nucleobase. This in turn results in a more efficient strategy for restoring the nucleotide for the next CRT cycle. A second advantage of 3'-OH unblocked reversible terminators is that many of these compounds show more favorable enzymatic incorporation and, in some cases, can be incorporated as well as a natural nucleotide with wild-type DNA polymerases (Wu et al., 2007; Litosh et al., 2011; Gardner et al., 2012; U.S. Pat. No. 7,897,737; U.S. Pat. No. 7,964,352; U.S. Pat. No. 8,148,503; U.S. Patent Appl. Publication 2011/0287427), although in other cases this efficiency has not been observed (Bowers et al., 2009; U.S. Pat. No. 7,476,734). One challenge for 3'-OH unblocked terminators is creating the appropriate modifications to the base that lead to termination of DNA synthesis after a single base addition. This is important because an unblocked 3'-OH group is the natural substrate for incorporating the next incoming nucleotide.

Next-generation sequencing (NGS) technologies have facilitated important biomedical discoveries, yet chemistry improvements are still needed for a number of reasons, including reduction of error rates, reduction of slow cycle times. To be effective in NGS assays, it is typically desirable for reversible terminators to exhibit a number of ideal properties including, for example, fast kinetics of nucleotide incorporation, single-base termination, high nucleotide selectivity, and/or rapid cleavage of the terminating group. Thus, there is a need for developing new nucleosides and nucleotides that meet these challenges.

SUMMARY OF THE INVENTION

In some aspects, the present disclosure provides novel compounds and compositions that are useful in efficient sequencing of genomic information in high throughput sequencing reactions. In another aspect, reagents and combinations of reagents that can efficiently and affordably provide genomic information are provided. In further aspects, the present invention provides libraries and arrays of reagents for diagnostic methods and for developing targeted therapeutics for individuals.

In some aspects, the present disclosure provides new compounds that may be used in DNA sequencing. For example, the present disclosure provides compounds of the formula:

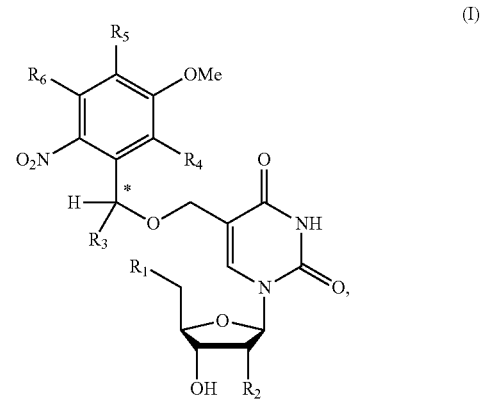

(I)

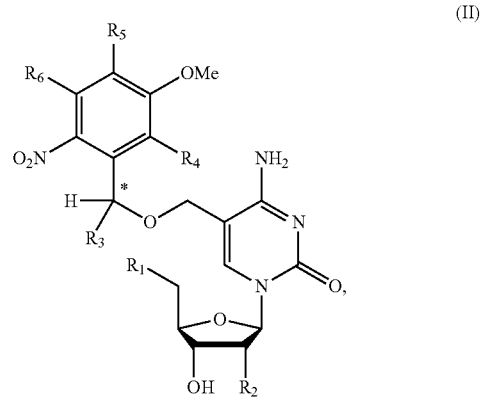

(II)

(III) 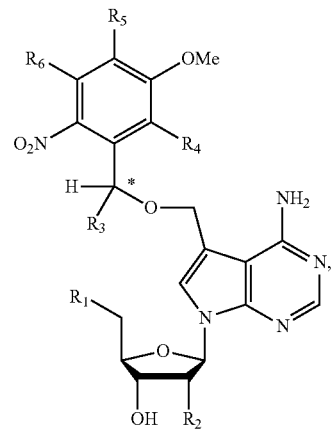

(IV) 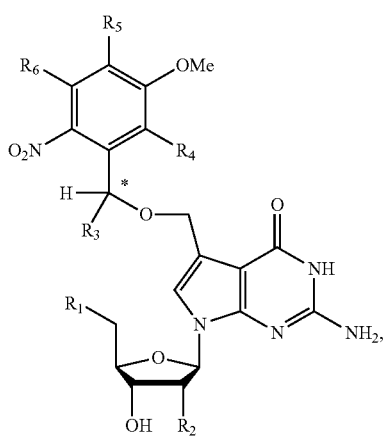

(V) 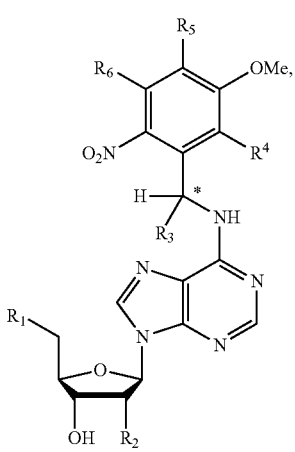

(VI) 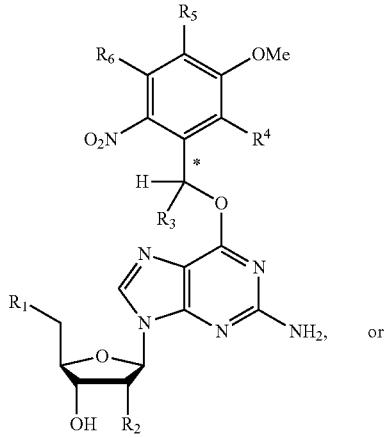

(VII) 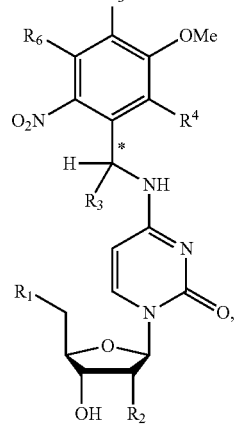

wherein:
R$_1$ is hydroxy, monophosphate, diphosphate, triphosphate, α-thiotriphosphate or polyphosphate;
R$_2$ is hydrogen or hydroxy;
R$_3$ is alkyl$_{(C \leq 8)}$ or substituted alkyl$_{(C \leq 8)}$;
R$_4$ is
  hydrogen, hydroxy, halo, amino, nitro, cyano, azido or mercapto;
  alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkyl-amino$_{(C \leq 6)}$, amido$_{(C \leq 6)}$, or a substituted version of any of these groups;
R$_5$ and R$_6$ are each independently:
  hydrogen, hydroxy, halo, amino, nitro, cyano, azido or mercapto;
  alkyl$_{(C \leq 6)}$, alkenyl$_{(C \leq 6)}$, alkynyl$_{(C \leq 6)}$, aryl$_{(C \leq 6)}$, aralkyl$_{(C \leq 8)}$, heteroaryl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkyl-amino$_{(C \leq 6)}$, amido$_{(C \leq 6)}$, or a substituted version of any of these groups;
a group of formula:

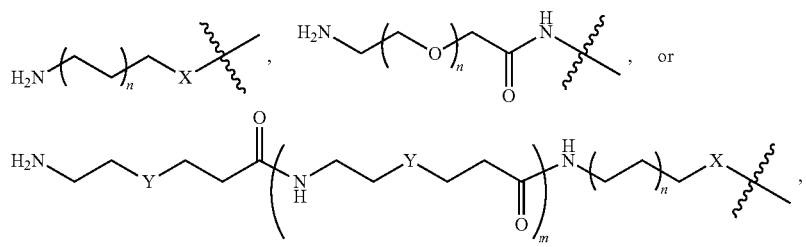

wherein

X is
—O—, —S—, or —NH—; or
alkanediyl$_{(C\leq 12)}$, alkenediyl$_{(C\leq 12)}$, alkynediyl$_{(C\leq 12)}$, or a substituted version of any of these groups;

Y is —O—, —NH—, alkanediyl$_{(C\leq 12)}$ or substituted alkane-diyl$_{(C\leq 12)}$;

n is an integer from 0-6; and m is an integer from 0-6; or a -linker-reporter;

or a salt, tautomer, or optical isomer thereof.

In some embodiments, the compounds are further defined as a compound of formulas I, II, III, IV, V, VI or VII. In some embodiments, $R_1$ is hydroxy, monophosphate, diphosphate, triphosphate, α-thiotriphosphate, or polyphosphate.

In some embodiments, $R_2$ is hydrogen, hydroxy. In some embodiments, $R_3$ is alkyl$_{(C\leq 8)}$, for example, alkyl$_{(C3-4)}$, including isopropyl or tert-butyl. In some embodiments, $R_4$ is hydrogen, nitro. In some embodiments, $R_5$ is hydrogen, iodo, or alkoxy$_{(C\leq 6)}$, including, for example, methoxy. In some embodiments, $R_5$ is a group of formula:

wherein
X is
—O—, —S—, or —NH—; or
alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; and
n is an integer from 0-6.

In some embodiments, X is alkynediyl$_{(C2-8)}$, for example, —C≡C—. In some embodiments, n is zero. In some embodiments, $R_5$ is a group of formula:

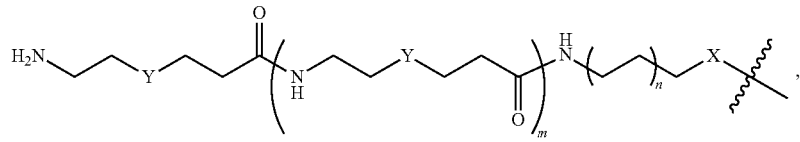

wherein
X is
—O—, —S—, or —NH—; or
alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups;
Y is —O—, —NH—, alkanediyl$_{(C\leq 12)}$ or substituted alkanediyl$_{(C\leq 12)}$;
n is an integer from 0-6; and
m is an integer from 0-6.

In some embodiments, X is alkynediyl$_{(C2-8)}$, for example, —C≡C—. In some embodiments, Y is —CH$_2$—. In some embodiments, n is zero. In some embodiments, m is zero. In some embodiments, $R_5$ is a -linker-reporter. In some embodiments, the linker is:

wherein
X is
—O—, —S—, or —NH—; or
alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; and
n is an integer from 0-6.

In some embodiments, X is alkynediyl$_{(C2-8)}$, for example, —C≡C—. In some embodiments, n is zero. In some embodiments, the linker is:

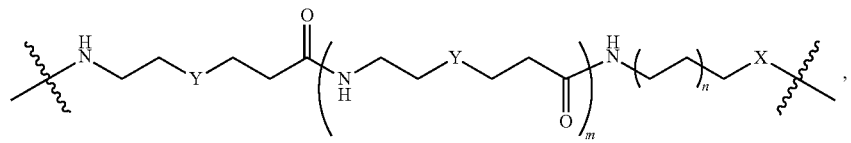

wherein
X is
—O—, —S—, or —NH—; or
alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups;

Y is —O—, —NH—, alkanediyl$_{(C\leq 12)}$ or substituted alkanediyl$_{(C\leq 12)}$;

n is an integer from 0-6; and m is an integer from 0-6.

In some embodiments, X is alkynediyl$_{(C2-8)}$, for example, —C≡C—. In some embodiments, Y is —CH$_2$—. In some embodiments, n is zero. In some embodiments, m is zero. In some embodiments, the reporter is based on a dye, wherein the dye is zanthene, fluorescein, rhodamine, BODIPY, cyanine, coumarin, pyrene, phthalocyanine, phycobiliprotein, or a squaraine dye. In some embodiments, the reporter is:

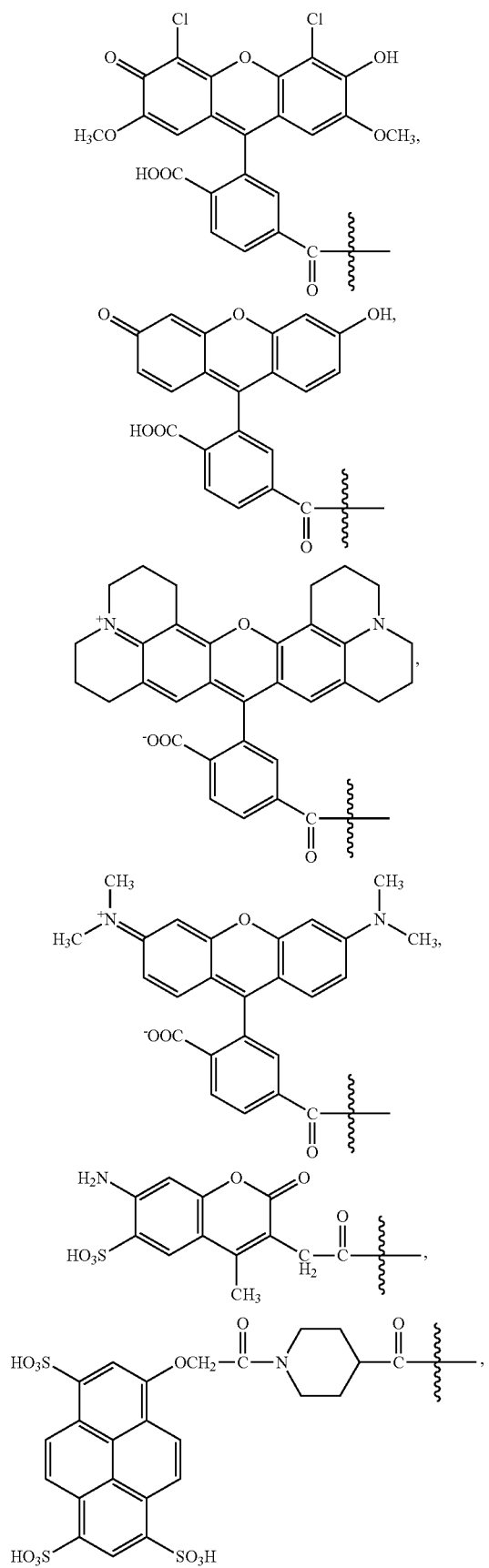
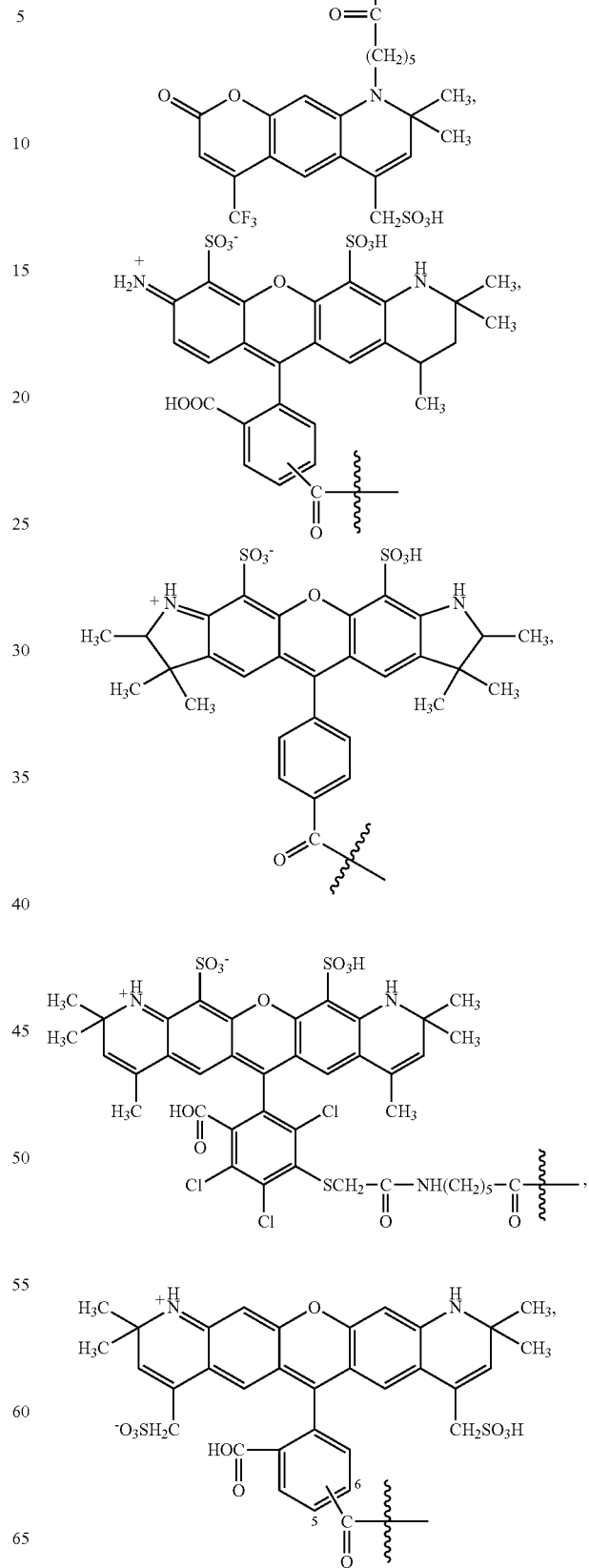

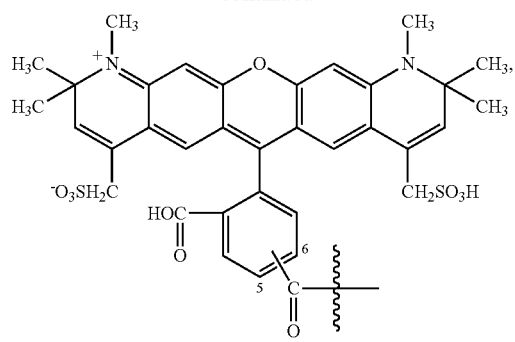
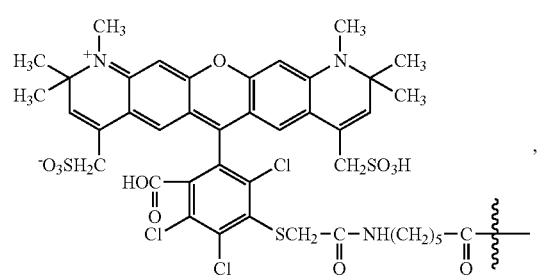
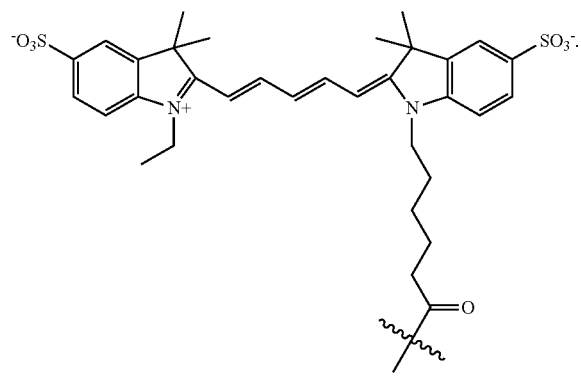
In some embodiments, $R_6$ is hydrogen. In some embodiments, the starred carbon atom is in the S configuration. In some embodiments, the starred carbon atom is in the R configuration. In some embodiments, the compound is further defined as:
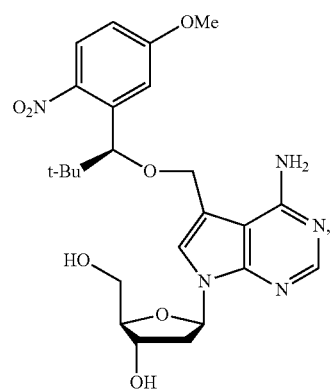
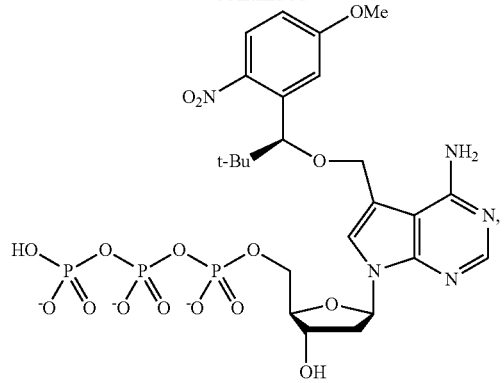
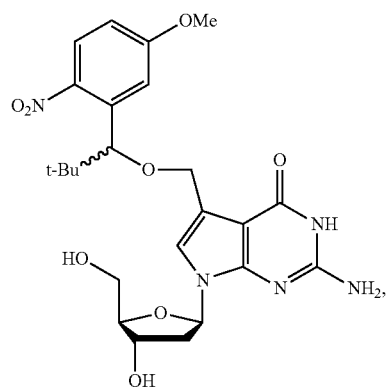
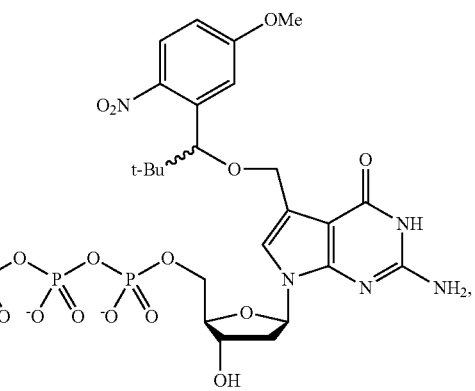
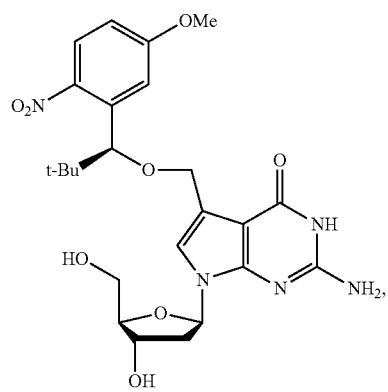

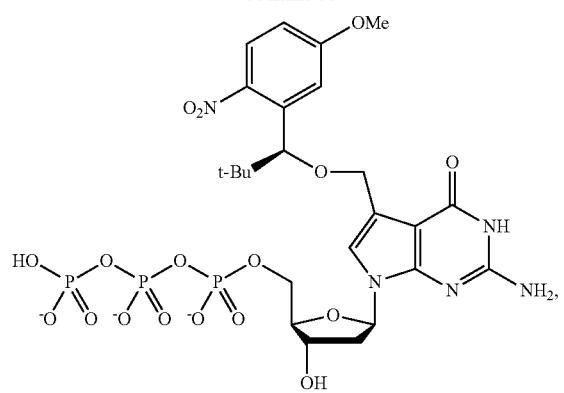
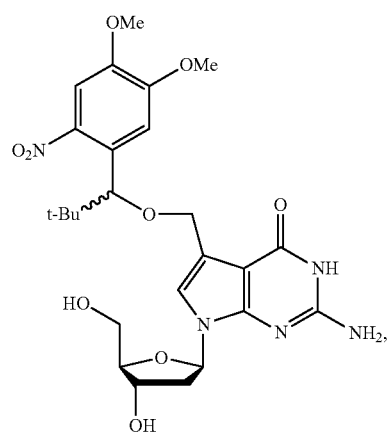
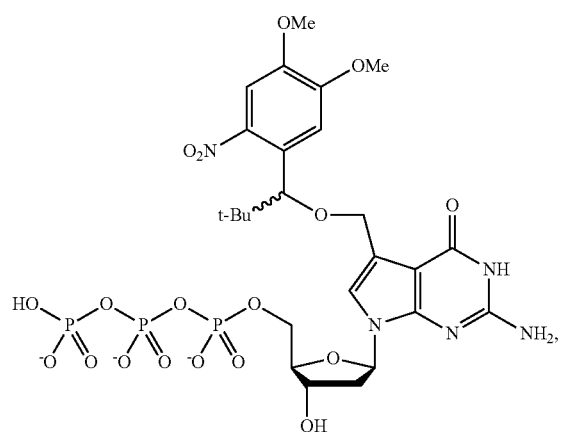
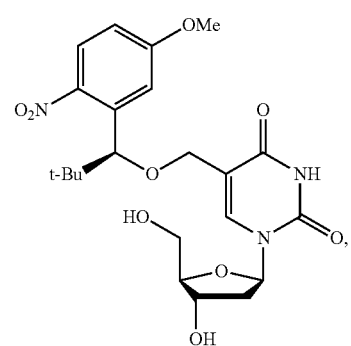
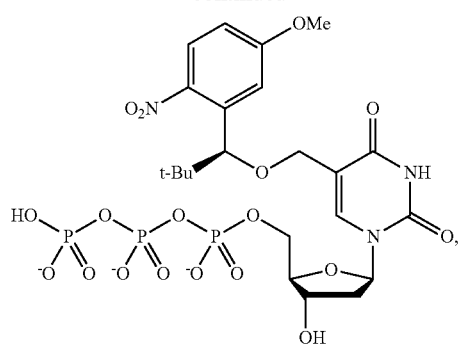
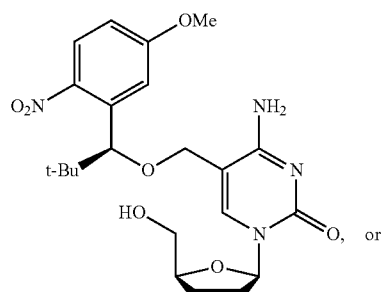
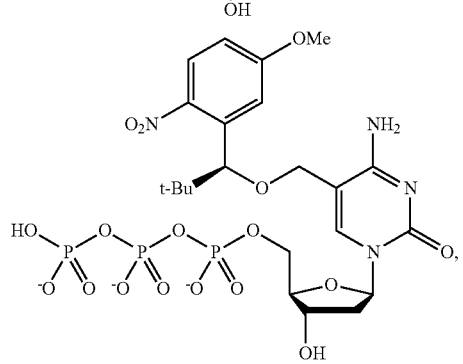
or a salt and/or protonated form of any of these formulas.
In some embodiments, the compound is further defined as:
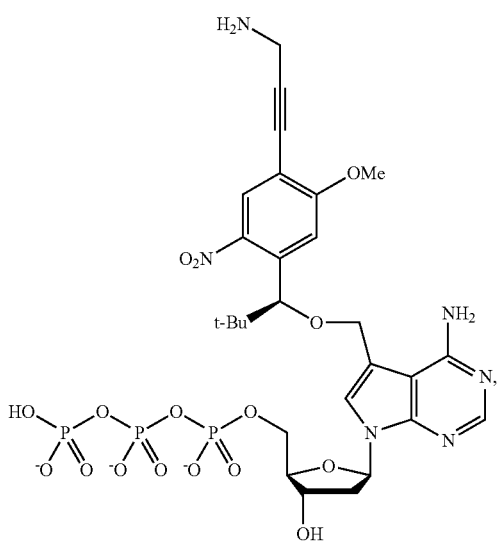

-continued
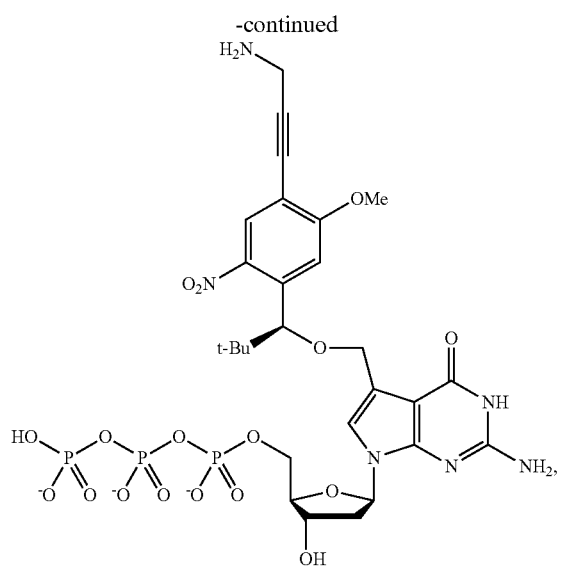
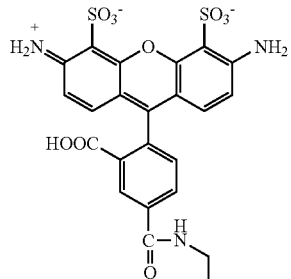
In some embodiments, the compound is further as:
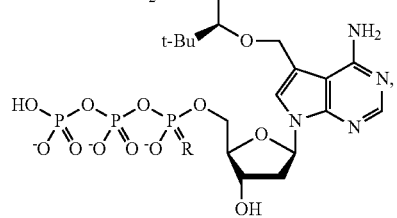
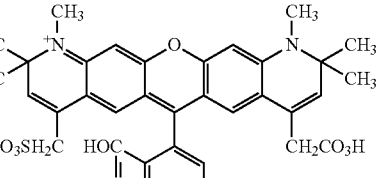
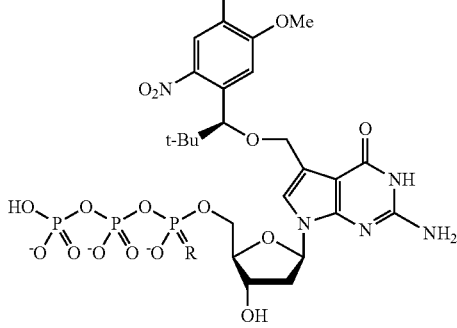
wherein R is =O or =S, or a salt and/or protonated form of any of these formulas.

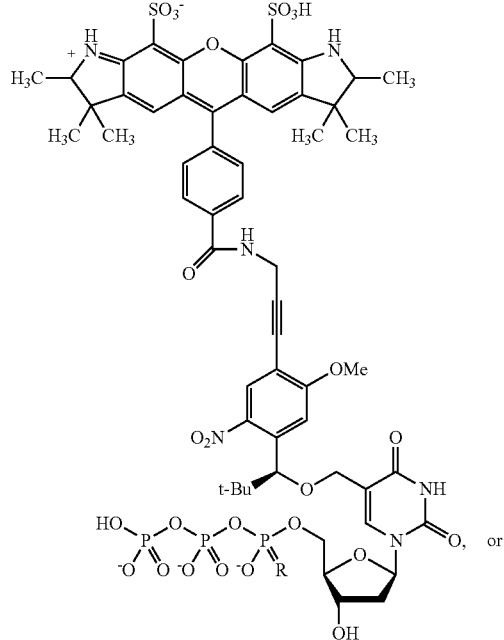
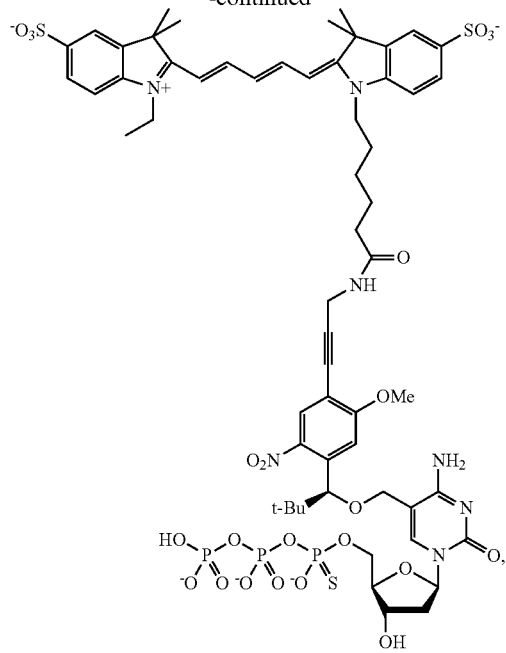
wherein R is =O or =S, or a salt and/or protonated form of any of these formulas.
In some embodiments, the compound is further defined as:
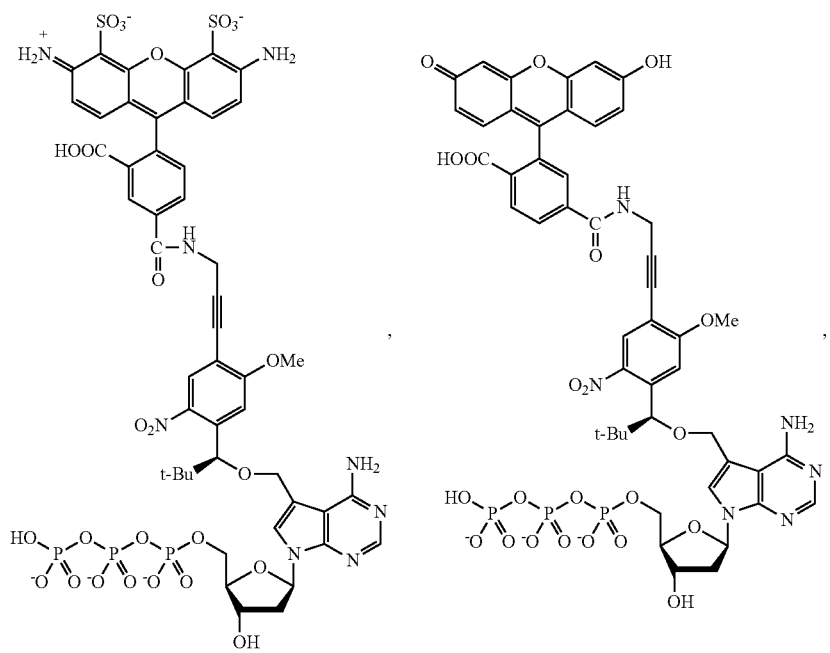

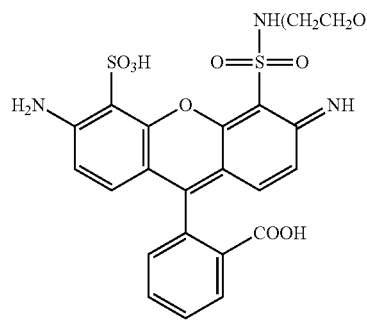
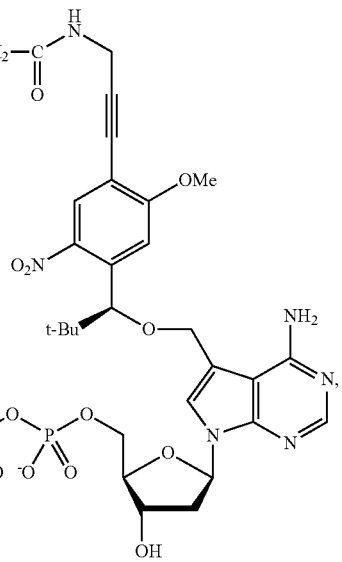
-continued
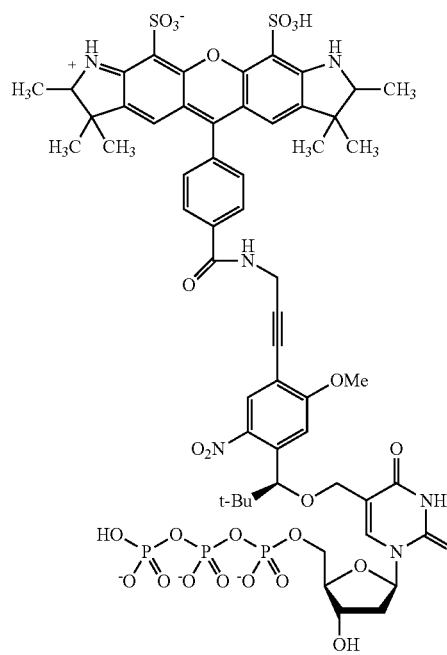
,
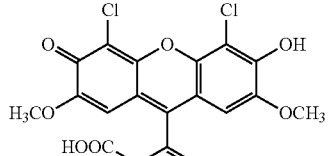
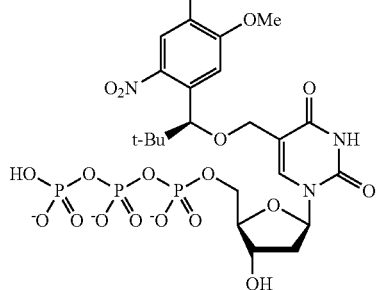
,

-continued

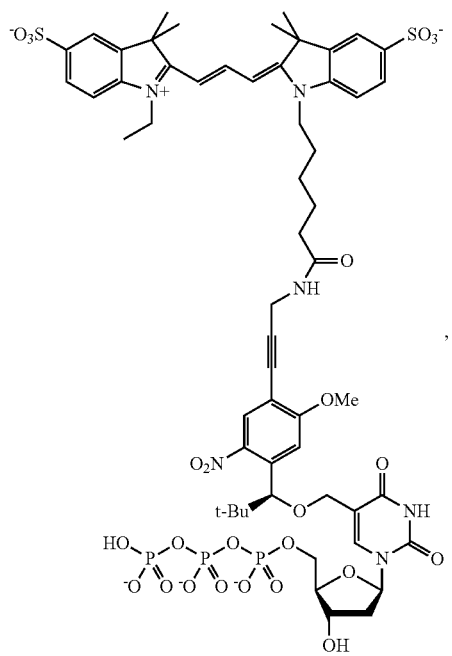

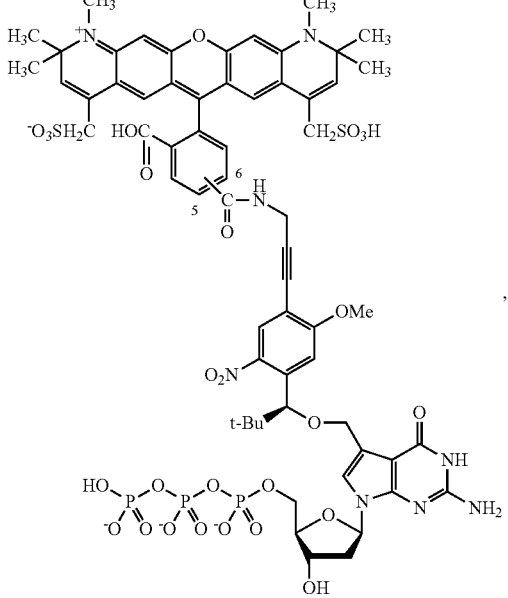

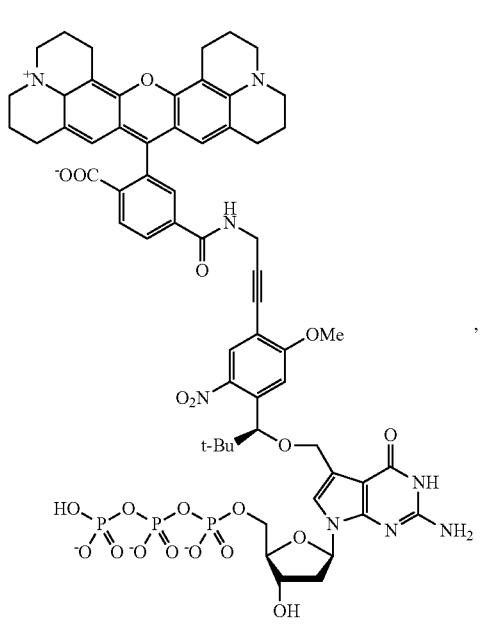, or

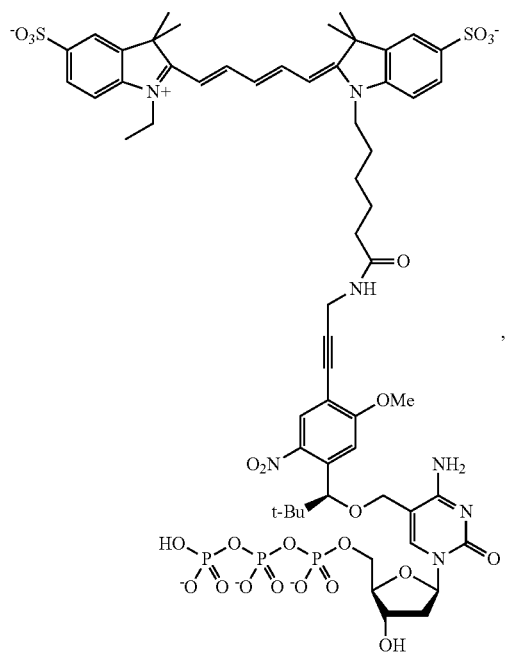

or a salt and/or protonated form of any of these formulas.

In another aspect of the invention there are provided methods of sequencing a target nucleic acid comprising the following steps:
(i) attaching the 5'-end of a primer to a solid surface;
(ii) hybridizing a target nucleic acid to the primer attached to the solid surface to form a hybridized primer/target nucleic acid complex;
(iii) obtaining a polymerase and one or more compounds described herein, with the proviso that compound of different formulas I-VII have different fluorophores;
(iv) reacting the hybridized primer/target nucleic acid complex with a polymerase and one or more of the compounds of step (iii) to form a growing primer strand via a polymerase reaction;
(v) imaging the growing primer strand to identify the incorporated compound of step (iv) via its fluorophore;
(vi) exposing the solid surface with the growing primer strand to a light source to remove a photocleavable terminating moiety of the formula:

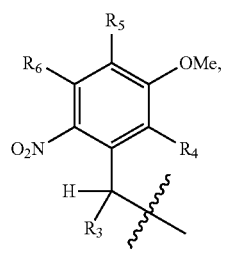

with the variables as defined herein referenced in step (iii), resulting in an extended primer with naturally-occurring components; and (vii) repeating steps (iv) through (vi) one or more times to identify a plurality of bases in the target nucleic acid, where the extended primer of step (vi) of the previous cycle reacts in place of the hybridized primer/target nucleic acid complex in step (iv) of the subsequent cycle.

In some embodiments, step (vi) is conducted in the presence of sodium azide. In some embodiments, the sodium azide concentration is from 0.1 mM to 10 mM, for examples, about 1 mM. In some embodiments, step (vi) is conducted in the presence of sodium acetate. In some embodiments, the sodium acetate concentration is from 0.1 mM to 10 mM, for example, about 1 mM.

In some embodiments, steps (v) or (vi) is conducted in the presence of thiourea. In some embodiments, the thiourea concentration is from 10 mM to 500 mM, for example, about 100 mM.

In some embodiments, step (vi) is conducted in the presence of dithiothreitol (DTT).

In another aspect, there are provided methods of sequencing a target nucleic acid comprising the following steps:
(i) attaching the 5'-end of a nucleic acid to a solid surface;
(ii) hybridizing a primer to the nucleic acid attached to the solid surface to form a hybridized primer/target nucleic acid complex;
(iii) obtaining a polymerase and one or more compounds described herein, with the proviso that compound of different formulas I-VII have different fluorophores
(iv) reacting the hybridized primer/target nucleic acid complex with a polymerase and one or more of the compounds of step (iii) to form a growing primer strand via a polymerase reaction;
(v) imaging the growing primer strand to identify the incorporated compound of step (iv) via its fluorophore;
(vi) exposing the solid surface with the growing primer strand to a light source to remove a photocleavable terminating moiety of the formula:

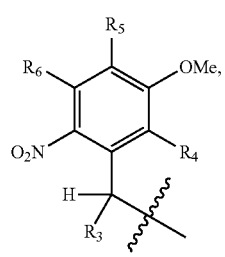

with the variables as defined herein, resulting in an extended primer with naturally-occurring components; and (vii) repeating steps (iv) through (vi) one or more times to identify a plurality of bases in the target nucleic acid, where the extended primer of step (vi) of the previous cycle reacts in place of the hybridized primer/target nucleic acid complex in step (iv) of the subsequent cycle.

In some embodiments, step (vi) is conducted in the presence of sodium azide. In some embodiments, step (vi) is conducted in the presence of dithiothreitol (DTT).

In some embodiments, the incorporation of at least one compound according to step (iv) occurs at about 70% to about 100% of the efficiency of incorporation of its natural nucleotide counterpart. In some embodiments, the incorporation efficiency occurs at about 85% to about 100%.

In some embodiments, the polymerase is selected from the group consisting of reverse transcriptase, terminal transferase, and DNA polymerase. In some embodiments, about 85% to about 100% of the photocleavable terminating moieties are removed by exposure to a light source in step (vi). In some embodiments, incorporation of at least one compound according to step (iv) is followed by termination of strand growth at an efficiency of from about 90% to about 100%.

In some embodiments, a pulsed multiline excitation detector is used for imaging in step (v).

In some embodiments, the method further comprises washing the growing primer strand prior after step (iv) or step (vi).

In some embodiments, the method further comprises, prior to step (iv), capping any primers or growing primer strands that did not react in step (iv).

In some embodiments, the method further comprises sequencing multiple target nucleic acids synchronistically.

In another aspect of the invention, there are provided methods of converting a non-naturally occurring component in a nucleic acid molecule into a naturally-occurring component comprising:
(i) incorporating a compound described herein;
(ii) exposing the resulting nucleic acid to a light source to remove a photocleavable terminating moiety of the formula:

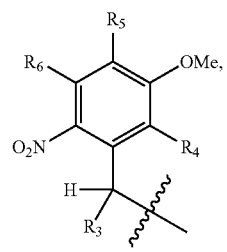

with the variables as defined herein, from the nucleic acid.

In some embodiments, the method further comprises converting non-naturally occurring components in multiple nucleic acid molecules into naturally-occurring components synchronistically. In some embodiments, the method further comprises terminating multiple nucleic acid syntheses synchronistically.

In another aspect, the invention provides methods of terminating a nucleic acid synthesis comprising the step of placing a 3'-OH unblocked nucleotide or nucleoside described above in the environment of a polymerase and allowing incorporation of the 3'-OH unblocked nucleotide or nucleoside into a nucleic acid molecule. In some embodiments, efficiency of termination of DNA synthesis upon incorporation of the 3'-OH unblocked nucleotide or nucleoside ranges from about 90% to about 100%. In some embodiments, the efficiency of incorporation of the 3'-OH unblocked nucleotide or nucleoside ranges from about 70% to about 100% compared to the efficiency of incorporation of a naturally-occurring nucleotide or nucleoside with the same base as the 3'-OH unblocked nucleotide or nucleoside.

In another aspect, the invention provides methods of performing Sanger or Sanger-type sequencing comprising using a compound described herein as a terminating nucleotide analog.

In another aspect, there are provided methods of determining the sequence of a target nucleic acid comprising
  (i) adding a target nucleic acid to a Sanger or Sanger-type sequencing apparatus,
  (ii) adding one or more compounds described herein to the sequencing apparatus, with the proviso that where more than one type of base is present, each base is attached to a different fluorophore;
  (iii) adding a complementary primer and a polymerase enzyme,
  (iv) performing a polymerase reaction to incorporate at least one of the compounds of step (ii) into a growing nucleic acid strand, and
  (v) analyzing the result of the Sanger sequencing reaction with fluorescence sequencing instrumentation or by pulsed multiline excitation fluorescence,
wherein steps (i)-(iii) can be performed in any order.

In some embodiments, incorporation of at least one compound according to step (iv) is followed by termination of strand growth at an efficiency of from about 90% to about 100%. In some embodiments, the incorporation of at least one compound according to step (iv) occurs at about 70% to about 100% of the efficiency of incorporation of a native substrate with the same base in the polymerase reaction. In some embodiments, the incorporation efficiency occurs at about 85% to about 100%. In some embodiments, the polymerase is selected from the group consisting of reverse transcriptase, terminal transferase, and DNA polymerase.

In another aspect, the invention provides methods of incorporating a non-naturally occurring component into a nucleic acid comprising:
  (i) adding a target nucleic acid to a sequencing apparatus;
  (ii) adding one or more compounds described herein to the sequencing apparatus, with the proviso that where more than one type of base is present, each base is attached to a different fluorophore;
  (iii) adding a polymerase enzyme; and
  (iv) performing a polymerase reaction to incorporate at least one of the compounds of step (ii) into a growing nucleic acid strand,
wherein steps (i)-(iii) can be performed in any order.

In some embodiments, the method further comprises:
  (v) analyzing the result of the polymerase chain reaction for incorporation of at least one compound from step (ii).

In some embodiments, incorporation of at least one compound according to step (iv) is followed by termination of strand growth at an efficiency of from about 90% to about 100%. In some embodiments, the incorporation of at least one compound according to step (iv) occurs at about 70% to about 100% of the efficiency of incorporation of native substrate with the same base in the polymerase reaction a native substrate with the same base in the polymerase reaction.

In another aspect, the invention provides methods of performing mini-sequencing or minisequencing-type sequencing comprising addition of a compound described herein to a mini-sequencing or minisequencing-type sequencing method.

In some embodiments of any of the methods described above, the compound is further defined as a compound of formula I, II, III, IV, V, VI, or VII.

In another aspect, the invention provides a system comprising:
  a flowcell comprising a plurality of beads, wherein:
    each bead attached to a DNA molecule, wherein a compound described herein has been incorporated into using a polymerase; and
    the flowcell is at least partially transparent to visible and UV light;
  an imaging device configured to capture images of the flowcell;
  a filter wheel comprising at least four spectral filters, wherein the filter wheel is configured to cycle between each filter;
  a lamp configured to create a light path from the flowcell through a filter in the filter wheel to the imaging device; and
  an ultraviolet light source configured to provide ultraviolet light to the DNA molecules on the flowcell.

In some embodiments, the flowcell is a microfluidic flowcell. In some embodiments, the system further comprises an objective lens between the filter wheel and the flowcell. In some embodiments, the system further comprises a mirror configured to direct the light path to the imaging device.

In some aspects, the present disclosure provides for cancer diagnostics that are fast, high-throughput, accurate and sensitive for early-stage detection to identify rare sequence variants that belong to a limited subpopulation of cells undergoing a cancerous transformation.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIGS. 5A & B—Optical Set-Up for UV Photochemical Cleavage Measurements. FIG. 5A shows a schematic of the modified 0.5 mL Eppendorf tube cut in half, PM100 power meter, a 1,000 μm pinhole cassette using a 3-axis manual translation stage to align the arc beam. FIG. 5B shows a sample holder and modified 0.5 mL Eppendorf tube with an internal alignment card to align the arc beam to the center of a 10 μL or 20 μL reaction sample.

DESCRIPTION OF ILLUSTRATIVE EMBODIMENTS

Figure 1:
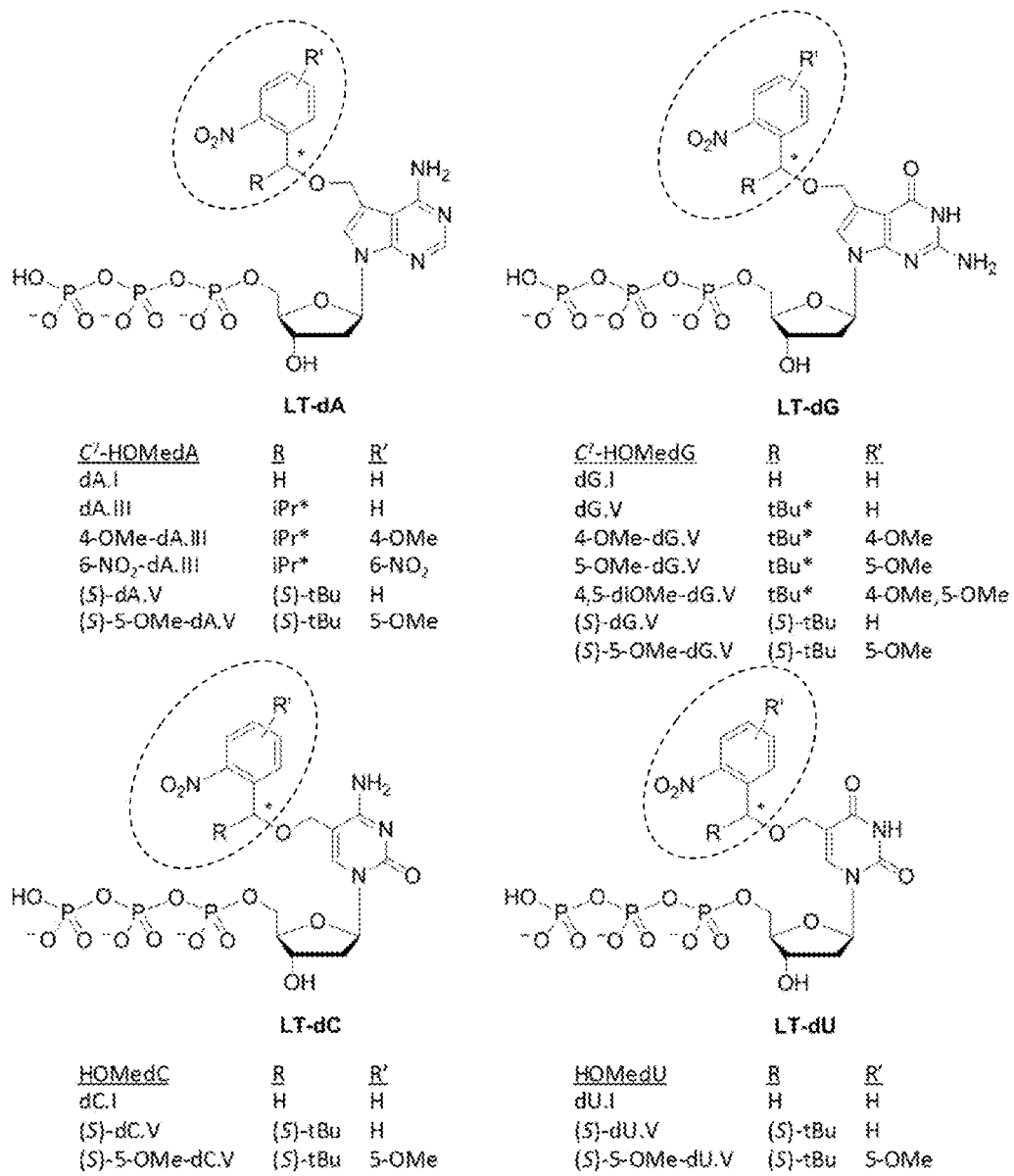
FIG. 1—Structures of 2-Nitrobenzyl Alkylated HOMedNTP Analogs. "R" is H, iso-propyl, or tert-butyl. "R'" is H, 4-OMe, 5-OMe, 4,5-di-OMe, or 6-$NO_2$. See keys for specific examples. "*" denotes two different stereochemical configurations at this carbon atom. The portion of the formulas within the dashed ellipsoids highlights the terminating functional groups that are cleaved upon exposure to UV light.

I. Reversible Terminators and Methods of Synthesis Thereof

In one aspect, the present disclosure provides new compounds that may be used to function as reversible terminators in a variety of different DNA sequencing applications. The compounds provided by the present disclosure are also referred to as reversible terminators, 3'-OH unblocked reversible terminators, and as Lightning Terminators™. In some embodiments, compounds of the following formulas are provided:

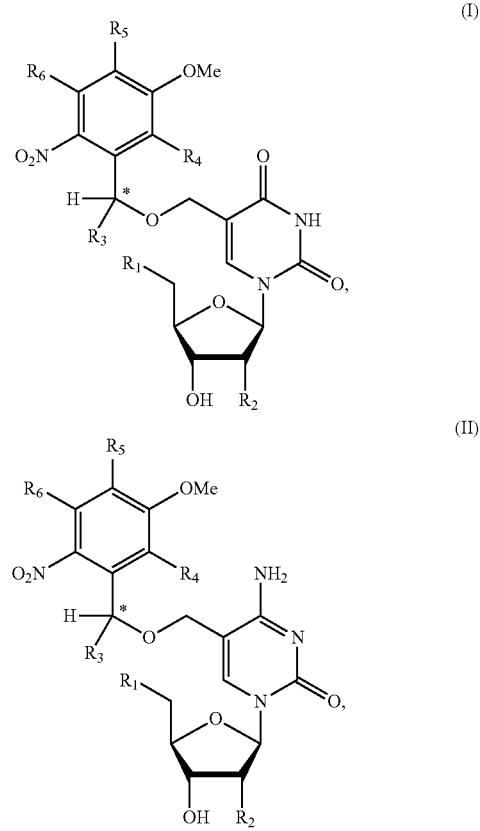

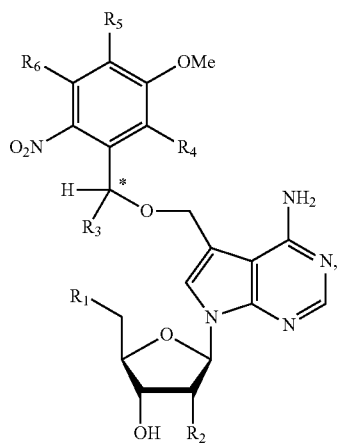

wherein:
R₁ is hydroxy, monophosphate, diphosphate, triphosphate, α-thiotriphosphate or polyphosphate;
R₂ is hydrogen or hydroxy;
R₃ is alkyl$_{(C≤8)}$ or substituted alkyl$_{(C≤8)}$;
R₄ is
  hydrogen, hydroxy, halo, amino, nitro, cyano, azido or mercapto;
  alkyl$_{(C≤6)}$, acyl$_{(C≤6)}$, alkoxy$_{(C≤6)}$, acyloxy$_{(C≤6)}$, alkylamino$_{(C≤6)}$, dialkyl-amino$_{(C≤6)}$, amido$_{(C≤6)}$, or a substituted version of any of these groups;
R₅ and R₆ are each independently:
  hydrogen, hydroxy, halo, amino, nitro, cyano, azido or mercapto;
  alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkyl-amino$_{(C≤6)}$, amido$_{(C≤6)}$, or a substituted version of any of these groups;
  a group of formula:

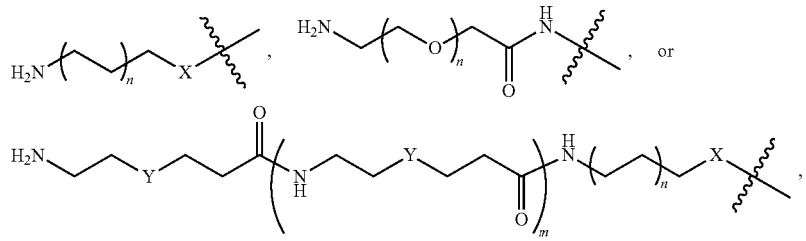

wherein

X is

—O—, —S—, or —NH—; or alkanediyl$_{(C≤12)}$, alkenediyl$_{(C≤12)}$, alkynediyl$_{(C≤12)}$, or a substituted version of any of these groups;

Y is —O—, —NH—, alkanediyl$_{(C≤12)}$ or substituted alkane-diyl$_{(C≤12)}$;

n is an integer from 0-6; and m is an integer from 0-6; or a -linker-reporter;

or a salt, tautomer, or optical isomer thereof

Dye-labeled α-tBu-5-OMe-2-nitrobenzyl alkylated hydroxymethyl nucleotides may be synthesized according to the following schemes and procedures.

A. Synthesis of dye labeled 7-[(S)-1-(5-methoxy-2-nitrophenyl)-2,2-dimethyl-propyloxy]methyl-7-deaza-2'-deoxyadenosine-5'-triphosphates Scheme 2a. Synthesis of dye labeled 7-[(S)-1-(5-methoxy-2-nitrophenyl)-2,2-dimethyl-propyloxy]methyl-7-deaza-2'-deoxyadenosine-5'-triphosphate.

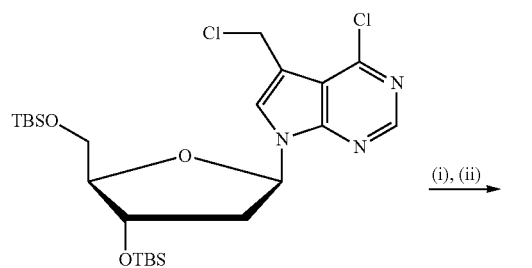

(i), (ii)

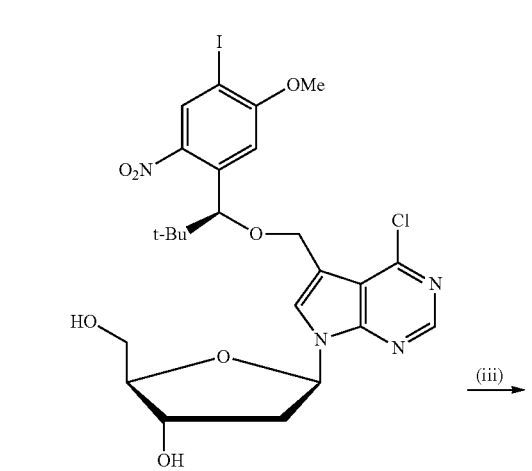

(iii)

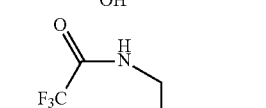

(iv)

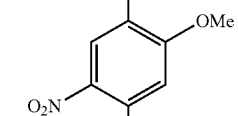

(v)

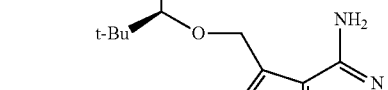

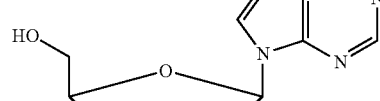

Reagents and conditions: (i) (S)-1-(5-methoxy-2-nitrophenyl)-2,2-dimethyl-1-propanol, 110° C.; (ii) N-Bu$_4$NF, THF, room temperature; (iii) NH$_3$, 1,4-dioxane/MeOH, 100° C.; (iv) N-propargyltrifluoroacetamide, Pd(PPh$_3$)$_4$(0), CuI, Et$_3$N, DMF; (v) POCl$_3$, (MeO)$_3$PO, 0° C.; (n-Bu$_3$NH)$_2$H$_2$P$_2$O$_7$, n-Bu$_3$N, DMF; 1M HNEt$_3$HCO$_3$.

Scheme 2b.
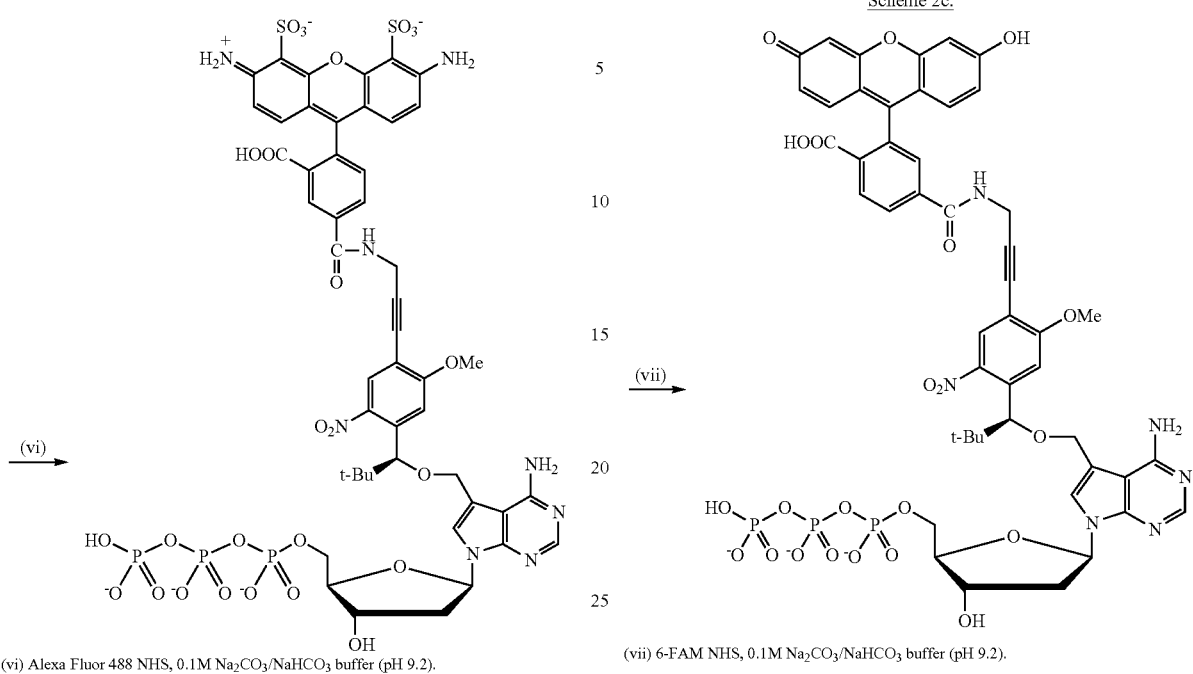
(vi) Alexa Fluor 488 NHS, 0.1M Na₂CO₃/NaHCO₃ buffer (pH 9.2).
Scheme 2c.
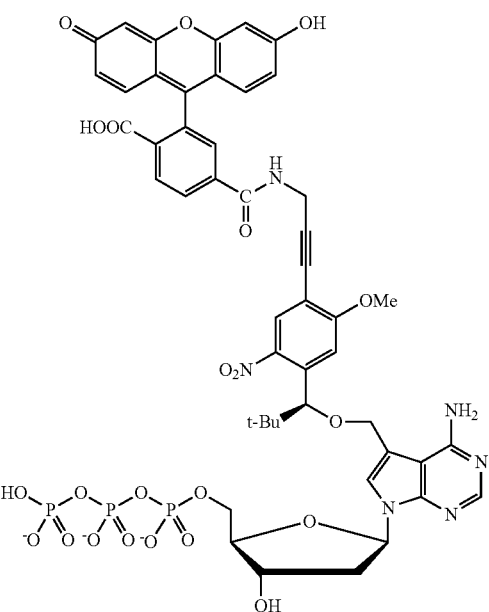
(vii) 6-FAM NHS, 0.1M Na₂CO₃/NaHCO₃ buffer (pH 9.2).
Scheme 2d.
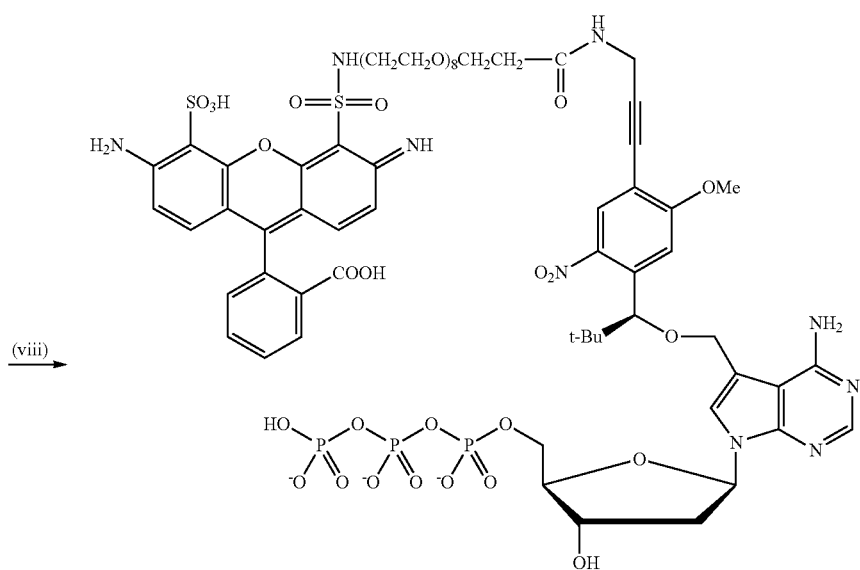
(viii) CF488A NHS, 0.1M Na₂CO₃/NaHCO₃ buffer (pH 9.2).

B. Synthesis of dye labeled 5-[(S)-1-(5-methoxy-2-nitrophenyl)-2,2-dimethyl-propyloxy]methyl-2'-deoxyuridine-5'-triphosphate Scheme 3a. Synthesis of dye labeled 5-[(S)-1-(5-methoxy-2-nitrophenyl)-2,2-dimethyl-propyloxy]methyl-2'-deoxyuridine-5'-triphosphate.

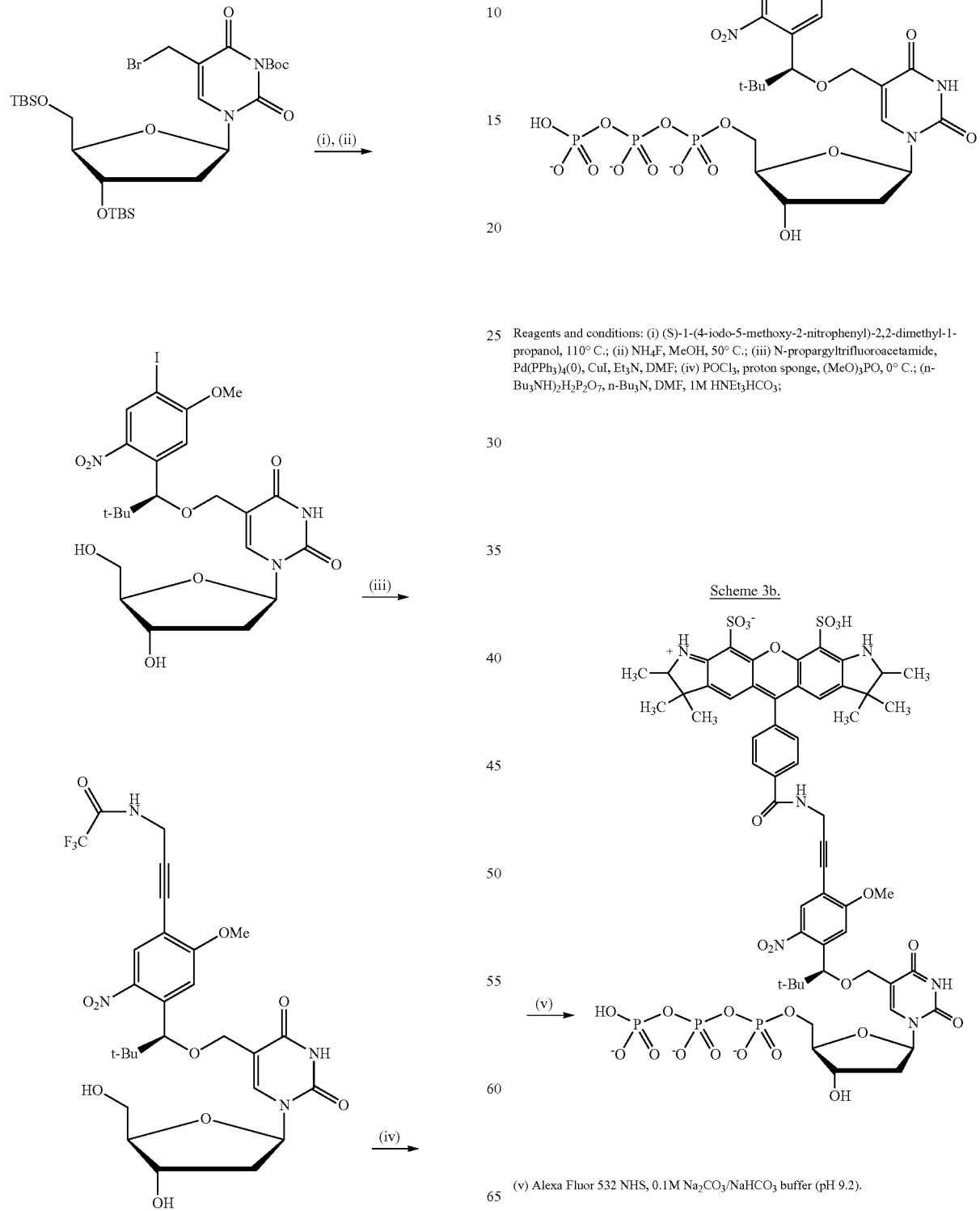

Reagents and conditions: (i) (S)-1-(4-iodo-5-methoxy-2-nitrophenyl)-2,2-dimethyl-1-propanol, 110° C.; (ii) NH$_4$F, MeOH, 50° C.; (iii) N-propargyltrifluoroacetamide, Pd(PPh$_3$)$_4$(0), CuI, Et$_3$N, DMF; (iv) POCl$_3$, proton sponge, (MeO)$_3$PO, 0° C.; (n-Bu$_3$NH)$_2$H$_2$P$_2$O$_7$, n-Bu$_3$N, DMF, 1M HNEt$_3$HCO$_3$;

Scheme 3b.

(v) Alexa Fluor 532 NHS, 0.1M Na$_2$CO$_3$/NaHCO$_3$ buffer (pH 9.2).

39
Scheme 3c.
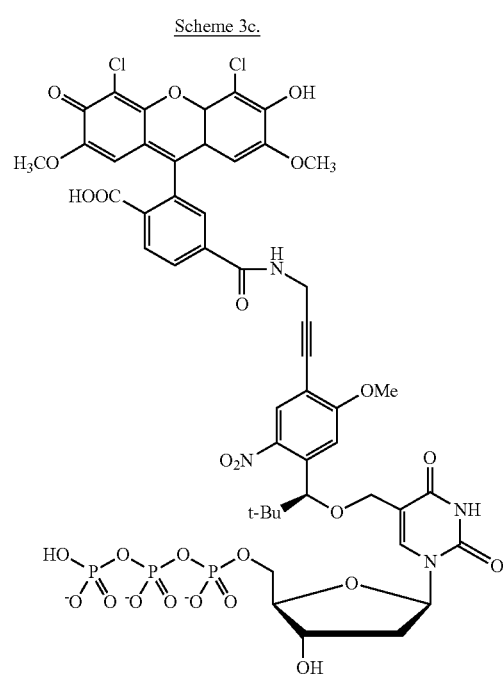
(v) 6-JOE NHS, 0.1M Na$_2$CO$_3$/NaHCO$_3$ buffer (pH 9.2).
Scheme 3d.
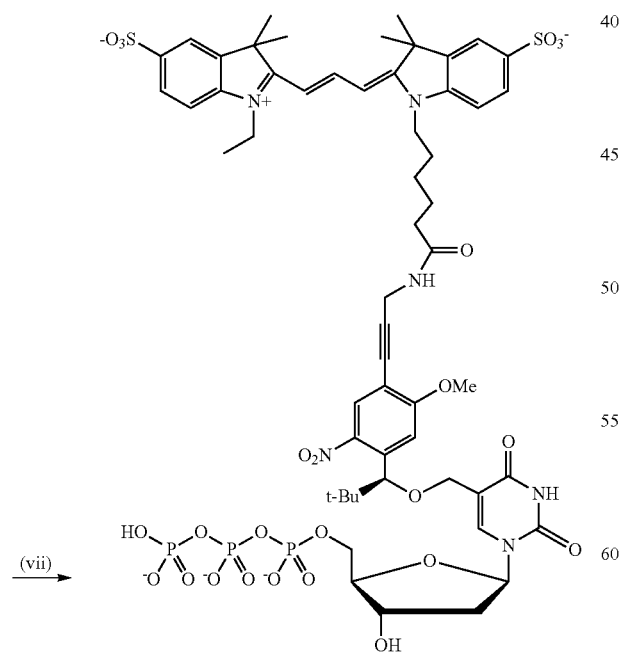
(v) Cy3 NHS, 0.1M Na$_2$CO$_3$/NaHCO$_3$ buffer (pH 9.2).
40
C. Synthesis of dye labeled 7-[(S)-1-(5-methoxy-2-nitrophenyl)-2,2-dimethyl-propyloxy]methyl-7-deaza-2'-deoxyguanosine-5'-triphosphate
Scheme 4a. Synthesis of dye labeled 7-[(S)-1-(5-methoxy-2-nitrophenyl)-2,2-dimethyl-propyloxy]methyl-7-deaza-2'-deoxyguanosine-5'-triphosphate.
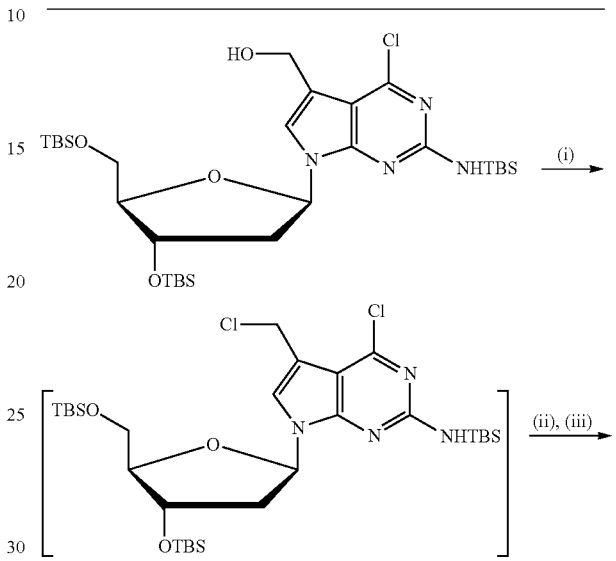
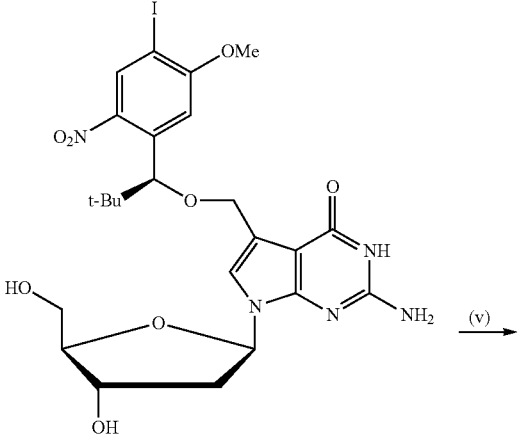

41

-continued

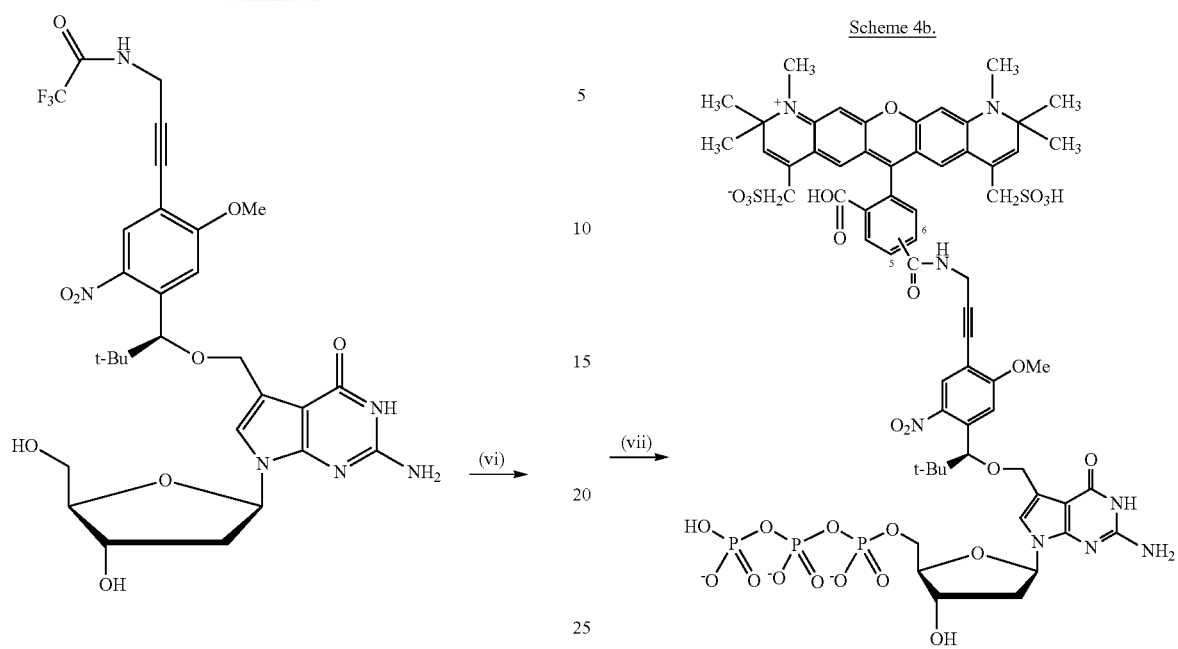

Reagents and conditions: (i) MsCl, DMAP, CH$_2$Cl$_2$, 0° C.; (ii) (S)-1-(4-iodo-5-methoxy-2-nitrophenyl)-2,2-dimethyl-1-propanol, 115° C.; (iii) n-Bu$_4$NF, THF, room temperature; (iv) syn-pyridine-2-aldoxime, 1,1,3,3-tetramethyl guanidine, 1,4-dioxane/DMF, 70° C.; (v) N-propargyltrifluoroacetamide, Pd(PPh$_3$)$_4$(0), CuI, Et$_3$N, DMF; (vi) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

42

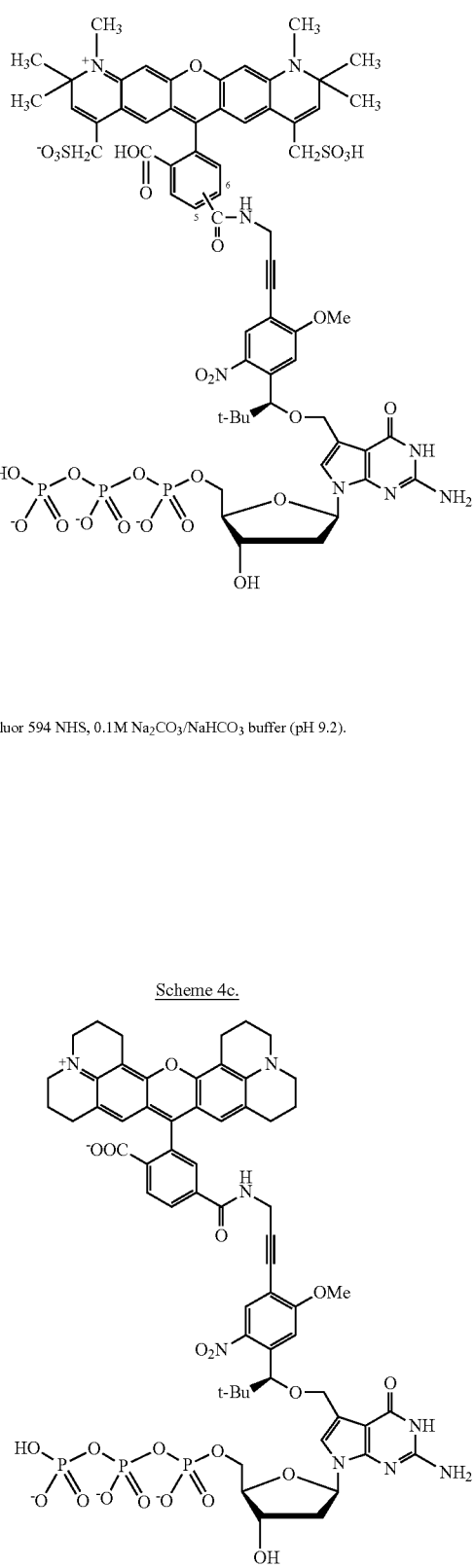

Scheme 4b.

(vii) Alexa Fluor 594 NHS, 0.1M Na$_2$CO$_3$/NaHCO$_3$ buffer (pH 9.2).

Scheme 4c.

(vii) 6-ROX NHS, 0.1M Na$_2$CO$_3$/NaHCO$_3$ buffer (pH 9.2).

D. Synthesis of dye labeled 5-[(S)-1-(5-methoxy-2-nitrophenyl)-2,2-dimethyl-propyloxy]methyl-2′-deoxycytidine-5′-triphosphate
Scheme 5a. Synthesis of dye labeled 5-[(S)-1-(5-methoxy-2-nitrophenyl)-2,2-dimethyl-propyloxy]methyl-2′-deoxycytidine-5′-triphosphate.
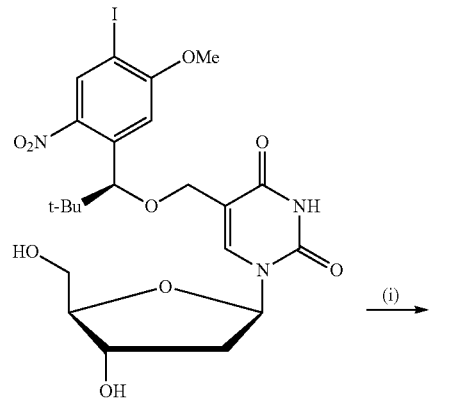
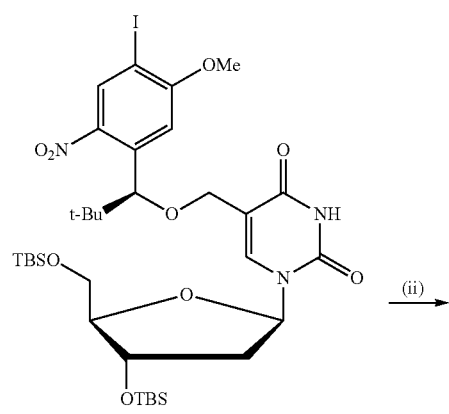
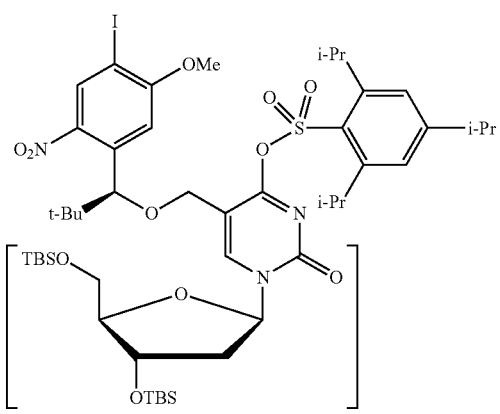
-continued
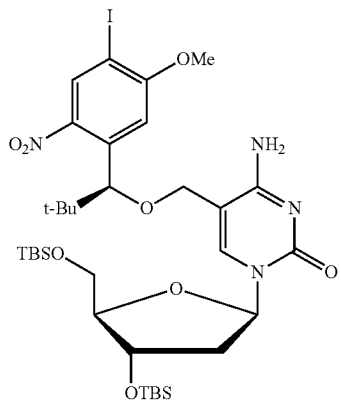
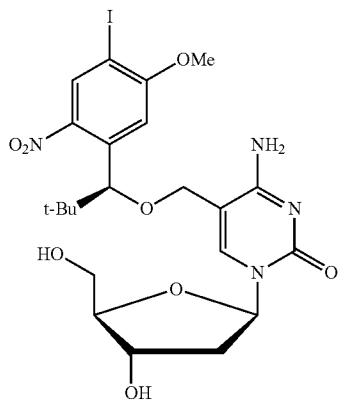
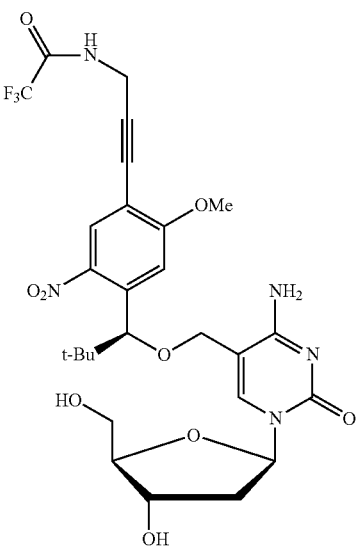

-continued

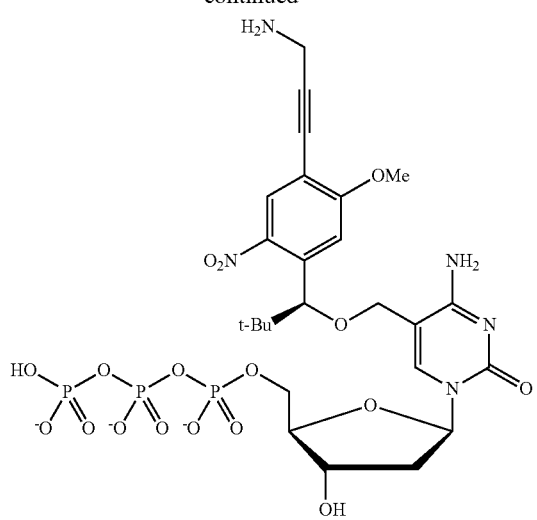

Scheme 5c.

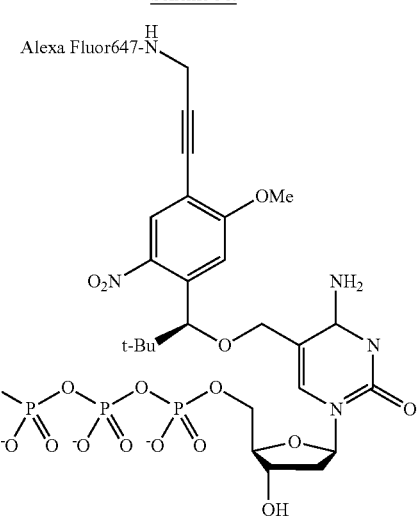

(vi) Alexa Fluor 647 NHS, 0.1M Na₂CO₃/ NaHCO₃ buffer (pH 9.2).

Reagents and conditions: (i) TBSCl, imidazole, DMF, room temperature; (ii) 2,4,6-triisopropylbenzenesulfonyl chloride, DMAP, Et₃N, CH₂Cl₂, room temperature; (iii) NH₃, 1,4-dioxane, 90° C.; (iv) n-Bu₄NF, THF, room temperature, 82%; (v) N-propargyltrifluoroacetamide, Pd(PPh₃)₄(0), CuI, Et₃N, DMF; (vi) POCl₃, proton sponge, (MeO)₃PO, 0° C.; (n-Bu₃NH)₂H₂P₂O₇, n-Bu₃N, DMF; 1M HNEt₃HCO₃.

Scheme 5b.

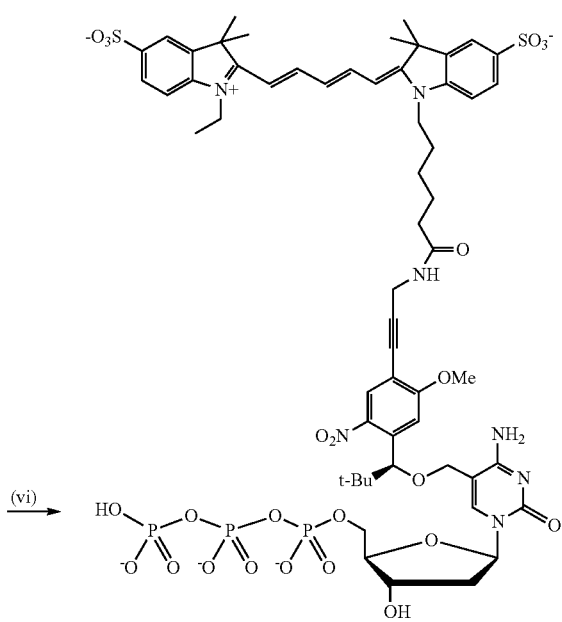

(vi) Cy5 NHS, 0.1M Na₂CO₃/NaHCO₃ buffer (pH 9.2).

In some embodiments, it was observed that the stereochemistry of the alkyl substituted at the α-carbon can improve the photochemical cleavage properties of a 2-nitrobenyl group. In some embodiments, it was observed that faster photochemical cleavage rates result by combining the stereospecific group at the α-carbon with another chemical group attached to the 2-nitrobenzyl ring. See, for example, FIG. 7.

Compounds of the present disclosure may be made using the methods described above and in the Example section below. For example, a summary of a synthesis for making α-tBu-5-OMe-2-nitrobenzyl alcohol, including an enantiopure form thereof, is provided in Example 8. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. For example, in some aspects of the present disclosure, substitution and its stereochemistry of the α-carbon of the benzyl ether of modified 5-hydroxymethyl pyrimidine or 7-hydroxymethyl-7-deazapurine bases affects biological function and cleavage rates of reaction of 3'-OH unblocked, base-modified dNTPs.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

In some embodiments, the 3'-OH unblocked reversible terminators provided herein have an alpha-thiophosphate group, preferably an alpha-thiotriphosphate group. See, for example, compounds 54b, 55b, 59b, 60b, 63b, 64b, 68b, and 69b, in Example 8 below. It is well known in the art that DNA polymerases exhibit 3'-5' exonuclease activity. The function of the 3'-5' exonuclease activity is to remove the just incorporated nucleotide from the primer strand. Many commercially available DNA polymerases delete or mutate the 3'-5' exonuclease domain to reduce this activity below detectable levels. Nonetheless, even low level activity of some DNA polymerases can result in poor sequence data quality due to dephasing of the primary signal. In some embodiments, the 3'-OH unblocked reversible terminators having alpha-thiotriphosphate groups may be used to reduce, minimize and/or eliminate the residual 3'-5' exonuclease activity. Without being bound by theory, it is well known in the art that alpha-thiotriphosphates are resistant to exonuclease activity. See, for example, European Patent EP 0 640 146 to Rosenthal and Brenner, which is incorporated herein by reference.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

The present disclosure further provides nucleotide and nucleoside compounds as well as salts, esters and phosphates thereof, that can be used in rapid DNA sequencing technology. However, it should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference. The compounds are optionally in the form of ribonucleoside triphosphates (NTPs) and deoxyribonucleoside triphosphates (dNTP). The nucleotide and nucleoside compounds in some cases include a chemically or enzymatically cleavable group labeled with a reporter group such as a fluorescent dye. The nucleotide and nucleoside compounds include chemically or enzymatically removable protecting groups that are designed to terminate DNA synthesis as well as cleave rapidly, so that these monomers can be used for rapid sequencing in a parallel format. The presence of such rapidly cleavable groups labeled with fluorescent dyes on the nucleotide and nucleoside compounds can enhance the speed and accuracy of sequencing of large oligomers of DNA in parallel, to allow, for example, rapid whole genome sequencing, and the identification of polymorphisms and other valuable genetic information.

These 3'-OH unblocked terminators are well-tolerated by a number of commercially available DNA polymerases, representing a key advantage over 3'-O-blocked terminators. The benzyl group of the compounds disclosed herein can also can be derivatized to include a selected fluorescent dye or other reporter group.

II. Properties of Reversible Terminators

As discussed above, in one aspect, there are provided novel alkylated 2-nitrobenzyl nucleotides with fast photochemical cleavage properties that may be used as improved reversible terminators for cyclic reversible terminator (CRT) sequencing applications. Such applications are described in Metzker (2005, 2010), which are both incorporated by reference herein. In some embodiments, there are provided modified 7-deaza-7-hydroxymethyl-2'-deoxyadenosine ($C^7$-HOMedA) (Rockhill et al., 1997) and 7-deaza-7-hydroxymethyl-2'-deoxyguanosine ($C^7$-HOMedG) (McDougall et al., 2001) along with HOMedC and HOMedU with a variety of substituted 2-nitrobenzyl groups. See FIG. 1. In some embodiments, the reversible terminators disclosed herein exhibit a number of suitable properties, including fast kinetics of nucleotide incorporation, single-base termination, high nucleotide selectivity, and/or rapid cleavage of the terminating group.

Chromatographic conditions were identified to separate $C^7$-HOMedA analogs into single diastereomeric nucleotides, with the first eluting isomer denoted as ds1 and the second as ds2. To evaluate the photochemical cleavage effect of the stereochemistry of an α-isopropyl group substitution with the 2-nitrobenzyl ring modifications of 4-methoxy (4-OMe) and 6-nitro (6-$NO_2$), three $C^7$-HOMedA analogs dA.III.a-dA.III.c, were synthesized, as well as the parent dA.I (see Examples section below). Incorporation assays were performed with these 2-nitrobenzyl alkylated $C^7$-HOMedATP analogs and then subjected to UV photochemical cleavage experiments in sodium azide solution (Table 1).

TABLE 1

Photochemical Cleavage Rates of $C^7$-HOMedA Analogs

| | $DT_{50}$ in 1 mM $NaN_3$ | |
|---|---|---|
| $C^7$-HOMedA analog | No DTT | 50 mM DTT |
| dA.I | 3.6 ± 0.1 | 3.5 ± 0.1 |
| dA.III.a ds1 | 4.5 ± 0.2 | 4.4 ± 0.2 |

TABLE 1-continued

Photochemical Cleavage Rates of $C^7$-HOMedA Analogs

| $C^7$-HOMedA analog | $DT_{50}$ in 1 mM $NaN_3$ | |
|---|---|---|
| | No DTT | 50 mM DTT |
| dA.III.a ds2 | 2.2 ± 0.1 | 2.1 ± 0.1 |
| dA.III.b ds1 | 7.0 ± 0.3 | 6.1 ± 0.4 |
| dA.III.b ds2 | 1.1 ± 0.1 | 1.0 ± 0.1 |
| dA.III.c ds1 | 3.4 ± 0.2 | 3.0 ± 0.2 |
| dA.III.c ds2 | 2.8 ± 0.2 | 2.5 ± 0.1 |

In all cases, the ds2 isomers of dA.III.a-dA.III.c showed faster photochemical cleavage rates (i.e., lower $DT_{50}$ values) by factors of 2.0×, 6.4×, and 1.2×, respectively, compared with those of their ds1 counterparts. Interestingly, the ds1 isomers exhibited similar (dA.III.c) or higher (dA.III.a or dA.III.b) $DT_{50}$ values compared with the parent dA.I analog. These data provide evidence that stereochemistry of the substituted α-isopropyl group is an important determinant, and coupled with a 4-OMe substitution, the dA.III.b ds2 analog produced the lowest $DT_{50}$ value for the α-isopropyl $C^7$-HOMedA set.

Previous work demonstrated that the α-tert-butyl analog dU.V exhibited excellent CRT properties such as single-base termination and high nucleotide selectivity (Litosh et al., 2011). This allowed to further examination of the stereospecific effect using a different α-substitution group coupled with various OMe ring substitutions by synthesizing four α-tert-butyl $C^7$-HOMedG analogs, dG.V.a-dG.V.d, along with the parent dG.I (FIG. 1). Consistent with the α-isopropyl-$C^7$-HOMedATP analogs, UV photochemical cleavage experiments revealed that ds2 isomers of dG.V.a-dG.V.d showed faster rates by factors of 3.1×, 4.5×, 4.4×, and 3.0×, respectively, compared with those of their ds1 counterparts (Table 2).

TABLE 2

Photochemical Cleavage Rates of $C^7$-HOMedG Analogs.

| $C^7$-HOMedG analog | $DT_{50}$ in 1 mM $NaN_3$ | |
|---|---|---|
| | No DTT | 50 mM DTT |
| dG.I | 9.2 ± 0.3 | 8.1 ± 0.2 |
| dG.V.a ds1 | 11.0 ± 0.4 | 10.7 ± 0.2 |
| dG.V.a ds2 | 3.6 ± 0.3 | 3.5 ± 0.3 |
| dG.V.b ds1 | 4.9 ± 0.3 | 4.6 ± 0.3 |
| dG.V.b ds2 | 1.1 ± 0.1 | 1.3 ± 0.2 |
| dG.V.c ds1 | 3.5 ± 0.3 | 3.0 ± 0.1 |
| dG.V.c ds2 | 0.8 ± 0.1 | 0.8 ± 0.1 |
| dG.V.d ds1 | 2.4 ± 0.1 | 2.3 ± 0.2 |
| dG.V.d ds2 | 0.8 ± 0.1 | 0.8 ± 0.1 |

Both 5-OMe ds1 and ds2 isomers exhibited faster photochemical cleavage rates of 1.4× fold each compared with the corresponding 4-OMe isomers. The bis-substituted 4,5-di-OMe ds1 isomer showed faster cleavage rates compared with mono-substituted 4-OMe (2.0×) or 5-OMe (1.5×) isomers. Conversely, the 5-OMe ds2 and 4,5-di-OMe ds2 isomers exhibited identical $DT_{50}$ values of just 0.8 sec. In the absence of an α-substitution group, Hasan et al. (1997) reported a rate increase of only 1.2× for a 5-OMe-2-nitrobenzyl analog over its corresponding parent. Comparison of ds1 and ds2 isomers of dG.V.c with dG.V.a revealed higher rate increases of 3.6× and 4.4×, respectively, suggesting that the stereospecific tert-butyl group enhances the effect of the 5-OMe group. With four-color CRT applications, this combination provides good flexibility in ring system utility, as a linker structure can also be attached to the 4-position to create dye-labeled analogs (U.S. Pat. Nos. 7,897,737 7,964,352, and 8,148,503; U.S. Patent Appl. Publication 2011/0287427; Metzker, 2010).

Figure 3:
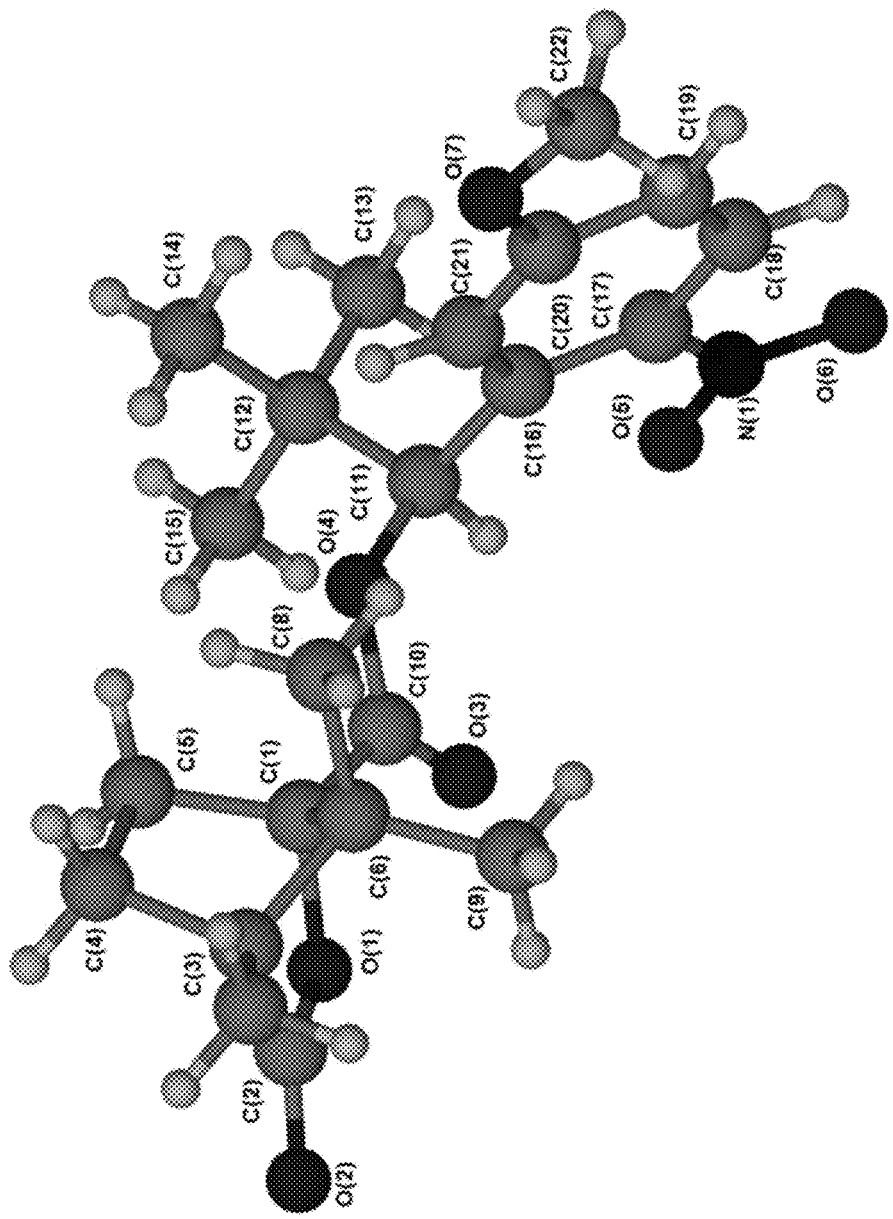
FIG. 3—X-ray Crystal Structure of (S)-1-(5-methoxy-2-nitrophenyl)-2,2-dimethyl-1-propyl(1S)-camphanate. Crystallographic measurements were made on a crystal of (S)-1-(5-methoxy-2-nitrophenyl)-2,2-dimethyl-1-propyl(1S)-camphanate with dimensions of 0.50 mm×0.05 mm×0.05 mm as described in Litosh et al. (2011), which is incorporated herein by reference. Data collection: CuKα radiation, $\lambda=1.54178$ Å, T=110±2° K, $2\theta_{max}=120.0°$, 32,513 reflections collected, 2,913 unique ($R_{int}=0.0517$). Final GooF=1.091, R1=0.0681, wR2=0.1695, R indices based on 2,913 reflections with I>2sigma(I) (refinement on $F^2$), 290 parameters, 43 restraints. Lp and absorption corrections applied, μ0.819 mm$^{-1}$. Absolute structure parameter: 0.05±0.09. X-Ray crystallography data: $C_{22}H_{29}NO_7$, M=419.46. Orthorhombic, a=6.29, b=15.00, c=22.27 Å (α, β, γ32 90°), V=2,099.29 Å$^3$, space group P2$_1$2$_1$2$_1$, Z=4, $D_c=1.327$ g/cm$^{-3}$, F(000)=896.

To determine the stereochemistry of these α-tert-butyl $C^7$-HOMedG analogs, the (1S)-camphanate of (R/S)-1-(5-methoxy-2-nitrophenyl)-2,2-dimethyl-1-propanol was resolved into its enantiopure (S) alcohol by fractional crystallization (Corrie et al., 1992) (FIG. 3). This (S) alcohol and (S)-α-tert-butyl-2-nitrobenzyl alcohol (U.S. Pat. No. 8,148, 503; Litosh et al., 2011) were each coupled to $C^7$-HOMedG (FIG. 1). RP-HPLC analysis of their corresponding triphosphates revealed that both ds2 isomers of dG.V.a and dG.V.c had identical peak retention times as that for dG.V and dG.VI, respectively, thus allowing us to determine that both ds2 isomers have the same (S) configuration at the α-carbon. By inference, the corresponding ds1 isomers of dG.V.a and dG.V.c have been assigned the (R) configuration.

Figure 7:
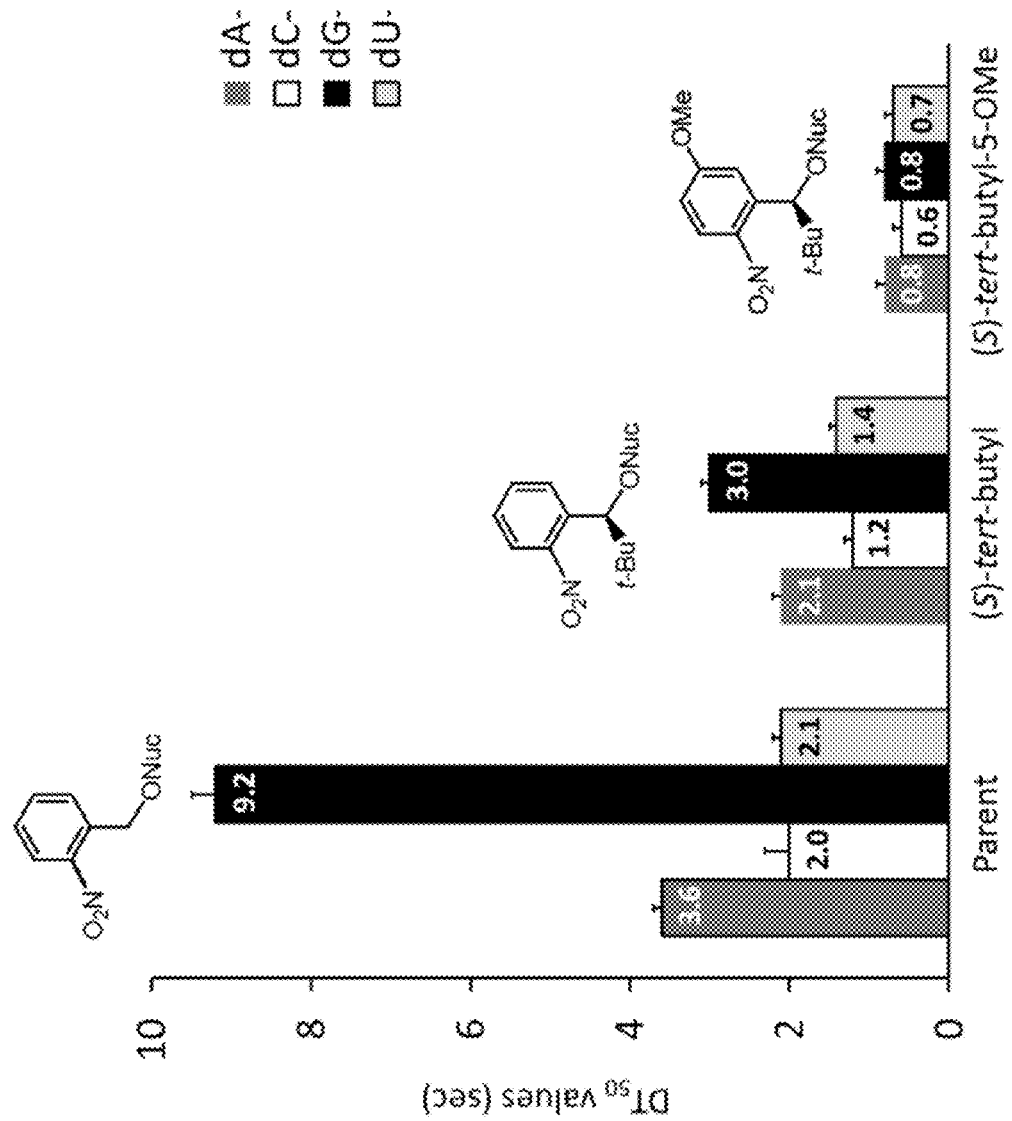
FIG. 7—tert-Butyl Substitution at the α-Carbon and Methoxy Substitution at the 5 Position Correlates with Improved Photochemical Cleavage Rates. This figure compares photochemical cleavage rates of the parent, (S)-α-tert-butyl, and (S)-α-tert-butyl-5-OMe 2-nitrobenzyl groups alkylated on C$^7$-HOMedA, HOMedC, C$^7$-HOMedG, and HOMedU nucleosides. Lower DT$_{50}$ values indicate faster photochemical cleavage rates.

These (S) alcohols were then coupled to the remaining nucleosides to examine the effect of the leaving group on the photochemical cleavage rate. For example, UV photochemical cleavage experiments revealed that $DT_{50}$ values for the parent 2-nitrobenzyl analogs varied from 2.0 sec for dC.I to 9.2 sec for dG.I (FIG. 7 and Table 3).

TABLE 3

Photochemical Cleavage Rates of Reversible Terminators

| Nucleotide analog | $DT_{50}$ in 1 mM $NaN_3$ | |
|---|---|---|
| | No DTT | 50 mM DTT |
| dA.I | 3.6 ± 0.1 | 3.5 ± 0.1 |
| dA.V | 2.1 ± 0.1 | 2.0 ± 0.2 |
| dA.VI | 0.8 ± 0.1[a] | 0.8 ± 0.1 |
| dC.I | 2.0 ± 0.3 | 1.6 ± 0.2 |
| dC.V | 1.2 ± 0.1 | 1.0 ± 0.2 |
| dC.VI | 0.6 ± 0.1[a] | 0.6 ± 0.1 |
| dG.I | 9.2 ± 0.3 | 8.1 ± 0.2 |
| dG.V | 3.0 ± 0.1 | 2.9 ± 0.2 |
| dG.VI | 0.8 ± 0.1 | 0.8 ± 0.1 |
| dU.I | 2.1 ± 0.1 | 1.7 ± 0.1 |
| dU.V | 1.4 ± 0.1 | 1.3 ± 0.1 |
| dU.VI | 0.7 ± 0.1[a] | 0.7 ± 0.1 |

[a]Transient product (TP) observed by gel electrophoresis; considered as cleaved product in $DT_{50}$ value.

Substitution of the benzylic carbon with (S)-tert-butyl resulted in increased cleavage rates by factors of 1.5×-3.1× and the additional substitution with a 5-OMe group further increased rates by factors of 3.0×-11.5× compared with the parent analogs. The greatest rate improvement was observed when comparing $C^7$-HOMedG analogs, reducing $DT_{50}$ values from 9.2 to 0.8 sec (FIG. 7, black bars). The complete set of (S)-5-OMe-α-tert-butyl reversible terminators showed a more narrow range of $DT_{50}$ values from 0.6 to 0.8 sec. These data suggest that the combined effects of the (S)-α-tert-butyl and 5-OMe groups play an important role in diminishing cleavage rate variation observed with particular nucleotide leaving groups, having the practical application of providing normalized and faster cleavage conditions for the CRT cycle. Unexpectedly, transient products were observed from incorporation assays for (S)-5-OMe-α-tert-butyl-$C^7$-HOMedA, -HOMedC and -HOMedU, but not —$C^7$-HOMedG, following brief exposure to UV light (HOMedU only shown in FIG. 2, left side). As the only difference being the just incorporated nucleotide, we hypothesize that the faster cleaving (S)-5-OMe-α-tert-butyl-2-nitrobenzyl group produces a more reactive 2-nitrosoketone by-product that attacks the 3'-terminal nucleotide of the growing primer strand.

Figure 2:
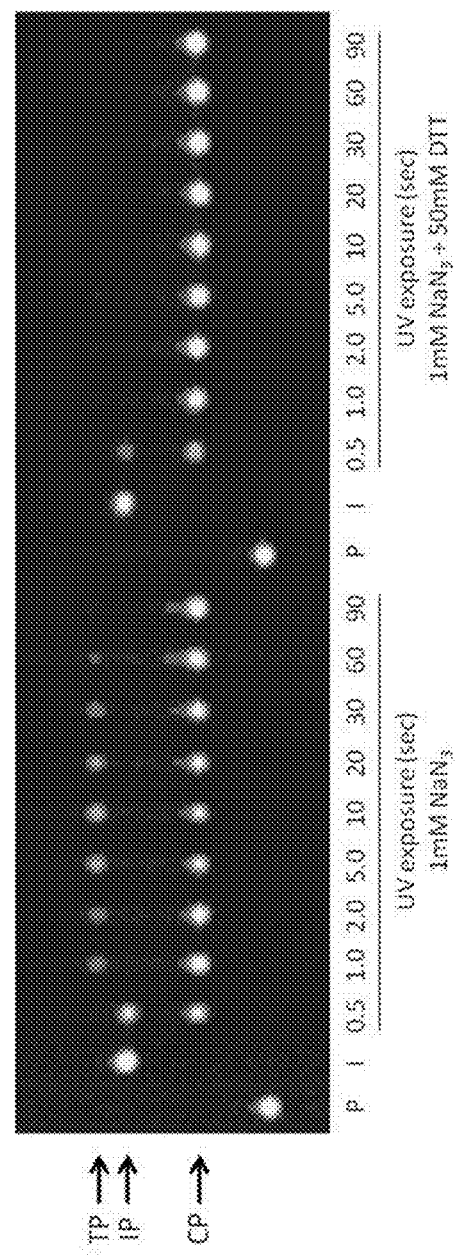
FIG. 2—Elimination of Transient Product (TP) with DTT. Fluorescent gel image of UV photochemical cleavage time series of dU.VI incorporated by Therminator polymerase in the presence of (A) 1 mM $NaN_3$ and (B) 1 mM $NaN_3$, 50 mM DTT. Lanes: "P" (primer) contains Therminator bound to oligoTemplate-4 hybridized with BODIPY-FL labeled primer-1 in 1× ThermoPol buffer (Wu et al., 2007; Litosh et al., 2011), "I" (incorporation) contains that found in lane "P" plus 100 nM dU.VI, and time point lanes contain that found in lane "I" plus listed times samples were exposed to 0.70 W/cm² 365 nm light. "IP" denotes incorporated product and "P" denotes cleaved product.

To investigate conditions to quench the nitroso intermediate, a number of amino and thiol agents were tested during UV photochemical cleavage experiments (FIG. 5). Of these, only dithiothreitol (DTT) (Cleland, 1964) eliminated the transient product (FIG. 2, right side). In some embodiments, the effective DTT concentration is from 1 mM to 1 M. In some embodiments, the effective DTT concentration is from 5 mM to 100 mM. In some embodiments, the effective DTT concentration is from 10 mM to 50 mM. In some embodiments, the effective DTT concentration is about 50 mM. In some embodiments, the photochemical cleavage step takes place in the presence of sodium azide. In some embodiments, the effective sodium azide concentration is from 0.1 mM to 1 M. In some embodiments, the effective sodium azide concentration is from 1 mM to 100 mM. In some embodiments, the effective sodium azide concentration is from 1 mM to 50 mM. In some embodiments, the effective sodium azide concentration is about 1 mM.

To test rate effects, UV photochemical cleavage experiments were repeated for all compounds in the presence of DTT, of which $DT_{50}$ values for several parent and ds1 isomers were reduced (Tables 1, 2, and 3). Barth et al. (2005) proposed that DTT attacks the nitroso group by nucleophilic addition, although a later review by Corrie (2005) describes protective thiols as unnecessary as the evidence for biological interference from of the nitrosoketone by-product remains minimal. In our examples described in this invention, DTT plays an important protective role against such undesired reactions.

The stereospecific (S) configuration of the α-substituted group combined with a 5-methoxy group were found to be determinants in creating fast-cleaving reversible terminators. The reactive nitrosoketone by-product can be effectively eliminated during photochemical cleavage in the presence of DTT, providing appropriate conditions in maintaining the biological integrity of the CRT reaction.

III. Nucleotide and Nucleoside Compounds and their Use in DNA Sequencing

The reversible terminators of the present invention may be used in DNA sequencing methods based on a variety of approaches, including:

"Sanger" or "dideoxy" methods, which involve the chain termination of DNA synthesis by the incorporation of 2',3'-dideoxynucleotides (ddNTPs) using DNA polymerase. See Metzker et al., 2005, which is incorporated herein by reference.

Sequencing-by-synthesis (SBS), which typically does not clearly delineate the different mechanics of sequencing DNA. See Metzker, 2010; Metzker 2005, which are incorporated herein by reference.

DNA polymerase-dependent strategies, which are also classified as cyclic reversible termination (CRT), single nucleotide addition (SNA, e.g., pyrosequencing), and real-time sequencing. See Metzker, 2010, which is incorporated herein by reference.

Single molecules sequencing using the Random Nick Sequencing (RNS) approach.

In some embodiments, the invention provides methods of sequencing a target nucleic acid comprising the following steps:
 (i) attaching the 5'-end of a primer to a solid surface;
 (ii) hybridizing a target nucleic acid to the primer attached to the solid surface;
 (iii) adding a compound according to any of structures described herein, with the proviso that where more than one type of base is present, each base is attached to a different reporter group;
 (iv) adding a nucleic acid replicating enzyme to the hybridized primer/target nucleic acid complex to incorporate the composition of step (iii) into the growing primer strand, wherein the incorporated composition of step (iii) terminates the polymerase reaction at an efficiency of between about 70% to about 100%;
 (v) washing the solid surface to remove unincorporated components;
 (vi) detecting the incorporated reporter group to identify the incorporated composition of step (iii);
 (vii) optionally adding one or more chemical compounds to permanently cap unextended primers;
 (viii) removing the terminating moiety comprising photochemically cleaving off the terminating moiety, resulting in an extended primer with 5-hydroxymethyl pyrimidine or 7-hydroxymethyl-7-deazapurine bases;
 (ix) washing the solid surface to remove the cleaved terminating group; and
 (x) repeating steps (iii) through (viii) one or more times to identify the plurality of bases in the target nucleic acid.

In some variations, the order of steps (iii) and (iv) is reversed. In further variations, the polymerase and the compound are added at the same time. In embodiments, they are in the same solution.

In another aspect the invention provides a method of sequencing a target nucleic acid comprising the following steps:
 (i) attaching the 5'-end of a target nucleic acid to a solid surface;
 (ii) hybridizing a primer to the target nucleic acid attached to the solid surface;
 (iii) adding a compound according to any of structures described herein, with the proviso that where more than one type of base is present, each base is attached to a different reporter group;
 (iv) adding a nucleic acid replicating enzyme to the hybridized primer/target nucleic acid complex to incorporate the composition of step (iii) into the growing primer strand, wherein the incorporated composition of step (iii) terminates the polymerase reaction at an efficiency of between about 70% to about 100%;
 (v) washing the solid surface to remove unincorporated components;
 (vi) detecting the incorporated reporter group to identify the incorporated composition of step (iii);
 (vii) optionally adding one or more chemical compounds to permanently cap unextended primers;
 (viii) removing the terminating moiety comprising photochemically cleaving off the terminating moiety, resulting in an extended primer with a 5-hydroxymethyl pyrimidine or 7-hydroxymethyl-7-deazapurine bases;
 (ix) washing the solid surface to remove the cleaved terminating group; and
 (x) repeating steps (iii) through (ix) one or more times to identify the plurality of bases in the target nucleic acid.

In some variations, the order of steps (iii) and (iv) is reversed.

In some embodiments the compound is incorporated by a nucleic acid replicating enzyme that is a DNA polymerase. In some embodiments the DNA polymerase is selected from the group consisting of Taq DNA polymerase, Klenow(exo−) DNA polymerase, Bst DNA polymerase, VENT® (exo−) DNA polymerase (DNA polymerase A cloned from *Thermococcus litoralis* and containing the D141A and E143A mutations), Pfu(exo–) DNA polymerase, and DEEPVENT™ (exo–) DNA polymerase (DNA polymerase A, cloned from the *Pyrococcus* species GB-D, and containing the D141A and E143A mutations). In some embodiments the DNA polymerase is selected from the group consisting of AMPLITAQ® DNA polymerase, FS (Taq DNA polymerase that contains the G46D and F667Y mutations), THERMOSEQUENASE™ DNA polymerase (Taq DNA polymerase that contains the F667Y mutation), THERMOSEQUENASE™ II DNA polymerase (blend of THERMOSEQUENASE™ DNA polymerase and *T. acidophilum* pyrophosphatase), THERMINATOR™ DNA polymerase (DNA polymerase A, cloned from the *Thermococcus* species 9° N-7 and containing the D141A, E143A and A485L mutations), THERMINATOR™ II DNA polymerase (THERMINATOR™ DNA polymerase that contains the additional Y409V mutation), and VENT® (exo–) A488L DNA polymerase (VENT® (exo–) DNA polymerase that contains the A488L mutation).

Compounds of the present disclosure may be made using the methods outlined in the Examples section. These methods can be further modified and optimized using the principles and techniques of organic chemistry as applied by a person skilled in the art. Such principles and techniques are taught, for example, in Wu et al. (2007; Litosh et al. (2011); Stupi et al. (2012); Gardner et al., 2012; U.S. Pat. Nos. 7,897,737, 7,964,352, and 8,148,503; U.S. Patent Appl. Publ. 2011/0287427, which is incorporated herein by reference.

In some embodiments, sample components enable the determination of SNPs. The method may be for the high-throughput identification of informative SNPs. The SNPs may be obtained directly from genomic DNA material, from PCR amplified material, or from cloned DNA material and may be assayed using a single nucleotide primer extension method. The single nucleotide primer extension method may comprise using single unlabeled dNTPs, single labeled dNTPs, single 3'-O-modified dNTPs, single base-modified 2'-dNTPs, single alpha-thio-dNTPs or single labeled 2',3'-dideoxynucleotides. The mini-sequencing method may comprise using single unlabeled dNTPs, single labeled dNTPs, single 3'-O-modified dNTPs, single base-modified 2'-dNTPs, single alpha-thio-dNTPs or single labeled 2',3'-dideoxynucleotides. The SNPs may be obtained directly from genomic DNA material, from PCR amplified material, or from cloned DNA materials.

A. Nucleotide and Nucleoside Compounds and their Use in CRT

In some aspects of the present invention, nucleotide and nucleoside compounds provided herein (reversible terminators) may be used in DNA sequencing technology based on cyclic reversible termination (CRT). CRT is a cyclic method of detecting the synchronistic, single base additions of multiple templates. This approach differentiates itself from the Sanger method (Metzker, 2005, which is incorporated herein by reference) in that it can be performed without the need for gel electrophoresis, a major bottleneck in advancing this field. Like Sanger sequencing, however, longer read-lengths translates into fewer sequencing assays needed to cover the entire genome. The CRT cycle typically comprises three steps, incorporation, imaging, and deprotection. The term "deprotection" may be used synonymously with "cleavage", so that the three steps could also be described as incorporation, imaging, and cleavage. For this procedure, cycle efficiency, cycle time, and sensitivity are important factors. The cycle efficiency is the product of deprotection and incorporation efficiencies and determines the CRT read-length. The CRT cycle time is the sum of incorporation, imaging, and deprotection times. For rapid CRT for whole genome sequencing, the nucleotide and nucleoside compounds as disclosed herein may be used, which can exhibit fast and efficient deprotection properties. These compounds can be labeled with reporter groups such as fluorescent dyes, attached directly to the benzyl group having an azido substitution on the alpha carbon, providing, e.g., fluorescent, reversible terminators with similar deprotection properties. It has remained difficult to accomplish the goal of long CRT reads because reversible terminators typically act as poor substrates with commercially available DNA polymerases. Modified nucleotide analogs of the present invention may be used to improve this technology by providing substrates that incorporate as well or better than a natural nucleotide with commercially available DNA polymerases.

Photocleavable groups attached to the base of a 3'-OH unblocked nucleotide, such as the groups described herein, can act as an effective reversible terminator and be efficiently incorporated by wild-type DNA polymerases. See Wu et al., 2007; Metzker, 2010; Litosh et al., 2011; Gardner et al., 2012; U.S. Pat. Nos. 7,897,737, 7,964,352, and 8,148,503; U.S. Patent Appl. Publ. 2011/0287427, which are incorporated herein by reference. For example, 5-hydroxymethyl-2'-deoxyuridine (HOMedU) is found naturally in the genomes of numerous bacteriophages and lower eukaryotes (Gommers-Ampt, 1995, which is incorporated herein by reference). Its hydroxymethyl group can serve as molecular handle to attach a small photocleavable terminating group. Other naturally occurring hypermodified bases that can be further modified in the manner described herein to function as reversible terminators include 5-hydroxymethyl-2'-deoxycytidine (HOMedC), which is found naturally in the genomes of T2, T4, and T6 bacteriophages (Wyatt & Cohen, 1953; Gommers-Ampt, 1995) and of mammals (Kriaucionis & Heintz, 2009; Tahiliani et al., 2009; Ito et al., 2010). The pyrrolopyrimidine ring structure (7-deazapurine) is also found naturally in nucleoside antibiotics (Carrasco & Vázquez, 1984, which is incorporated herein by reference) and tRNA bases (Limbach, et al., 1994, which is incorporated herein by reference), and the compounds 7-deaza-7-hydroxymethyl-2'-deoxyadenosine ($C^7$-HOMedA) (Rockhill et al., 1997) and 7-deaza-7-hydroxymethyl-2'-deoxyguanosine ($C^7$-HOMedG) (McDougall et al., 2001) may also be further modified in the manner described herein to function as reversible terminators.

In some embodiments described herein, the photocleavable group is a substituted 2-nitrobenzyl nucleotide, which may be efficiently photochemically cleaved, for example, with 365 nm UV light. See U.S. Patent Appl. Publ. 2010/0041041, which is incorporated herein by reference. It is generally understood the wavelengths >300 nm are used to minimize damage to DNA and proteins (Corrie, 2005) with several specific wavelengths other than 365 nm being 340 nm (Kaplan et al., 1978) and 355 nm (Seo, 2005).

In some embodiments, the 3'-OH unblocked reversible terminators described herein typically have several advantages, including, for example, that photocleavage of only a single bond removes both the terminating and fluorophore groups from the nucleobase. This in turn may be used to more efficiently restore the nucleotide for a subsequent CRT cycle. A second advantage of 3'-OH unblocked reversible terminators provided herein is that many of these compounds show more favorable enzymatic incorporation and, in some embodiments, can be incorporated as readily as a natural nucleotide with wild-type DNA polymerases.

One challenge for 3'-OH unblocked terminators is creating the appropriate modifications to the base that lead to termination of DNA synthesis after a single base addition. This is typically important because an unblocked 3'-OH group is the natural substrate for incorporating the next incoming nucleotide. The compounds described herein address this challenge. For example, in some embodiments, there the reversible terminators provided herein lead to termination of DNA synthesis after a single base addition.

In some embodiments, the compounds disclosed herein may be used in CRT to read directly from genomic DNA. Fragmented genomic DNA can be hybridized to a high-density oligonucleotide chip containing priming sites that span selected chromosomes. Each priming sequence is separated by the estimated read-length of the CRT method. Between base additions, a fluorescent imager can simultaneously image the entire high-density chip, marking significant improvements in speed and sensitivity. In specific embodiments, a fluorophore, which is attached to the benzyl group having an azido substitution on the alpha carbon or its derivatives described herein, is removed by a specific chemical or enzymatic reaction releasing the benzyl group for the next round of base addition. In another specific embodiments, a fluorophore, which is attached to the benzyl group having an amide substitution on the alpha carbon or its derivatives described herein, is removed by a specific enzymatic or chemical reaction releasing the benzyl group for the next round of base addition. After approximately 500 CRT cycles, the complete and contiguous genome sequence information can then be compared to the reference human genome to determine the extent and type of sequence variation in an individual's sample. Reversible terminators that exhibit higher incorporation and deprotection efficiencies will typically achieve higher cycle efficiencies, and thus longer read-lengths.

CRT Efficiency is defined by the formula: $(RL)^{Ceff}=0.5$, where RL is the read-length in bases and Ceff is the overall cycle efficiency. In other words, a read-length of 7 bases could be achieved with an overall cycle efficiency of 90%, 70 bases could be achieved with a cycle efficiency of 99% and 700 bases with a cycle efficiency of 99.9%. The efficiency of incorporation of compounds according to the invention may range from about 70% to about 100% of the incorporation of the analogous native nucleoside. Preferably, the efficiency of incorporation will range from about 85% to about 100%. Photochemical cleavage efficiencies will preferably range from about 85% to about 100%. Further, termination of nucleic acid extension will range from about 90% to about 100% upon incorporation of compounds according to the invention. Nucleotide and nucleoside compounds in one embodiment have a cycle efficiency of at least 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%.

Another aspect of the present invention is directed towards the use of pyrosequencing, which is a non-electrophoretic, bioluminescence method that measures the release of inorganic pyrophosphate (PPi) by proportionally converting it into visible light by a series of enzymatic reactions (Ronaghi et al., 1998, which is incorporated herein by reference). Unlike other sequencing approaches that use modified nucleotides to terminate DNA synthesis, the pyrosequencing assay manipulates DNA polymerase by the single addition of a dNTP in limiting amounts. DNA polymerase then extends the primer upon incorporation of the complementary dNTP and pauses. DNA synthesis is reinitiated following the addition of the next complementary dNTP in the dispensing cycle. The order and intensity of the light peaks are recorded as flowgrams, revealing the underlying DNA sequence. For homopolymer repeats up to six nucleotides, the number of dNTPs added is directly proportional to the light signal. Homopolymer repeats greater than six nucleotide can result in insertion errors, which are the most common error type for pyrosequencing. Modified nucleotide analogs of the present invention may improve this technology by accurate sequencing through homopolymer repeats, particularly those greater than six nucleotides in length.

Another aspect of the present invention is directed towards the use of Sanger sequencing, for example, as applied to heterozygote detection. Despite much advancement, improvements in the dideoxy-BigDye terminator sequencing chemistry for accurate heterozygote detection are needed. It is generally believed that a uniform peak height distribution in the primary data makes base-calling and heterozygote detection more reliable and accurate. The termination pattern in Sanger sequencing is primarily due to sequence-dependent bias incorporation by DNA polymerase, which can selectively incorporate natural nucleotides over modified nucleotides (Metzker et al., 1998, which is incorporated herein by reference). These bias incorporation effects are more pronounced with the dye-terminator chemistry than with the dye-primer chemistry. This can be attributed to effects of the large fluorescent dye structures attached to the terminating nucleotide, lowering enzyme activity at least 10-fold to that of the natural substrate. Thus, the reduction of bias incorporation effects by DNA polymerase towards dye-labeled terminators could lead to improved heterozygote detection. Modified nucleotide analogs of the present invention may improve this technology by incorporating as well or better than a natural nucleotide, thus eliminating incorporation bias in Sanger sequencing.

Another aspect of the present invention is directed towards the use of clonally amplified templates and single DNA molecule templates. The front-end of NGS technologies can be partitioned into two camps: clonally amplified templates from single DNA molecules and single DNA molecule templates. It is well recognized in the art that DNA can be immobilized to a solid surface by either attaching a primer to said surface and hybridizing a target nucleic acid to said primer (U.S. Pat. No. 5,770,367; Harris et al., 2008, which are incorporated herein by reference) or by attaching a target nucleic acid to said surface by clonally amplification and hybridizing a primer to said target nucleic acid (Dressman et al., 2003; Margulies et al., 2005, which are incorporated herein by reference). Either immobilization configuration can be used in the present invention for then binding a DNA polymerase to initiate either the CRT method or the pyrosequencing method.

An aspect, the present invention is directed towards the use of single template molecules, that consist of large DNA fragments (i.e., 0.1-0.5 megabase). In some embodiments, an adaptor-free strategy called Random Nick Sequencing (RNS) can be employed. It has several advantages including (a) no requirement for PCR or adaptor ligation, (b) redundant sequencing of the same template to improve accuracy, and (c) visible sequencing reaction sites across the single molecule template providing localized de novo assemblies. For example, the PCR process creates mutations in clonally amplified templates that masquerade as sequence variants. AT-rich and GC-rich target sequences may also show amplification bias in product yield, resulting in their underrepresentation in genome alignments and assemblies. Knowing the location of sequencing reactions for a given single molecule template will simplify the location assignment and organization of complex genomic and structural regions in the assembly of genomes.

Figure 13:
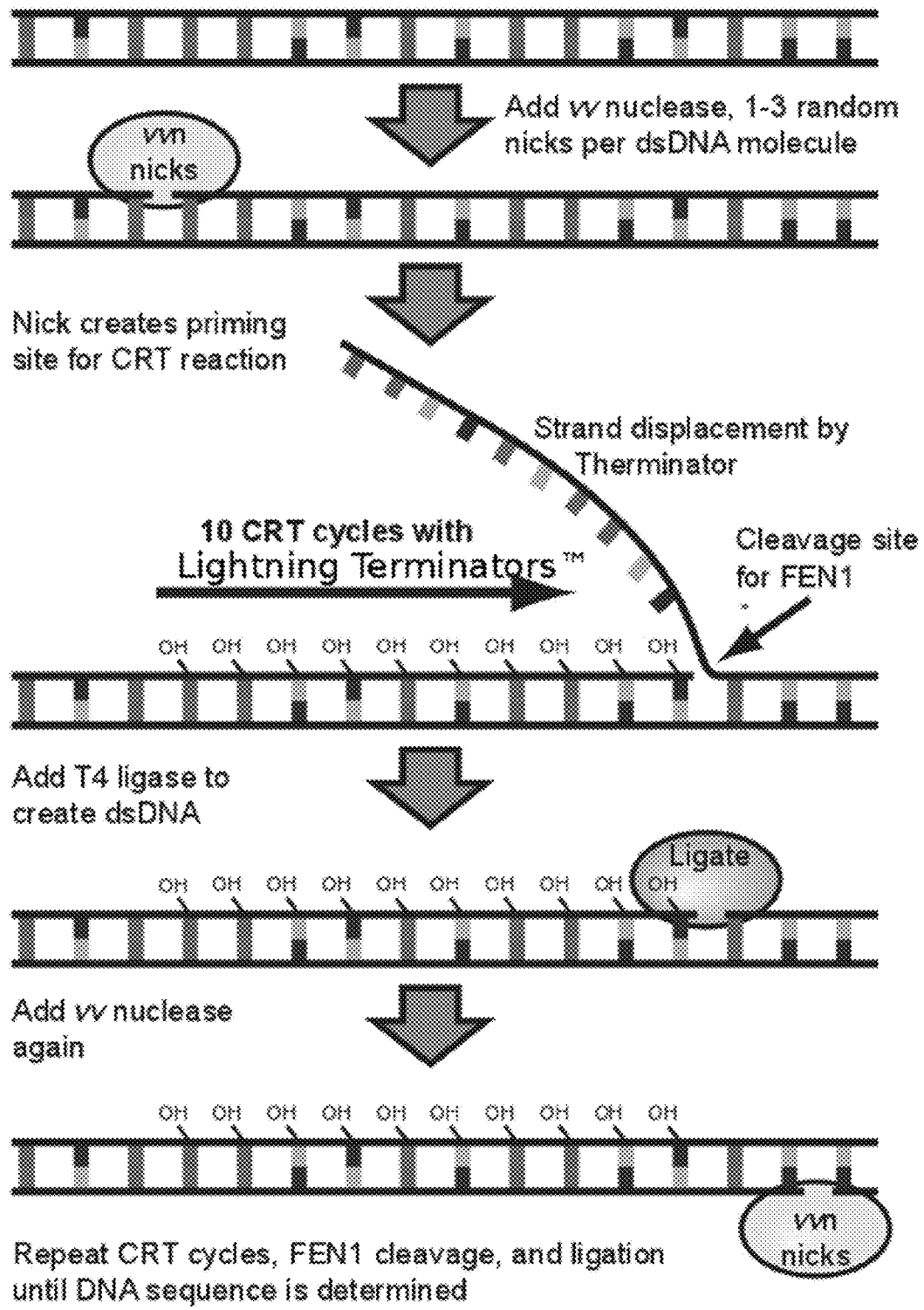
FIG. 13—Diagram of the Random Nick Sequencing (RNS) method. Lightning Terminators™ denoted in the figure are comprised of the reversible terminators of the present invention.

In RNS approach, sugar-nonspecific nucleases such as that isolated from *Vibrio vulnificus* (vvn) create random single-stranded nicks in dsDNA and digest both ssDNA and RNA (See Hsia et al., 2005). Vvn binding occurs in the minor groove of DNA, avoiding sequence-dependent recognition of nucleobases. This represents an advantage in nicking along a DNA molecule in a random fashion without sequence-dependent bias. The upstream strand of the nick becomes a priming site for polymerase to begin the RNS reaction. For this approach to work in some embodiments, the polymerase must be able to displace the downstream strand while extending the upstream strand. Several well-known DNA polymerases that possess this property include φ29 (See Soengas et al., 1995, which is incorporated herein by reference) and Bst (See Aliotta et al., 1996, which is incorporated herein by reference) polymerases. Vent(exo–) (see Gardner et al., 1999, which is incorporated herein by reference) and Therminator™ polymerases also show strand displacement properties, albeit maybe limited to 50 bases before stalling. Following UV cleavage, hydroxymethyl nucleotides are created which serve as excellent template bases for subsequent rounds of RNS (FIG. 13). The strand displacement during RNS creates a bifurcated dsDNA (flap) structure similar to that created with the Invader assay (See Lyamichev et al., 1999). Flap endonucleases (FEN1) are known to cleave these bifurcated structures as shown in FIG. 13, generating a downstream 5'-$PO_4$ end strand without a nucleotide gap (Kaiser et al., 1999). This creates a ligatable substrate to repair the dsDNA molecule for subsequent rounds of RNS.

B. Polymerase Assays

Another aspect of the present invention is directed towards the use of polymerase assays. Natural and modified nucleotides were tested for incorporation efficiency using the "polymerase end point assay" (Wu et al., 2007, which is incorporated herein by reference). This assay examines incorporation efficiency on matched and mismatched template bases. Incorporation efficiency is measured by determining the concentration at which the compound incorporates on half the primer-template complexes ($IC_{50}$). Titrations of increasing compound concentration were performed to generate curves from which the $IC_{50}$ can be determined.

The sequence of the template DNA is selected depending on which compound will be tested. For example, the first interrogation base after the primer in the template sequence is the complement base of the compound when measuring incorporation efficiency, and one of three mismatched bases when measuring mismatch discrimination properties.

To the annealed reaction, a DNA polymerase (e.g., THERMINATOR™ DNA polymerase, 0.25 units per reaction, New England Biolabs), 1× Thermopol Buffer, and a known concentration of either natural or modified nucleotide are added to each 10 μL reaction and incubated at 75° C. for 10 minutes, cooled on ice, and quenched with 10 μL of stop solution (98% formamide: 10 mM $Na_2EDTA$, pH=8.0, 25 mg/ml Blue Dextran). Stopped reactions are heated to 75° C. for 30 seconds to denature the DNA, and then placed on ice. The extension products are analyzed on a 10% Long Ranger (Lonza) polyacrylamide gel using an ABI model 377 DNA sequencer. Additional details are provided in Example 1, below.

C. Mismatch Discrimination and Termination

Another aspect of the present invention is directed towards improved discrimination against mismatch incorporation, for example, through the use of the reversible terminators described herein. It has been reported that substitution at the α-carbon of the 2-nitrobenzyl group can increase the rate of the cleavage reaction (Reichmanis et al., 1985; Cameron and Frechet, 1991; Hasan et al., 1997, all three are incorporated herein by reference). Without being bound by theory, the results presented herein suggest that substitution at the α-carbon of the 2-nitrobenzyl group can also affect the termination of DNA synthesis for 3'-OH unblocked nucleotide triphosphates and improve discrimination against mismatch incorporation. Furthermore, and based on the results discussed in greater detail below, it was found that the stereochemistry of the substitution of α-carbon of the 2-nitrobenzyl group can have a significant impact on the extent of mismatch discrimination and the rate of the cleavage reaction. Without being bound by theory, at least two factors were found to typically influence termination of DNA synthesis after a single incorporation: a) substitution at the α-carbon of the 2-nitrobenzyl group, and b) substitution at the 2-position of the benzyl ring.

D. UV-Cleavage Rates

Another aspect of the present invention is directed towards providing reversible terminators with improved UV-cleavage rates. Cleavage of the terminating substituted 2-nitrobenyl group when analogs are incorporated into the primer strand with 365 nm UV light allows for the next cycle of incorporation to resume. Without being bound by theory, at least two factors were found typically influence UV-cleavage rates of incorporated nucleotide analogs: a) stereo-chemistry of the α-carbon substitution of the 2-nitrobenzyl group, and b) substitution on the benzyl ring.

E. Next-Generation Sequencing (NGS) Technologies

Another aspect of the present invention is directed towards applying the reversible terminators and methods provided herein to next-generation sequencing methods. Sequencing technologies include a number of methods that are grouped broadly as (a) template preparation, (b) sequencing and imaging, and (c) data analysis. The unique combination of specific protocols distinguishes one technology from another and determines the type of data produced from each platform. These differences in data output present challenges when comparing platforms based on data quality and cost. Although quality scores and accuracy estimates are provided by each manufacturer, there is no consensus that a 'quality base' from one platform is equivalent to that from another platform. The compounds and methods described herein may be used in combination with and/or applied to one or more of the template formats described below.

Methods used in preparing templates for NGS reactions include: clonally amplified templates originating from single DNA molecules, and single DNA molecule templates. Sequencing methods that use DNA polymerases are classified as cyclic reversible termination (CRT), single-nucleotide addition (SNA) and real-time sequencing. Sequencing by ligation (SBL), an approach in which DNA polymerase is replaced by DNA ligase, has also been used in the NGS technologies. See, e.g., Shendure et al., 2005 and Valouev et al., 2008, which are incorporated herein by reference. Imaging methods coupled with these sequencing strategies range from measuring bioluminescent signals to four-color imaging of single molecular events. In some embodiments, such combined methods are further combined with suitable information technology systems capable of handling the voluminous data produced by NGS platforms, including aspects related to data storage, tracking and quality control. See Pop & Salzberg, 2008, which is incorporated herein by reference.

a) Template Preparation

In some embodiments, the present invention is directed towards applying and/or combining the reversible terminators and sequencing methods with one or more templates or template preparation methods. For example, in some embodiments, robust template preparation methods are used. These produce representative, non-biased sources of nucleic acid material from the genome under investigation. In some embodiments, the method involves randomly breaking genomic DNA into smaller sizes from which either fragment templates or mate-pair templates are created. In some embodiments, for example those associated with NGS technologies, the template is attached or immobilized to a solid surface or support. The immobilization of spatially separated template sites may be used to allow for thousands to billions of sequencing reactions to be performed simultaneously.

Clonally Amplified Templates.

In some embodiments, the present invention comprises the use of clonally amplified templates or clonally amplified template preparation methods. For example, such templates may be used with imaging systems that have not been designed to detect single fluorescent events. For example, two common amplification methods are emulsion PCR (also called emPCR) and solid-phase amplification. See Dressman et al., 2003 and Fedurco et al., 2006, which are both incorporated herein by reference. In some embodiments, emPCR may be used to prepare sequencing templates in a cell-free system, which has the advantage of avoiding the arbitrary loss of genomic sequences—a problem that is typically inherent in bacterial cloning methods. In some embodiments, a library of fragment or mate-pair targets is created, and adaptors containing universal priming sites are ligated to the target ends, allowing complex genomes to be amplified with common PCR primers. For example, after ligation, the DNA is separated into single strands and captured onto beads under conditions that favor one DNA molecule per bead. See Metzker 2010, FIG. 1a, which is incorporated herein by reference. For example, after the successful amplification and enrichment of emPCR beads, millions can be immobilized in a polyacrylamide gel on a standard microscope slide (used with the Polonator instrument; See, e.g., Shendure et al., 2005, which is incorporated herein by reference), chemically crosslinked to an aminocoated glass surface (used with the Life/APG SOLiD and Polonator instruments; see, e.g., Kim et al., 2007, which is incorporated herein by reference) or deposited into either individual PicoTiterPlate (PTP) wells (used with the Roche/454 instrument; Margulies et al., 2005, which is incorporated herein by reference) or IonChip well (used with the Ion Torrent instrument; Rothberg et al., 2011, which is incorporated herein by reference) in which the NGS chemistry can be performed. In some embodiments, solid-phase amplification may be used to produce randomly distributed, clonally amplified clusters from fragment or mate-pair templates on a glass slide. See Metzker 2010, FIG. 1b, which is incorporated herein by reference. In some embodiments, high-density forward and reverse primers are covalently attached to the slide, and the ratio of the primers to the template on the support defines the surface density of the amplified clusters. In some embodiments, solid-phase amplification may be used to produce 100-200 million spatially separated template clusters (Illumina/Solexa), providing free ends to which a universal sequencing primer can be hybridized to initiate the NGS reaction. See Bentley et al., 2008, which is incorporated herein by reference.

Single-Molecule Templates.

In some embodiments, the present invention comprises the use of single-molecule templates or single-molecule template preparation methods. Although clonally amplified methods offer certain advantages over bacterial cloning, some of the protocols are cumbersome to implement and require a large amount of genomic DNA material (3-20 µg). The preparation of single-molecule templates is typically more straightforward and requires less starting material (<1 µg). In some embodiments, these methods do not require PCR, which typically create mutations in clonally amplified templates that masquerade as sequence variants. AT-rich and GC-rich target sequences may also show amplification bias in product yield, which results in their underrepresentation in genome alignments and assemblies. In some embodiments, quantitative applications, such as RNA-seq may be used. See Wang et al., 2009, which is incorporated herein by reference. Such applications typically perform more effectively with non-amplified template sources, which do not alter the representational abundance of mRNA molecules. In some embodiments, and before the NGS reaction is carried out, single molecule templates are usually immobilized on solid supports using one of at least three different approaches. In the first approach, which may be used in some embodiments, spatially distributed individual primer molecules are covalently attached to the solid support (See Harris et al., 2008). The template, which may be prepared, for example, by randomly fragmenting the starting material into small sizes (for example, ~200-250 bp) and adding common adaptors to the fragment ends, is then hybridized to the immobilized primer. See Metzker 2010, FIG. 1c, which is incorporated herein by reference. In the second approach, which may be used in some embodiments, spatially distributed single-molecule templates are covalently attached to the solid support (See Harris et al., 2008) by priming and extending single-stranded, single-molecule templates from immobilized primers. See Metzker 2010, FIG. 1c, which is incorporated herein by reference. In some embodiments, a common primer is then hybridized to the template. See Metzker 2010, FIG. 1d, which is incorporated by reference. In either approach, DNA polymerase may be used, for example, to bind to the immobilized primed template configuration to initiate the NGS reaction. In a third approach, which may be used in some embodiments, spatially distributed single polymerase molecules are attached to the solid support (see Eid et al., 2009, which is incorporated herein by reference), to which a primed template molecule is bound (see Metzker 2010, FIG. 1e, which is incorporated herein by reference). In general, see U.S. Pat. Nos. 7,329,492 and 6,255,083, which are incorporated herein by reference. Larger DNA molecules (up to tens of thousands of base pairs) may be used with this technique, for example, and, unlike the first two approaches, the third approach can be used with real-time methods, resulting in potentially longer read lengths.

b) Sequencing and Imaging

There are fundamental differences in sequencing clonally amplified and single-molecule templates. Clonal amplification may be used in some embodiments to yield populations of identical templates, each of which has undergone the sequencing reaction. Upon imaging, the observed signal is a consensus of the nucleotides or probes added to the identical templates for a given cycle. Typically, this places a greater demand on the efficiency of the addition process, as incomplete extension of the template ensemble results in lagging-strand dephasing (also called type 2 dephasing). The addition of multiple nucleotides or probes can also occur in a given cycle, resulting in leading-strand dephasing (also called type 1 dephasing). The concept of dephasing was described by Cheeseman (See U.S. Pat. No. 5,302,509, which is incorporated herein by reference). Signal dephasing increases fluorescence noise, causing base-calling errors and shorter reads (See Erlich et al., 2008). Because dephasing is not an issue with single-molecule templates, the requirement for cycle efficiency is relaxed. Single molecules, however, are susceptible to multiple nucleotide or probe additions in any given cycle. Here, deletion errors may be observed to occur, in some embodiments, owing to quenching effects between adjacent dye molecules or no signal will be detected because of the incorporation of dark nucleotides or probes. In the following sections, sequencing and imaging strategies that use both clonally amplified and single-molecule templates are discussed. In some aspects of the present inventions, the reversible terminators the method of use provided herein may be applied and/or used in combination with any one or more of the DNA polymerase-dependent strategies, including, for example, CRT, SNA, and real-time sequencing. In some embodiments, compounds of the present invention and their method of use can be applied to and/or used in combination with the CRT method.

There are several commercially available NGS system that imaging fluorescent signals for single DNA molecules (See Harris et al., 2008; Eid et al., 2009, both of which are incorporated herein by reference). Resolving single molecules on the array can be done it at 100× magnification with a high sensitivity CCD camera, so long as the individual DNA molecules are separated by a distance that approximates the diffraction limit of light (i.e., 250 nm). Variations can occur that can depend on magnification and surface flatness, which should be obvious to one of ordinary skill in the art. One technique that is widely used to detection fluorescent signals from single molecules is total internal reflection fluorescence (TIRF) microscopy. (See Axelrod, 1989, which is incorporated herein by reference). Other techniques that can be used in the present invention that are known in the art include, but not limited to, scanning near-field optical microscopy (SNOM; See Moyer et al., 1993, which is incorporated herein by reference).

F. Imaging System

Figure 8:
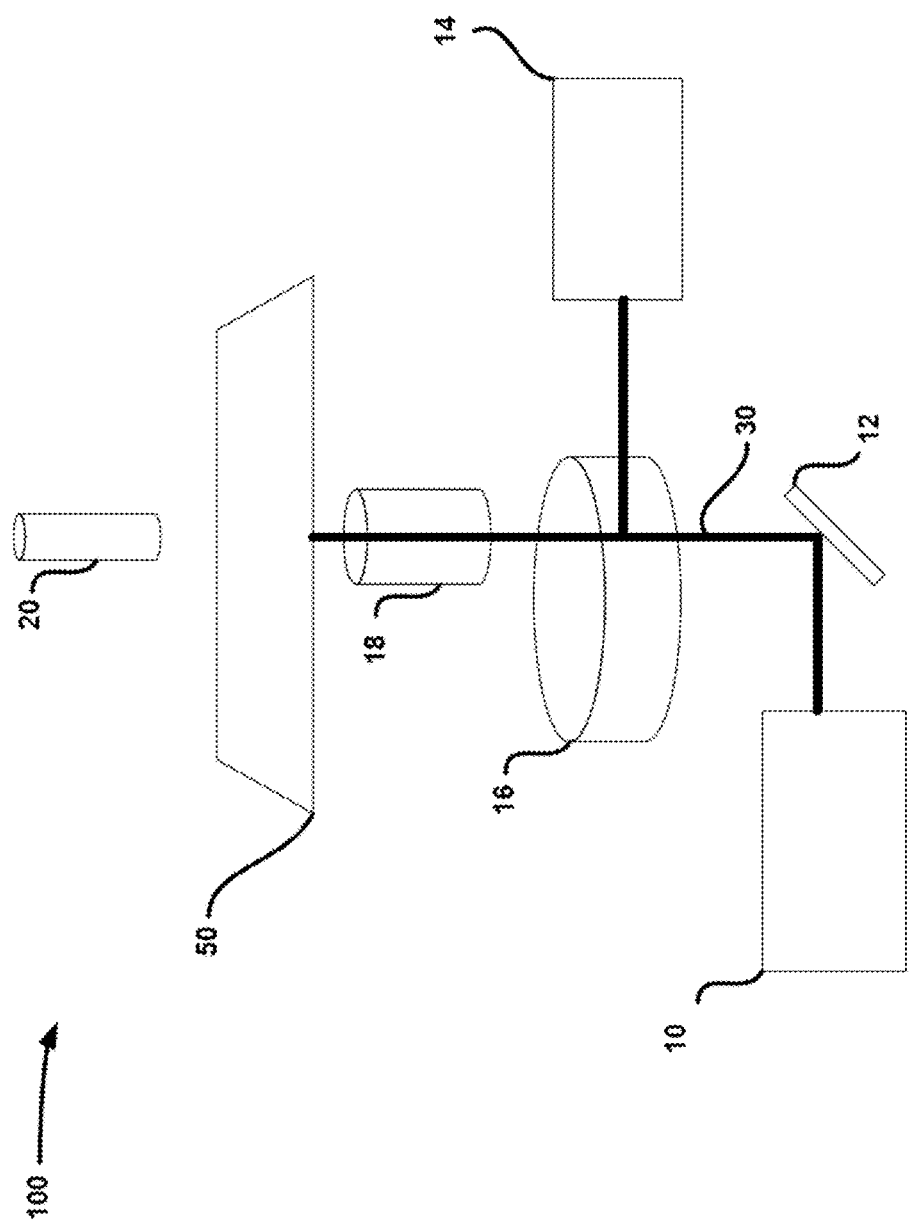
FIG. 8. A schematic representation of a system for imaging fluorescent beads on a flowcell.

FIG. 8 illustrates an embodiment of an imaging system 100 for imaging fluorescent signals derived from clonally amplified template. System 100 is configured to image a microfluidic flowcell 50 that has been prepared with micron beads comprising the DNA of interest.

A range of imaging technologies, such as standard four-color imaging or color-blind pulse-multiline excitation, may be used in various embodiments in combination with the 3'-OH unblocked reversible terminators. The illustrated embodiment is configured for standard four-colored imaging.

System 100 comprises an imaging device 10 (e.g., a digital camera, photocell, etc.) configured to capture fluorescent signals derived from emPCR amplified template beads immobilized in microfluidic flowcell 50.

Lamp 14 (e.g., a xenon lamp) creates a light path 30 between microfluidic flowcell 50 and imaging device 10. Light from lamp 14 travels to filter wheel 16. In the illustrated embodiment, filter wheel 16 is motorized and comprises four spectral filters such that four-color images may be captured. Filter wheel 16 is configured to switch between each of the four spectral filters at each tile position so that imaging device 10 may capture four-color images from the incorporated 3'-OH unblocked reversible terminators.

A portion of the light from lamp 14 travels from filter wheel 16 through objective lens 18 to microfluidic flowcell 50. Another portion of the light from lamp 14 travels from filter wheel 16 to imaging device 10. In the illustrated embodiment, light path 30 is directed to imaging device 10 using mirror 12. In other embodiments no such mirrors may be necessary, while in still other embodiments, two or more mirrors may be required.

System 100 also comprises an ultraviolet (UV) light source 20 configured to provide UV light to flowcell 50. UV light source 20 may be a light-emitting diode (LED) in some embodiments, or may be any other source of UV light.

G. Minimizing Ozone Contamination

In another aspect, this invention provides sequences methods that minimize the effects of ozone contamination. Ozone ($O_3$) is an allotrope of oxygen and has both beneficial and detrimental attributes to life on earth. For example, ozone is created in the stratosphere by high energy radiation from the sun that splits molecular oxygen ($O_2$) into two atoms, which then combine with different $O_2$ molecules to form $O_3$. This stratospheric layer protects living organisms on the planet from harmful ultraviolet radiation produced by the sun. At the ground level or troposphere, however, ozone is considered an air pollutant. Ozone is also created under smog conditions where sunlight acts on the combination of oxides of nitrogen and volatile organic compounds that are produced by industrial facilities, electric utilities, motor vehicle exhaust, gasoline vapors, and chemical solvents (See EPA, 2011). Ozone levels increase during the hot summer months, and the effects of ozone damage increase with increasing relative humidity levels. Tropospheric ozone causes severe damage to crops and forests (See Hewitt et al., 1990), numerous respiratory problems in animals and humans (See Fairchild et al., 1959; Bhalla, 1994), as well as adverse effects with many consumer products including automobile tires (See Crabtree and Kemp, 1946), dyes found in textile materials (See Salvin and Walker, 1955) as well as fluorescent dyes used in molecular biology.

From a chemical perspective, ozone is an electrophilic agent that is most reactive with electron pairs commonly found in olefinic compounds (i.e., chemicals that contain carbon-carbon double bonds). There has been extensive research dedicated to the chemistry of ozone, which is called ozonation. An extensive two volume book series provides a comprehensive review that describes the properties of ozone itself and the numerous reactions it can undergo with organic substrates. Volume 1 of this series is dedicated almost exclusively to the reaction of ozone with olefinic compounds (See Bailey, 1978; Bailey 1982), for which Volume 1 and 2 are incorporated by reference.

Dyes and dye intermediates are well known in the literature and with the majority of dye types in use today having been discovered more than a century ago (Gordon and Gregory, 1983). Dyes can be grouped into classes based on how they are used or based on their chemical structures (Gordon, 2009). For the latter, dyes have been classified into the general classes of (i) azo, (ii) anthraquinone, (iii) benzodifuranone, (iv) polycyclic aromatic carbonyl, (v) indigoid, (vi) polymethine and related dyes (i.e., cyanine), (vii) styryl, (viii) di- and triaryl carbonium and related dyes (i.e., fluorescein, rhodamine and their sulfonated derivatives), (ix) phthalocyanine, (x) quinophthalone, (xi) sulfur, (xii) nitro and nitroso, and (xiii) miscellaneous (i.e., coumarin and BODIPY) (Gregory, 2009). Most, if not all, dyes and dye intermediates have a multiplicity of carbon-carbon double bonds that make them sensitive to ozonation. In the mid 1970s, Lofquist and colleagues taught the general conclusion that most dyes would be susceptible to ozonolysis (See U.S. Pat. No. 3,822,996; U.S. Pat. No. 3,859,045; U.S. Pat. No. 3,917,499.

The effect of ozone exposure to dyed fabrics is dye fading (e.g., loss of dyefastness), which was first reported in 1955. Salvin and Walker coined the term "O-fading", which in their service test of drapery fabrics revealed that ozone caused significant dye fading when exposed to several blue anthraquinone dyes, (i.e., Eastman Blue GLF, Amacel Blue, and Interchemical Blue B) as well as yellow and red anthraquinone dyes (See Salvin, 1955). Other examples of anthraquinone dyes, such as C.I. Basic Blue 47 (See U.S. Pat. No. 3,822,996) and Disperse Blue 3 (See U.S. Pat. No. 3,859, 045) have been reported to be susceptible to O-fading. High humidity enhances O-fading (See U.S. Pat. No. 3,917,449;

U.S. Pat. No. 4,737,155; U.S. Pat. No. 3,822,996; U.S. Pat. No. 4,304,568), and for fabrics, it has been suggested that the moisture provides the dye sufficient mobility to diffuse to the surface of the material where the ozonation reaction occurs (See U.S. Pat. No. 4,737,155).

Fluorescent dyes, such as those belonging to the polymethine class, have also been reported susceptibility to ozonation reactions, which reduce their fluorescent signal intensities. For example, Cy3 and Cy5 dyes have been widely used in microarray technologies for gene expression, genotyping, and resequencing applications (See Gershon, 2004). Fare and colleagues showed results that Cy5 and its sulfonated derivative Alexa Fluor 647 were susceptible to ozone damage at exposure levels of 5 to 10 ppb within 10 to 30 sec (See Fare et al., 2003). Fluorescent intensity levels were also reduced for Cy3 and its sulfonated derivative Alexa Fluor 555 at higher ozone levels (>100 ppb). Kadushin and Getts note that the starting signal can degrade to ~10% in 1-5 min (See U.S. Patent Appl. Publication 2004/0110196).

There a large number of chemical reagents, which act as antiozonants. Examples include para-phenyldiamine, dihydroquinoline, thiourea (See U.S. Pat. No. 4,737,155; U.S. Pat. No. 4,631,066), saturated alkyl substituted thiourea, alkyl and aryl phosphites (See U.S. Pat. No. 3,822,996), ethoxylated aliphatic tertinary amines (See U.S. Pat. No. 3,859,045), substituted piperidine thiourea (See U.S. Pat. No. 4,304,568), substituted oxadiazine thiones and substituted thiazine thiones (See U.S. Pat. No. 4,304,568), acrylic polymerase, copolymers of methacrylate or ethylacrylate (See U.S. Patent Appl. Publication 2004/0110196), and polythiourea (See U.S. Pat. No. 3,917,449). For the present invention, thiourea may be used in some embodiments, in one or more solutions to prevent the ozonolysis of fluorescent dyes in the sequencing reaction. WO 2012/037394, which is incorporated herein by reference, provides methods for using thiourea in combination with methods involving NGS technologies. In some embodiments, the imaging and/or photochemical cleavage steps may be performed in the presence of thiourea, for example, at the concentrations disclosed in the invention summary above.

H. Sample Preparation

Figure 9:
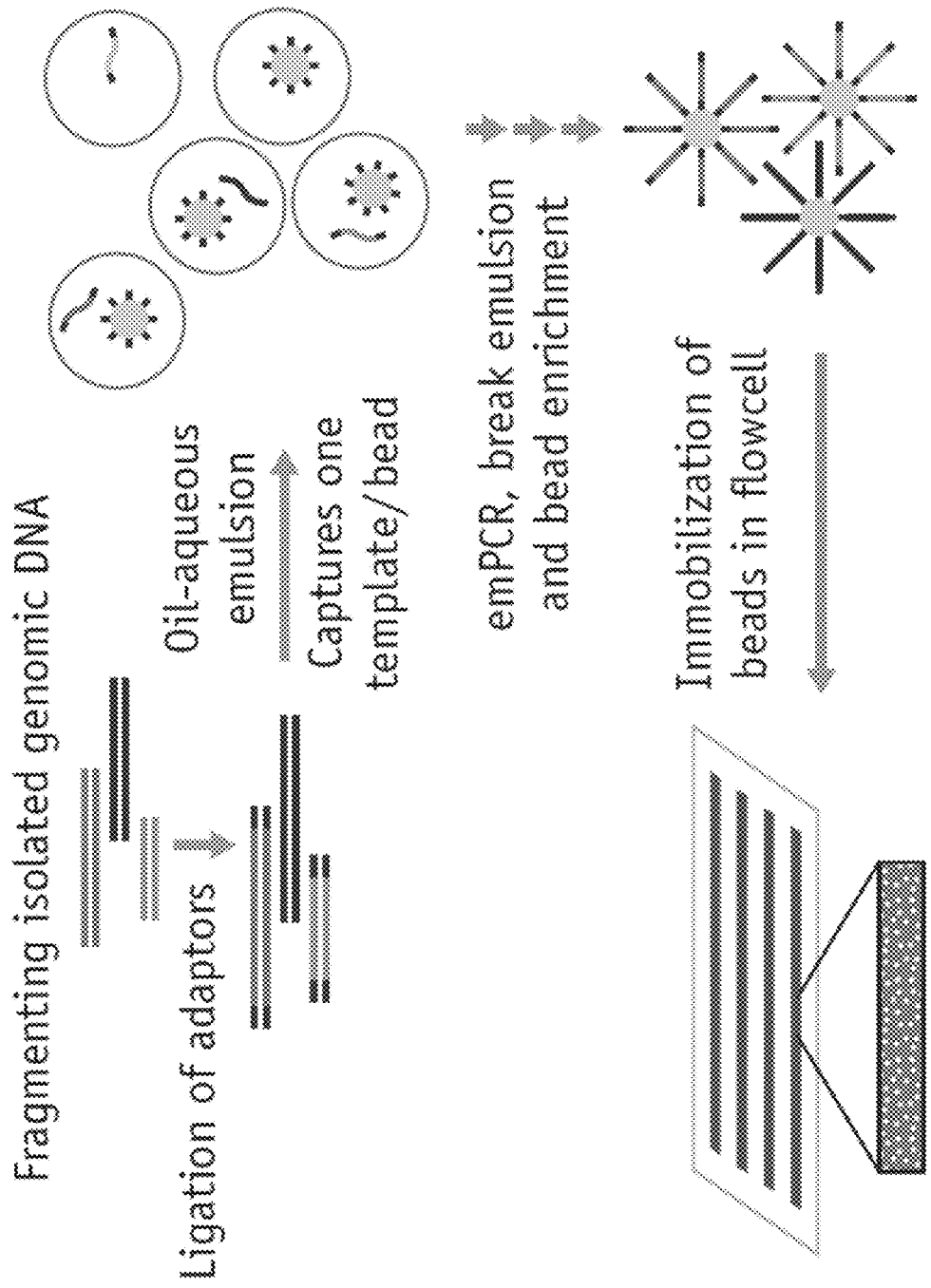
FIG. 9—Example of Bead Preparation and Immobilization Method. Schematic illustration of the steps of an exemplary mpreparing a bead sample on a flowcell.

Methods to prepare the DNA of interest for NGS analysis include, for example, clonally-amplified and non-amplified (i.e., single molecule) templates. In some embodiments, emulsion PCR (emPCR) may be used. As shown in FIG. 9, samples may be prepared as follows. First, genomic DNA is isolated. The DNA is then fragmented into smaller pieces. Then, common adaptors are ligated to the ends of those fragments. The adaptor-ligated DNA molecules are then separated into single strands and captured onto 1 µm size beads under conditions that favor one DNA molecule per bead. An oil-aqueous emulsion creates individual aqueous droplets that encapsulate these bead-DNA complexes. PCR amplification is performed within these droplets to create beads containing $10^4$-$10^6$ copies of the same template sequence. Following successful amplification and enrichment, tens of millions to hundreds of millions of emPCR beads are then chemically immobilized to microfluidic flowcell 50. In some embodiments, flowcell 50 may comprise eight channels and may be made of glass.

I. System Operation

Figure 10:
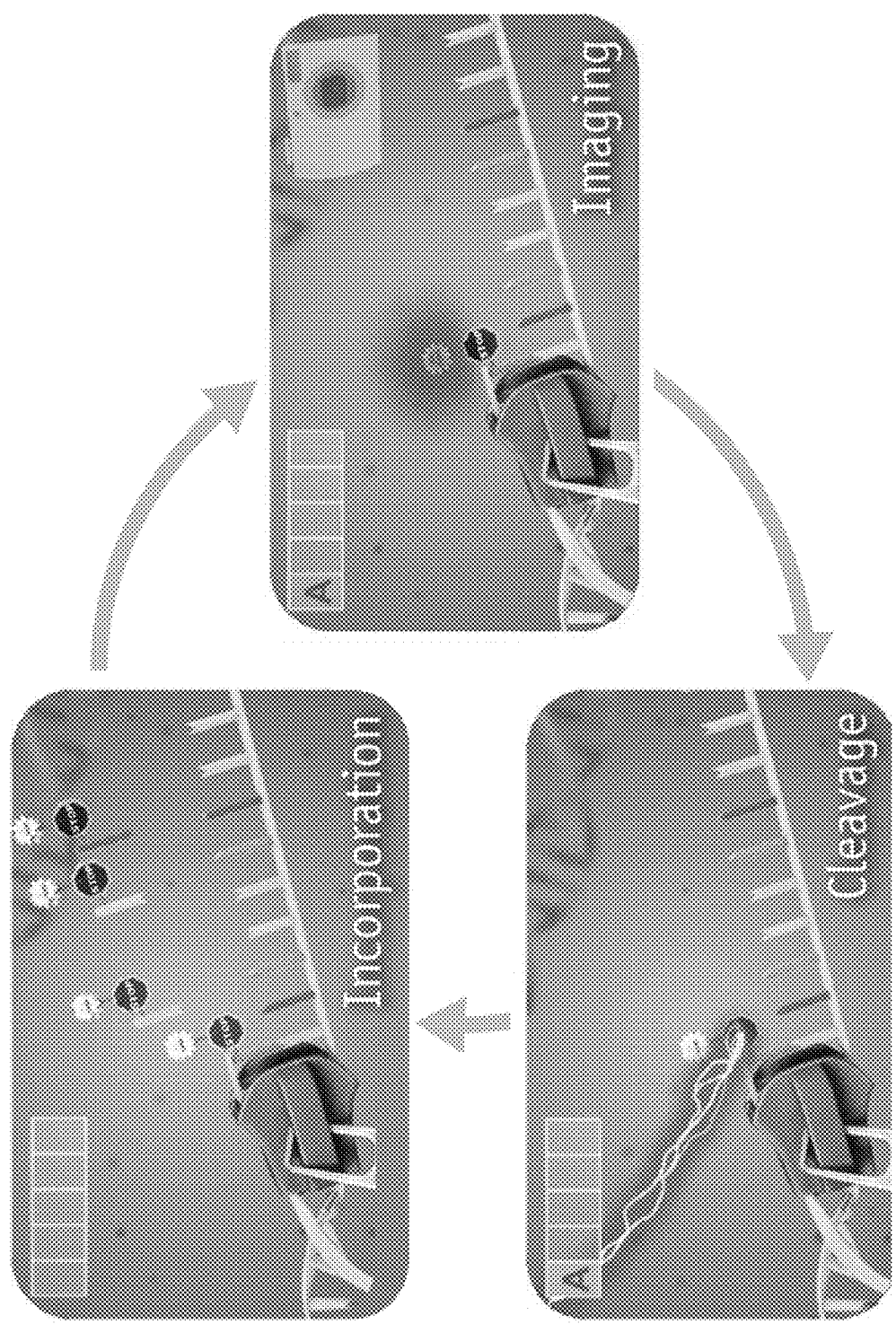
FIG. 10. Schematic illustration of the steps of incorporation, fluorescence imaging, and photochemical cleavage in a CRT cycle.

Once flowcell 50 is prepared with beads, flowcell 50 may be placed in the sequencing system 100. FIG. 10 illustrates the typical steps in one CRT cycle. A single DNA molecule is depicted for illustrative purposes, but those skilled in the art would understand that this process is performed on many DNA molecules.

First, in the incorporation step, 3'-OH reversible terminators are incorporated using DNA polymerase (depicted as a zipper) as discussed above.

Next, fluorescently-labeled DNA molecules are imaged. Lamp 14 is activated such that light path 30 is created from flowcell 50 to imaging device 10. Imaging device 10 captures images through the each of the four spectral filters of filter wheel 16. Using filter-wheel 16, each spectral channel is imaged in a tiled fashion to capture fluorescent signals within microfluidic flowcell 50. Base calling is then performed from processed fluorescent intensities of individual beads (i.e., a purified blue signal may be called an "A" base as the 3'-OH reversible terminator was labeled with a blue dye). The read length of the CRT method is a direct function of the number cycles that are executed (see Metzker 2010; Metzker, 2005, which are incorporated herein by reference).

Photochemical cleavage may then be performed. Using UV light source 20, UV light is shined upon flowcell 50. The UV light photochemically cleaves away the terminating group and the fluorescent group. In this manner, the modified nucleic acid is restored to its native state.

Figure 11:
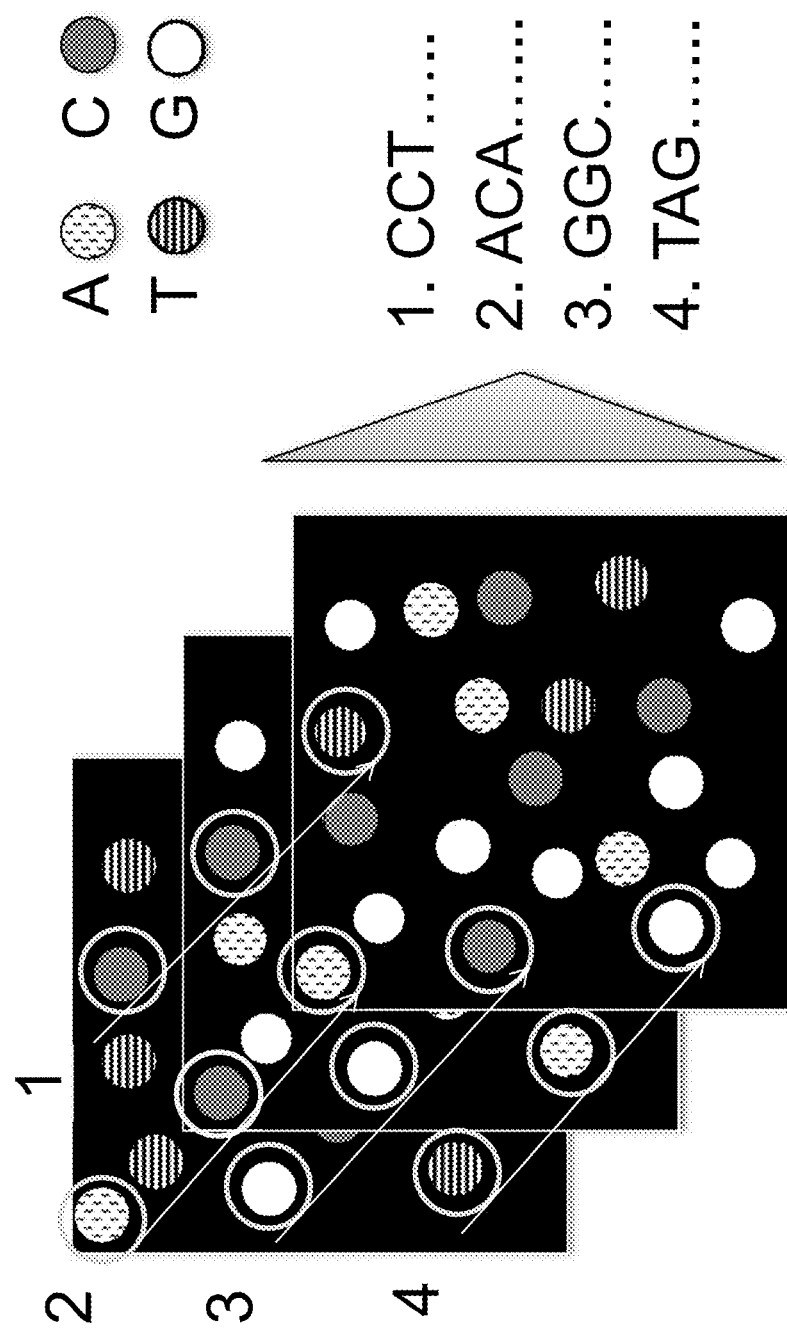
FIG. 11. Illustration of tile images from three CRT cycles and subsequent base-calling from individual beads.
Figure 12:
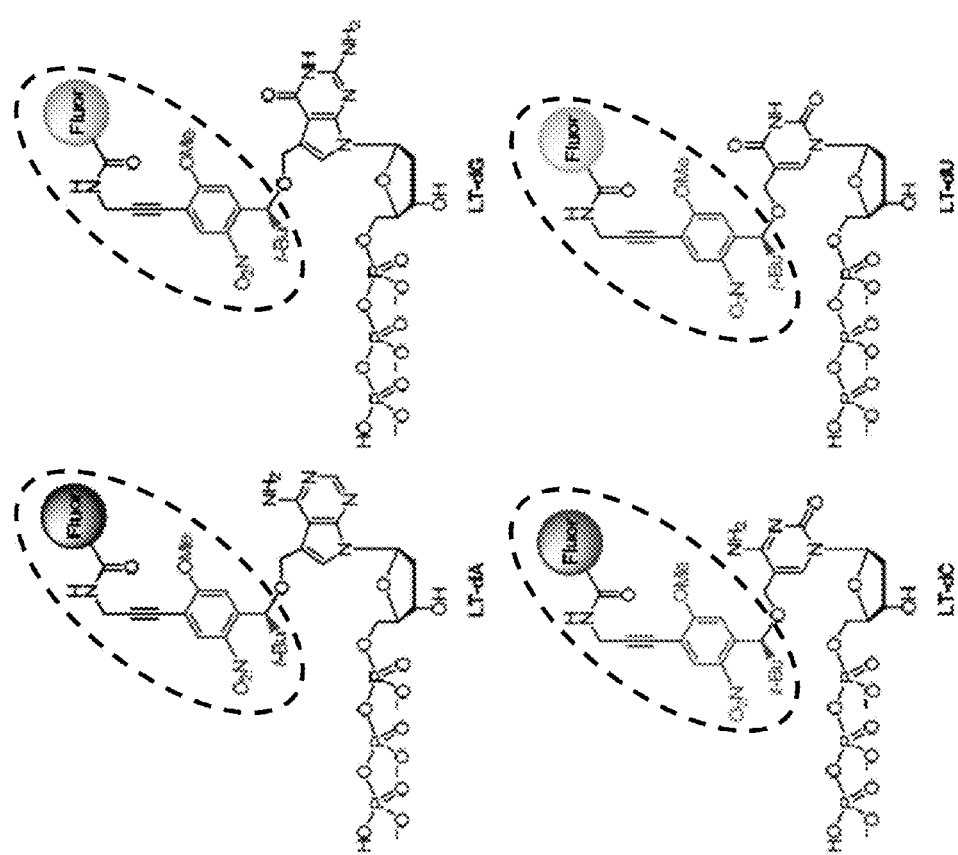
FIG. 12—Chemical Formulas of 3'-OH Reversible Terminators Attached to Generic Dyes ("Fluor"). The portion of the formulas encompassed by the dashed ellipsoid denotes the dye-labeled terminating functional groups and that are cleaved upon exposure to UV light.

A wash is then supplied, washing away the terminating group and fluorescent groups. The incorporation, imaging, cleaving and washing steps may be performed for as many CRT cycles as desired. FIG. 11 illustrates four-color tile images from three cycles and subsequent base-calling from individual beads.

IV. Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

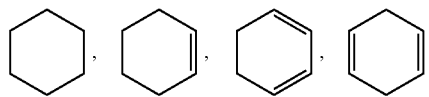

and

.

As will be understood by a person of skill in the art, no one such ring atom forms part of more than one double bond. The symbol "∿∿", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀▬" means a single bond where the group attached to the thick end of the wedge is "out of the page." The symbol "▬▬▬▬" means a single bond where the group attached to the thick end of the wedge is "into the page". The symbol "∿∿" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

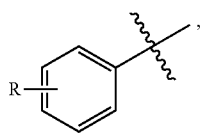

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

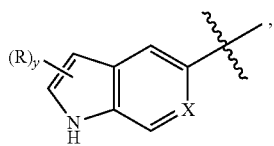

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$," or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$—(methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

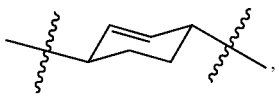 [SMILES: *C1C=CC(*)CC1]

are non-limiting examples of alkenediyl groups.

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

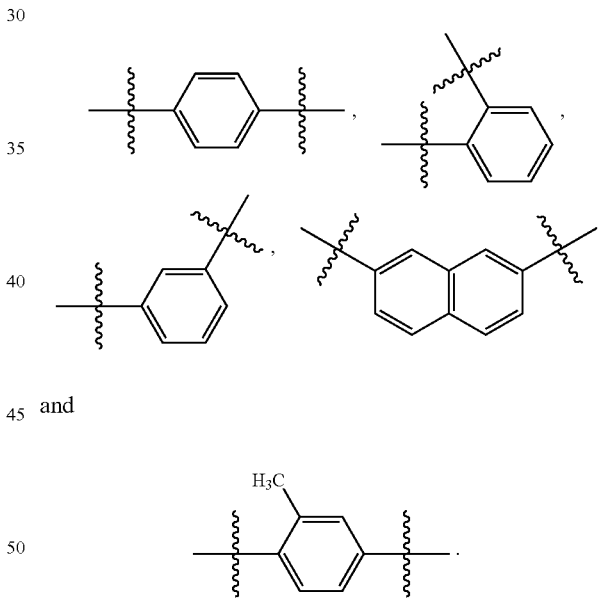

and

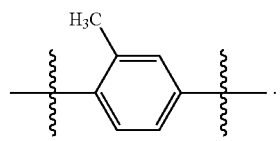 [SMILES: *c1ccc(*)c(C)c1]

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

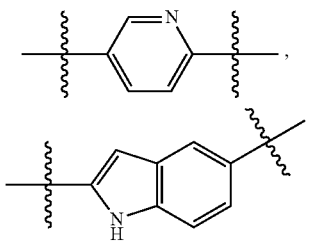

and

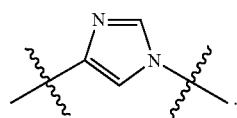 [SMILES: *c1cn(*)cn1]

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O— cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH— alkanediyl-, —NH— alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The terms "nucleotide base", "nucleobase" or simply "base", as used herein, refers to a substituted or unsubstituted nitrogen-containing parent heteroaromatic ring of a type that is commonly found in nucleic acids, as well as natural, substituted, modified, or engineered variants or analogs of the same. In a typical embodiment, the nucleobase is capable of forming Watson-Crick and/or Hoogsteen hydrogen bonds with an appropriately complementary nucleobase. Exemplary nucleobases include, but are not limited to, purines such as 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine;

7-deaza-purines such as 7-deazaadenine (7-deaza-A), 7-deazaguanine (7-deaza-G), 7-deaza-7-hydroxymethyladenine, 7-deaza-7-aminomethyladenine and 7-deaza-7-hydroxymethylguanine;

pyrimidines such as cytosine (C), 5-propynylcytosine, isocytosine, 5-hydroxylmethylcytosine (HOMeC), 5-aminomethyl-cytosine, thymine (T), 4-thiothymine (4sT), 5,6-dihydrothymine, $O^4$-methylthymine, uracil (U), 4-thiouracil (4sU), 5-hydroxylmethyluracil (HOMeU), 5-aminomethyl-uracil, and 5,6-dihydrouracil (dihydrouracil; D);

indoles such as nitroindole and 4-methylindole; pyrroles such as nitropyrrole; nebularine; base (Y); etc.

Additional exemplary nucleobases can be found in Lehninger, 2005, which is incorporated by reference, and the references cited therein.

The term "nucleoside" as used herein, refers to a glycosylamine consisting of a nucleobase bound to a five-carbon sugar, typically a ribose or a deoxyribose. Examples of these include, but are not limited to, cytidine, 2'-deoxycytidine, 5-hydroxylmethylcytidine, 2'-deoxy-5-hydroxylmethylcytidine, 5-aminomethylcytidine, 2'-deoxy-5-aminomethylcytidine, uridine, 2'-deoxyuridine, 5-hydroxylmethyluridine, 2'-deoxy-5-hydroxylmethyluridine, 5-aminomethyluridine, 2'-deoxy-5-aminomethyluridine, adenosine, 2'-deoxyadenosine, 7-deaza-7-hydroxymethyladenosine, 2'-deoxy-7-deaza-7-hydroxymethyladenosine, 7-deaza-7-aminomethyladenosine, 2'-deoxy-7-deaza-7-aminomethyladenosine, guanosine, 2'-deoxyguanosine, 7-deaza-7-hydroxymethyl guanosine, 2'-deoxy-7-deaza-7-hydroxymethyl, 7-deaza-7-aminomethyl guanosine, 2'-deoxy-7-deaza-7-aminomethyl guanosine, thymidine, and 2'-deoxythymidine.

A "nucleotide" is composed of a nucleoside with one, two, three or more phosphate groups bound in a chain to the 5-carbon sugar of the nucleoside.

The term "dephasing" is a pheonmenon that occurs with step-wise addition methods, including but not limited to CRT, SNA, and SBL methods, when growing primers move out of synchronicity for any given cycle. Lagging strand or type 2 dephasing (for example, n−1 from the expected cycle) result from incomplete extension, and leading strand or type 1 dephasing (for example, n+1) result from the addition of multiple nucleotides or probes in a population of identical templates.

The term "dark nucleotide" or "dark probe" refers to a nucleotide or probe that does not contain a fluorescent label. It can be generated from its cleavage and carry-over from the previous cycle or be hydrolyzed in situ from its dye-labeled counterpart in the current cycle.

Unless specified otherwise, a "linker" refers to one or more divalent groups (linking members) that function as a covalently-bonded molecular bridge between two other groups. A linker may contain one or more linking members and one or more types of linking members. Exemplary linking members include: —C(O)NH—, —C(O)O—, —NH—, —S—, —S(O)$_n$— where n is 0, 1 or 2, —O—, —OP(O)(OH)O—, —OP(O)(O$^-$)O—, alkanediyl, alkenediyl, alkynediyl, arenediyl, heteroarenediyl, or combinations thereof. Some linkers have pendant side chains or pendant functional groups (or both). Examples of such pendant moieties are hydrophilicity modifiers, for example, solubilizing groups like, e.g., —SO$_3$H or —SO$_3^-$. In some embodiments, a linker may connect a reporter to another moiety such as a chemically or enzymatically reactive group (e.g., a cleavable or non-cleavable terminating moiety). In other embodiments, a linker connects a reporter to a biological and non-biological component, for example, a nucleobase, a nucleoside or a nucleotide. In further embodiments, a linker connects chemically reactive groups to a nucleobase, a nucleoside or a nucleotide. The moiety formed by a linker bonded to a reporter may be designated -L-Reporter. Depending on such factors as the molecules to be linked and the conditions in which the method of strand synthesis is performed, the linker may vary in length and composition for optimizing properties such as stability, length, FRET efficiency, resistance to certain chemicals and/or temperature parameters, and be of sufficient stereo-selectivity or size to operably link a label to a nucleotide such that the resultant conjugate is useful in optimizing a polymerization reaction. Linkers can be employed using standard chemical techniques and include but not limited to, amine linkers for attaching labels to nucleotides (see, for example, Hobbs and Trainor, U.S. Pat. No. 5,151,507, which is incorporated herein by reference); a linker typically contain a primary or secondary amine for operably linking a label to a nucleotide; and a rigid hydrocarbon arm added to a nucleotide base (see, for example, Service, 1998, which is incorporated herein by reference). Some exemplary linking methodologies for attachment of reporters to base molecules are provided in U.S. Pat. Nos. 4,439,356 and 5,188,934; European Patent Appl. 87310256.0; International Appl. PCT/US90/05565 and Barone et al., 2001, each of which is incorporated herein by reference in its entirety.

A "cleavable linker" is a linker that has one or more cleavable groups that may be broken by the result of a reaction or condition. The term "cleavable group" refers to a moiety that allows for release of a portion, e.g., a fluorogenic or fluorescent moiety. Such cleavage is typically chemically, photochemically or enzymatically mediated. Exemplary enzymatically cleavable groups include phosphates, or groups attached via a peptide bond.

As used herein, the term "IC$_{50}$" refers to but not limited to the concentration of a nucleotide analog at which its incorporation on a primer-template complex yields equal numbers of moles of substrate and product and/or could be defined, but not limited to, incorporation efficiency measured by determining the concentration at which the compound incorporates on half the primer-template complexes.

As used herein, the term "oligonucleotide" refers to DNA fragments of 2 to 200 covalently linked nucleotides.

As used herein, the term "reporter" refers to a chemical moiety that is able to produce a detectable signal directly or indirectly. Examples of reporters include fluorescent dye groups, radioactive labels or groups effecting a signal through chemiluminescent or bioluminescent means. Examples fluorescent dye groups include zanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, and a squaraine dye. Additional examples, of fluorescent dye groups that may be used in some embodiments of the present invention are disclosed throughout this Specification and in Haugland, 2005 and U.S. Pat. Nos. 4,439,356 & 5,188,934, which are incorporated by reference herein. Examples of radioactive labels that may be used as reporters in some embodiments of the present invention, which are well known in the art such as $^{35}$S, $^{3}$H, $^{32}$P, or $^{33}$P. Examples of reporters that function by chemiluminescent or bioluminescent means and that may be used as reporters in some embodiments of the present invention are described in Nieman, 1989; Given & Schowen, 1989; Orosz et al., 1996; and Hastings, 1983, which are incorporated by reference herein.

As used herein, the term "template" can refer to an oligonucleotide serving as the complimentary strand for DNA synthesis (incorporation) or a recombinant DNA molecule that is made up of a known region, usually a vector or adaptor sequence to which a universal primer can bind, and the target sequence, which is typically an unknown portion to be sequenced.

The term "fragment templates" refers to a library of fragments that have been prepared by randomly shearing genomic DNA into small sizes of <1 kb and ligating adaptors to each end of the fragment. These templates generally require less DNA than would be needed for a mate-pair library.

The term "mate-pair templates" refers to a genomic library that has prepared by circularizing sheared of fragmented DNA that has been selected for a given size, (examples include 2 kb or 5 kb or 10 kb or 20 kb or any other desired size), therefore bringing the ends that were previously distant from one another into close proximity. Cutting these circles into linear DNA fragments creates mate-pair templates.

As used herein, the term "primer" refers to an oligonucleotide that is hybridized to a complement sequence on the template strand (usually a known sequence) used to initiate DNA synthesis (incorporation).

When used herein in the scientific or technical sense, the term "incorporation" refers to a nucleotide or nucleotide analog forming a complement base-pair with the template strand and a covalent bond to a primer strand by a polymerase. The primer-template complex is extended one or more bases from the initial primer strand.

As used herein, the term "cleavage" refers to the removal of the terminating group by chemical cleavage, enzymatic cleavage or the like.

As used herein, the term "incorporation cycle" refers to the incorporation of a nucleotide or nucleotide analog by a polymerase, the detection and identification of said nucleotide or nucleotide analog, and if a nucleotide analog, cleavage of the terminating group and, if originally present on the nucleotide analog, fluorescent dye group from said analog.

As used herein, the term "misincorporation" refers to a nucleotide or nucleotide analog forming a non-complement base-pair with the template strand and a covalent bond to a primer by a polymerase. The primer-template complex is extended one or more bases from the initial primer strand.

As used herein, the term "discrimination" refers the $IC_{50}$ concentration differences for misincorporation versus incorporation of nucleotide or nucleotide analogs by a polymerase.

As used herein, the term "termination" refers to the incorporation of a nucleotide or nucleotide analog forming a complement or non-complement base-pair with the template strand and a covalent bond to a primer by a polymerase. The primer-template complex is extended only one base from the initial primer strand or growing primer strand for any given incorporation cycle.

The terms "terminating moiety" and "terminating group" as used herein, are synonymous, referring to a small chemical group (e.g., <500 daltons, excluding any modification, such a linker or linker/dye) that when attached to at least one part of a nucleoside (i.e., sugar or nucleobase) or nucleotide (i.e., sugar, nucleobase, or phosphate group) confers substantial termination properties to the nucleoside or nucleotide. In some embodiments, the terminating moiety is further modified with a linker and/or a linker attached to a dye. In preferred embodiments, the terminating properties of such a modified terminating group is not substantially altered.

As used herein, the term "$DT_{50}$" refers to the amount of time required to cleavage 50% of the base analog incorporated in the primer-template complex.

The term "analog" as used herein, is understood as being a substance which does not comprise the same basic carbon skeleton and carbon functionality in its structure as a "given compound", but which can mimic the given compound by incorporating one or more appropriate substitutions such as for example substituting carbon for heteroatoms.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Reagents and Materials.

All reagents were purchased from commercial sources and used as received, unless otherwise noted.

Spectroscopic and Analytical Instrumentation.

$^1$H NMR, $^{13}$C NMR, and $^{31}$P NMR spectra were recorded on a Bruker DPX 400 spectrometer as previously described in Wu et al. (2007), which is incorporated herein by reference. Mass spectra analyses were provided by the Mass Spectrometry Laboratory at the MD Anderson Cancer Center (Houston, Tex.) and the Core Mass Spectrometry Facility at Rice University (Houston, Tex.). X-ray crystallography was performed by the X-ray Diffraction Laboratory at Texas A&M University (College Station, Tex.). UV/Vis measurements were taken using a Beckman DU-800 spectrophotometer. Anion exchange chromatography was performed using a Q Sepharose FF column (2.5×20 cm) with a linear gradient of 75% triethylammonium bicarbonate (TEAB, 0.1 M) in 25% acetonitrile to 75% TEAB (1.5 M) in 25% acetonitrile over 240 min at a flow rate of 4.5 mL per min. Reverse-phase high performance liquid chromatography (RP-HPLC) was performed using a Beckman System Gold equipped with a 128 solvent module and 166 UV detector or 168 photodiode array UV/Vis detector. RP-HPLC for nucleosides and nucleotide analogs was performed using a 4.6 mm×250 mm Aquapore OD-300 $C_{18}$ column, with buffer A containing 100 mM triethylammonium acetate (TEAA), pH 7.0, and buffer B containing 100 mM TEAA, pH 7.0, 70% acetonitrile (v/v).

Example 2

Synthesis of α-Substituted 2-Nitrobenzyl Alcohols (R/S)-1-(2-Nitrophenyl)-2-methyl-1-propanol Synthesis of (R/S)-1-(2-nitrophenyl)-2-methyl-1-propanol was previously reported. See Litosh et al. (2011), which is incorporated herein by reference.

(R/S)-1-(2-Nitrophenyl)-2,2-dimethyl-1-propanol

Synthesis of (R/S)-1-(2-nitrophenyl)-2,2-dimethyl-1-propanol was previously reported. See Litosh et al. (2011), which is incorporated herein by reference.

(R/S)-1-(2,6-Dinitrophenyl)-2-methyl-1-propanol

Scheme S1. Synthesis of (R/S)-1-(2,6-dinitrophenyl-2-methyl-1-propanol.

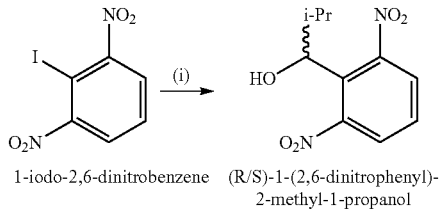

1-iodo-2,6-dinitrobenzene    (R/S)-1-(2,6-dinitrophenyl)-2-methyl-1-propanol

Reagents and conditions: (i) PhMgBr, THF, minus 50° C.; i-PrCHO, minus 50° C. to room temperature, 30%.

To a solution of 1-iodo-2,6-dinitrobenzene (Smith and Ho, 1990), which is incorporated herein by reference) (1.55 g, 5.27 mmol) in anhydrous THF (18 mL) at minus 50° C. under a nitrogen atmosphere, phenylmagnesium bromide (2 M in THF, 3.2 mL, 6.4 mmol) was added dropwise at a rate such that the temperature would not exceed minus 45° C. Upon completion of the addition, the mixture was stirred at minus 50° C. for five min, followed by addition of isobutyraldehyde (0.96 mL, 11 mmol). The mixture was gradually warmed up to room temperature, quenched with saturated $NH_4Cl$ solution (10 mL), and then diluted with water (50 mL). The mixture was extracted with $CH_2Cl_2$ (100 mL) three times. The combined organic phase was washed with brine (50 mL), dried over $Na_2SO_4$, concentrated in vacuo, and the residue was purified by silica gel column chromatography to yield (R/S)-1-(2,6-dinitrophenyl)-2-methyl-1-propanol (0.375 g, 30%) as a yellow oil. $^1$H NMR (400 MHz, $CDCl_3$): δ 7.82 (d, 2H, J=8.0 Hz, Ph-H), 7.59 (t, 1H, J=8.0 Hz, Ph-H), 4.83 (dd, 1H, J=9.2 and 7.6 Hz, Ph-CH), 2.87 (d, 1H, J=7.6 Hz, OH), 2.19 (m, 1H, CH), 1.12 (d, 3H, J=6.4 Hz, $CH_3$), 0.76 (d, 3H, J=6.8 Hz, $CH_3$).

(R/S)-1-(4-Methoxy-2-nitrophenyl)-2-methyl-1-propanol

Scheme S2. Synthesis of (R/S)-1-(4-methoxy-2-nitrophenyl)-2-methyl-1-propanol.

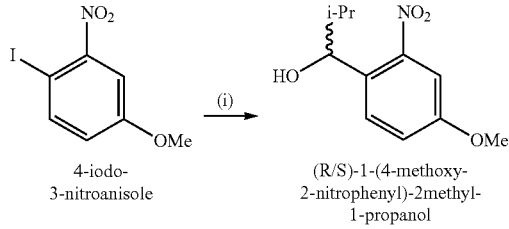

4-iodo-3-nitroanisole    (R/S)-1-(4-methoxy-2-nitrophenyl)-2methyl-1-propanol

Reagents and conditions: (i) PhMgCl, THF, minus 40° C.; i-PrCHO, minus 40° C. to room temperature, 67%.

To a solution of 4-iodo-3-nitroanisole (2.79 g, 10.0 mmol) in anhydrous THF (20 mL) at minus 40° C. under a nitrogen atmosphere, phenylmagnesium chloride (2 M in THF, 6.0 mL, 12 mmol) was added dropwise at a rate such that the temperature would not exceed minus 35° C. Upon completion of the addition, the mixture was stirred at minus 40° C. for five min, followed by addition of isobutyraldehyde (1.8 mL, 20 mmol). The mixture was gradually warmed to room temperature, quenched with saturated $NH_4Cl$ solution (5.0 mL), diluted with $CH_2Cl_2$ (100 mL) and washed with water (100 mL). The organic phase was separated, and the aqueous phase was extracted with $CH_2Cl_2$ (50 mL) three times. The combined organic phase was washed with brine (40 mL), dried over $Na_2SO_4$, concentrated in vacuo, and the residue was purified by silica gel column chromatography to yield (R/S)-1-(4-methoxy-2-nitrophenyl)-2-methyl-1-propanol (1.5 g, 67%) as a light yellow oil. $^1$H NMR (400 MHz, $CDCl_3$): δ 7.61 (d, 1H, J=8.8 Hz, Ph-H), 7.34 (d, 1H, J=2.8 Hz, Ph-H), 7.15 (dd, 1H, J=8.8 and 2.8 Hz, Ph-H), 4.92 (dd, 1H, J=5.6 and 3.2 Hz, Ph-CH), 2.46 (br s, 1H, OH), 2.00 (m, 1H, CH), 0.97 (d, 3H, J=6.4 Hz, $CH_3$), 0.86 (d, 3H, J=6.8 Hz, $CH_3$).

(R/S)-1-(4-Methoxy-2-nitrophenyl)-2,2-dimethyl-1-propanol

Scheme S3. Synthesis of (R/S)-1-(4-methoxy-2-nitrophenyl)-2,2-dimethy-1-propanol.

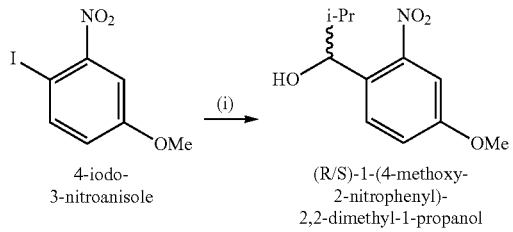

4-iodo-3-nitroanisole    (R/S)-1-(4-methoxy-2-nitrophenyl)-2,2-dimethyl-1-propanol Reagents and conditions: (i) PhMgCl, THF, minus 40° C.; $(CH_3)_3CCHO$, minus 40° C. to room temperature, 74%.

To a solution of 4-iodo-3-nitroanisole (2.38 g, 8.50 mmol) in anhydrous THF (10 mL) at minus 40° C. under a nitrogen atmosphere, phenylmagnesium chloride (2 M in THF, 4.7 mL, 9.4 mmol) was added dropwise at a rate such that the temperature would not exceed minus 35° C. Upon completion of the addition, the mixture was stirred at minus 40° C. for one hour, followed by addition of trimethylacetaldehyde (1.13 mL, 10.2 mmol). The mixture was stirred at minus 40° C. for two hours and then at room temperature for another one hour. The reaction was quenched with brine (100 mL), and the mixture was extracted with $CH_2Cl_2$ (40 mL) three times. The combined organic phase was dried over $Na_2SO_4$ and concentrated in vacuo, and the residue was purified by silica gel column chromatography to yield racemic (R/S)-1-(4-methoxy-2-nitrophenyl)-2,2-dimethyl-1-propanol (1.52 g, 74%). $^1$H NMR (400 MHz, $CDCl_3$): δ 7.67 (d, 1H, J=9.2 Hz, Ph-H), 7.22 (d, 1H, J=2.4 Hz, Ph-H), 7.12 (dd, 1H, J=8.8 and 2.8 Hz, Ph-H), 5.27 (d, 1H, J=4.0 Hz, Ph-CH), 3.86 (s, 3H, $OCH_3$), 2.01 (d, 1H, J=4.0 Hz, OH), 0.86 (s, 9H, $C(CH_3)_3$).

(R/S)-1-(5-Methoxy-2-nitrophenyl)-2,2-dimethyl-1-propanol and (S)-1-(5-methoxy-2-nitro-phenyl)-2,2-dimethyl-1-propanol Scheme S4. Synthesis of (R/S)-1-(5-methoxy-2-nitrophenyl)-2,2-dimethyl-1-propanol and (S)-1-(5-methoxy-2-nitrophenyl)-2,2-dimethyl-1-propanol.

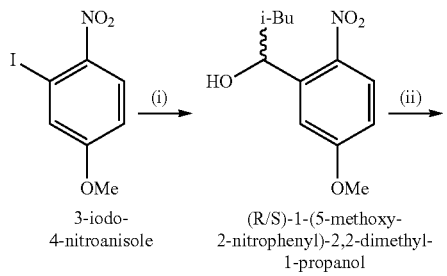

3-iodo-4-nitroanisole    (R/S)-1-(5-methoxy-2-nitrophenyl)-2,2-dimethyl-1-propanol

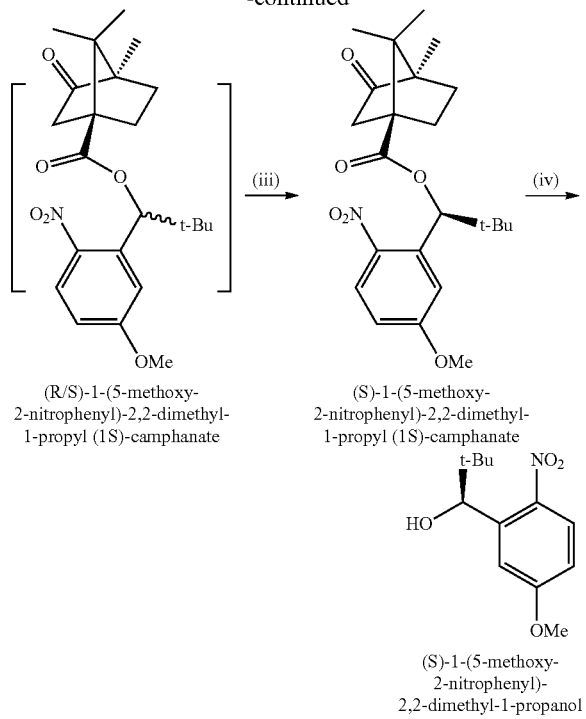

(R/S)-1-(5-methoxy-2-nitrophenyl)-2,2-dimethyl-1-propyl (1S)-camphanate (S)-1-(5-methoxy-2-nitrophenyl)-2,2-dimethyl-1-propyl (1S)-camphanate (S)-1-(5-methoxy-2-nitrophenyl)-2,2-dimethyl-1-propanol Reagents and conditions: (i) PhMgCl, anhydrous THF, minus 40° C; (CH$_3$)$_3$CCHO, minus 40° C. to room temperature, 88%; (ii) (1S)-camphanic acid choride, DMAP, CH$_2$Cl$_2$, room temperature; (iii) fractional crystallization from ethyl acetate/hexane, 43%; (iv) K$_2$CO$_3$, MeOH, reflux, 99%

To a solution of 3-iodo-4-nitroanisole (2.79 g, 10.0 mmol) in anhydrous THF (10 mL) at minus 40° C. under a nitrogen atmosphere, phenylmagnesium chloride (2 M in THF, 4.2 mL, 8.3 mmol) was added dropwise at a rate such that the temperature would not exceed minus 35° C. Upon completion of the addition, the mixture was stirred at minus 40° C. for two hours, followed by addition of trimethylacetaldehyde (1.1 mL, 10 mmol). The mixture was stirred at minus 40° C. for two hours and then at room temperature for another one hour. The reaction was then quenched with brine (100 mL), and the mixture was extracted with CH$_2$Cl$_2$ (40 mL) three times. The combined organic phase was dried over Na$_2$SO$_4$, concentrated in vacuo, and the residue was purified by silica gel column chromatography to yield racemic (R/S)-1-(5-methoxy-2-nitrophenyl)-2,2-dimethyl-1-propanol (1.76 g, 88%). $^1$H NMR (400 MHz, CDCl$_3$): δ 7.89 (d, 1H, J=9.2 Hz, Ph-H), 7.27 (d, 1H, J=2.8 Hz, Ph-H), 6.84 (dd, 1H, J=8.8 and 2.8 Hz, Ph-H), 5.62 (d, 1H, J=4.0 Hz, PhCH), 3.89 (s, 3H, OCH$_3$), 2.08 (d, 1H, J=4.0 Hz, OH), 0.89 (s, 9H, C(CH$_3$)$_3$).

To a solution of racemic (R/S)-1-(5-methoxy-2-nitrophenyl)-2,2-dimethyl-1-propanol (1.75 g, 7.3 mmol) and DMAP (2.92 g, 23.9 mmol) in anhydrous CH$_2$Cl$_2$ (10 mL), (1S)-camphanic chloride (Corrie et al., 1992) which is incorporated by reference) (2.6 g, 12 mmol) was added, and the mixture was stirred overnight at room temperature under a nitrogen atmosphere. The reaction mixture was diluted with CH$_2$Cl$_2$ (50 mL) and washed with saturated NaHCO$_3$ solution (50 mL). The organic phase was dried over Na$_2$SO$_4$, concentrated in vacuo, and the residue was purified by silica gel column chromatography to yield (R/S)-1-(5-methoxy-2-nitrophenyl)-2,2-dimethyl-1-propyl(1S)-camphanate (2.5 g, 85%, 1:1 mixture of diastereomers). The camphanate was dissolved in ethyl acetate (30 mL) followed by slow addition of hexane (120 mL) with stirring. Needle crystals formed gradually from the solution over a two-hour period. The crystals were collected by filtration to yield pure single diastereomer (S)-1-(5-methoxy-2-nitrophenyl)-2,2-dimethyl-1-propyl(1S)-camphanate. The filtrate was concentrated in vacuo, and the crystallization process was repeated twice to provide additional (S)-1-(5-methoxy-2-nitrophenyl)-2,2-dimethyl-1-propyl(1S)-camphanate (total 1.08 g, 43%). $^1$H NMR (400 MHz, CDCl$_3$): δ 8.04 (d, 1H, J=9.2 Hz, Ph-H), 7.27 (d, 1H, J=2.8 Hz, Ph-H), 6.88 (dd, 1H, J=2.8 and 8.8 Hz, Ph-H), 6.81 (3, 1H, Ph-CH), 3.87 (s, 3H, OCH$_3$), 2.36 (m, 1H, CH), 1.92 (m, 2H, CH$_2$), 1.66 (m, 1H, CH), 1.12 (s, 3H, CH$_3$), 1.06 (s, 3H, CH$_3$), 1.02 (s, 3H, CH$_3$), 0.95 (s, 9H, C(CH$_3$)$_3$).

Method for Obtaining X-Ray Crystallography Data:

Crystallographic measurements were made on a crystal of (S)-1-(5-methoxy-2-nitrophenyl)-2,2-dimethyl-1-propyl (1S)-camphanate with dimensions of 0.50 mm×0.05 mm×0.05 mm as described by Litosh et at (2011), which is incorporated herein by reference. See FIG. 3.

Data Collection:

CuKα radiation, λ=1.54178 Å, T=110±2° K, 2θ=120.0°, 32,513 reflections collected, 2,913 unique (R$_{int}$=0.0517). Final GooF=1.091, R1=0.0681, wR2=0.1695, R indices based on 2,913 reflections with I>2sigma(I) (refinement on F$^2$), 290 parameters, 43 restraints. Lp and absorption corrections applied, μ=0.819 mm$^{-1}$. Absolute structure parameter: 0.05±0.09.

X-Ray Crystallography Data:

C$_{22}$H$_{29}$NO$_7$, M=419.46. Orthorhombic, a=6.29, b=15.00, c=22.27 Å (α, β, γ=90°), V=2,099.29 Å$^3$, space group P2$_1$2$_1$2$_1$, Z=4, D$_c$=1.327 g/cm$^{-3}$, F(000)=896.

A mixture of (S)-1-(5-methoxy-2-nitrophenyl)-2,2-dimethyl-1-propyl(1S)-camphanate (590 mg, 1.4 mmol) and K$_2$CO$_3$ (389 mg, 2.8 mmol) in methanol (MeOH, 25 mL) was heated to reflux for one hour, then cooled down, concentrated in vacuo, and diluted with CH$_2$Cl$_2$ (50 mL). The organic phase was washed with brine (50 mL), dried over Na$_2$SO$_4$, concentrated in vacuo, and the residue was purified by silica gel column chromatography to yield enantiopure (S)-1-(5-methoxy-2-nitrophenyl)-2,2-dimethyl-1-propanol (333 mg, 99%). $^1$H NMR was identical with that of the racemic alcohol.

(R/S)-1-(4,5-Dimethoxy-2-nitrophenyl)-2,2-dimethyl-1-propanol

Scheme S5. Synthesis of (R/S)-1-(4,5-dimethoxy-2-nitrophenyl)-2,2-dimethyl-1-propanol.

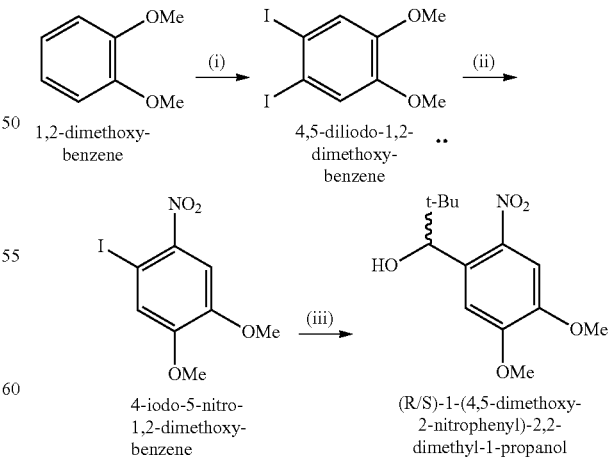

1,2-dimethoxy-benzene 4,5-diliodo-1,2-dimethoxy-benzene 4-iodo-5-nitro-1,2-dimethoxy-benzene (R/S)-1-(4,5-dimethoxy-2-nitrophenyl)-2,2-dimethyl-1-propanol Reagents and conditions: (i) ICl, CH$_3$COOH, 100° C., 62%; (ii) HNO$_3$, CH$_3$COOH, room temperature, 75%; (iii) PhMgCl, THF, minus 40° C.; (CH$_3$)$_3$CCHO, minus 40° C. to room temperature, 20%.

1,2-Dimethoxybenzene (5.0 g, 36 mmol) was dissolved in acetic acid (10 mL), and the solution was cooled in an ice-water bath followed by dropwise addition of iodine chloride (8.7 g, 54 mmol). After 10 min, the reaction mixture was heated to 100° C. for two hours and then cooled to room temperature. Needle crystals that precipitated from solution were filtered and washed with acetic acid (5.0 mL) three times. The crystals were dried overnight under high vacuum to yield 4,5-diiodo-1,2-dimethoxybenzene (8.8 g, 62%). NMR (400 MHz, CDCl$_3$): δ 7.28 (s, 2H, Ph-H), 3.85 (s, 6H, OCH$_3$).

4,5-Diiodo-1,2-dimethoxybenzene (8.8 g, 23 mmol) was added into acetic acid (300 mL), and the mixture was heated to 100° C. to dissolve the solid. The clear mixture was then cooled to room temperature followed by dropwise addition of nitric acid (68-70%, 120 mL). The reaction mixture was stirred at room temperature overnight and then poured into ice-water (200 mL). The mixture was extracted by CH$_2$Cl$_2$ (100 mL) three times. The combined organic phase was washed with saturated NaHCO$_3$ solution (200 mL), brine (100 mL), and dried over Na$_2$SO$_4$, concentrated in vacuo, and the residue was purified by silica gel column chromatography to yield 4-iodo-5-nitro-1,2-dimethoxybenzene (5.25 g, 75%). $^1$H NMR (400 MHz, CDCl$_3$): δ 7.60 (s, 1H, Ph-H), 7.38 (s, 1H, Ph-H), 3.98 (s, 3H, OCH$_3$), 3.92 (s, 3H, OCH$_3$).

To a solution of 4-iodo-5-nitro-1,2-dimethoxybenzene (4.6 g, 15 mmol) in anhydrous THF (10 mL) at minus 40° C. under a nitrogen atmosphere, phenylmagnesium chloride (2 M in THF, 7.5 mL, 15 mmol) was added dropwise at a rate such that the temperature would not exceed minus 35° C. Upon completion of the addition, the mixture was stirred at minus 40° C. for two hours, followed by addition of trimethyl acetaldehyde (2.0 mL, 18 mmol). The mixture was stirred at minus 40° C. for two hours and then at room temperature for another one hour. The reaction was quenched with brine (100 mL), and the mixture was extracted with CH$_2$Cl$_2$ (40 mL) three times. The combined organic phase was dried over Na$_2$SO$_4$ and concentrated in vacuo, and the residue was purified by silica gel column chromatography to yield racemic (R/S)-1-(4,5-dimethoxy-2-nitrophenyl)-2,2-dimethyl-1-propanol (0.8 g, 20%). $^1$H NMR (400 MHz, CDCl$_3$): δ 7.41 (1, 1H, Ph-H), 7.21 (s, 1H, Ph-H), 5.60 (s, 1H, PhCH), 3.95 (s, 3H, OCH$_3$), 3.92 (s, 3H, OCH$_3$), 0.90 (s, 9H, (CH$_3$)$_3$).

Example 3

Synthesis of 7-HOMe-7-Deaza-2'-Deoxyadenosine Triphosphate Analogs 7-(2-nitrobenzyloxy)methyl-7-deaza-2'-deoxyadenosine-5'-triphosphate Scheme S6. Synthesis of 7-(2-nitrobenzyloxy)methyl-7-deaza-2'-dexyadenosine-5'-triphosphate.

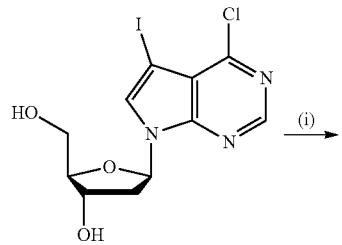

1

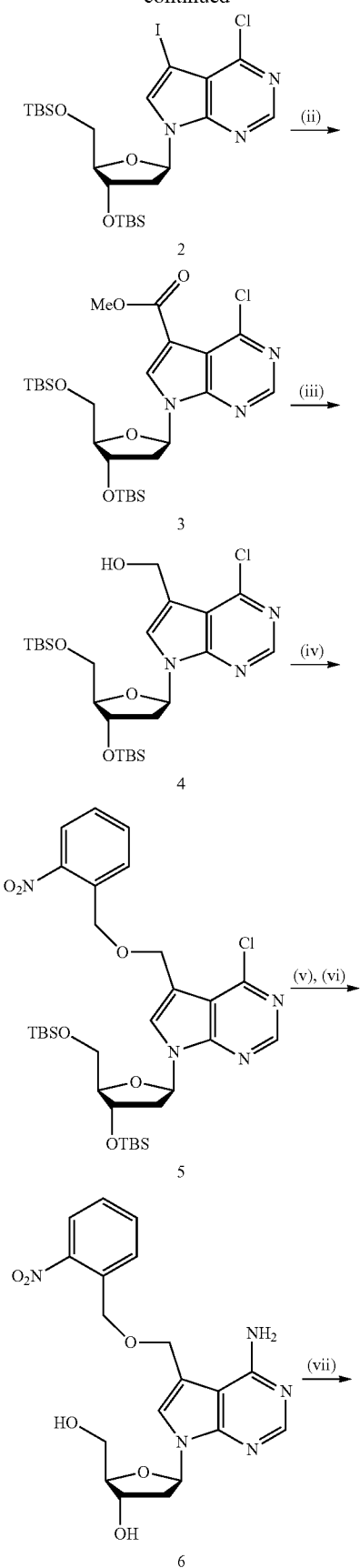

Reagents and conditions: (i) TBSCl, imidazole, DMF, room temperature, 87%; (ii) CO, PdCl$_2$[PhCN]$_2$, MeOH/1, 4-dioxane, 50° C., 98%; (iii) LiBH$_4$, MeOH, THF, reflux, 45%; (iv) 2-nitrobenzyl bromide, n-Bu$_4$NBr, CH$_2$Cl$_2$/aq. NaOH, room temperature, 50%; (v) n-Bu$_4$NF, THF, 0° C. to room temperature; (vi) NH$_3$, 1-4-dioxane/MeOH, 100° C., 91% for two steps; (vii) POCl$_3$, (MeO)$_3$PO, minus 40° C.; (n-Bu$_3$NH)$_2$H$_2$P$_2$O$_7$, n-Bu$_3$N, DMF; 1M HNEt$_3$HCO$_3$.

Compound 1 (Seela et al. (2005), which is incorporated herein by reference), (0.79 g, 2.0 mmol) was evaporated from anhydrous pyridine (2.0 mL) three times and dissolved in anhydrous DMF (4.0 mL). tert-Butyldimethylsilyl chloride (0.90 g, 6.0 mmol) and imidazole (0.82 g, 12 mmol) were added, and the mixture was stirred at room temperature for 16 hours. The reaction was concentrated in vacuo and purified by silica gel chromatography to yield 9-[β-D-3',5'-O-bis-(tert-butyldimethylsilyl)-2'-deoxyribofuranosyl]-6-chloro-7-iodo-7-deazapurine 2 (1.08 g, 87%) as a white foam. $^1$H NMR (400 MHz, CDCl$_3$): δ 8.61 (s, 1H, H-2), 7.81 (s, 1H, H-8), 6.74 (t, 1H, J=6.4 Hz, H-1'), 4.56 (m, 1H, H-4'), 4.01 (m, 1H, H-3'), 3.87 (dd, 1H, H-5'a), 3.79 (dd, 1H, H-5'b), 2.39 (m, 2H, H-2'a and H-2'b), 0.96 (s, 9H, (CH$_3$)$_3$CSi), 0.91 (s, 9H, (CH$_3$)$_3$CSi), 0.18 (2s, 6H, (CH$_3$)$_2$Si), 0.15 (s, 6H, (CH$_3$)$_2$Si).

To a solution of compound 2 (1.55 g, 2.48 mmol) in anhydrous 1,4-dioxane (42 mL) and anhydrous MeOH (42 mL), triethylamine (0.87 mL) was added. After stirring for 10 min under a CO atmosphere, bis(benzonitrile)dichloropalladium (II) (0.05 g, 0.13 mmol) was added, and the reaction was stirred at 50° C. for 48 hours under a CO atmosphere. The mixture was then concentrated in vacuo, and the residue was purified by silica gel chromatography to yield 9-[β-D-3',5'-O-bis-(tert-butyldimethylsilyl)-2'-deoxyribofuranosyl]-6-chloro-7-methoxycarbonyl-7-deazapurine 3 (1.36 g, 98%) as a viscous oil. $^1$H NMR (400 MHz, CDCl$_3$): δ 8.69 (s, 1H, H-2), 8.31 (s, 1H, H-8), 6.77 (t, 1H, J=6.8 Hz, H-1'), 4.58 (m, 1H, H-4'), 4.06 (m, 1H, H-3'), 3.90 (s, 3H, CH$_3$O), 3.87 (dd, 1H, H-5'a), 3.81 (dd, 1H, H-5'b), 2.42 (m, 2H, H-2'a and H-2'b), 0.93 (s, 18H, (CH$_3$)$_3$CSi), 0.13 (s, 6H, (CH$_3$)$_2$Si), 0.12 (s, 6H, (CH$_3$)$_2$Si).

To a solution of compound 3 (0.28 g, 0.50 mmol) in anhydrous THF (4.0 mL), lithium borohydride (44 mg, 2.0 mmol) was added, followed by MeOH (0.1 mL). The reaction mixture was stirred at room temperature for 10 min and then heated to reflux for 45 min. Upon cooling to room temperature, the mixture was diluted with CH$_2$Cl$_2$ (20 mL) and water (2.0 mL). The organic layer was separated, washed with brine (5.0 mL) two times, dried over Na$_2$SO$_4$, and concentrated in vacuo. The residue was purified by silica gel chromatography to yield 9-[β-D-3',5'-O-bis-(tert-butyldimethylsilyl)-2'-deoxyribofuranosyl]-6-chloro-7-hydroxymethyl-7-deazapurine 4 (0.12 g, 45%) as a white foam. $^1$H NMR (400 MHz, CDCl$_3$): δ 8.62 (s, 1H, H-8), 7.61 (s, 1H, H-2), 6.75 (dd, 1H, J=6.0 and 7.2 Hz, H-1'), 4.96 (AB d, 1H, J=11.6 Hz, 7-CH$_2$a), 4.91 (AB d, 1H, J=11.6 Hz, 7-CH$_2$b), 4.57 (m, 1H, H-4'), 4.00 (m, 1H, H-3'), 3.80 (m, 2H, H-5'a and H-5'b), 2.44 (m, 1H, H-2'a), 2.04 (m, 1H, H-2'b), 0.91 (2 s, 18H, (CH$_3$)$_3$CSi), 0.11 (2 s, 12H, (CH$_3$)$_2$Si).

To a solution of compound 4 (30 mg, 0.057 mmol) in CH$_2$Cl$_2$ (2.0 mL), n-Bu$_4$NBr (9 mg, 0.029 mmol), 2-nitrobenzyl bromide (37 mg, 0.17 mmol) and NaOH solution (1 M, 2.0 mL) were added. The reaction mixture was stirred vigorously at room temperature for 48 hours in the dark. The organic layer was separated, dried over Na$_2$SO$_4$, concentrated in vacuo, and the residue was purified by silica gel chromatography to yield 9-[β-D-3',5'-O-bis-(tert-butyldimethylsilyl)-2'-deoxyribofuranosyl]-6-chloro-7-(2-nitrobenzyloxy)methyl-7-deazapurine 5 (19 mg, 50%) as a viscous oil. $^1$H NMR (400 MHz, CDCl$_3$): δ 8.63 (s, 1H, H-2), 8.06 (dd, 1H, J=8.4 and 1.2 Hz, Ph-H), 7.84 (d, 1H, J=7.6 Hz, Ph-H), 7.64 (s, 1H, H-8), 7.62 (m, 1H, Ph-H), 7.43 (t, 1H, Ph-H), 6.75 (dd, 1H, J=7.2 and 6.0 Hz, H-1'), 5.03 (s, 2H, PhCH$_2$), 4.95 (AB d, 1H, J=12.0 Hz, 7-CH$_2$a), 4.88 (AB d, 1H, J=12.0 Hz, 7-CH$_2$b), 4.59 (m, 1H, H-4'), 4.00 (m, 1H, H-3'), 3.80 (m, 2H, H-5'a and H-5'b), 2.48 (m, 1H, H-2'a), 2.37 (m, 1H, H-2'b), 0.92 (2 s, 18H, (CH$_3$)$_3$CSi), 0.11 (s, 6H, (CH$_3$)$_2$Si), 0.10 (s, 6H, (CH$_3$)$_2$Si).

A solution of n-Bu$_4$NF (17 mg, 0.054 mmol) in THF (1.0 mL) was added to a solution of compound 5 (18 mg, 0.028 mmol) in THF (1.0 mL) at 0° C. The reaction mixture was gradually warmed to room temperature and stirred for two hours. The mixture was concentrated in vacuo, dissolved in 1,4-dioxane (2.0 mL), followed by addition of NH$_3$ in MeOH solution (7 M, 4.0 mL). The mixture was transferred to a sealed tube and stirred at 100° C. for 16 hours, then cooled to room temperature, concentrated in vacuo, and the residue was purified by silica gel chromatography to yield 7-(2-nitrobenzyloxyl)methyl-7-deaza-2'-deoxyadenosine 6 (10 mg, 91%) as a white foam. $^1$H NMR (400 MHz, DMSO-d$_6$): δ 8.08 (s, 1H, H-2), 8.06 (m, 1H, Ph-H), 7.75 (m, 2H, Ph-H), 7.58 (m, 1H, Ph-H), 7.42 (s, 1H, H-8), 6.64 (bs, 2H, D$_2$O exchangeable, 6-NH$_2$), 6.48 (dd, 1H, J=2.0 and 6.0 Hz, H-1'), 5.25 (d, 1H, J=4.0 Hz, D$_2$O exchangeable, 3'-OH), 5.08 (t, 1H, J=5.6 Hz, D$_2$O exchangeable, 5'-OH), 4.90 (s, 2H, PhCH$_2$), 4.75 (AB dd, 2H, 7-CH$_2$), 4.33 (m, 1H, H-3'), 3.81 (m, 1H, H-4'), 3.54 (m, 2H, H-5'a and H-5'b), 2.47 (m, 1H, H-2'a), 2.15 (m, 1H, H-2'b).

Compound 6 (6 mg, 0.014 mmol) was phosphorylated with POCl$_3$ (2.6 μL, 0.028 mmol) and proton sponge (6 mg, 0.028 mmol) in trimethylphosphate (0.25 mL) at minus 40° C. for four hours under a nitrogen atmosphere. A solution of bis-tri-n-butylammonium pyrophosphate (66 mg, 0.14 mmol) and tri-n-butylamine (28 μL) in anhydrous DMF (0.28 mL) was added. After 30 min of stirring, triethylammonium bicarbonate buffer (1 M, pH 7.5; 1.0 mL) was added. The reaction was stirred at room temperature for one hour and then concentrated in vacuo. The residue was dissolved in water (2.0 mL), filtered, and purified using RP-HPLC (see above) to yield 7-(2-nitro-benzyloxy)methyl-7-deaza-2'-deoxyadenosine-5'-triphosphate dA.I. HRMS (ESI): For the molecular ion $C_{19}H_{23}N_5O_{15}P_3$ [M−H]⁻, the calculated mass was 654.0403, and the observed mass was 654.0397.

7-[1-(2-nitrophenyl)-2-methyl-propyloxy]methyl-7-deaza-2'-deoxyadenosine-5'-triphosphate Scheme S7. Synthesis of 7-[1-(2-nitrophenyl)-2-methyl-propyloxy]methyl-7-deaza-2'-deoxyadenosine-5'-triphosphate.

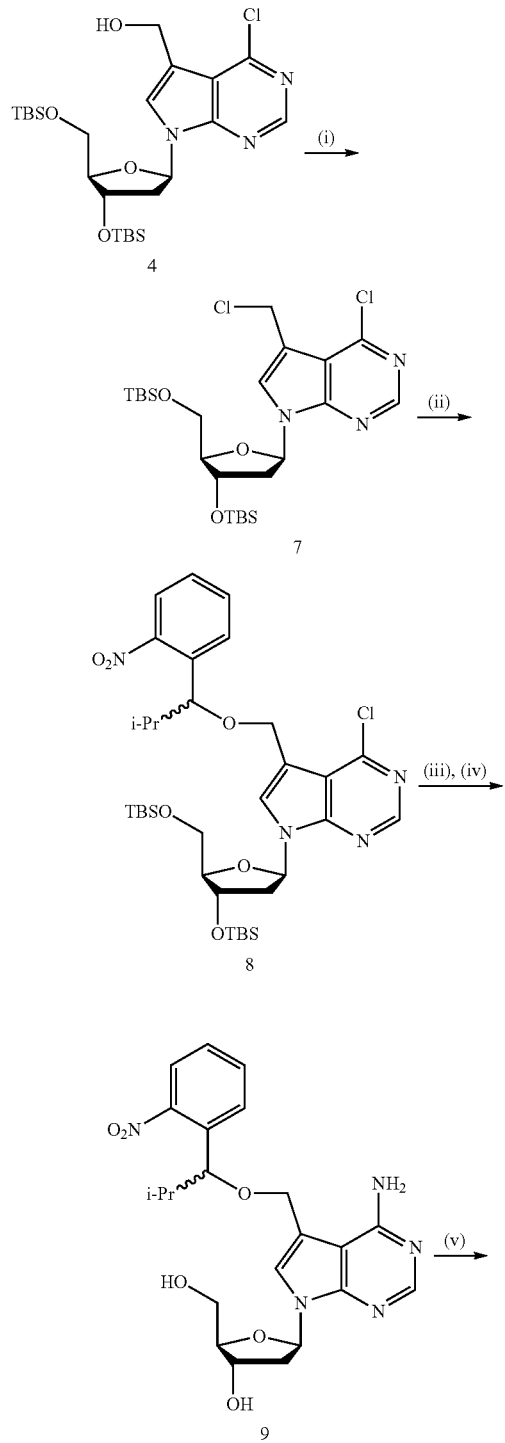

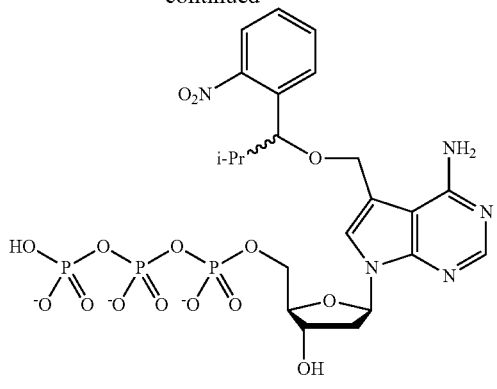

dA.III.a

Reagents and conditions: (i) TsCl, DMAP, CH₂Cl₂, room temperature, 39%; (ii) racemic (R/S)-1-(2-nitrophenyl)-2-methyl-propanol, neat, 105° C., 54%; (iii) n-Bu₄NF, THF, 0° C. to room temperature; (iv) NH₃, 1,4-dioxane/MeOH, 100° C., 76% for two steps; (v) POCl₃, (MeO)₃PO, minus 40° C. to 0° C.; (n-Bu₃NH)₂H₂P₂O₇, n-Bu₃N, DMF; 1M HNEt₃HCO₃.

To a solution of compound 4 (0.26 g, 0.49 mmol) in anhydrous CH₂Cl₂ (12 mL), 4-dimethylaminopyridine (DMAP; 0.15 g, 1.2 mmol) and tosyl chloride (0.11 g, 0.58 mmol) were added. The reaction mixture was stirred at room temperature for 18 hours and then concentrated in vacuo. The residue was purified by silica gel chromatography to yield 9-[β-D-3',5'-O-bis-(tert-butyldimethylsilyl)-2'-deoxyribofuranosyl]-6-chloro-7-chloromethyl-7-deazapurine 7 (0.103 g, 39%) as a viscous oil. ¹H NMR (400 MHz, CDCl₃): δ 8.64 (s, 1H, H-2), 7.72 (s, 1H, H-8), 6.73 (t, 1H, J=6.8 Hz, H-1'), 4.95 (AB d, J=12.4 Hz, 7-CH₂ₐ), 4.91 (AB d, J=12.0 Hz, 7-CH₂ᵦ), 4.58 (m, 1H, H-3'), 4.00 (m, 1H, H-4'), 3.82 (m, 2H, H-5'a and H-5'b), 2.41 (m, 2H, H-2'a and H-2'b), 0.95 (s, 9H, (CH₃)₃CSi), 0.93 (s, 9H, (CH₃)₃CSi), 0.12 (s, 6H, (CH₃)₂Si), 0.11 (s, 6H, (CH₃)₂Si).

Compound 7 (54 mg, 0.10 mmol) and racemic (R/S)-1-(2-nitrophenyl)-2-methyl-propanol (191 mg, 0.98 mmol) were dissolved in anhydrous CH₂Cl₂ (10 mL). The solvent was removed in vacuo, and the residue was heated for one hour under a nitrogen atmosphere, then dissolved in minimum amount of ethyl acetate and purified by silica gel chromatography to yield 9-[β-D-3',5'-O-bis-(tert-butyldimethylsilyl)-2'-deoxy-ribofuranosyl]-6-chloro-7-[1-(2-nitro-phenyl)-2-methyl-propyloxy]methyl-7-deazapurine 8 (38 mg, 54%) as a 1:1 mixture of two diastereomers. ¹H NMR (400 MHz, CDCl₃) for diastereomers: δ 8.60 and 8.59 (2 s, 1H, H-2), 7.83 (m, 1H, Ph-H), 7.79 (m, 1H, Ph-H), 7.56 (m, 1H, Ph-H), 7.48 and 7.47 (2 s, 1H, H-8), 7.38 (m, 1H, Ph-H), 6.70 (m, 1H, H-1'), 4.81 (m, 1H, Ph-CH), 4.70 (m, 1H, 7-CH₂a), 4.58 (m, 2H, 7-CH₂b and H-3'), 3.99 (m, 1H, H-4'), 3.78 (m, 2H, H-5'a and H-5'b), 2.48 (m, 1H, H-2'a), 2.35 (m, 1H, H-2'b), 1.96 (m, 1H, CH), 0.98 and 0.96 (2 d, 3H, CH₃), 0.93 (2 s, 9H, (CH₃)₃CSi), 0.89 (2 s, 9H, (CH₃)₃CSi), 0.82 and 0.78 (2 d, 3H, CH₃), 0.12 (2 s, 6H, (CH₃)₂Si), 0.08 and 0.07 (2 s, 3H, (CH₃)₂Si), 0.06 and 0.05 (2 s, 3H, (CH₃)₂Si).

A solution of n-Bu₄NF (44 mg, 0.14 mmol) in THF (2.0 mL) was added to a solution of compound 8 (38 mg, 0.05 mmol) in THF (2.0 mL) at 0° C. The reaction was gradually warmed to room temperature and stirred for two hours. The mixture was concentrated in vacuo, dissolved in 1,4-dioxane (4.0 mL), followed by addition of NH₃ in MeOH solution (7 M, 8.0 mL). The mixture was transferred to a sealed tube, stirred at 100° C. for 24 hours, cooled to room temperature, and then concentrated in vacuo. The residue was purified by silica gel chromatography to yield 7-[1-(2-nitrophenyl)-2-methyl-propyloxy]methyl-7-deaza-2'-deoxyadenosine 9 (19 mg, 76%) as a 1:1 mixture of two diastereomers. $^1$H NMR (400 MHz, DMSO-d$_6$) for diastereomers: δ 8.06 and 8.04 (2 s, 1H, H-2), 7.90 (m, 1H, Ph-H), 7.67 (m, 2H, Ph-H), 7.56 (m, 2H, Ph-H), 7.19 and 7.16 (2 s, 1H, H-8), 6.63 (bs, 2H, D$_2$O exchangeable, 6-NH$_2$), 6.39 (m, 1H, H-1'), 5.23 (m, 1H, D$_2$O exchangeable, 3'-OH), 5.00 (m, 1H, D$_2$O exchangeable, 5'-OH), 4.72 (2 d, 1H, Ph-CH), 4.45 (s, 2H, 7-CH$_2$), 4.30 (m, 1H, H-3'), 3.77 (m, 1H, H-4'), 3.49 (m, 2H, H-5'a and H-5'b), 2.40 (m, 1H, H-2'a), 2.12 (m, 1H, H-2'b), 1.94 (m, 1H, CH), 0.87 (m, 3H, CH$_3$), 0.74 (m, 3H, CH$_3$).

Compound 9 (19 mg, 0.041 mmol) was phosphorylated with POCl$_3$ (16 μL, 0.16 mmol) and proton sponge (18 mg, 0.082 mmol) in trimethylphosphate (0.4 mL) at minus 40° C. for five hours under a nitrogen atmosphere. A solution of bis-tri-n-butylammonium pyrophosphate (97 mg, 0.20 mmol) and tri-n-butylamine (40 μL) in anhydrous DMF (0.40 mL) was added. After 30 min of stirring, triethylammonium bicarbonate buffer (1 M, pH 7.5; 10 mL) was added. The reaction was stirred at room temperature for one hour and then concentrated in vacuo. The residue was dissolved in water (5.0 mL), filtered, and purified by anion exchange chromatography. The fractions containing triphosphate were combined and lyophilized to yield 7-[1-(2-nitrophenyl)-2-methyl-propyloxy]methyl-7-deaza-2'-deoxyadenosine-5'-triphosphate dA.III.a as a 1:1 mixture of two diastereomers, which were separated using RP-HPLC to yield the single diastereomers dA.III.a ds1 and dA.III.a ds2. In all cases, diastereomer 1 (ds1) eluted faster than diastereomer 2 (ds2) by RP-HPLC. HRMS (ESI): For the molecular ion C$_{22}$H$_{29}$N$_5$O$_{15}$P$_3$ [M–H]$^-$, the calculated mass was 696.0873, and the observed mass was 696.0864.

7-[1-(4-Methoxy-2-nitrophenyl)-2-methyl-propyloxy]methyl-7-deaza-2'-deoxyadenosine-5'-triphosphate Scheme S8. Synthesis of 7-[1-(4-methoxy-2-nitrophenyl)-2-methyl-propyloxy]methyl-7-deaza-2'-dexyadenosine-5'-triphosphate.

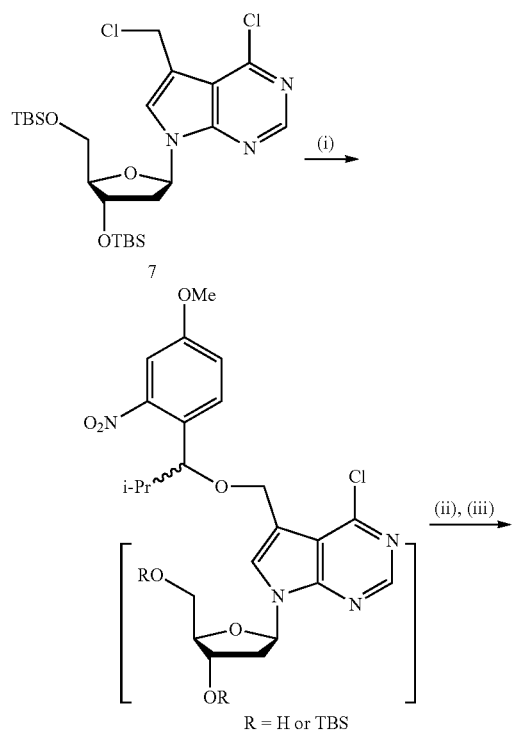

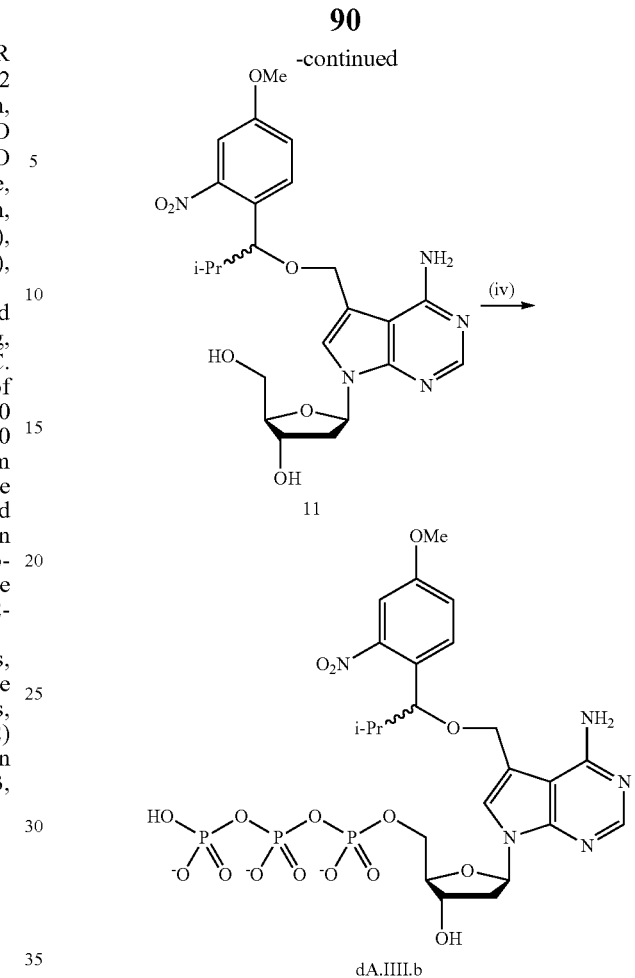

Reagents and conditions: (i) racemic (R/S)-1-(4-methoxy-2-nitrophenyl)-2-methyl-1-propanol, 108° C.; (ii) n-Bu$_4$NF, THF, 0° C. to room temperature; (iii) NH$_3$, 1,4-dioxane/MeOH, 100° C., 32% for three steps; (iv) POCl$_3$, (MeO)$_3$PO, 0° C.; (n-Bu$_3$NH)$_2$H$_2$P$_2$O$_7$; n-Bu$_3$N, DMF; 1M HNEt$_3$HCO$_3$.

Compound 7 (103 mg, 0.19 mmol) and racemic (R/S)-1-(4-methoxy-2-nitrophenyl)-2-methyl-1-propanol (428 mg, 1.9 mmol) were dissolved in anhydrous CH$_2$Cl$_2$ (3.0 mL). The solvent was removed in vacuo, and the residue was heated at 108° C. for 30 min under a nitrogen atmosphere, cooled to room temperature, dissolved in minimum amount of ethyl acetate, and purified by silica gel chromatography to yield 6-chloro-7-[1-(4-methoxy-2-nitrophenyl)-2-methyl-propyloxy]methyl-7-deazapurine 2'-deoxyribonucleosides 10. The sample was dissolved in THF (8.0 mL), cooled to 0° C., and then added to a solution of n-Bu$_4$NF (68 mg, 0.22 mmol) in THF (2.0 mL). The reaction was gradually warmed to room temperature and stirred for 30 min. The mixture was concentrated in vacuo, dissolved in 1,4-dioxane (8.0 mL), followed by addition of NH$_3$ in MeOH (7 N, 24 mL). The mixture was transferred to a sealed tube and stirred at 100° C. for 16 hours, then cooled to room temperature, and concentrated in vacuo. The residue was purified by silica gel chromatography to yield 7-[1-(4-methoxy-2-nitrophenyl)-2-methyl-propyloxy]methyl-7-deaza-2'-deoxyadenosine 11 (30 mg, 32% for three steps) as a 1:1 mixture of two diastereomers. $^1$H NMR (400 MHz, DMSO-d$_6$) for diastereomers: δ 8.06 and 8.05 (2 s, 1H, H-2), 7.57 and 7.54 (2 d, 1H, J=8.8 Hz, Ph-H), 7.47 and 7.44 (2 d, 1H, J=2.6 Hz, Ph-H), 7.33 and 7.27 (2 dd, J=8.8 and 2.6 Hz, 1H, Ph-H), 7.18 and 7.15 (2 s, 1H, H-8), 6.63 (bs, 2H, D$_2$O exchangeable, 6-NH$_2$), 6.43 (m, 1H, H-1'), 5.24 (m, 1H, D$_2$O exchangeable, 3'-OH), 5.03 (m, 1H, D$_2$O exchangeable, 5'-OH), 4.55 (m, 2H, Ph-CH, 7-CH$_2$a), 4.30 (m, 2H, 7-CH$_2$b and H-3'), 3.86 and 3.84 (2 s, 3H, MeO), 3.78 (m, 1H, H-4'), 3.48 (m, 2H, H-5'), 2.45 (m, 1H, H-2'a), 2.12 (m, 1H, H-2'b), 1.93 (m, 1H, CH(CH$_3$)$_2$), 0.88 (m, 3H, CH$_3$), 0.74 and 0.71 (2 d, J=6.8 Hz, 3H, CH$_3$).

Compound 11 (28 mg, 0.06 mmol) was phosphorylated with POCl$_3$ (11 µL, 0.12 mmol) and proton sponge (25 mg, 0.12 mmol) in trimethylphosphate (0.35 mL) at 0° C. for two hours under a nitrogen atmosphere. A solution of bis-tri-n-butylammonium pyrophosphate (237 mg, 0.50 mmol) and tri-n-butylamine (100 µL) in anhydrous DMF (1.0 mL) was added. After 10 min of stirring, triethylammonium bicarbonate buffer (1 M, pH 7.5; 10 mL) was added. The reaction was stirred at room temperature for one hour and then concentrated in vacuo. The residue was dissolved in 20% aqueous acetonitrile (10 mL), filtered, and purified by anion exchange chromatography. The fractions containing triphosphate were combined and lyophilized to yield 7-[1-(4-methoxy-2-nitro-phenyl)-2-methyl-propyloxy]methyl-7-deaza-2'-deoxyadenosine-5'-triphosphate dA.III.b as a 1:1 mixture of two diastereomers, which were separated using RP-HPLC to yield the single diastereomers dA.III.b ds1 and dA.III.b ds2. HRMS (ESI): For the molecular ion C$_{23}$H$_{31}$N$_5$O$_{16}$P$_3$ [M–H]$^-$, the calculated mass was 726.0979, and the observed mass was 726.0984.

7-[1-(2,6-Dinitrophenyl)-2-methyl-propyloxy]methyl-7-deaza-2'-deoxyadenosine-5'-triphosphate Scheme S9. Synthesis of 7-[1-2,6-dinitrophenyl)-2-methyl-propyloxy]methyl-7-deaza-2'-deoxy-adenosine-5'-triphosphate.

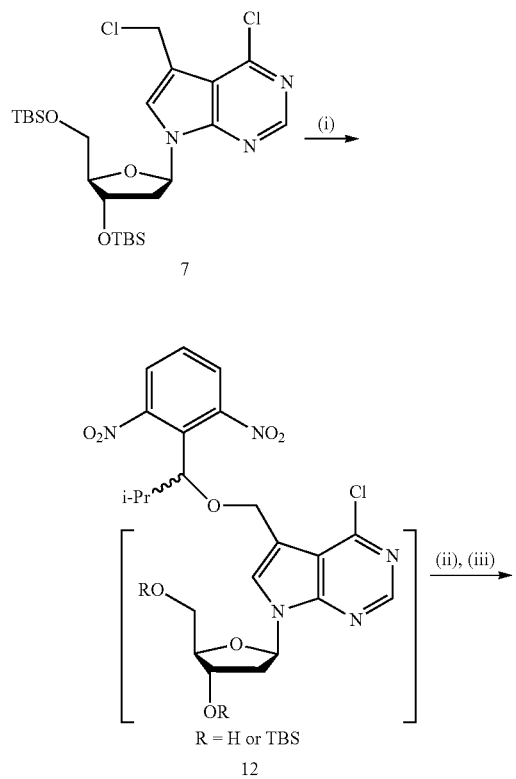

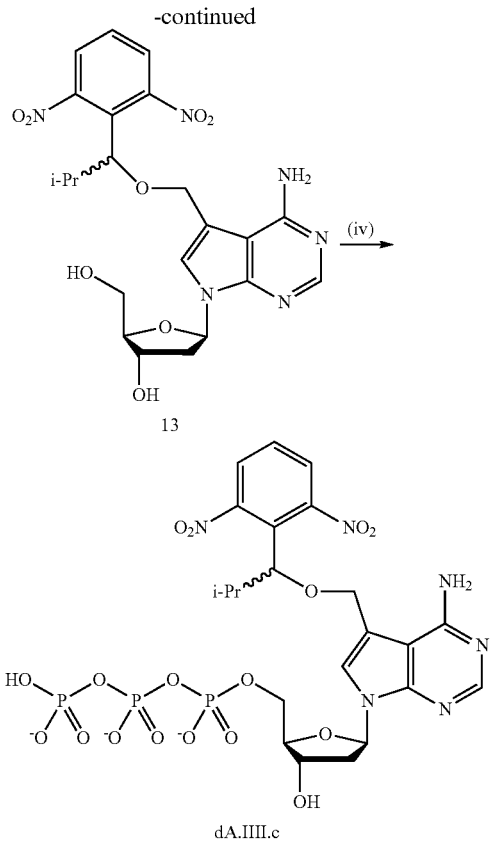

Reagents and conditions: (i) racemic (R/S)-1-(2,6-dinitrophenyl)-2-methyl-1-propanol, 108° C.; (ii) n-Bu$_4$NF, THF, 0° C. to room temperature; (iii) NH$_3$, 1,4-dioxane/MeOH, 100° C., 38% for three steps; (iv) POCl$_3$, (MeO)$_3$PO, 0° C.; (n-Bu$_3$NH)$_2$H$_2$P$_2$O$_7$, n-Bu$_3$N, DMF; 1M HNEt$_3$HCO$_3$.

Compound 7 (109 mg, 0.20 mmol) and racemic (R/S)-1-(2,6-dinitrophenyl)-2-methyl-1-propanol (448 mg, 1.9 mmol) were dissolved in anhydrous CH$_2$Cl$_2$ (10 mL). The solvent was removed in vacuo, and the residue was heated at 108° C. for 30 min under a nitrogen atmosphere, then dissolved in minimum amount of ethyl acetate and purified by silica gel chromatography to yield 6-chloro-7-[1-(2,6-dinitrophenyl)-2-methyl-propyloxy]methyl-7-deazapurine-2'-deoxyribo-nucleosides 12. The sample was dissolved in THF (5.0 mL), cooled to 0° C., and then added a solution of n-Bu$_4$NF (31 mg, 0.10 mmol) in THF (2.0 mL). The reaction was gradually warmed to room temperature and stirred for two hours. The mixture was concentrated in vacuo, dissolved in 1,4-dioxane (4.0 mL), followed by addition of NH$_3$ in MeOH (7 N, 18 mL). The mixture was transferred to a sealed tube, stirred at 100° C. for 36 hours, cooled to room temperature, and then concentrated in vacuo. The residue was purified by silica gel chromatography to yield 7-[1-(2,6-dinitrophenyl)-2-methyl-propyloxy]methyl-7-deaza-2'-deoxyadenosine 13 (38 mg, 38% for three steps) as a 1:1 mixture of two diastereomers. $^1$H NMR (400 MHz, DMSO-d$_6$) for diastereomers: δ 8.17 (m, 1H, Ph-H), 8.07 and 8.06 (2 s, 1H, H-2), 7.85 (m, 1H, Ph-H), 7.69 (m, 1H, Ph-H), 7.20 and 7.18 (2 s, 1H, H-8), 6.57 (bs, 2H, D$_2$O exchangeable, 6-NH$_2$), 6.46 (m, 1H, H-1'), 5.26 (d, J=3.6 Hz, 1H, D$_2$O exchangeable, 3'-OH), 5.01 (m, 1H, D$_2$O exchangeable, 5'-OH), 4.60 (m, 2H, Ph-CH and 7-CH$_2$a), 4.29 (m, 1H, 7-CH$_2$b), 4.13 (m, 1H, H-3'), 3.80 (m, 1H, H-4'), 3.51 (m, 2H, H-5'a and H-5'b), 2.49 (m, 1H, CH(CH$_3$)$_3$), 2.16 (m, 2H, H-2'a and H-2'b), 0.91 (m, 3H, CH₃), 0.65 (m, 3H, CH₃). ToF-MS (ESI): For the molecular ion $C_{22}H_{27}N_6O_8$ [M+H]⁻, the calculated mass was 503.1890, and the observed mass was 503.2029.

Compound 13 (30 mg, 0.06 mmol) was phosphorylated with POCl₃ (17 µL, 0.18 mmol) and proton sponge (26 mg, 0.12 mmol) in trimethylphosphate (0.4 mL) at 0° C. for four hours under a nitrogen atmosphere. A solution of bis-tri-n-butylammonium pyrophosphate (285 mg, 0.6 mmol) and tri-n-butylamine (120 µL) in anhydrous DMF (1.2 mL) was added. After 30 min of stirring, triethylammonium bicarbonate buffer (1 M, pH 7.5; 10 mL) was added. The reaction was stirred for one hour at room temperature and then concentrated in vacuo. The residue was dissolved in 20% aqueous acetonitrile (10 mL), filtered, and purified by anion exchange chromatography. The fractions containing triphosphate were combined and lyophilized to yield 7-[1-(2,6-dinitrophenyl)-2-methyl-propyloxy]methyl-7-deaza-2'-deoxyadenosine-5'-triphosphate dA.III.c as a 1:1 mixture of two diastereomers which were separated using RP-HPLC to yield the single diastereomers dA.III.c ds1 and dA.III.c ds2. HRMS (ESI): For the molecular ion $C_{22}H_{28}N_6O_{17}P_3$ [M–H]⁻, the calculated mass was 741.0724, and the observed mass was 741.0731.

7-[(S)-1-(2-Nitrophenyl)-2,2-dimethyl-propyloxy]methyl-7-deaza-2'-deoxyadenosine-5'-triphosphate Scheme S10. Synthesis of 7-[(S)-1-(2-nitrophenyl)-2,2-dimethyl-propyloxy]methyl-7-deaza-2'-deoxyadenosine-5'-triphosphate.

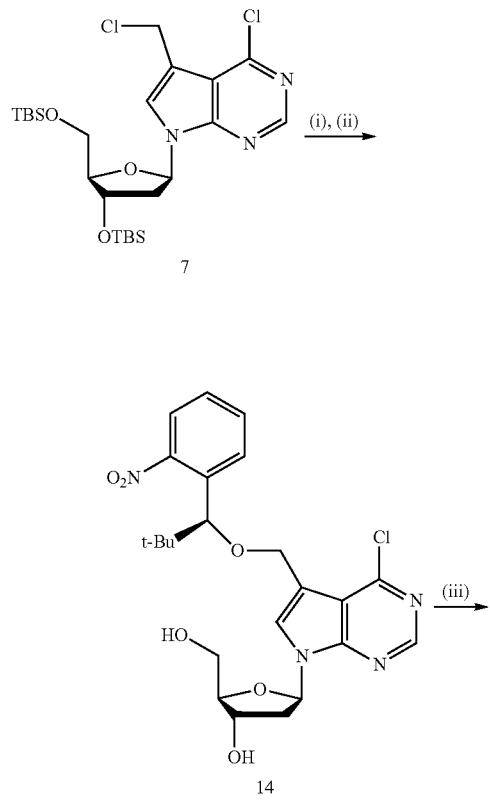

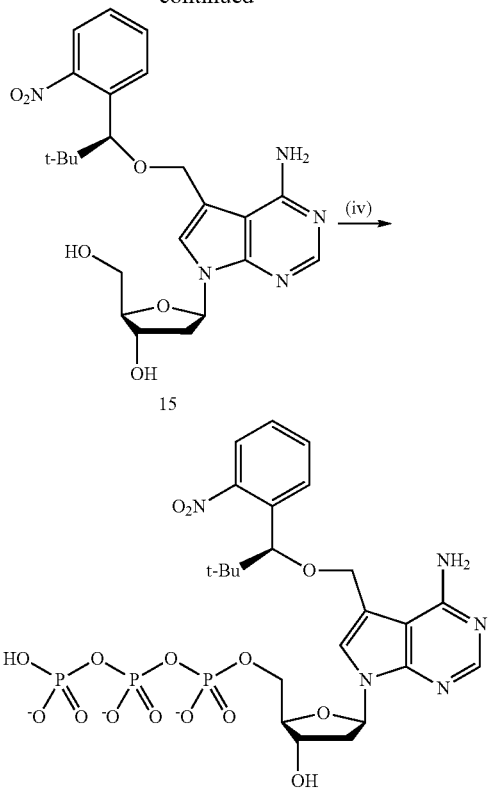

dA.V

Reagents and conditions: (i) (S)-1-(2-nitrophenyl)-2,2-dimethyl-1-propanol, 110° C.; (ii) n-Bu₄NF, THF, room temperature; 75% for two steps; (iii) NH₃, 1,4-dioxane/MeOH, 100° C., 93%; (iv) POCl₃, (MeO)₃PO, 0° C.; (n-Bu₃NH)₂H₂P₂O₇, n-Bu₃N, DMF; 1M HNEt₃HCO₃.

Compound 7 (130 mg, 0.24 mmol) and (S)-1-(2-nitrophenyl)-2,2-dimethyl-1-propanol (290 mg, 1.4 mmol) were heated at 110° C. for 45 min under a nitrogen atmosphere. The reaction mixture was cooled to room temperature and dissolved in THF (10 mL) followed by addition of n-Bu₄NF (189 mg, 0.60 mmol). The mixture was stirred at room temperature for two hours and then concentrated in vacuo. The residue was dissolved in CH₂Cl₂ (20 mL) and washed with brine (30 mL), and the aqueous phase was extracted with CH₂Cl₂ (20 mL) two times. The combined organic phase was dried over Na₂SO₄, concentrated in vacuo, and the residue was purified by silica gel chromatography to yield 6-chloro-9-[β-D-2'-deoxyribofuranosyl]-7-[(S)-1-(2-nitrophenyl)-2,2-dimethyl-propyloxy]methyl-7-deazapurine 14 (90 mg, 75%). ¹H NMR (400 MHz, CDCl₃): δ 8.51 (s, 1H, H-2), 7.68 (m, 2H, Ph-H), 7.45 (t, 1H, J=7.2 Hz, Ph-H), 7.38 (s, 1H, H-8), 7.29 (t, 1H, J=7.2 Hz, Ph-H), 6.39 (dd, 1H, J=6.0 and 8.0 Hz, H-1'), 4.97 (s, 1H, Ph-CH), 4.70 (m, 3H, 7-CH₂ and H-3'), 4.16 (m, 1H, H-4'), 3.83 (m, 2H, H-5'), 2.80 (m, 1H, H-2'a), 2.35 (m, 1H, H-2'b), 0.82 (s, 9H, C(CH₃)₃).

Compound 14 (90 mg, 0.18 mmol) was dissolved in 1,4-dioxane (8.0 mL) followed by addition of NH₃ in MeOH (7 N, 16 mL). The mixture was transferred to a sealed tube and stirred at 100° C. for 24 hours, cooled to room temperature, and then concentrated in vacuo. The residue was purified by silica gel chromatography to yield 7-[(S)-1-(2-nitrophenyl)-2,2-dimethyl-propyloxy]methyl-7-deaza-2'-deoxyadenosine 15 (80 mg, 93%). ¹H NMR (400 MHz, DMSO-d₆): δ 8.09 (s, 1H, H-2), 7.91 (dd, 1H, J=1.2 and 8.0 Hz, Ph-H), 7.71 (m, 2H, Ph-H), 7.58 (m, 1H, Ph-H), 7.24 (s, 1H, H-8), 6.68 (bs, 2H, D₂O exchangeable, 6-NH₂), 6.46 (dd, 1H, J=6.0 and 8.0 Hz, H-1'), 5.27 (d, 1H, D₂O exchangeable, 3'-OH), 5.06 (t, 1H, D₂O exchangeable, 5'-OH), 4.87 (s, 1H, Ph-CH), 4.65 (d, 1H, J=12.8 Hz, 7-CH₂a), 4.49 (m, 1H, H-3'), 4.36 (d, 1H, 7-CH₂b), 3.80 (m, 1H, H-4'), 3.49 (m, 2H, H-5'), 2.45 (m, 1H, H-2'a), 2.17 (m, 1H, H-2'b), 0.75 (s, 9H, C(CH₃)₃).

Compound 15 (25 mg, 0.053 mmol) was phosphorylated with POCl₃ (22 μL, 0.24 mmol) and proton sponge (23 mg, 0.11 mmol) in trimethylphosphate (0.35 mL) at 0° C. for 4.5 hours under a nitrogen atmosphere. A solution of bis-tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to yield 7-[(S)-1-(2-nitrophenyl)-2,2-dimethyl-propyloxy]methyl-7-deaza-2'-deoxyadenosine-5'-triphosphate dA.V, which was further purified using RP-HPLC. HRMS (ESI): For the molecular ion C₂₃H₃₁N₅O₁₅P₃ [M−H]⁻, the calculated mass was 710.1029, and the observed mass was 710.1032.

7-[(S)-1-(5-Methoxy-2-nitrophenyl)-2,2-dimethyl-propyloxy]methyl-7-deaza-2'-deoxyadenosine-5'-triphosphate Scheme S11. Synthesis of 7-[(S)-1-(5-methoxy-2-nitrophenyl)-2,2-dimethyl-propyloxy]methyl-7-deaza-2'-deoxyadenosine-5'-triphosphate.

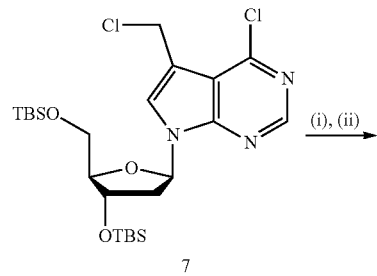

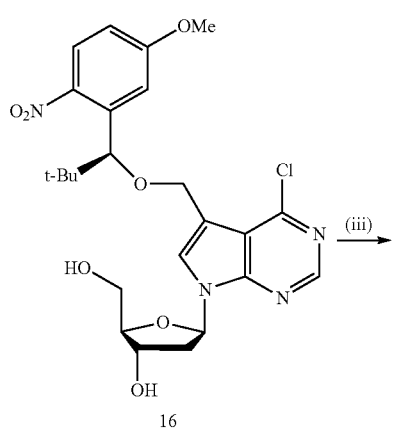

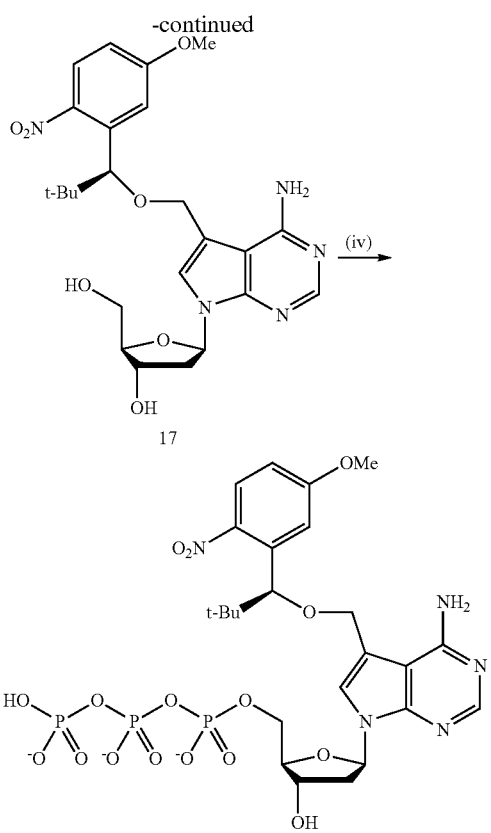

Reagents and conditions: (i) (S)-1-(5-methoxy-2-nitrophenyl)-2,2-dimethyl-1-propanol, 110° C.; (ii) n-Bu₄NF, THF, room temperature; 78% for two steps; (iii) NH₃, 1,4-dioxane/MeOH, 100° C., 74%; (iv) POCl₃, (MeO)₃PO, 0° C.; (n-Bu₃NH)₂H₂P₂O₇, n-Bu₃N, DMF; 1M HNEt₃HCO₃.

Compound 7 (165 mg, 0.30 mmol) and (S)-1-(5-methoxy-2-nitrophenyl)-2,2-dimethyl-1-propanol (330 mg, 1.4 mmol) were heated at 110° C. for 45 min under a nitrogen atmosphere. The reaction mixture was cooled to room temperature and dissolved in THF (10 mL), followed by addition of n-Bu₄NF (236 mg, 0.75 mmol). The mixture was stirred at room temperature for two hours and then concentrated in vacuo. The residue was dissolved in CH₂Cl₂ (40 mL) and washed with brine (50 mL), and the aqueous phase was extracted with CH₂Cl₂ (40 mL) two times. The combined organic phase was dried over Na₂SO₄, concentrated in vacuo, and the residue was purified by silica gel chromatography to yield 6-chloro-9-[β-D-2'-deoxyribofuranosyl]-7-[(S)-1-(5-methoxy-2-nitrophenyl)-2,2-dimethyl-propyloxy]methyl-7-deazapurine 16 (122 mg, 78%). ¹H NMR (400 MHz, CDCl₃): δ 8.55 (s, 1H, H-2), 7.79 (d, 1H, J=9.2 Hz, Ph-H), 7.35 (s, 1H, H-8), 7.15 (d, 1H, J=3.2 Hz, Ph-H), 6.68 (dd, 1H, J=3.2 and 9.2 Hz, Ph-H), 6.33 (dd, 1H, J=5.6 and 8.8 Hz, H-1'), 5.26 (s, 1H, Ph-CH), 4.85 (d, 1H, J=8.8 Hz, 7-CH₂a), 4.75 (m, 1H, H-3'), 4.70 (d, 1H, J=8.8 Hz, 7-CH₂b), 4.13 (m, 1H, H-4'), 3.95 (m, 1H, H-5'a), 3.83 (s, 3H, OCH₃), 3.78 (m, 1H, H-5'b), 2.86 (m, 1H, H-2'a), 2.30 (m, 1H, H-2'b), 0.83 (s, 9H, C(CH₃)₃).

Compound 16 (120 mg, 0.23 mmol) was dissolved in 1,4-dioxane (10 mL) followed by addition of NH₃ in MeOH (7 N, 10 mL). The mixture was transferred to a sealed tube and stirred at 100° C. for 24 hours, then cooled to room temperature, concentrated in vacuo, and the residue was purified by silica gel chromatography to yield 7-[(S)-1-(5-methoxy-2- nitrophenyl)-2,2-dimethyl-propyloxy]methyl-7-deaza-2'-deoxyadenosine 17 (87 mg, 74%). ¹H NMR (400 MHz, DMSO-d₆): δ 8.06 (s, 1H, H-2), 7.97 (d, 1H, J=9.2 Hz, Ph-H), 7.22 (s, 1H, H-8), 7.08 (d, 1H, J=2.8 Hz, Ph-H), 7.05 (dd, 1H, J=2.8 and 9.2 Hz, Ph-H), 6.66 (bs, 2H, D₂O exchangeable, 6-NH₂), 6.42 (dd, 1H, J=6.0 and 8.0 Hz, H-1'), 5.25 (d, 1H, D₂O exchangeable, 3'-OH), 5.15 (s, 1H, Ph-CH), 5.03 (t, 1H, D₂O exchangeable, 5'-OH), 4.64 (d, 1H, J=12.8 Hz, 7-CH₂a), 4.43 (d, 1H, J=12.8 Hz, 7-CH₂b), 4.30 (m, 1H, H-3'), 3.84 (s, 3H, OCH₃), 3.77 (m, 1H, H-4'), 3.45 (m, 2H, H-5'), 2.43 (m, 1H, H-2'a), 2.14 (m, 1H, H-2'b), 0.75 (s, 9H, C(CH₃)₃).

Compound 17 (21 mg, 0.042 mmol) was phosphorylated with POCl₃ (40 μL, 0.43 mmol) and proton sponge (18 mg, 0.084 mmol) in trimethylphosphate (0.35 mL) at 0° C. for 7.5 hours under a nitrogen atmosphere. A solution of bis-tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to yield 7-[(S)-1-(5-methoxy-2-nitrophenyl)-2,2-dimethyl-propyloxy]methyl-7-deaza-2'-deoxyadenosine-5-'-triphosphate dA.VI, which was further purified using RP-HPLC. HRMS (ESI): For the molecular ion C₂₄H₃₃N₅O₁₆P₃ [M−H]⁻, the calculated mass was 740.1135, and the observed mass was 740.1156.

Example 4

Synthesis of 7-HOMe-7-Deaza-2'-deoxyguanosine Triphosphate Analogs 7-(2-nitrobenzyloxyl)methyl-7-deaza-2'-deoxyguanosine-5'-triphosphate

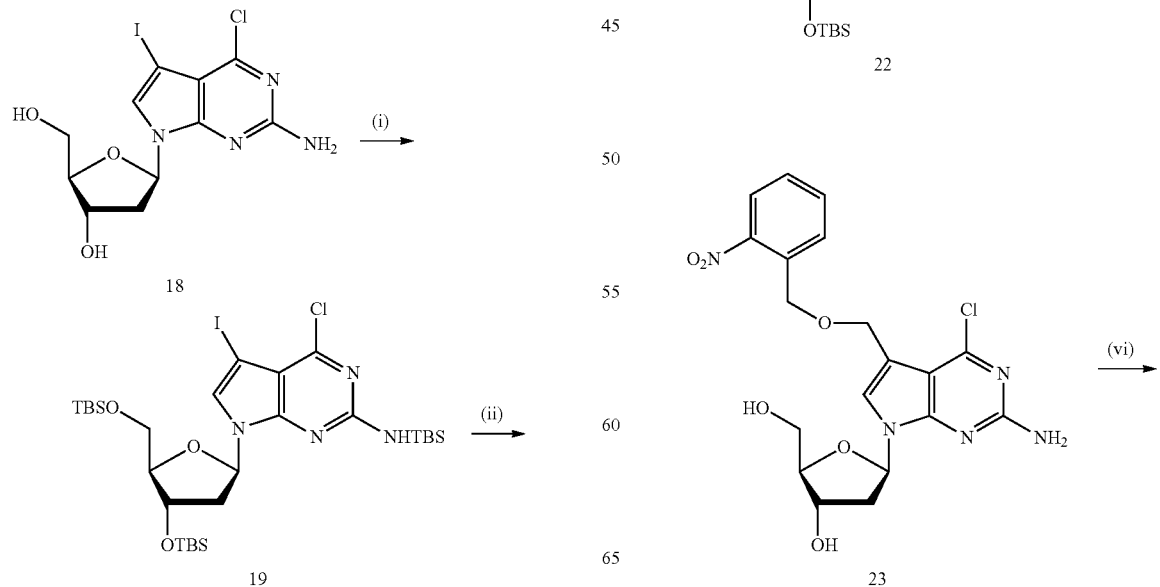

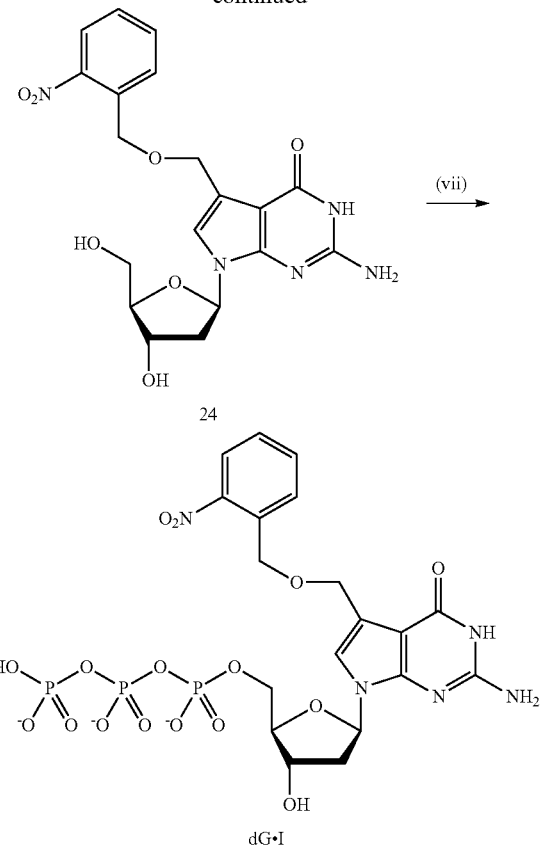

dG•I

Reagents and conditions: (i) TBSCl, imidazole, DMF, room temperature, 60%; (ii) CO, PdCl₂[PhCN]₂, MeOH/1,4-dioxane, 50° C., 91%; (iii) LiBH₄, MeOH, THF, reflux, 54%; (iv) 2-nitrobenzyl bromide, n-Bu₄NBr, CH₂Cl₂/aq. NaOH, room temperature, 48%; (v) n-Bu₄NF, THF, 0° C. to room temperature, 95%; (vi) DABCO, H₂O, reflux, 30%; (vii) POCl₃, proton sponge, (MeO)₃PO, 0° C; (n-Bu₃NH)₂H₂P₂O₇, n-Bu₃N, DMF; 1M HNEt₃HCO₃.

Compound 18 (Seela and Peng, 2005, which is incorporated by reference herein) (1.35 g, 3.29 mmol) was evaporated from anhydrous pyridine (3.0 mL) three times and then dissolved in anhydrous DMF (6.0 mL). tert-Butyldimethylsilyl chloride (5.95 g, 39.5 mmol) and imidazole (5.37 g, 78.9 mmol) were added, and the mixture was stirred at 50° C. for 48 hours with additional tert-butyldimethylsilyl chloride (2.97 g, 19.7 mmol) and imidazole (2.69 g, 39.4 mmol) being added every six hours. The reaction mixture was concentrated in vacuo and purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-iodo-7-deazapurine 19 (1.48 g, 60% yield) as a white foam. $^1$H NMR (400 MHz, CDCl₃): δ 7.35 (s, 1H, H-8), 6.53 (t, 1H, J=6.0 Hz, H-1'), 4.70 (s, 1H, 2-NH), 4.47 (m, 1H, H-3'), 3.97 (m, 1H, H-4'), 3.78 (m, 2H, H-5'a and H-5'b), 2.23 (m, 2H, H-2'a and H-2'b), 0.98 (s, 9H, (CH₃)₃CSi), 0.95 (s, 9H, (CH₃)₃CSi), 0.90 (s, 9H, (CH₃)₃CSi), 0.29 (2 s, 6H, (CH₃)₂Si), 0.13 (2 s, 6H, CH₃)₂Si), 0.09 (s, 6H, CH₃)₂Si).

A solution of compound 19 (720 mg, 0.96 mmol) was dissolved in anhydrous 1,4-dioxane (30 mL). Anhydrous MeOH (30 mL) and triethylamine (0.58 mL) were added, and the mixture was stirred for 10 min under a CO atmosphere, followed by addition of bis(benzonitrile)dichloropalladium (II) (20 mg, 0.05 mmol). The reaction was stirred at 58° C. for 24 hours under a CO atmosphere, and then concentrated in vacuo. The residue was purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-methoxycarbonyl-7-deazapurine 20 (600 mg, 91%) as a viscous oil. $^1$H NMR (400 MHz, CDCl₃): δ 7.92 (s, 1H, H-8), 6.57 (dd, 1H, J=8.0 and 6.0 Hz, H-1'), 4.78 (s, 1H, 2-NH), 4.49 (m, 1H, H-3'), 4.02 (m, 1H, H-4'), 3.85 (s, 3H, CH₃), 3.81 (m, 2H, H-5'a and H-5'b), 2.25 (m, 2H, H-2'a and H-2'b), 0.98 (s, 9H, (CH₃)₃CSi), 0.93 (s, 9H, (CH₃)₃CSi), 0.92 (s, 9H, (CH₃)₃CSi), 0.31 (s, 6H, (CH₃)₂Si), 0.13 (2 s, 6H, (CH₃)₂Si), 0.11 (s, 6H, (CH₃)₂Si).

To a solution of compound 20 (1.11 g, 1.63 mmol) in anhydrous THF (56 mL), lithium borohydride (143 mg, 6.5 mmol) was added, followed by MeOH (0.94 mL). The reaction mixture was heated to reflux for one hour. Upon cooling to room temperature, the reaction mixture was diluted with CH₂Cl₂ (700 mL) and quenched with water (70 mL). The organic phase was separated, dried over Na₂SO₄, and concentrated in vacuo. The residue was purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-hydroxymethyl-7-deazapurine 21 (0.58 g, 54%) as a viscous oil. $^1$H NMR (400 MHz, CDCl₃): δ 7.16 (s, 1H, H-8), 6.56 (t, 1H, J=6.4 Hz, H-1'), 4.79 (AB d, J=13.6 Hz, 7-CH₂a), 4.75 (AB d, J=13.6 Hz, 7-CH₂b), 4.70 (s, 1H, 2-NH), 4.50 (m, 1H, H-3'), 3.96 (m, 1H, H-4'), 3.76 (m, 2H, H-5'a and H-5'b), 2.23 (m, 2H, H-2'a and H-2'b), 0.98 (s, 9H, (CH₃)₃CSi), 0.94 (s, 9H, (CH₃)₃CSi), 0.92 (s, 9H, (CH₃)₃CSi), 0.30 (s, 3H, (CH₃)₂Si), 0.29 (s, 3H, (CH₃)₂Si), 0.11 (s, 6H, (CH₃)₂Si), 0.10 (s, 6H, (CH₃)₂Si).

To a solution of compound 21 (150 mg, 0.23 mmol) in CH₂Cl₂ (3.0 mL), n-Bu₄NBr (37 mg, 0.12 mmol), 2-nitrobenzyl bromide (148 mg, 0.68 mmol) and NaOH solution (1 M, 3.0 mL) were added. The reaction mixture was stirred vigorously at room temperature for two days in the dark. The organic phase was separated, dried over Na₂SO₄, concentrated in vacuo, and purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-(2-nitrobenzyloxyl)methyl-7-deazapurine 22 (87 mg, 48%) as a viscous oil. $^1$H NMR (400 MHz, CDCl₃): δ 8.06 (dd, 1H, J=8.0 and 1.2 Hz, Ph-H), 7.87 (d, 1H, J=7.2 Hz, Ph-H), 7.61 (dt, 1H, J=7.6 and 1.2 Hz, Ph-H), 7.43 (m, 1H, Ph-H), 7.20 (s, 1H, H-8), 6.56 (dd, 1H, J=7.6 and 6.0 Hz, H-1'), 4.99 (s, 2H, PhCH₂), 4.83 (AB d, 1H, J=11.4 Hz, 7-CH₂a), 4.75 (AB d, 1H, J=11.4 Hz, 7-CH₂b), 4.67 (s, 1H, 2-NH), 4.50 (m, 1H, H-3'), 3.96 (m, 1H, H-4'), 3.77 (m, 2H, H-5'a and H-5'b), 2.25 (m, 2H, H-2'a and H-2'b), 0.98 (s, 9H, (CH₃)₃CSi), 0.92 (s, 18H, (CH₃)₃CSi), 0.30 (s, 3H, (CH₃)₂Si), 0.29 (s, 3H, (CH₃)₂Si), 0.09 (m, 12H, (CH₃)₂Si).

A solution of n-Bu₄NF (123 mg, 0.39 mmol) in THF (2.0 mL) was added dropwise to a solution of compound 22 (105 mg, 0.13 mmol) in THF (3.0 mL) at 0° C. The reaction mixture was stirred at 0° C. for one hour and then at room temperature for two hours. The mixture was concentrated in vacuo and purified by silica gel chromatography to yield 2-amino-6-chloro-9-[β-D-2'-deoxy-ribofuranosyl]-7-(2-nitrobenzyloxyl)methyl-7-deazapurine 23 (57 mg, 95%) as a yellow foam. $^1$H NMR (400 MHz, DMSO-d6): δ, 8.02 (m, 1H, Ph-H), 7.74 (m, 2H, Ph-H), 7.55 (m, 1H, Ph-H), 7.41 (s, 1H, H-8), 6.73 (s, 2H, D₂O exchangeable, NH₂), 6.41 (dd, 1H, J=8.4 and 6.0 Hz, H-1'), 5.26 (d, 1H, D₂O exchangeable, 3'-OH), 4.91 (t, 1H, D₂O exchangeable, 5'-OH), 4.88 (s, 2H, Ph-CH₂), 4.66 (dd, 2H, J=11.6 Hz, 7-CH₂), 4.31 (m, 1H, H-3'), 3.78 (m, 1H, H-4'), 3.50 (m, 2H, H-5'), 2.38 (m, 1H, H-2'a), 2.15 (m, 1H, H-2'b).

A mixture of 23 (38 mg, 0.085 mmol) and 1,4-diazabicyclo[2.2.2]octane (11 mg, 0.1 mmol) in water (4.0 mL) was heated to reflux for four hours under a nitrogen atmosphere. Water was removed in vacuo, and the residue was evaporated from MeOH (3.0 mL) three times, and purified by silica gel chromatography to yield 7-(2-nitrobenzyloxyl)methyl-7-deaza-2'-deoxyguanosine 24 (11 mg, 30%). $^1$H NMR (400 MHz, DMSO-d6): δ 10.4 (s, 1H, D$_2$O exchangeable, N—H), 8.03 (dd, 1H, J=8.4 and 0.8 Hz, Ph-H), 7.83 (d, 1H, J=7.6 Hz, Ph-H), 7.73 (m, 1H, Ph-H), 7.55 (m, 1H, Ph-H), 6.92 (s, 1H, H-8), 6.28 (m, 1H, H-1'), 6.26 (bs, 2H, D$_2$O exchangeable, NH$_2$), 5.21 (d, 1H, D$_2$O exchangeable, 3'-OH), 4.89 (t, 1H, D$_2$O exchangeable, 5'-OH), 4.88 (s, 2H, Ph-CH$_2$), 4.60 (dd, 2H, 7-CH$_2$), 4.28 (m, 1H, H-3'), 3.74 (m, 1H, H-4'), 3.48 (m, 2H, H-5'), 2.32 (m, 1H, H-2'a), 2.08 (m, 1H, H-2'b).

Compound 24 (11 mg, 0.025 mmol) was phosphorylated with POCl$_3$ (15 μL, 0.05 mmol) and proton sponge (11 mg, 0.05 mmol) in trimethylphosphate (0.3 mL) at 0° C. for two hours under a nitrogen atmosphere. A solution of bis-tri-n-butylammonium pyrophosphate (118 mg, 0.25 mmol) and tri-n-butylamine (50 μL) in anhydrous DMF (0.5 mL) was added. After 30 min of stirring, triethylammonium bicarbonate buffer (1 M, pH 7.5; 5.0 mL) was added. The reaction was stirred at room temperature for one hour and then concentrated in vacuo. The residue was dissolved in water (10 mL), filtered, and purified by anion exchange chromatography. The fractions containing triphosphate were combined and lyophilized to give 7-(2-nitrobenzyloxyl)methyl-7-deaza-2'-deoxyguanosine-5'-triphosphate dG.I, which was further purified using RP-HPLC. HRMS (ESI): For the molecular ion C$_{19}$H$_{23}$N$_5$O$_{16}$P$_3$ [M–H]$^-$, the calculated mass was 670.0353, and the observed mass was 670.0344.

7-[1-(2-Nitrophenyl)-2,2-dimethyl-propyloxy]methyl-7-deaza-2'-deoxyguanosine-5'-triphosphate Scheme S13. Synthesis of 7-[1-(2-nitrophenyl)-2,2-dimethyl-propyloxy]methyl-7-deaza-2'-deoxy-guanosine-5'-triphosphate.

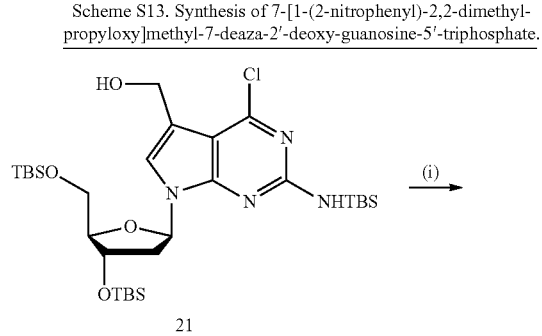

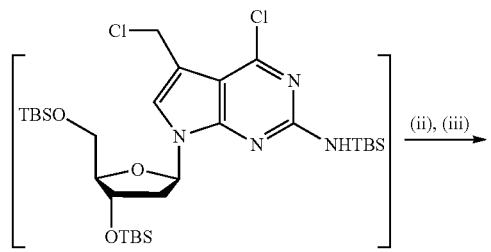

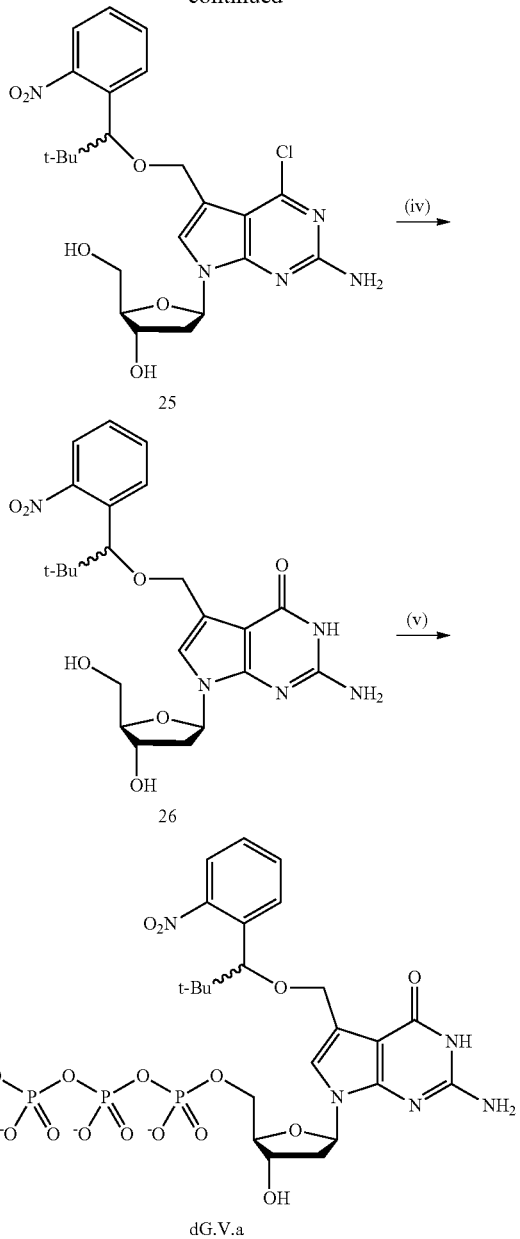

dG.V.a

Reagents and conditions: (i) MsCl, DMAP, CH$_2$Cl$_2$, 0° C.; (ii) racemic (R/S)-1-(2-nitrophenyl)-2,2-dimethyl-1-propanol, 115° C.; (iii) n-Bu$_4$NF, THF, room temperature, 26% for three steps; (iv) syn-pyridine-2-aldoxime, 1,1,3,3-tetramethyl guanidine, 1,4-dioxane/DMF, 70° C., 70%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

DMAP (148 mg, 1.2 mmol) and MsCl (71 μL, 0.9 mmol) were added to a solution of compound 21 (200 mg, 0.30 mmol) in anhydrous CH$_2$Cl$_2$ (5.0 mL) at 0° C. under a nitrogen atmosphere. The reaction was stirred at 0° C. for 10 min and diluted with CH$_2$Cl$_2$ (15 mL). The solution was applied on a short silica gel plug (2×3 cm) and was eluted quickly with hexane/ethyl acetate/triethylamine solvent system (volume ratio: 80/20/0.5). The eluent was concentrated in vacuo, and the residue was mixed with racemic (R/S)-1-(2-nitrophenyl)-2,2-dimethyl-1-propanol (500 mg, 2.4 mmol). The mixture was heated at 115° C. for 45 min under a nitrogen atmosphere, cooled to room temperature and then dissolved in THF (10 mL) followed by addition of n-Bu$_4$NF (283 mg, 0.90 mmol). The mixture was stirred at room temperature for four hours and then concentrated in vacuo. The residue was dissolved in CH₂Cl₂ (25 mL) and washed with brine (25 mL), and the aqueous phase was extracted with CH₂Cl₂ (25 mL) two times. The combined organic phase was dried over Na₂SO₄, concentrated in vacuo, and the residue was purified by silica gel chromatography to yield 2-amino-6-chloro-9-[β-D-2'-deoxyribofuranosyl]-7-[1-(2-nitrophenyl)-2,2-dimethyl-propyloxy]methyl-7-deazapurine 25 (40 mg, 26% for three steps) as a 1:1 mixture of two diastereomers.

To a solution of compound 25 (40 mg, 0.08 mmol) in 1,4-dioxane (1.0 mL) and DMF (2.0 mL), syn-pyrimidine-2-aldoxime (180 mg, 1.5 mmol) and 1,1,3,3-tetramethyl guanidine (211 μL, 1.68 mmol) were added. The mixture was heated at 70° C. overnight under a nitrogen atmosphere. The reaction mixture was diluted with CH₂Cl₂ (20 mL) and washed sequentially with acetic acid solution (0.1 M, 30 mL), saturated NaHCO₃ solution (30 mL), and brine (30 mL). The organic phase was dried over Na₂SO₄, concentrated in vacuo, and the residue was purified by silica gel chromatography to yield 7-[1-(2-nitrophenyl)-2,2-dimethyl-propyloxy]methyl-7-deaza-2'-deoxyguanosine 26 (27 mg, 70%) as a 1:1 mixture of two diastereomers. ¹H NMR (400 MHz, MeOH-d₄) for diastereomers: δ 7.79 (m, 1H, Ph-H), 7.73 (m, 1H, Ph-H), 7.56 (m, 1H, Ph-H), 7.39 (m, 1H, Ph-H), 6.87 and 6.86 (2 s, 1H, H-8), 6.30 (m, 1H, H-1'), 4.99 and 4.97 (2 s, 1H, Ph-CH), 4.63-4.36 (m, 3H, 7-CH₂ and H-3'), 3.91 (m, 1H, H-4'), 3.69 (m, 2H, H-5'), 2.48 (m, 1H, H-2'a), 2.20 (m, 1H, H-2'b), 0.79 and 0.77 (2 s, 9H, (CH₃)₃).

Compound 26 (25 mg, 0.05 mmol) was phosphorylated with POCl₃ (20 μL, 0.21 mmol) and proton sponge (21 mg, 0.1 mmol) in trimethylphosphate (0.35 mL) at 0° C. for 3.5 hours under a nitrogen atmosphere. A solution of bis-tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 7-[1-(2-nitrophenyl)-2,2-dimethyl-propyloxy]methyl-7-deaza-2'-deoxyguanosine-5'-triphosphate dG.V.a as a 1:1 mixture of two diastereomers, which were separated using RP-HPLC to yield the single diastereomers dG.V.a ds1 and dG.V.a ds2. HRMS (ESI): For the molecular ion C₂₃H₃₁N₅O₁₆P₃ [M–H]⁻, the calculated mass was 726.0979, and the observed mass was 726.0992.

7-[(S)-1-(2-Nitrophenyl)-2,2-dimethyl-propyloxy]methyl-7-deaza-2'-deoxyguanosine-5'-triphosphate

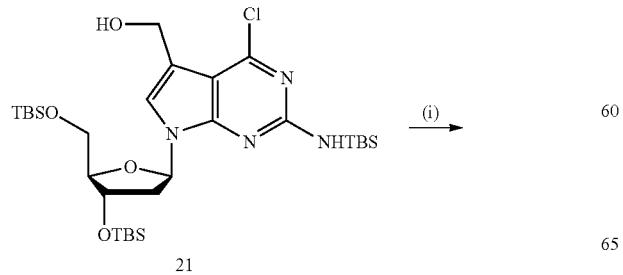

Scheme S14. Synthesis of 7-[(S)-1-(2-nitrophenyl)-2,2-dimethyl-propyloxy]methyl-7-deaza-2'-deoxy-guanosine-5'-triphosphate.

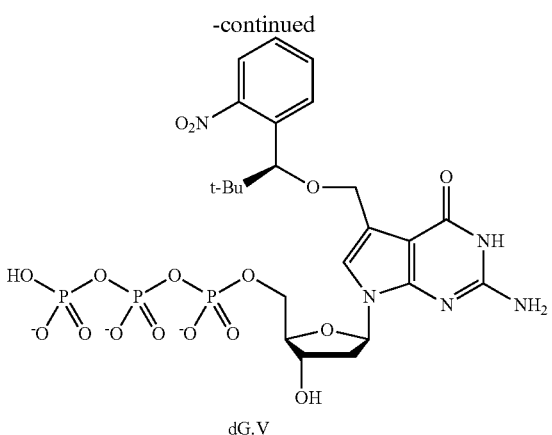

dG.V

Reagents and conditions: (i) MsCl, DMAP, CH₂Cl₂, 0° C.; (ii) (S)-1-(2-nitrophenyl)-2,2-dimethyl-1-propanol, 115° C.; (iii) n-Bu₄NF, THF, room temperature, 35% for three steps; (iv) NaOMe, MeOH, reflux, 74%; (v) 1,4-dioxane, 2M NaOH, reflux, 33%; (vi) POCl₃, proton sponge, (MeO)₃PO, 0° C.; (n-Bu₃NH)₂H₂P₂O₇, n-Bu₃N, DMF; 1M HNEt₃HCO₃.

DMAP (224 mg, 1.8 mmol) and MsCl (107 µL, 1.4 mmol) were added to a solution of compound 21 (300 mg, 0.46 mmol) in anhydrous CH₂Cl₂ (10 mL) at 0° C. under a nitrogen atmosphere. The reaction was stirred at 0° C. for 10 min and diluted with CH₂Cl₂ (20 mL). The solution was applied on a short silica gel plug (2×3 cm) and was eluted quickly with hexane/ethyl acetate/triethylamine solvent system (volume ratio 80/20/0.5). The eluent was concentrated in vacuo, and residue was mixed with (S)-1-(2-nitrophenyl)-2,2-dimethyl-1-propanol (520 mg, 2.5 mmol). The mixture was heated at 115° C. for 45 min under a nitrogen atmosphere, cooled to room temperature and dissolved in THF (20 mL) followed by addition of n-Bu₄NF (491 mg, 1.6 mmol). The mixture was stirred at room temperature for four hours and then concentrated in vacuo. The residue was dissolved in CH₂Cl₂ (20 mL) and washed with brine (30 mL), and the aqueous phase was extracted with CH₂Cl₂ (20 mL) two times. The combined organic phase was dried over Na₂SO₄, concentrated in vacuo, and the residue was purified by silica gel chromatography to yield 2-amino-6-chloro-9-[β-D-2'-deoxyribofuranosyl]-7-[(S)-1-(2-nitrophenyl)-2,2-dimethyl-propyloxy]methyl-7-deazapurine 27 (81 mg, 35% for three steps). ¹H NMR (400 MHz, MeOH-d₄): δ 7.79 (m, 2H, Ph-H), 7.60 (dt, 1H, J=1.2 and 8.0 Hz, Ph-H), 7.46 (dt, 1H, J=1.2 and 8.0 Hz, Ph-H), 7.27 (s, 1H, H-8), 6.47 (dd, 1H, J=6.4 and 8.0 Hz, H-1'), 4.98 (s, 1H, Ph-CH), 4.71 (d, 1H, J=12.4 Hz, 7-CH₂a), 4.50 (m, 1H, H-3'), 4.47 (d, 1H, J=12.4 Hz, 7-CH₂b), 3.96 (m, 1H, H-4'), 3.73 (m, 2H, H-5'), 2.59 (m, 1H, H-2'a), 2.30 (m, 1H, H-2'b), 0.80 (s, 9H, (CH₃)₃).

Compound 27 (104 mg, 0.21 mmol) was dissolved in a solution of sodium methoxide in MeOH (0.5 M, 10 mL), and the mixture was heated to reflux for one hour under a nitrogen atmosphere. The reaction mixture was cooled to room temperature, neutralized with acetic acid, and then concentrated in vacuo. The residue was purified by silica gel chromatography to yield 2-amino-6-methoxy-9-[β-D-2'-deoxyribofuranosyl]-7-[(S)-1-(2-nitrophenyl)-2,2-dimethyl-propyloxy]methyl-7-deazapurine 28 (75 mg, 74%). ¹H NMR (400 MHz, CDCl₃): δ 7.74 (m, 2H, Ph-H), 7.52 (t, 1H, J=8.0 Hz, Ph-H), 7.36 (t, 1H, J=8.0 Hz, Ph-H), 6.71 (s, 1H, H-8), 6.47 (dd, 1H, J=5.6 and 9.6 Hz, H-1'), 5.04 (s, 1H, Ph-CH), 4.71 (m, 1H, H-3'), 4.47 (dd, 2H, J=12 Hz, 7-CH₂), 4.15 (m, 1H, H-4'), 3.94 (s, 3H, OCH₃), 3.76 (m, 2H, H-5'), 3.01 (m, 1H, H-2'a), 2.19 (m, 1H, H-2'b), 0.82 (s, 9H, (CH₃)₃).

Compound 28 (70 mg, 0.14 mmol) was dissolved in 1,4-dioxane (6.0 mL) followed by addition of an aqueous solution of sodium hydroxide (2 M, 12 mL). The mixture was heated to reflux for four days under a nitrogen atmosphere, cooled to room temperature, neutralized with dilute hydrochloric acid (1 M), and concentrated in vacuo. The residue was evaporated from MeOH (5.0 mL) three times and then purified by silica gel chromatography to yield 7-[(S)-1-(2-nitrophenyl)-2,2-dimethyl-propyloxy]methyl-7-deaza-2'-deoxyguanosine 29 (22 mg, 33%). Starting material 28 (42 mg, 60%) was also recovered from the reaction. ¹H NMR (400 MHz, CDCl₃): δ 11.02 (br s, 1H, NH), 7.69 (m, 2H, Ph-H), 7.52 (t, 1H, J=7.2 Hz, Ph-H), 7.33 (t, 1H, J=7.2 Hz, Ph-H), 6.66 (s, 1H, H-8), 6.13 (t, 1H, J=6.8 Hz, H-1'), 6.03 (br s, 2H, 6-NH₂), 4.92 (s, 1H, Ph-CH), 4.77 (m, 1H, H-3'), 4.57 (d, 1H, J=12.8 Hz, 7-CH₂a), 4.12 (m, 1H, H-4'), 3.05 (d, 1H, J=12.8 Hz, 7-CH₂b), 3.75 (m, 2H, H-5'), 2.87 (m, 1H, H-2'a), 2.29 (m, 1H, H-2'b), 0.76 (s, 9H, (CH₃)₃).

Compound 29 (16 mg, 0.033 mmol) was phosphorylated with POCl₃ (17 µL, 0.18 mmol) and proton sponge (14 mg, 0.066 mmol) in trimethylphosphate (0.35 mL) at 0° C. for four hours under a nitrogen atmosphere. A solution of bis-tri-n-butylammonium pyrophosphate (237 mg, 0.50 mmol) and tri-n-butylamine (100 µL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 7-[(S)-1-(2-nitrophenyl)-2,2-dimethyl-propyloxy]methyl-7-deaza-2'-deoxyguanosine-5'-triphosphate dG.V, which was further purified using RP-HPLC conditions. The retention time of dG.V was identical to that of dG.V.a ds2 by RP-HPLC analysis using the same condition (data not shown). HRMS (ESI): For the molecular ion C₂₃H₃₁N₅O₁₆P₃ [M−H]⁻, the calculated mass was 726.0979, and the observed mass was 726.0986.

7-[1-(4-Methoxy-2-nitrophenyl)-2,2-dimethyl-propyloxy]methyl-7-deaza-2'-deoxyguanosine-5'-triphosphate Scheme S15. Synthesis of 7-[1-(4-methoxy-2-nitrophenyl)-2,2-dimethyl-propyloxy]methyl-7-deaza-2'-deoxyguanosine-5'-triphosphate.

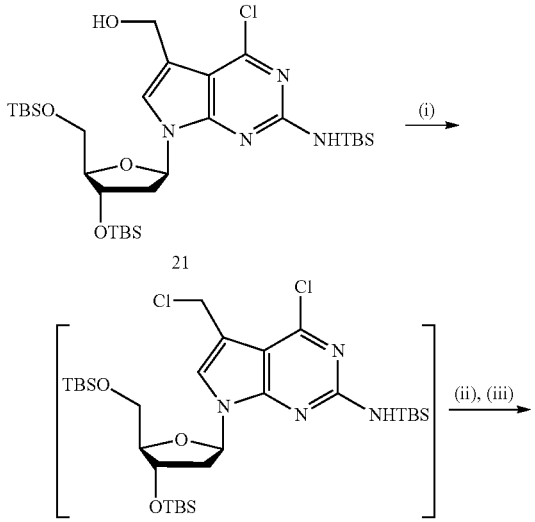

-continued

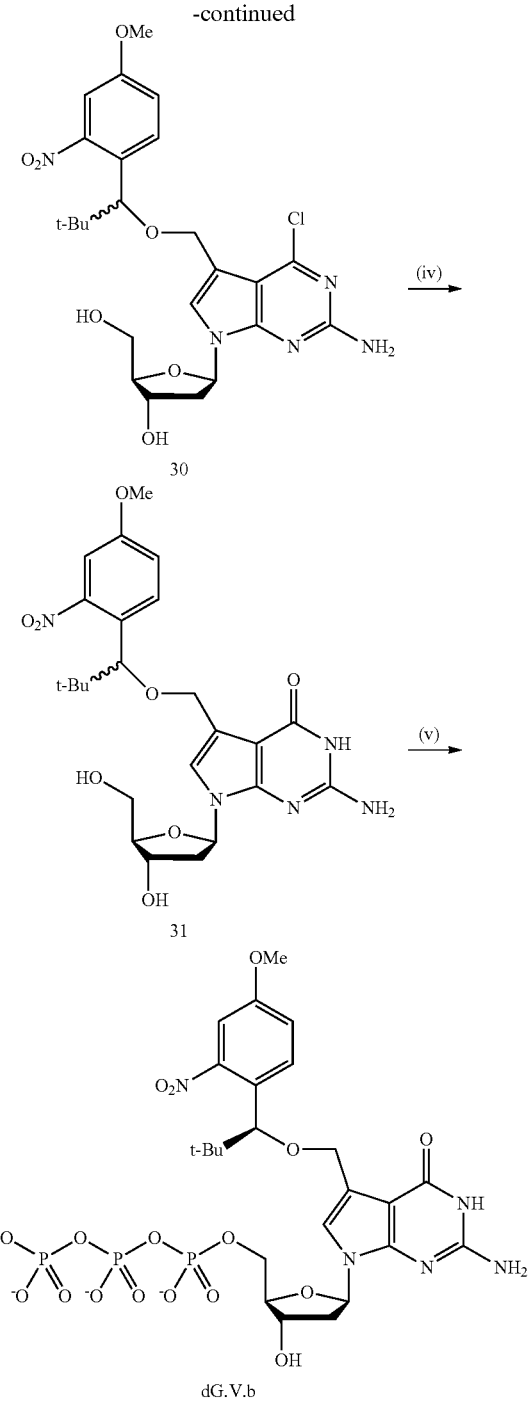

dG.V.b

Reagents and conditions: (i) MsCl, DMAP, CH$_2$Cl$_2$, 0° C.; (ii) racemic (R/S)-1-(4-methoxy-2-nitrophenyl)-2,2-dimethyl-1-propanol, 115° C.; (iii) n-Bu$_4$NF, THF, room temperature, 21% for three steps; (iv) syn-pyridine-2-aldoxime, 1,1,3,3-tetramethyl guanidine, 1,4-dioxane/DMF, 70° C., 59%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

DMAP (346 mg, 2.8 mmol) and MsCl (165 µL, 2.1 mmol) were added to a solution of compound 21 (470 mg, 0.72 mmol) in anhydrous CH$_2$Cl$_2$ (5.0 mL) at 0° C. under a nitrogen atmosphere. The reaction was stirred at 0° C. for 10 min and diluted with CH$_2$Cl$_2$ (20 mL). The solution was applied on a short silica gel plug (2×3 cm) and was eluted quickly with hexane/ethyl acetate/triethylamine solvent system (volume ratio 80/20/0.5). The eluent was concentrated in vacuo, and the residue was mixed with racemic (R/S)-1-(4-methoxy-2-nitrophenyl)-2,2-dimethyl-1-propanol (1.6 g, 6.69 mmol). The mixture was heated to 115° C. for 45 min under a nitrogen atmosphere, cooled to room temperature, and dissolved in THF (20 mL) followed by addition of n-Bu$_4$NF (788 mg, 2.5 mmol). The mixture was stirred at room temperature for four hours and then concentrated in vacuo. The residue was dissolved in CH$_2$Cl$_2$ (20 mL) and washed with brine (30 mL), and the aqueous phase was extracted with CH$_2$Cl$_2$ (20 mL) two times. The combined organic phase was dried over Na$_2$SO$_4$, concentrated in vacuo, and the residue was purified by silica gel chromatography to yield 2-amino-6-chloro-9-[β-D-2'-deoxyribofuranosyl]-7-[(S)-1-(4-methoxy-2-nitrophenyl)-2,2-dimethyl-propyloxy]-methyl-7-deazapurine 30 (80 mg, 21% for three steps) as a 1:1 mixture of two diastereomers.

To a solution of compound 30 (80 mg, 0.15 mmol) in 1,4-dioxane (1.0 mL) and DMF (2.0 mL), syn-pyrimidine-2-aldoxime (366 mg, 3.0 mmol) and 1,1,3,3-tetramethyl guanidine (414 µL, 3.3 mmol) were added, and the mixture was heated at 70° C. overnight under a nitrogen atmosphere. The reaction mixture was diluted with CH$_2$Cl$_2$ (20 mL) and washed sequentially with acetic acid (0.1 M, 30 mL), saturated NaHCO$_3$ solution (30 mL), and brine (30 mL). The organic phase was dried over Na$_2$SO$_4$, concentrated in vacuo, and the residue was purified by silica gel chromatography to yield 7-[(S)-1-(4-methoxy-2-nitrophenyl)-2,2-dimethyl-propyloxy]methyl-7-deaza-2'-deoxy-guanosine 31 (45 mg, 59%) as a 1:1 mixture of two diastereomers. $^1$H NMR (400 MHz, DMSO-d$_6$) for diastereomers: δ 10.31 (br s, 1H, D$_2$O exchangeable, NH), 7.63 and 7.62 (2 d, 1H, J=2.8 Hz, Ph-H), 7.41 and 7.40 (2 d, 1H, J=2.8 Hz, Ph-H), 7.27 (m, 1H, Ph-H), 6.98 and 6.96 (2 s, 1H, H-8), 6.28 (m, 1H, H-1'), 6.22 (br s, 2H, D$_2$O exchangeable, NH$_2$), 5.22 (d, 1H, D$_2$O exchangeable, 3'-OH), 4.88 (t, 1H, D$_2$O exchangeable, 5'-OH), 4.73 and 4.71 (2 s, 1H, Ph-CH), 4.47-4.24 (m, 3H, 7-CH$_2$ and H-3'), 3.85 and 3.83 (2 s, 3H, OCH$_3$), 3.74 (m, 1H, H-4'), 3.48 (m, 2H, H-5'), 2.28 (m, 1H, H-2'a), 2.06 (m, 1H, H-2'b), 0.80 and 0.78 (2 s, 9H, (CH$_3$)$_3$).

Compound 31 (25 mg, 0.048 mmol) was phosphorylated with POCl$_3$ (15 µL, 0.18 mmol) and proton sponge (21 mg, 0.10 mmol) in trimethylphosphate (0.35 mL) at 0° C. for 3.5 hours under a nitrogen atmosphere. A solution of bis-tri-n-butylammonium pyrophosphate (237 mg, 0.50 mmol) and tri-n-butylamine (100 µL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 7-[1-(4-methoxy-2-nitrophenyl)-2,2-dimethyl-propyloxy]methyl-7-deaza-2'-deoxyguanosine-5'-triphosphate dG.V.b as a 1:1 mixture of two diastereomers, which were separated using RP-HPLC to yield the single diastereomers dG.V.b ds1 and dG.V.b ds2. HRMS (ESI): For the molecular ion $C_{24}H_{33}N_5O_{17}P_3$ [M–H]⁻, the calculated mass was 756.1084, and the observed mass was 756.1101.

7-[1-(5-Methoxy-2-nitrophenyl)-2,2-dimethyl-propyloxy]methyl-7-deaza-2'-deoxyguanosine-5'-triphosphate Scheme S16. Synthesis of 7-[1-(5-methoxy-2-nitrophenyl)-2,2-dimethyl-propyloxy]methyl-7-deaza-2'-deoxyguanosine-5'-triphosphate.

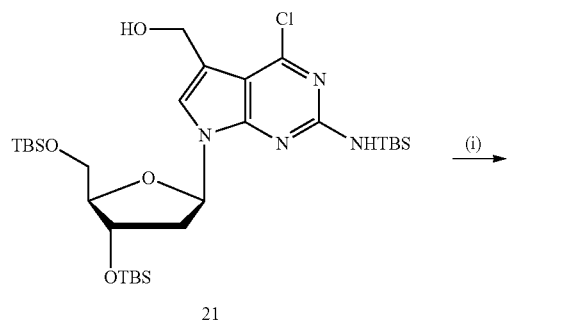

21

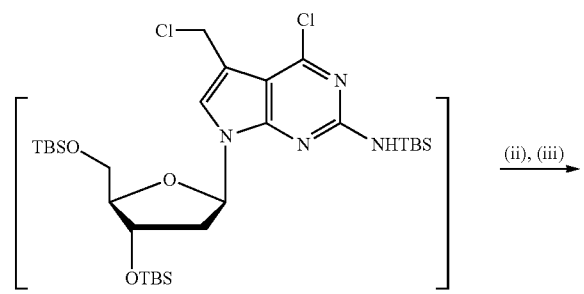

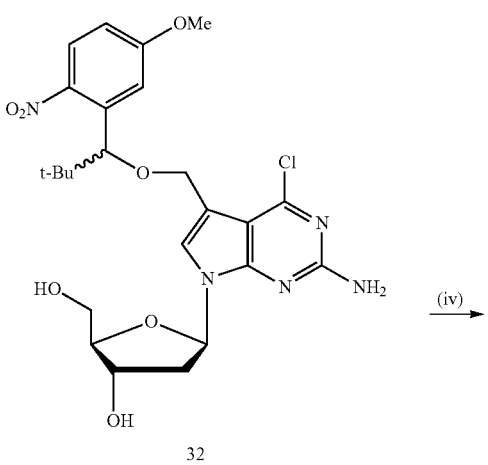

32

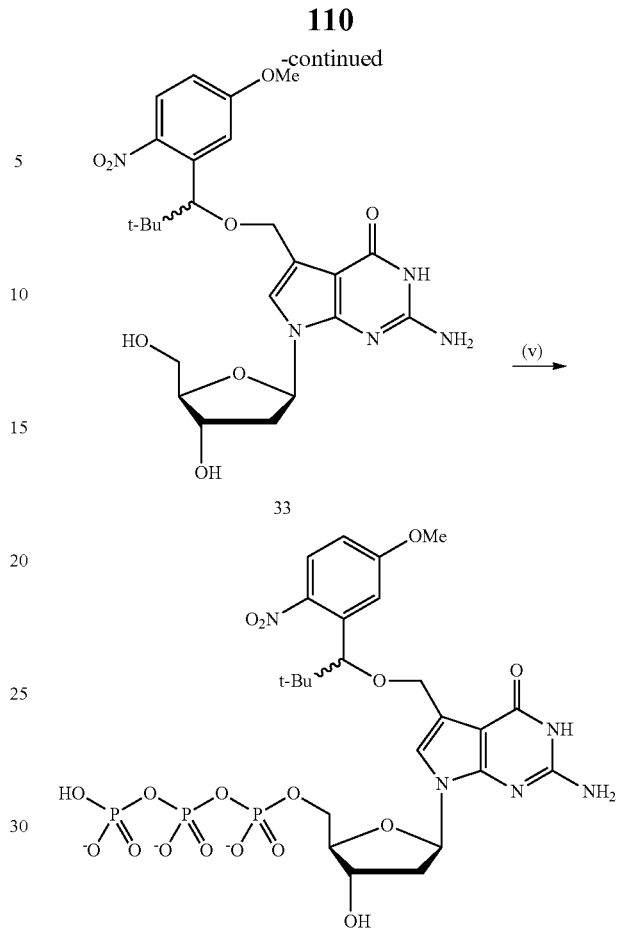

33 dG.V.c

Reagents and conditions: (i) MsCl, DMAP, CH₂Cl₂, 0° C.; (ii) racemic (R/S)-1-(5-methoxy-2-nitrophenyl)-2,2-dimethyl-1-propanol, 115° C.; (iii) n-Bu₄NF, THF, room temperature, 24% for three steps; (iv) syn-pyridine-2-aldoxime, 1,1,3,3-tetramethyl guanidine, 1,4-dioxane/DMF, 70° C., 57%; (v) POCl₃, proton sponge, (MeO)₃PO, 0° C.; (n-Bu₃NH)₂H₂P₂O₇, n-Bu₃N, DMF; 1M HNEt₃HCO₃.

DMAP (302 mg, 2.5 mmol) and MsCl (145 µL, 1.9 mmol) were added to a solution of compound 21 (410 mg, 0.62 mmol) in anhydrous CH₂Cl₂ (5.0 mL) at 0° C. under a nitrogen atmosphere. The reaction was stirred at 0° C. for 10 min and diluted with CH₂Cl₂ (20 mL). The solution was applied on a short silica gel plug (2×3 cm) and was eluted quickly with a hexane/ethyl acetate/triethylamine solvent system (volume ratio: 80/20/0.5). The eluent was concentrated in vacuo, and residue was mixed with racemic (R/S)-1-(5-methoxy-2-nitrophenyl)-2,2-dimethyl-1-propanol (800 mg, 2.2 mmol). The mixture was heated at 115° C. for 45 min under a nitrogen atmosphere, cooled to room temperature, and dissolved in THF (10 mL) followed by addition of n-Bu₄NF (683 mg, 3.3 mmol). The mixture was stirred at room temperature for four hours and then concentrated in vacuo. The residue was dissolved in CH₂Cl₂ (20 mL) and washed with brine (30 mL), and the aqueous phase was extracted with CH₂Cl₂ (20 mL) two times. The combined organic phase was dried over Na₂SO₄, concentrated in vacuo, and the residue was purified by silica gel chromatography to yield 2-amino-6-chloro-9-[β-D-2'-deoxyribofuranosyl]-7-[1-(5-methoxy-2-nitrophenyl)-2,2-dimethyl-propyloxy]methyl-7-deazapurine 32 (80 mg, 24% for three steps) as a 1:1 mixture of two diastereomers. ¹H NMR (400 MHz, CDCl₃) for diastereomers: δ 7.86 and 7.83 (2 d, 1H, J=8.8 Hz, Ph-H), 7.19 and 7.17 (2 d, 1H, J=2.8 Hz, Ph-H), 6.91 and 6.90 (2 s, 1H, H-8), 6.80 and 6.75 (2 dd, 1H, J=0.8 and 8.8 Hz, Ph-H), 6.17 (m, 1H, H-1'), 5.23 and 5.21 (2 s, 1H, Ph-CH), 5.01 and 5.00 (2 br s, 2H, NH₂), 4.73 (m, 1H, H-3'), 4.65-4.49 (m, 2H, 7-CH$_2$), 4.14 (m, 1H, H-4'), 3.84 (m, 5H, H-5' and OCH$_3$), 2.78 (m, 1H, H-2'a), 2.33 (m, 1H, H-2'b), 0.82 and 0.81 (2 s, 9H, (CH$_3$)$_3$).

To a solution of compound 32 (80 mg, 0.15 mmol) in 1,4-dioxane (1.0 mL) and DMF (2.0 mL), syn-pyrimidine-2-aldoxime (360 mg, 3.0 mmol) and 1,1,3,3-tetramethyl guanidine (414 μL, 3.3 mmol) were added, and the mixture was heated at 70° C. overnight under a nitrogen atmosphere. The reaction mixture was diluted with CH$_2$Cl$_2$ (20 mL) and washed sequentially with acetic acid (0.1 M, 30 mL), saturated NaHCO$_3$ solution (30 mL), and brine (30 mL). The organic phase was dried over Na$_2$SO$_4$, concentrated in vacuo, and the residue was purified by silica gel chromatography to yield 7-[1-(5-methoxy-2-nitrophenyl)-2,2-dimethyl-propyloxy]methyl-7-deaza-2'-deoxyguanosine 33 (43 mg, 57%) as a 1:1 mixture of two diastereomers. $^1$H NMR (400 MHz, DMSO-d$_6$) for diastereomers: δ 10.34 (br s, 1H, D$_2$O exchangeable, NH), 7.92 and 7.89 (2 d, 1H, J=8.8 Hz, Ph-H), 7.15 (m, 1H, Ph-H), 6.95 (m, 1H, Ph-H), 6.82 and 6.81 (2 s, 1H, H-8), 6.22 (m, 3H, 2H D$_2$O exchangeable, H-1' and NH$_2$), 5.19 (d, 1H, D$_2$O exchangeable, 3'-OH), 5.12 and 5.10 (2 s, 1H, Ph-CH), 4.84 (t, 1H, D$_2$O exchangeable, 5'-OH), 4.47-4.31 (m, 2H, 7-CH$_2$), 4.24 (m, 1H, H-3'), 3.85 and 3.83 (2 s, 3H, OCH$_3$), 3.71 (m, 1H, H-4'), 3.44 (m, 2H, H-5'), 2.24 (m, 1H, H-2'a), 2.01 (m, 1H, H-2'b), 0.76 and 0.74 (2 s, 9H, (CH$_3$)$_3$).

Compound 33 (20 mg, 0.04 mmol) was phosphorylated with POCl$_3$ (25 μL, 0.27 mmol) and proton sponge (16 mg, 0.08 mmol) in trimethylphosphate (0.30 mL) at 0° C. for six hours under a nitrogen atmosphere. A solution of bis-tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 7-[1-(5-methoxy-2-nitrophenyl)-2,2-dimethyl-propyloxy]methyl-7-deaza-2'-deoxyguanosine-5'-triphosphate dG.V.c as a 1:1 mixture of two diastereomers, which were separated using RP-HPLC to yield the single diastereomers dG.V.c ds1 and dG.V.c ds2. HRMS (ESI): For the molecular ion C$_{24}$H$_{33}$N$_5$O$_{17}$P$_3$ [M−H]$^-$, the calculated mass was 756.1084, and the observed mass was 756.1088.

7-[1-(4,5-Dimethoxy-2-nitrophenyl)-2,2-dimethyl-propyloxy]methyl-7-deaza-2'-deoxyguanosine-5'-triphosphate Scheme S17. Synthesis of 7-[1-(4,5-dimethoxy-2-nitrophenyl)-2,2-dimethyl-propyloxy]methyl-7-deaza-2'-deoxyguanosine-5'-triphosphate.

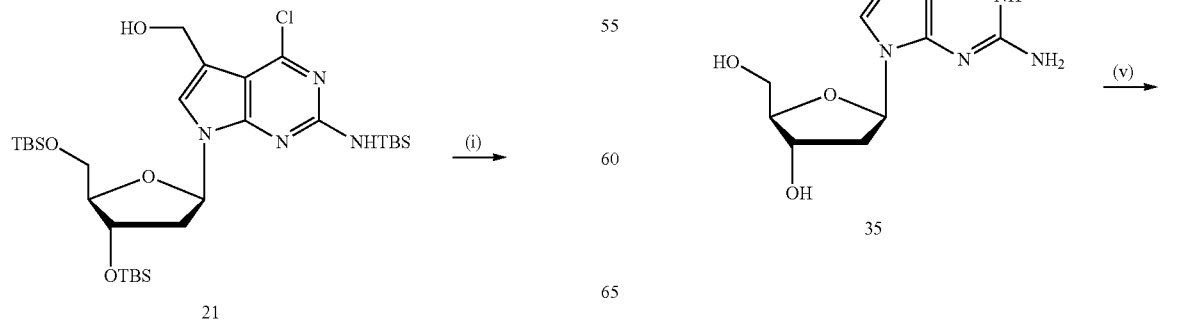

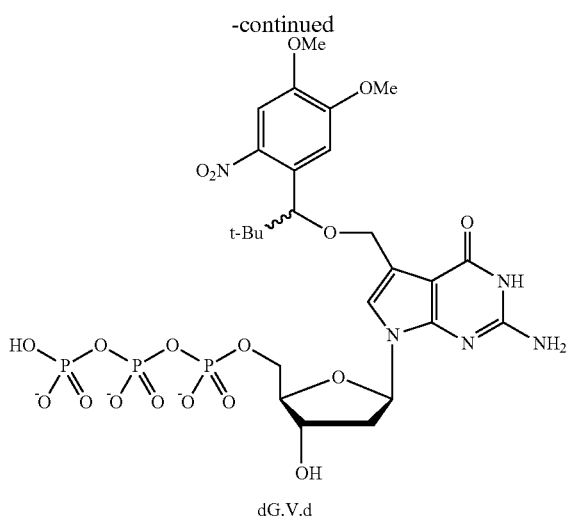

dG.V.d

Reagents and conditions: (i) MsCl, DMAP, CH$_2$Cl$_2$, 0° C.; (ii) racemic (R/S)-1-(4,5-dimethoxy-2-nitrophenyl)-2,2-dimethyl-1-propanol, 115° C.; (iii) n-Bu$_4$NF, THF, room temperature, 23% for three steps; (iv) syn-pyridine-2-aldoxime, 1,1,3,3-tetramethyl guanidine, dioxane/DMF, 70° C., 68%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

DMAP (273 mg, 2.2 mmol) and MsCl (130 µL, 1.7 mmol) were added to a solution of compound 21 (370 mg, 0.56 mmol) in anhydrous CH$_2$Cl$_2$ (5.0 mL) at 0° C. under a nitrogen atmosphere. The reaction was stirred at 0° C. for 30 min and diluted with CH$_2$Cl$_2$ (25 mL). The solution was applied on a short silica gel plug (2×3 cm) and was eluted quickly with a hexane/ethyl acetate/triethylamine solvent system (volume ratio: 80/20/0.5). The eluent was concentrated in vacuo, and the residue was mixed with racemic (R/S)-1-(4,5-dimethoxy-2-nitrophenyl)-2,2-dimethyl-1-propanol (800 mg, 3.0 mmol). The mixture was heated at 115° C. for 45 min under a nitrogen atmosphere, cooled to room temperature and dissolved in THF (10 mL) followed by addition of n-Bu$_4$NF (530 mg, 1.7 mmol). The mixture was stirred at room temperature for two hours and then concentrated in vacuo. The residue was dissolved in CH$_2$Cl$_2$ (40 mL) and washed with brine (50 mL), and the aqueous phase was extracted with CH$_2$Cl$_2$ (40 mL) two times. The combined organic phase was dried over Na$_2$SO$_4$ and concentrated in vacuo, and the residue was purified by silica gel chromatography to yield 2-amino-6-chloro-9-[β-D-2'-deoxyribofuranosyl]-7-[1-(4,5-dimethoxy-2-nitrophenyl)-2,2-dimethyl-propyloxy]methyl-7-deazapurine 34 (70 mg, 23% for three steps) as a 1:1 mixture of two diastereomers. $^1$H NMR (400 MHz, CDCl$_3$) for diastereomers: δ 7.42 and 7.39 (2 s, 1H, Ph-H), 7.15 and 7.13 (2 s, 1H, Ph-H), 6.89 and 6.84 (2 s, 1H, H-8), 6.12 (m, 1H, H-1'), 5.22 and 5.16 (2 s, 1H, Ph-CH), 5.10 and 5.08 (2 bs, 2H, NH$_2$), 4.71-4.41 (m, 3H, H-3' and 7-CH$_2$), 4.13 (m, 1H, H-4'), 3.94 (4 s, 7H, OCH$_3$×2 and H-5'a), 3.78 (m, 1H, H-5'b), 2.90 (m, 1H, H-2'a), 2.25 (m, 1H, H-2'b), 0.82 and 0.80 (2 s, 9H, (CH$_3$)$_3$).

To a solution of compound 34 (65 mg, 0.11 mmol) in 1,4-dioxane (1.0 mL) and DMF (2.0 mL), syn-pyrimidine-2-aldoxime (292 mg, 2.4 mmol) and 1,1,3,3-tetramethyl guanidine (330 µL, 2.6 mmol) were added, and the mixture was heated at 70° C. overnight under a nitrogen atmosphere. The reaction mixture was diluted with CH$_2$Cl$_2$ (40 mL) and washed sequentially with acetic acid (0.1 M, 50 mL), saturated NaHCO$_3$ solution (50 mL), and brine (50 mL). The organic phase was dried over Na$_2$SO$_4$, concentrated in vacuo, and the residue was purified by silica gel chromatography to yield 7-[1-(4,5-dimethoxy-2-nitrophenyl)-2,2-dimethyl-propyloxy]methyl-7-deaza-2'-deoxyguanosine 35 (42 mg, 68%) as a 1:1 mixture of two diastereomers. $^1$H NMR (400 MHz, DMSO-d$_6$) for diastereomers: δ 10.33 (br s, 1H, D$_2$O exchangeable, NH), 7.47 and 7.44 (2 s, 1H, Ph-H), 7.16 and 7.15 (2 s, 1H, Ph-H), 6.83 and 6.82 (2 s, 1H, H-8), 6.22 (m, 3H, 2H D$_2$O exchangeable, NH$_2$ and H-1'), 5.18 (br s, 1H, D$_2$O exchangeable, 3'-OH), 5.06 and 5.04 (2 s, 1H, Ph-CH), 4.83 (t, 1H, D$_2$O exchangeable, 5'-OH), 4.44-4.23 (m, 3H, 7-CH$_2$ and H-3'), 3.82 (4 s, 6H, OCH$_3$×2), 3.70 (m, 1H, H-4'), 3.42 (m, 2H, H-5'), 2.22 (m, 1H, H-2'a), 2.01 (m, 1H, H-2'b), 0.77 and 0.75 (2 s, 9H, (CH$_3$)$_3$).

Compound 35 (40 mg, 0.073 mmol) was phosphorylated with POCl$_3$ (14 µL, 0.15 mmol) and proton sponge (31 mg, 0.15 mmol) in trimethylphosphate (0.35 mL) at 0° C. for two hours under a nitrogen atmosphere. A solution of bis-tri-n-butylammonium pyrophosphate (237 mg, 0.50 mmol) and tri-n-butylamine (100 µL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 7-[1-(4,5-dimethoxy-2-nitrophenyl)-2,2-dimethyl-propyloxy]methyl-7-deaza-2'-deoxyguanosine-5'-triphosphate dG.V.d as a 1:1 mixture of two diastereomers, which were separated using RP-HPLC to yield the single diastereomers dG.V.d ds1 and dG.V.d ds2. HRMS (ESI): For the molecular ion C$_{25}$H$_{35}$N$_5$O$_{18}$P$_3$ [M−H]$^-$, the calculated mass was 786.1190, and the observed mass was 786.1206.

7-[(S)-1-(5-Methoxy-2-nitrophenyl)-2,2-dimethyl-propyloxy]methyl-7-deaza-2'-deoxyguanosine-5'-triphosphate Scheme S18. Synthesis of 7-[(S)-1-(5-methoxy-2-nitrophenyl)-2,2-dimethyl-propyloxy]methyl-7-deaza-2'-deoxyguanosine-5'-triphosphate.

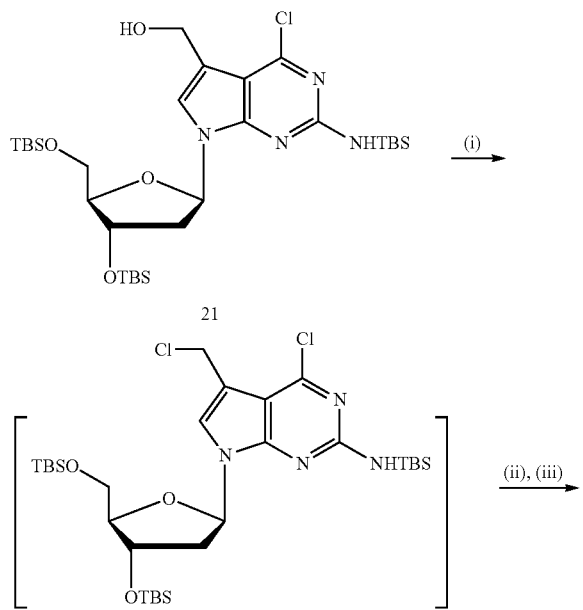

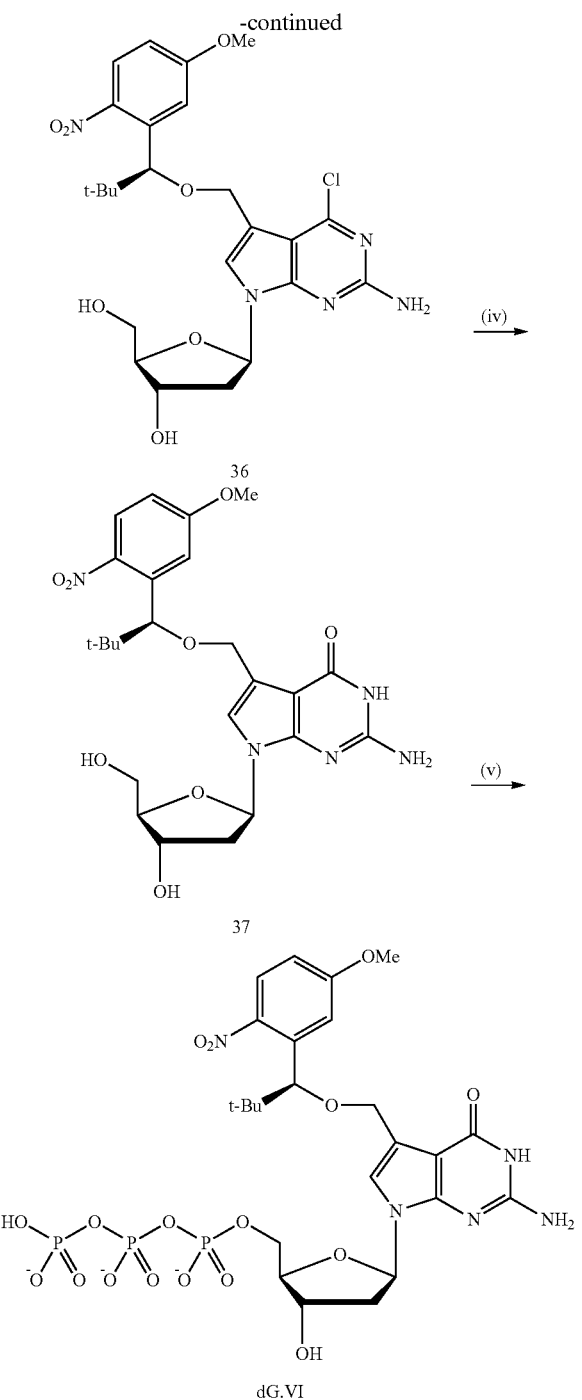

dG.VI

Reagents and conditions: (i) MsCl, DMAP, CH$_2$Cl$_2$, 0° C.; (ii) (S)-1-(5-methoxy-2-nitrophenyl)-2,2-dimethyl-1-propanol, 115° C.; (iii) n-Bu$_4$NF, THF, room temperature, 27% for three steps; (iv) syn-pyridine-2-aldoxime, 1,1,3,3-tetramethyl guanidine, 1,4-dioxane/DMF, 70° C., 76%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

DMAP (224 mg, 1.8 mmol) and MsCl (106 μL, 1.4 mmol) were added to a solution of compound 21 (300 mg, 0.46 mmol) in anhydrous CH$_2$Cl$_2$ (5.0 mL) at 0° C. under a nitrogen atmosphere. The reaction was stirred at 0° C. for 10 min and diluted with CH$_2$Cl$_2$ (20 mL). The solution was applied on a short silica gel plug (2×3 cm) and was eluted quickly with a hexane/ethyl acetate/triethylamine solvent system (volume ratio: 80/20/0.5). The eluent was concentrated in vacuo, and residue was mixed with (S)-1-(5-methoxy-2-nitrophenyl)-2,2-dimethyl-1-propanol (500 mg, 2.1 mmol). The mixture was heated at 115° C. for 45 min under a nitrogen atmosphere, cooled to room temperature and dissolved in THF (10 mL) followed by addition of n-Bu$_4$NF (507 mg, 1.6 mmol). The mixture was stirred at room temperature for four hours and then concentrated in vacuo. The residue was dissolved in CH$_2$Cl$_2$ (20 mL) and washed with brine (30 mL), and the aqueous phase was extracted with CH$_2$Cl$_2$ (20 mL) two times. The combined organic phase was dried over Na$_2$SO$_4$, concentrated in vacuo, and the residue was purified by silica gel chromatography to yield 2-amino-6-chloro-9-[β-D-2'-deoxyribofuranosyl]-7-[(S)-1-(5-methoxy-2-nitrophenyl)-2,2-dimethyl-propyloxy]-methyl-7 deazapurine 36 (67 mg, 27% for three steps). $^1$H NMR (400 MHz, CDCl$_3$): δ 7.82 (d, 1H, J=8.8 Hz, Ph-H), 7.16 (d, 1H, J=2.8 Hz, Ph-H), 6.90 (s, 1H, H-8), 6.72 (dd, 1H, J=8.8 and 2.8 Hz, Ph-H), 6.12 (dd, 1H, J=9.2 and 6.0 Hz, H-1'), 5.22 (s, 1H, Ph-CH), 5.15 (br s, 2H, NH$_2$), 4.69-4.55 (m, 3H, H-3' and 7-CH$_2$), 4.11 (m, 1H, H-4'), 3.92 (m, 1H, H-5'a), 3.82 (s, 3H, OCH$_3$), 3.73 (m, 1H, H-5'b), 2.81 (m, 1H, H-2'a), 2.21 (m, 1H, H-2'b), 0.82 (s, 9H, (CH$_3$)$_3$).

To a solution of compound 36 (65 mg, 0.12 mmol) in 1,4-dioxane (1.0 mL) and DMF (2.0 mL), syn-pyrimidine-2-aldoxime (292 mg, 2.4 mmol) and 1,1,3,3-tetramethyl guanidine (331 μL, 2.6 mmol) were added, and the mixture was heated at 70° C. overnight under a nitrogen atmosphere. The reaction mixture was diluted with CH$_2$Cl$_2$ (20 mL) and washed sequentially with acetic acid (0.1 M, 30 mL), saturated NaHCO$_3$ solution (30 mL), and brine (30 mL). The organic phase was dried over Na$_2$SO$_4$, concentrated in vacuo, and the residue was purified by silica gel chromatography to yield 7-[(S)-1-(5-methoxy-2-nitrophenyl)-2,2-dimethyl-propyloxy]methyl-7-deaza-2'-deoxyguanosine 37 (48 mg, 76%). $^1$H NMR (400 MHz, DMSO-d$_6$): δ 10.37 (br s, 1H, D$_2$O exchangeable, NH), 7.95 (d, 1H, J=9.2 Hz, Ph-H), 7.18 (d, 1H, J=2.8 Hz, Ph-H), 7.03 (dd, 1H, J=9.2 and 2.8 Hz, Ph-H), 6.84 (s, 1H, H-8), 6.23 (m, 3H, 2H D$_2$O exchangeable, NH$_2$ and H-1'), 5.20 (d, 1H, D$_2$O exchangeable, 3'-OH), 5.13 (s, 1H, Ph-CH), 4.84 (t, 1H, D$_2$O exchangeable, 5'-OH), 4.48 (d, 1H, J=12.0 Hz, 7-CH$_2$a), 4.32 (d, 1H, J=12.0 Hz, 7-CH$_2$b), 4.27 (m, 1H, H-3'), 3.88 (s, 3H, OCH$_3$), 3.73 (m, 1H, H-4'), 3.46 (m, 2H, H-5'), 2.30 (m, 1H, H-2'a), 2.05 (m, 1H, H-2'b), 0.77 (s, 9H, (CH$_3$)$_3$).

Compound 37 (10 mg, 0.02 mmol) was phosphorylated with POCl$_3$ (26 μL, 0.26 mmol) and proton sponge (8 mg, 0.04 mmol) in trimethylphosphate (0.3 mL) at 0° C. for 6.5 hours under a nitrogen atmosphere. A solution of bis-tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (10 mL), filtered, and purified by anion exchange chromatography. The fractions containing triphosphate were combined and lyophilized to give 7-[(S)-1-(5-methoxy-2-nitrophenyl)-2,2-dimethyl-propyloxy]methyl-7-deaza-2'-deoxyguanosine-5'-triphosphate dG.VI, which was further purified using RP-HPLC. The retention time of dG.VI was identical to that of dG.V.c ds2 by RP-HPLC analysis under the same condition. HRMS (ESI): For the molecular ion $C_{24}H_{33}N_5O_{17}P_3$ [M–H]⁻, the calculated mass was 756.1084, and the observed mass was 756.1101.

Example 5

Synthesis of 5-HOMe-2'-Deoxyuridine Triphosphate Analog

5-[(S)-1-(5-Methoxy-2-nitrophenyl)-2,2-dimethyl-propyloxy]methyl-2'-deoxyuridine-5'-triphosphate Scheme S19. Synthesis of 5-[(S)-1-(5-methoxy-2-nitrophenyl)-2,2-dimethyl-propyloxy]methyl-2'-deoxyuridine-5'-triphosphate.

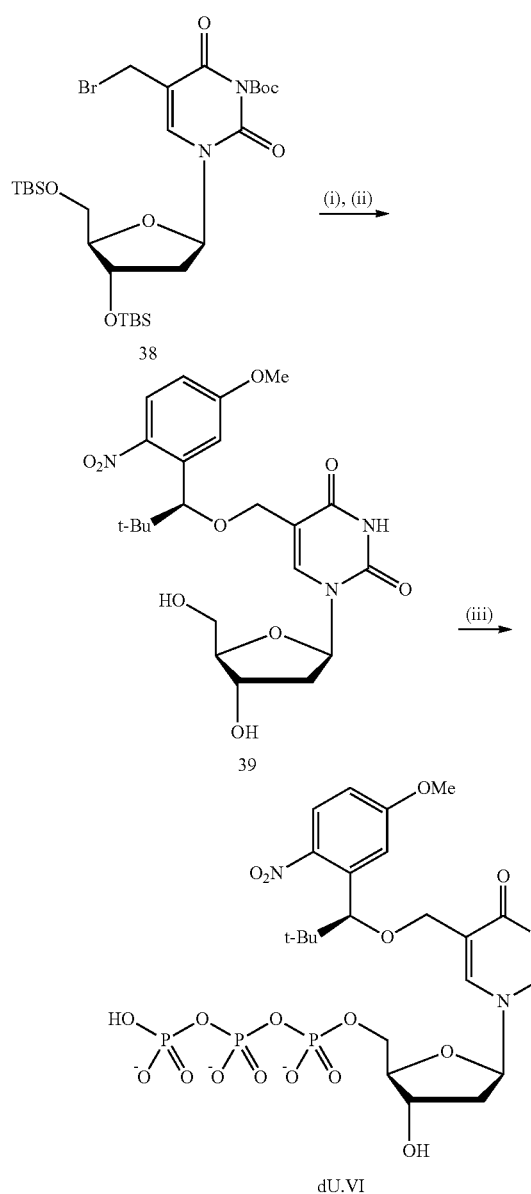

Reagents and conditions: (i) (S)-1-(5-methoxy-2-nitrophenyl)-2,2-dimethyl-1-propanol, 110° C.; (ii) NH₄F, MeOH, 50° C., 56% for two steps; (iii) POCl₃, proton sponge, (MeO)₃PO, 0° C.; (n-Bu₃NH)₂H₂P₂O₇, n-Bu₃N, DMF; 1M HNEt₃HCO₃.

Compound 38 (Litosh et al., 2011, which is incorporated herein by reference) (315 mg, 0.49 mmol) and (S)-1-(5-methoxy-2-nitrophenyl)-2,2-dimethyl-1-propanol (490 mg, 2.1 mmol) were heated at 110° C. for 45 min under a nitrogen atmosphere. The mixture was cooled down to room temperature, dissolved in MeOH (10 mL), and followed by addition of NH₄F (400 mg, 11 mmol). The mixture was stirred at 50° C. for 12 hours, concentrated in vacuo, dissolved in CH₂Cl₂ (50 mL), and washed with brine (50 mL). The organic phase was dried over Na₂SO₄, concentrated in vacuo, and the residue was purified by silica gel chromatography to yield 5-[(S)-1-(5-methoxy-2-nitrophenyl)-2,2-dimethyl-propyloxy]methyl-2'-deoxyuridine 39 (130 mg, 56%). ¹H NMR (400 MHz, CDCl₃): δ 9.14 (br s, 1H, NH), 7.90 (d, 1H, J=9.2 Hz, Ph-H), 7.67 (s, 1H, H-6), 7.17 (d, 1H, J=2.8 Hz, Ph-H), 6.84 (dd, 1H, J=9.2 and 2.8 Hz, Ph-H), 6.18 (t, 1H, J=6.4 Hz, H-1'), 5.22 (s, 1H, Ph-CH), 4.56 (m, 1H, H-3'), 4.24 (d, 1H, J=12.4 Hz, 5-CH₂a), 4.15 (d, 1H, J=12.4 Hz, 5-CH₂b), 4.00 (m, 1H, H-4'), 3.90 (m, 1H, H-5'a), 3.88 (s, 3H, OCH₃), 3.81 (m, 1H, H-5'b), 2.35 (m, 2H, H-2), 0.83 (s, 9H, C(CH₃)₃).

Compound 39 (30 mg, 0.065 mmol) was phosphorylated with POCl₃ (9 µL, 0.097 mmol) and proton sponge (28 mg, 0.13 mmol) in trimethylphosphate (0.35 mL) at 0° C. for one hour under a nitrogen atmosphere. A solution of tri-n-butylammonium pyrophosphate (147 mg, 0.32 mmol) and tri-n-butylamine (64 µL) in anhydrous DMF (0.64 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (10 mL), filtered, and purified by anion exchange chromatography. The fractions containing triphosphate were combined and lyophilized to yield 5-[(S)-1-(5-methoxy-2-nitrophenyl)-2,2-dimethyl-propyloxy]methyl-2'-deoxyuridine-5'-triphosphate dU.VI, which was further purified using RP-HPLC. HRMS (ESI): For the molecular ion $C_{22}H_{31}N_3O_{18}P_3$ [M–H]⁻, the calculated mass was 718.0815, and the observed mass was 718.0824.

Example 6

Synthesis of 5-HOMe-2'-Deoxycytidine Triphosphate Analogs 5-(2-nitrobenzyloxyl)methyl-2'-deoxycytidine-5'-triphosphate Scheme S20. Synthesis of 5-(2-nitrobenzyloxy)methyl-2'-deoxcytidine-5'-triphosphate.

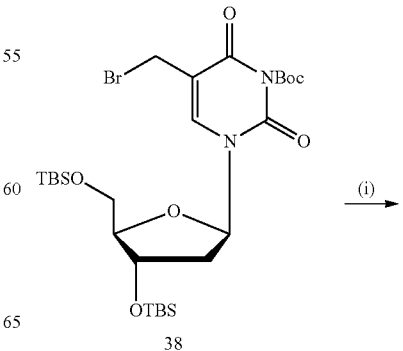

38

119
-continued

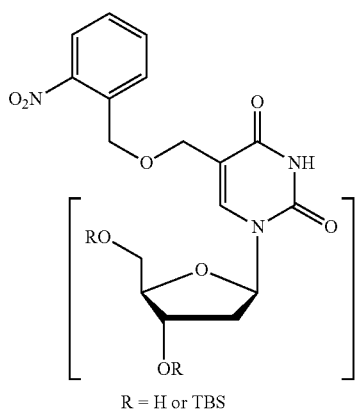

R = H or TBS

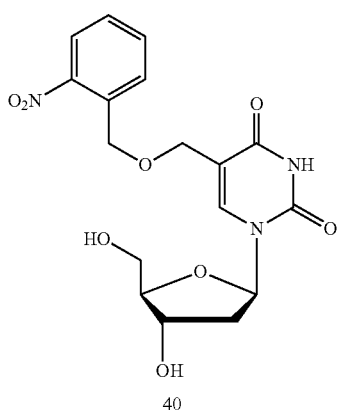

40

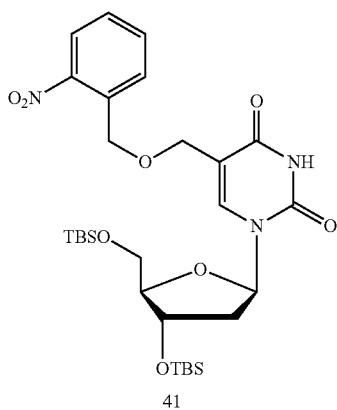

41

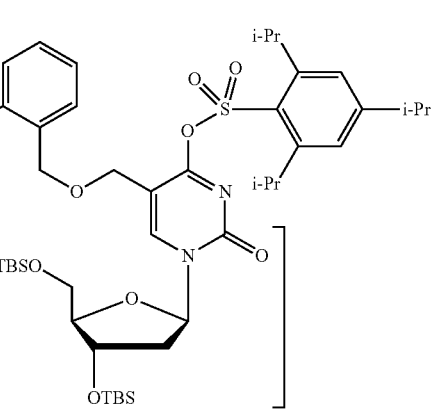

120
-continued

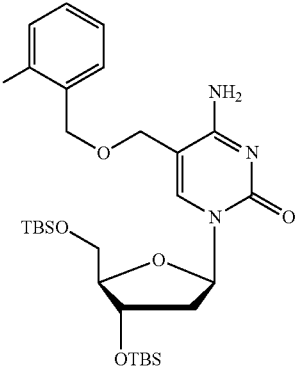

42

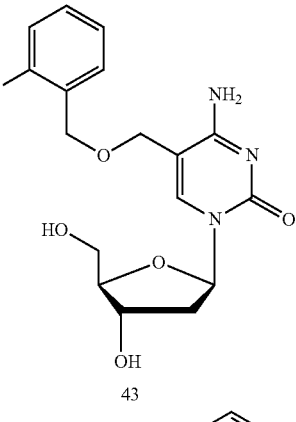

43

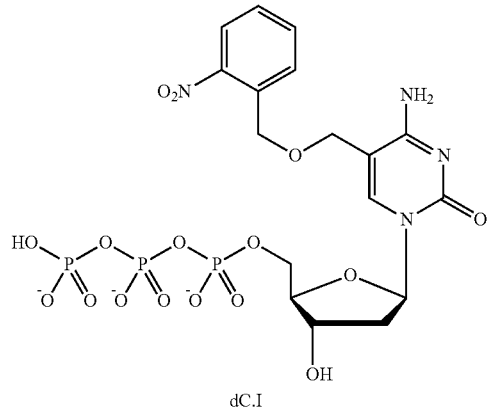

dC.I

Reagents and conditions: (i) 2-nitrobenzyl alcohol, 110° C.; (ii) n-Bu₄NF, THF, room temperature, 53% for two steps; (iii) TBSCl, imidazole, DMF, room temperature, 80%; (iv) 2,4,6-triisopropylbenzenesulfonyl chloride, DMAP, Et₃N, CH₂Cl₂, room temperature; (v) NH₃, 1,4-dioxane, 90° C., 69% for two steps; (vi) n-Bu₄NF, THF, room temperature, 96%; (vii) POCl₃, proton sponge, (MeO)₃PO, 0° C.; (n-Bu₃NH)₂H₂P₂O₇, n-Bu₃N, DMF; 1M HNEt₃HCO₃.

Compound 38 (300 mg, 0.46 mmol) and 2-nitrobenzyl alcohol (500 mg, 3.3 mmol) were heated at 110° C. for 45 min under a nitrogen atmosphere. The mixture was cooled to room temperature, dissolved in THF (20 mL) followed by addition of n-Bu₄NF (362 mg, 1.2 mmol). The mixture was stirred at room temperature for four hours, concentrated in vacuo, and the residue was purified by silica gel chromatography to yield 5-(2-nitrobenzyloxyl)methyl-2'-deoxyuridine 40 (Litosh et al., 2011, which is incorporated herein by reference) (95 mg, 53%). $^1$H NMR (400 MHz, CDCl$_3$): δ 8.45 (br s, 1H, NH), 8.05 (s, 1H, H-6), 8.02 (d, J=8.0 Hz, 1H, Ph-H), 7.80 (d, 1H, J=8.0 Hz, Ph-H), 7.69 (t, 1H, J=8.0 Hz, Ph-H), 7.43 (t, 1H, J=8.0 Hz, Ph-H), 6.21 (t, 1H, J=6.0 Hz, H-1'), 4.94 (dd, J=14.4 Hz, 2H, Ph-CH$_2$), 4.66 (m, 1H, H-3'), 4.35 (s, 2H, 5-CH$_2$), 3.95 (m, 3H, H-4' and H-5'), 2.42 (m, 1H, H-2'a), 2.30 (m, 1H, H-2'b).

To a solution of compound 40 (Litosh et al., 2011, which is incorporated herein by reference) (70 mg, 0.18 mmol) in anhydrous DMF (2.0 mL), TBSCl (60 mg, 0.40 mmol) and imidazole (54 mg, 0.80 mmol) were added. The mixture was stirred at room temperature overnight under a nitrogen atmosphere, concentrated in vacuo, dissolved in CH$_2$Cl$_2$ (20 mL), and washed with saturated NaHCO$_3$ solution (30 mL). The organic and aqueous phases were separated, and the aqueous phase was extracted with CH$_2$Cl$_2$ (20 mL) two times. The combined organic phase was dried with Na$_2$SO$_4$, concentrated in vacuo, and the residue was purified by silica gel chromatography to yield 3',5'-O-bis-(tert-butyldimethylsilyl)-5-(2-nitrobenzyloxy)-methyl-2'-deoxyuridine 41 (90 mg, 80%). $^1$H NMR (400 MHz, CDCl$_3$): δ 8.04 (d, J=8.0 Hz, 1H, Ph-H), 7.98 (br s, 1H, NH), 7.80 (d, 1H, J=8.0 Hz, Ph-H), 7.74 (s, 1H, H-6), 7.64 (q, 1H, J=8.0 Hz, Ph-H), 7.44 (t, 1H, J=8.0 Hz, Ph-H), 6.21 (q, 1H, J=6.0 Hz, H-1'), 4.95 (s, 2H, Ph-CH$_2$), 4.41 (m, 1H, H-3'), 4.34 (dd, 2H, J=11.6 Hz, 5-CH$_2$), 3.96 (m, 1H, H-4'), 3.79 (m, 2H, H-5'), 2.29 (m, 1H, H-2'a), 2.05 (m, 1H, H-2'b), 0.89 (2 s, 18H, C(CH$_3$)$_3$), 0.08 (4 s, 12H, CH$_3$).

2,4,6-Triisopropyl benzenesulfonyl chloride (176 mg, 0.59 mmol) was added to a solution of compound 41 (85 mg, 0.14 mmol), DMAP (19 mg, 0.16 mmol), and triethylamine (0.18 mL, 1.3 mmol) in anhydrous CH$_2$Cl$_2$ (5.0 mL). The mixture was stirred at room temperature overnight under a nitrogen atmosphere, concentrated in vacuo, and the residue was dissolved in a solution of NH$_3$ in 1,4-dioxane (0.5 M, 15 mL). The mixture was transferred into a sealed tube and was heated at 90° C. overnight. The mixture was cooled to room temperature, concentrated in vacuo, dissolved in CH$_2$Cl$_2$ (30 mL), and washed with brine (30 mL). The organic and aqueous phases were separated, and the aqueous phase was extracted with CH$_2$Cl$_2$ (30 mL) two times. The combined organic phase was dried over Na$_2$SO$_4$, concentrated in vacuo, and the residue was purified by silica gel column chromatography to yield 3',5'-O-bis-(tert-butyldimethylsilyl)-5-(2-nitrobenzyloxyl)methyl-2'-deoxycytidine 42 (60 mg, 69% for two steps). $^1$H NMR (400 MHz, CDCl$_3$): δ 8.08 (d, J=8.0 Hz, 1H, Ph-H), 7.81 (s, 1H, H-6), 7.65 (m, 2H, Ph-H), 7.64 (q, 1H, J=8.0 Hz, Ph-H), 7.49 (m, 1H, Ph-H), 6.29 (t, 1H, J=6.4 Hz, H-1'), 5.75 (br s, 1H, NH$_2$), 4.85 (dd, 2H, J=13.6 Hz, Ph-CH$_2$), 4.41 (s, 2H, 5-CH$_2$), 4.34 (m, 1H, H-3'), 3.95 (m, 1H, H-4'), 3.89 (dd, 1H, J=2.8 Hz, H-5'a), 3.76 (dd, 1H, J=2.8 Hz, H-5'b), 2.46 (m, 1H, H-2'a), 1.98 (m, 1H, H-2'b), 0.92 and 0.89 (2 s, 18H, C(CH$_3$)$_3$), 0.11-0.08 (4 s, 12H, CH$_3$).

To a solution of compound 42 (55 mg, 0.09 mmol) in THF (10 mL), n-Bu$_4$NF (63 mg, 0.20 mmol) was added. The mixture was stirred at room temperature for four hours and concentrated in vacuo, and the residue was purified by silica gel column chromatography to yield 5-(2-nitrobenzyloxyl)methyl-2'-deoxycytidine 43 (34 mg, 96%). $^1$H NMR (400 MHz, DMSO-d$_6$): δ 8.05 (d, J=8.0 Hz, 1H, Ph-H), 7.89 (s, 1H, H-6), 7.74 (m, 2H, Ph-H), 7.55 (m, 1H, Ph-H), 7.39 (br s, 1H, D$_2$O exchangeable, NH$_2$), 6.74 (br s, 1H, D$_2$O exchangeable, NH$_2$), 6.12 (t, 1H, J=6.4 Hz, H-1'), 5.21 (br s, 1H, D$_2$O exchangeable, 3'-OH), 4.99 (br s, 1H, D$_2$O exchangeable, 5'-OH), 4.81 (s, 2H, Ph-CH$_2$), 4.30 (dd, 2H, J=11.6 Hz, 5-CH$_2$), 4.20 (m, 1H, H-3'), 3.76 (m, 1H, H-4'), 3.55 (m, 2H, H-5'), 2.11 (m, 1H, H-2'a), 1.95 (m, 1H, H-2'b).

Compound 43 (32 mg, 0.081 mmol) was phosphorylated with POCl$_3$ (30 μL, 0.32 mmol) and proton sponge (35 mg, 0.16 mmol) in trimethylphosphate (0.35 mL) at 0° C. for three hours under a nitrogen atmosphere. A solution of tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 5-(2-nitrobenzyloxyl)methyl-2'-deoxycytidine-5'-triphosphate dC.I, which was further purified using RP-HPLC. HRMS (ESI): For the molecular ion C$_{17}$H$_{22}$N$_4$O$_{16}$P$_3$ [M–H]$^-$, the calculated mass was 631.0244, and the observed mass was 631.0258.

5-[(S)-1-(2-nitrophenyl)-2,2-dimethyl-propyloxy]methyl-2'-deoxycytidine-5'-triphosphate

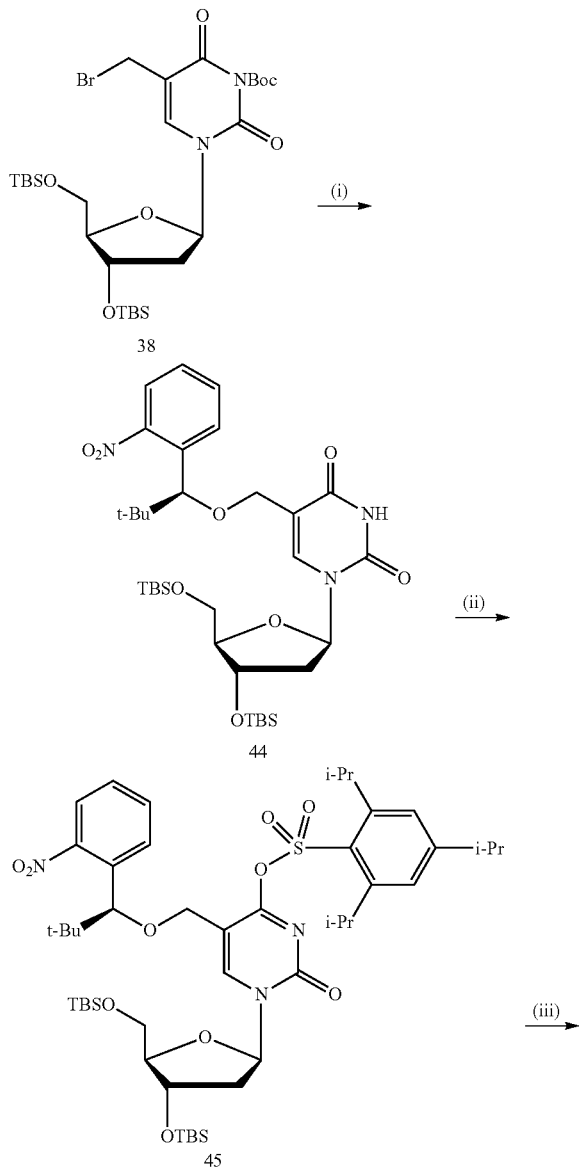

Scheme S21. Synthesis of 5-[(S)-1-(2-nitrophenyl)-2,2-dimethyl-propyloxy]methyl-2'-deoxycytidine-5'-triphosphate.

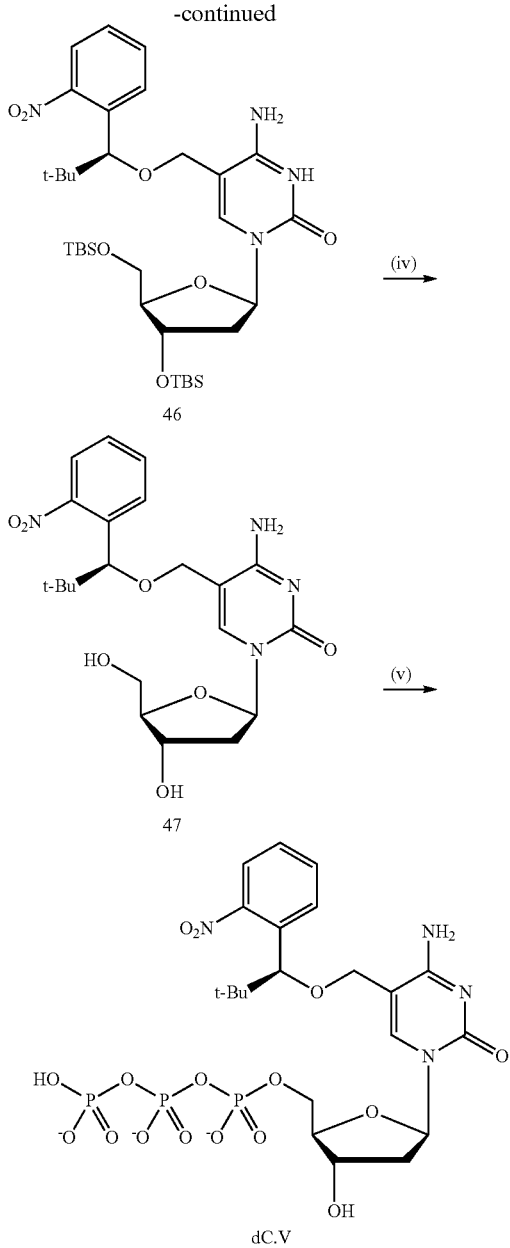

Reagents and conditions: (i) (S)-1-(2-nitrophenyl)-2,2-dimethyl-1-propanol, 110° C., 21%; (ii) 2,4,6-triisopropylbenzenesulfonyl chloride, DMAP, Et₃N, CH₂Cl₂, room temperature, 31%; (iii) NH₃, 1,4-dioxane, 90° C., 91%; (iv) n-Bu₄NF, THF, room temperature, 82%; (v) POCl₃, proton sponge, (MeO)₃PO, 0° C.; (n-Bu₃NH)₂H₂P₂O₇, n-Bu₃N, DMF; 1M HNEt₃HCO₃.

Compound 38 (Litosh et al., 2011, which is incorporated herein by reference) (520 mg, 0.80 mmol) and (S)-1-(2-nitrophenyl)-2,2-dimethyl-1-propanol (580 mg, 2.8 mmol) were heated at 110° C. for one hour under a nitrogen atmosphere. The mixture was cooled down to room temperature, dissolved in a minimum amount of ethyl acetate, and purified by silica gel chromatography to yield 3',5'-O-bis-(tert-butylsimethylsilyl)-5-[(S)-1-(2-nitrophenyl)-2,2-dimethyl-propyloxy]methyl-2'-deoxyuridine 44 (115 mg, 21%). (3' or 5')-O-(tert-butylsimethylsilyl)-5-[(S)-1-(2-nitrophenyl)-2,2-dimethyl-propyloxy]methyl-2'-deoxyuridine (78 mg, 17%) and 5-[(S)-1-(2-nitrophenyl)-2,2-dimethyl-propyloxy]methyl-2'-deoxyuridine (16 mg, 4%) was also obtained from the reaction. $^1$H NMR (400 MHz, CDCl₃): δ 8.97 (s, 1H, NH), 7.76 (d, 2H, J=8.0 Hz, Ph-H), 7.60 (m, 2H, Ph-H and H-6), 7.41 (s, 1H, Ph-H), 6.29 (dd, 1H, J=6.0 and 7.6 Hz, H-1'), 4.97 (s 1H, Ph-CH), 4.42 (m, 1H, H-3'), 4.28 (AB d, 1H, J=12.0 Hz, 5-CH₂a), 4.06 (AB d, 1H, J=12.0 Hz, 5-CH₂b), 3.92 (m, 1H, H-4'), 3.76 (m, 2H, H-5'), 2.30 (m, 1H, H-2'a), 2.05 (m, 1H, H-2'b), 0.95 (s, 9H, (CH₃)₃CSi), 0.90 (s, 9H, (CH₃)₃CSi), 0.83 (s, 9H, (CH₃)₃C), 0.12 (s, 3H, CH₃Si), 0.09 (s, 3H, CH₃Si), 0.07 (s, 3H, CH₃Si), 0.06 (s, 3H, CH₃Si). 2,4,6-Triisopropyl benzenesulfonyl chloride (61 mg, 0.20 mmol) was added to a solution of compound 44 (110 mg, 0.16 mmol), DMAP (20 mg, 0.17 mmol), and triethylamine (63 µL, 0.45 mmol) in anhydrous CH₂Cl₂ (3.0 mL). The mixture was stirred at room temperature for 36 hours under a nitrogen atmosphere, concentrated in vacuo, and the residue was purified by silica gel column chromatography to give 3',5'-O-bis-(tert-butylsimethylsilyl)-5-[(S)-1-(2-nitrophenyl)-2,2-dimethyl-propyloxy]methyl-O⁴-(2,4,6-triisopropylbenzenesulfonyl)-2'-deoxyuridine 45 (47 mg, 31%). $^1$H NMR (500 MHz, CDCl₃): δ 8.08 (s, 1H, H-6), 7.80 (dd, 1H, J=1.2 and 8.0 Hz, Ph-H), 7.78 (dd, 1H, J=1.6 and 8.0 Hz, Ph-H), 7.67 (m, 1H, Ph-H), 7.46 (m, 1H, Ph-H), 7.20 (s, 2H, Ph-H), 6.09 (t, 1H, J=6.4 Hz, H-1'), 4.98 (s, 1H, Ph-CH), 4.35 (m, 1H, H-3'), 4.25 (AB d, 1H, J=11.6 Hz, 5-CH₂a), 4.11 (AB d, 1H, J=11.6 Hz, 5-CH₂b), 3.97 (m, 1H, H-4'), 3.79 (dd, 1H, J=3.6 and 11.6 Hz, H-5'a), 3.74 (dd, 1H, J=11.6 and 3.6 Hz, H-5'b), 2.90 (m, 1H, CH), 2.50 (m, 2H, H-2'), 1.98 (m, 2H, CH), 1.31-1.22 (m, 18H, (CH₃)₂CH×3), 0.88 (2 s, 18H, (CH₃)₃CSi×2), 0.87 (s, 9H, (CH₃)₃C), 0.07 (s, 6H, (CH₃)₂Si), 0.06 (s, 6H, (CH₃)₂Si).

A solution of NH₃ in 1,4-dioxane (0.5 M, 2.0 mL) was added to a solution of compound 45 (47 mg, 0.05 mmol) in anhydrous 1,4-dioxane (2.0 mL). The mixture was transferred into a sealed tube and was heated at 90° C. for ten hours. The mixture was cooled to room temperature, concentrated in vacuo and the residue was purified by silica gel column chromatography to yield 3',5'-O-bis-(tert-butyldimethylsilyl)-5-[(S)-1-(2-nitrophenyl)-2,2-dimethyl-propyloxy]-methyl-2'-deoxycytidine 46 (31 mg, 91%). $^1$H NMR (400 MHz, CDCl₃): δ 7.67 (m, 3H, Ph-H), 7.53 (s, 1H, H-6), 7.45 (m, 1H, Ph-H), 6.30 (t, 1H, J=6.6 Hz, H-1'), 5.72 (br s, 2H, NH₂), 4.88 (s, 1H, Ph-CH), 4.32 (m, 1H, H-3'), 4.28 (AB d, 1H, J=12.8 Hz, 5-CH₂a), 4.08 (AB d, 1H, J=12.8 Hz, 5-CH₂b), 3.87 (m, 1H, H-4'), 3.74 (dd, 1H, J=3.6 and 14.8 Hz, H-5'a), 3.66 (dd, 1H, J=3.6 and 11.3 Hz, H-5'b), 2.41 (m, 1H, H-2'a), 2.03 (m, 1H, H-2'b), 0.90 (s, 9H, (CH₃)₃CSi), 0.87 (s, 9H, (CH₃)₃CSi), 0.83 (s, 9H, C(CH₃)₃), 0.09 (2 s, 6H, (CH₃)₂Si), 0.06 (2 s, 6H, (CH₃)₂Si).

A solution of n-Bu₄NF (28 mg, 0.09 mmol) in THF (1.0 mL) was added to a solution of compound 46 (20 mg, 0.03 mmol) in THF (2.0 mL). The mixture was stirred at room temperature for 30 min and concentrated in vacuo, and the residue was purified by silica gel column chromatography to yield 5-[(S)-1-(2-nitrophenyl)-2,2-dimethyl-propyloxy]methyl-2'-deoxycytidine 47 (11 mg, 82%). $^1$H NMR (400 MHz, CD₃OD): δ 7.87 (s, 1H, H-6), 7.82 (dd, 1H, J=1.2 and 8.4 Hz, Ph-H), 7.76 (dd, 1H, J=1.6 and 8.0 Hz, Ph-H), 7.68 (m, 1H, Ph-H), 7.51 (m, 1H, Ph-H), 6.23 (t, 1H, J=6.6 Hz, H-1'), 4.94 (s, 1H, Ph-CH), 4.44 (AB d, 1H, J=13.2 Hz, 5-CH₂a), 4.34 (m, 1H, H-3'), 4.11 (AB d, 1H, J=13.2 Hz, 5-CH₂b), 3.88 (m, 1H, H-4'), 3.71 (dd, 1H, J=3.2 and 12.0 Hz, H-5'a), 3.63 (dd, 1H, J=4.0 and 12.0 Hz, H-5'b), 2.35 (m, 1H, H-2'a), 2.14 (m, 1H, H-2'b), 0.80 (s, 9H, C(CH₃)₃).

Compound 47 (11 mg, 0.025 mmol) was phosphorylated with POCl₃ (7 µL, 0.075 mmol) and proton sponge (11 mg, 0.05 mmol) in trimethylphosphate (0.3 mL) at 0° C. for three hours under a nitrogen atmosphere. A solution of tri-n-butylammonium pyrophosphate (59 mg, 0.125 mmol) and tri-n-butylamine (30 µL) in anhydrous DMF (0.25 mL) was added. After 5 min of stirring, triethylammonium bicarbonate buffer (1 M, pH 7.5; 5.0 mL) was added. The reaction was stirred at room temperature for one hour and then lyophilized to dryness. The residue was dissolved in water (5.0 mL), filtered, and purified by anion exchange chromatography. The fractions containing triphosphate were combined and lyophilized to give 5-[(S)-1-(2-nitrophenyl)-2,2-dimethyl-propyloxy]methyl-2'-deoxycytidine-5'-triphosphate dC.V, which was further purified using by RP-HPLC. HRMS (ESI): For the molecular ion $C_{21}H_{30}N_4O_{16}P_3$ [M−H]−, the calculated mass was 687.0870, and the observed mass was 687.0873.

5-[(S)-1-(5-Methoxy-2-nitrophenyl)-2,2-dimethyl-propyloxy]methyl-2'-deoxycytidine-5'-triphosphate

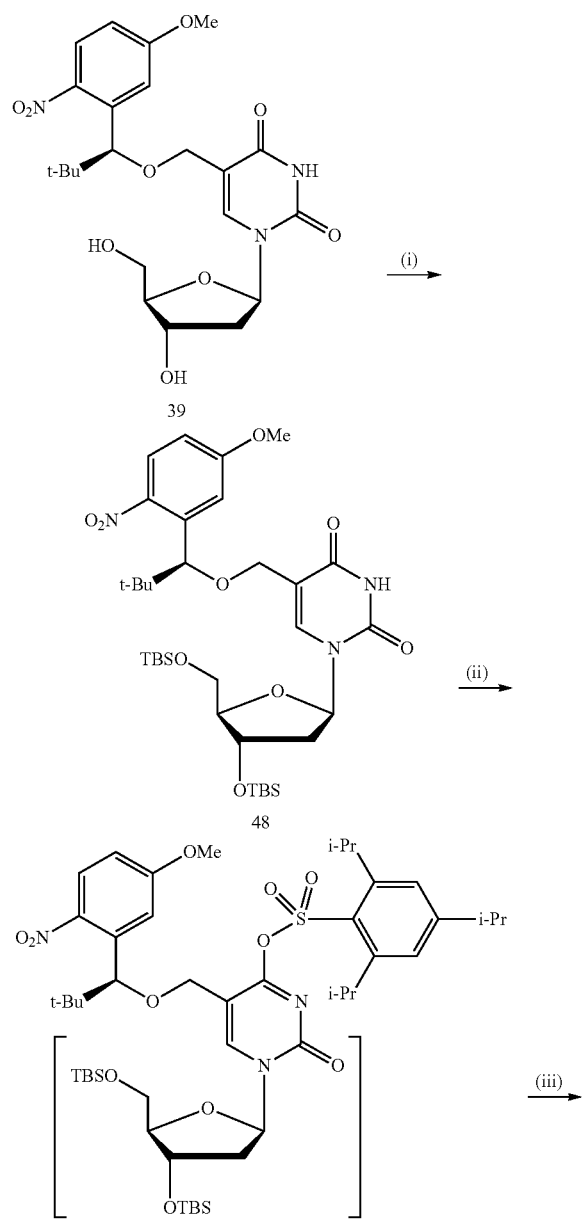

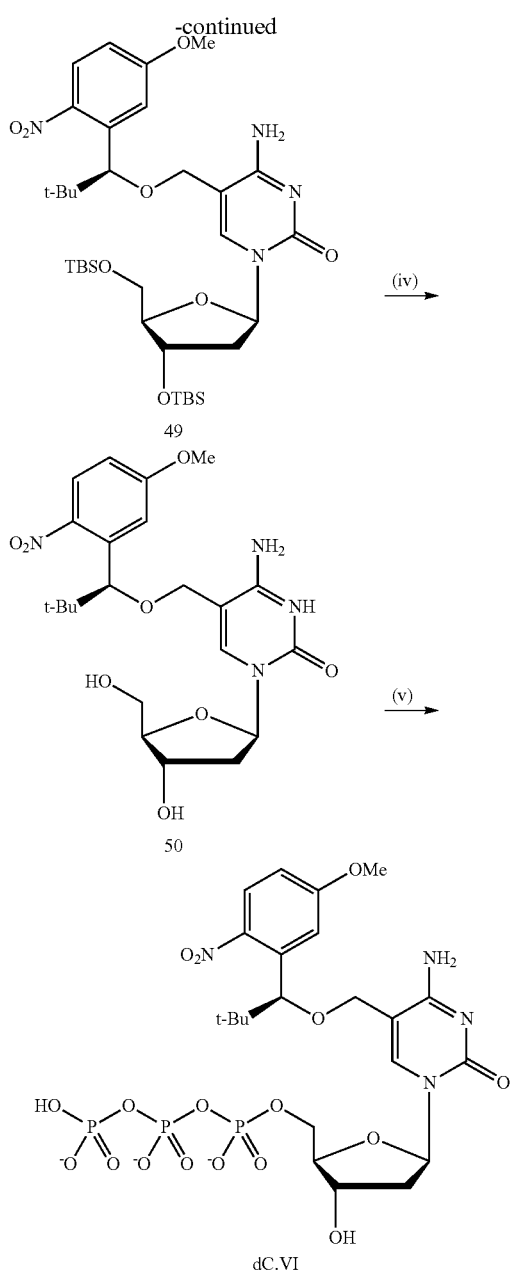

Reagents and conditions: (i) TBSCl, imidazole, DMF, room temperature, 70%; (ii) 2,4,6-triisopropylbenzenesulfonyl chloride, DMAP, Et$_3$N, CH$_2$Cl$_2$, room temperature; (iii) NH$_3$, 1,4-dioxane, 90° C., 65% for two steps; (iv) n-Bu$_4$NF, THF, room temperature, 82%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

To a solution of compound 39 (235 mg, 0.49 mmol) in anhydrous DMF (3.0 mL), TBSCl (320 mg, 0.8 mmol) and imidazole (109 mg, 1.6 mmol) were added. The mixture was stirred at room temperature for six hours, concentrated in vacuo, dissolved in CH$_2$Cl$_2$ (20 mL), and washed with saturated NaHCO$_3$ solution (50 mL). The organic and aqueous phases were separated, and the aqueous phase was extracted with CH$_2$Cl$_2$ (30 mL) three times. The combined organic phase was dried with Na$_2$SO$_4$, concentrated in vacuo, and the residue was purified by silica gel chromatography to yield 3',5'-O-bis-(tert-butyldimethylsilyl)-5-[(S)-1-(5-methoxy-2-nitrophenyl)-2,2-dimethyl-propyloxy]methyl-2'-deoxyuridine 48 (245 mg, 70%). $^1$H NMR (400 MHz, CDCl$_3$): δ 8.00

(br s, 1H, NH), 7.88 (d, J=9.2 Hz, 1H, Ph-H), 7.60 (s, 1H, H-6), 7.22 (d, 1H, J=2.8 Hz, Ph-H), 6.84 (dd, 1H, J=2.8 and 8.0 Hz, Ph-H), 6.25 (dd, 1H, J=5.6 and 8.0 Hz, H-1'), 5.23 (s, 1H, Ph-CH), 4.40 (m, 1H, H-3'), 4.26 (d, 1H, J=12 Hz, 5-CH$_2$a), 4.11 (d, 1H, J=12 Hz, 5-CH$_2$b), 3.89 (m, 4H, OCH$_3$ and H-4'), 3.78 (m, 2H, H-5'), 2.27 (m, 1H, H-2'a), 2.04 (m, 1H, H-2'b), 0.90 and 88 (2 s, 18H, SiC(CH$_3$)$_3$), 0.84 (s, 9H, C(CH$_3$)$_3$), 0.08 (3 s, 12H, CH$_3$).

2,4,6-Triisopropyl benzenesulfonyl chloride (363 mg, 1.2 mmol) was added to a solution of compound 48 (170 mg, 0.24 mmol), DMAP (32 mg, 0.26 mmol), and triethylamine (0.34 mL, 2.4 mmol) in anhydrous CH$_2$Cl$_2$ (8.0 mL). The mixture was stirred at room temperature overnight under a nitrogen atmosphere, concentrated in vacuo, and the residue was dissolved in a solution of NH$_3$ in 1,4-dioxane (0.5 M, 20 mL). The mixture was transferred into a sealed tube and was heated at 90° C. overnight. The mixture was cooled to room temperature, concentrated in vacuo, dissolved in CH$_2$Cl$_2$ (20 mL), and washed with brine (50 mL). The organic and aqueous phases were separated, and the aqueous phase was extracted with CH$_2$Cl$_2$ (30 mL) three times. The combined organic phase was dried over Na$_2$SO$_4$, concentrated in vacuo, and the residue was purified by silica gel column chromatography to yield 3',5'-O-bis-(tert-butyldimethylsilyl)-5-[(S)-1-(5-methoxy-2-nitrophenyl)-2,2-dimethyl-propyloxy]methyl-2'-deoxycytidine 49 (110 mg, 65% for two steps). $^1$H NMR (400 MHz, DMSO-d$_6$): δ 7.96 (d, J=8.8 Hz, 1H, Ph-H), 7.50 (br s, 1H, NH$_2$), 7.38 (s, 1H, H-6), 7.08 (dd, 1H, J=2.8 and 8.8 Hz, Ph-H), 7.04 (d, 1H, J=2.8 Hz, Ph-H), 6.80 (br s, 1H, NH$_2$), 6.13 (t, 1H, J=6.4 Hz, H-1'), 5.09 (s, 1H, Ph-CH), 4.31 (m, 1H, H-3'), 4.25 (d, 1H, J=12.8 Hz, 5-CH$_2$a), 4.08 (d, 1H, J=12.8 Hz, 5-CH$_2$b), 3.87 (s, 3H, OCH$_3$), 3.76 (m, 1H, H-4'), 3.64 (m, 2H, H-5'), 3.76 (dd, 1H, J=2.8 Hz, H-5'b), 2.10 (m, 1H, H-2'a), 2.00 (m, 1H, H-2'b), 0.87 (s, 9H, C(CH$_3$)$_3$), 0.78 and 0.76 (2 s, 18H, SiC(CH$_3$)$_3$), 0.07, 0.06, −0.01, and −0.04 (4 s, 12H, SiCH$_3$).

To a solution of compound 49 (130 mg, 0.18 mmol) in THF (10 mL), n-Bu$_4$NF (141 mg, 0.44 mmol) was added. The mixture was stirred at room temperature for four hours, concentrated in vacuo, and the residue was purified by silica gel column chromatography to yield 5-[(S)-1-(5-methoxy-2-nitrophenyl)-2,2-dimethyl-propyloxy]methyl-2'-deoxycytidine 50 (72 mg, 82%). $^1$H NMR (400 MHz, DMSO-d$_6$): δ 7.99 (d, J=8.0 Hz, 1H, Ph-H), 7.65 (s, 1H, H-6), 7.42 (br s, 1H, D$_2$O exchangeable, NH$_2$a), 7.06 (m, 2H, Ph-H), 6.72 (br s, 1H, D$_2$O exchangeable, NH$_2$b), 6.11 (t, 1H, J=6.4 Hz, H-1'), 5.17 (d, 1H, D$_2$O exchangeable, 3'-OH), 5.12 (s, 1H, Ph-CH), 4.78 (t, 1H, D$_2$O exchangeable, 5'-OH), 4.25 (d, 1H, J=12.4 Hz, 5-CH$_2$a), 4.15 (m, 1H, H-3'), 4.05 (d, 1H, J=12.4 Hz, 5-CH$_2$b), 3.87 (s, 3H, OCH$_3$), 3.72 (m, 1H, H-4'), 3.44 (m, 2H, H-5'), 3.76 (dd, 1H, J=2.8 Hz, H-5'b), 2.08 (m, 1H, H-2'a), 1.95 (m, 1H, H-2'b), 0.77 (s, 9H, C(CH$_3$)$_3$).

Compound 50 (20 mg, 0.043 mmol) was phosphorylated with POCl$_3$ (24 μL, 0.26 mmol) and proton sponge (19 mg, 0.086 mmol) in trimethylphosphate (0.3 mL) at 0° C. for six hours under a nitrogen atmosphere. A solution of tri-n-butylammonium pyrophosphate (237 mg, 0.50 mmol) and tri-n-butylamine (100 μL) in anhydrous DMF (1.0 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (20 mL), filtered, and purified by anion exchange chromatography. The fractions containing triphosphate were combined and lyophilized to give 5-[(S)-1-(5-methoxy-2-nitrophenyl)-2,2-dimethyl-propyloxy]methyl-2'-deoxycytidine-5'-triphosphate dC.VI, which was further purified using RP-HPLC. HRMS (ESI): For the molecular ion C$_{22}$H$_{32}$N$_4$O$_{17}$P$_3$ [M−H]$^-$, the calculated mass was 719.0975, and the observed mass was 719.0983.

Example 7

Synthesis of (R/S)-1-(4-iodo-5-methoxy-2-nitrophenyl)-2,2-dimethyl-1-propanol and (S)-1-(4-iodo-5-methoxy-2-nitrophenyl)-2,2-dimethyl-1-propanol Scheme S23.

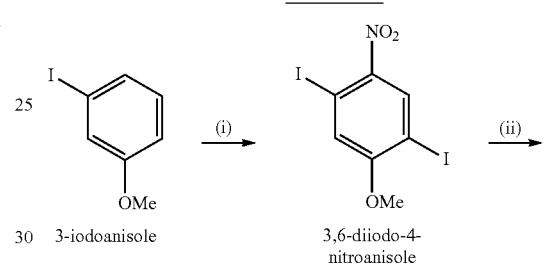

3-iodoanisole 3,6-diiodo-4-nitroanisole

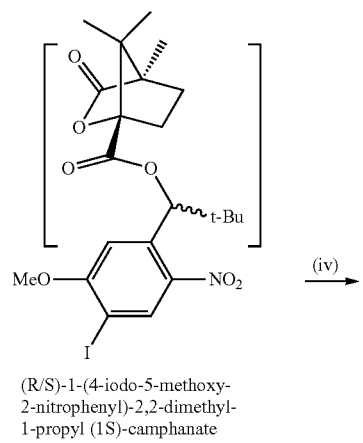

(R/S)-1-(4-iodo-5-methoxy-2-nitrophenyl)-2,2-dimethyl-1-propanol (R/S)-1-(4-iodo-5-methoxy-2-nitrophenyl)-2,2-dimethyl-1-propyl (1S)-camphanate

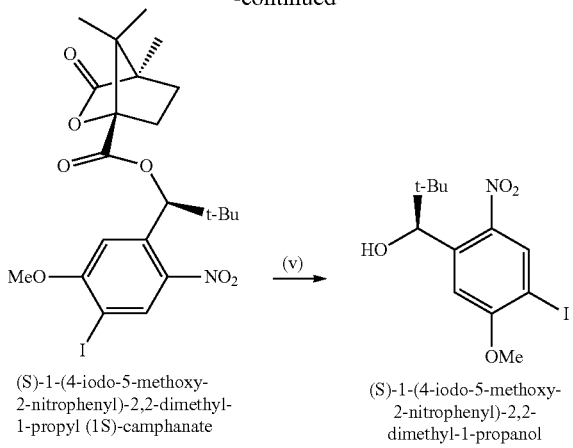

(S)-1-(4-iodo-5-methoxy-2-nitrophenyl)-2,2-dimethyl-1-propyl (1S)-camphanate (S)-1-(4-iodo-5-methoxy-2-nitrophenyl)-2,2-dimethyl-1-propanol Synthesis of (R/S)-1-(4-iodo-5-methoxy-2-nitrophenyl)-2,2-dimethyl-1-propanol and (S)-1-(4-iodo-5-methoxy-2-nitrophenyl)-2,2-dimethyl-1-propanol. (i) NaNO₂, CH₃COOH, HNO₃, room temperature; I₂, 60° C., 25% for two steps (80% pure); (ii) PhMgCl, (CH₃)₃CCHO, THF, minus 40° C. to room temperature, 72%; (iii) (1S)-camphanic acid chloride, DMAP, CH₂Cl₂, room temperature 80%; (iii) fractional crystallization from ethanol, 63%; (iv) K₂CO₃, MeOH, reflux.

Nitric acid (68-70%, 125 mL) was slowly mixed with glacial acetic acid (125 ml) at room temperature, followed by addition of NaNO₂ (400 mg, 5.8 mmol) and 3-iodoanisole (10 g, 42.7 mmol). After the reaction was stirred at room temperature for 24 hours, I₂ (10.8 g, 42.7 mmol) was added and the mixture was stirred at 60° C. overnight. The reaction mixture was poured into ice-water (500 ml) and extracted by CH₂Cl₂ (100 ml) three times. The combined organic phase was neutralized with saturated NaHCO₃ solution (500 ml), washed with aqueous solution of Na₂S₂O₃ (20%, 100 ml), dried over Na₂SO₄, and concentrated in vacuo. The residue was purified by silica gel column chromatography to yield crude 3,6-diiodo-4-nitroanisole (5.4 g), which is mixed with one unknown by-product (20%) and used in the next step without further purification. $^1$H NMR (400 MHz, CDCl₃): δ 8.42 (s, 1H, Ph-H), 7.33 (s, 1H, Ph-H), 3.97 (s, 3H, OCH₃).

To a solution of crude 3,6-diiodo-4-nitroanisole (770 mg, 80% purity, 1.52 mmol) in anhydrous THF (10 mL) at minus 40° C. under a nitrogen atmosphere, phenylmagnesium chloride (2 M in THF, 0.46 mL, 0.92 mmol) was added dropwise at a rate such that the temperature would not exceed minus 35° C. Upon completion of the addition, the mixture was stirred at minus 40° C. for two hours, followed by addition of trimethylacetaldehyde (0.22 mL, 1.97 mmol). The mixture was stirred at minus 30° C. for two hours and then at room temperature for another one hour. The reaction was then quenched with brine (1.0 mL), diluted with CH₂Cl₂ (100 mL), and the solution was washed with CH₃COOH (0.1 N, 50 ml) and brine (50 ml) sequentially. The organic phase was dried over Na₂SO₄, concentrated in vacuo, and the residue was purified by silica gel column chromatography to yield racemic (R/S)-1-(4-iodo-5-methoxy-2-nitrophenyl)-2,2-dimethyl-1-propanol (399 mg, 72%). $^1$H NMR (400 MHz, CDCl₃): δ 8.32 (s, 1H, Ph-H), 7.17 (s, 1H, Ph-H), 5.60 (d, 1H, J=4.0 Hz, PhCH), 3.98 (s, 3H, OCH₃), 2.12 (d, 1H, J=4.0 Hz, OH), 0.89 (s, 9H, C(CH₃)₃).

To a solution of racemic (R/S)-1-(4-iodo-5-methoxy-2-nitrophenyl)-2,2-dimethyl-1-propanol (395 mg, 1.1 mmol) and DMAP (263 mg, 2.16 mmol) in anhydrous CH₂Cl₂ (5.0 mL), (1S)-camphanic chloride (Corrie et al., 1992, which is incorporated by reference) (350 mg, 1.62 mmol) was added, and the mixture was stirred overnight at room temperature under a nitrogen atmosphere. The reaction mixture was diluted with CH₂Cl₂ (50 mL) and washed with saturated NaHCO₃ solution (50 mL). The organic phase was dried over Na₂SO₄, concentrated in vacuo, and the residue was purified by silica gel column chromatography to yield (R/S)-1-(4-iodo-5-methoxy-2-nitrophenyl)-2,2-dimethyl-1-propyl(1S)-camphanate (490 mg, 80%, 1:1 mixture of diastereomers).

(R/S)-1-(4-Iodo-5-methoxy-2-nitrophenyl)-2,2-dimethyl-1-propyl(1S)-camphanate (3.4 g) was dissolved in boiling ethanol (150 ml), the solution was kept in a warm oil bath and slowly cooled to room temperature and stood overnight. Needle crystals were formed gradually and collected by filtration to yield pure single diastereomer (R)-1-(4-iodo-5-methoxy-2-nitrophenyl)-2,2-dimethyl-1-propyl(1S)-camphanate (870 mg, 51%). The remaining mother liquor was concentrated in vacuo, and the residue was dissolved again in boiling ethanol (150 ml), and the solution was quickly cooled to room temperature and needle crystals were formed within two hours. The crystals were collected by filtration to yield pure single diastereomer (S)-1-(4-iodo-5-methoxy-2-nitrophenyl)-2,2-dimethyl-1-propyl(1S)-camphanate. The crystallization process was repeated twice to yield additional pure (S)-diastereomer (total 1.07 g, 63%). $^1$H NMR (400 MHz, CDCl₃) for (R)-1-(4-iodo-5-methoxy-2-nitrophenyl)-2,2-dimethyl-1-propyl(1S)-camphanate: δ 8.48 (s, 1H, Ph-H), 6.94 (s, 1H, Ph-H), 6.84 (s, 1H, Ph-CH), 3.93 (s, 3H, OCH₃), 2.42 (m, 1H, CH), 2.11 (m, 1H, CH), 1.92 (m, 1H, CH₂), 1.75 (m, 1H, CH₂), 1.11 (s, 3H, CH₃), 1.05 (s, 3H, CH₃), 0.97 (s, 9H, C(CH₃)₃), 0.86 (s, 3H, CH₃). $^1$H NMR (400 MHz, CDCl₃) for (S)-1-(4-iodo-5-methoxy-2-nitrophenyl)-2,2-dimethyl-1-propyl(1S)-camphanate: δ 8.48 (s, 1H, Ph-H), 6.95 (s, 1H, Ph-H), 6.80 (s, 1H, Ph-CH), 3.96 (s, 3H, OCH₃), 2.37 (m, 1H, CH), 1.92 (m, 2H, CH₂), 1.66 (m, 1H, CH), 1.14 (s, 3H, CH₃), 1.07 (s, 3H, CH₃), 1.06 (s, 3H, CH₃), 0.98 (s, 9H, C(CH₃)₃).

A mixture of (S)-1-(4-iodo-5-methoxy-2-nitrophenyl)-2,2-dimethyl-1-propyl(1S)-camphanate (1.1 g, 2.0 mmol) and K₂CO₃ (552 mg, 4.0 mmol) in methanol (50 mL) was heated to reflux for one hour, then cooled down, concentrated in vacuo, and diluted with CH₂Cl₂ (50 mL). The organic phase was washed with brine (50 mL), dried over Na₂SO₄, concentrated in vacuo, and the residue was purified by silica gel column chromatography to yield enantiopure (S)-1-(4-iodo-5-methoxy-2-nitrophenyl)-2,2-dimethyl-1-propanol (720 mg, 98%). $^1$H NMR (400 MHz, CDCl₃): δ 8.32 (s, 1H, Ph-H), 7.17 (s, 1H, Ph-H), 5.60 (d, 1H, J=4.0 Hz, PhCH), 3.98 (s, 3H, OCH₃), 2.12 (d, 1H, J=4.0 Hz, OH), 0.89 (s, 9H, C(CH₃)₃).

Example 8

Dye-labeled tBu-5-OMe-2-nitrobenzyl Alkylated Hydroxymethyl Nucleotides Synthesis Synthesis of (R/S)-1-(4-iodo-5-methoxy-2-nitrophenyl)-2,2-dimethyl-1-propanol and (S)-1-(4-iodo-5-methoxy-2-nitrophenyl)-2,2-dimethyl-1-propanol Scheme S24.

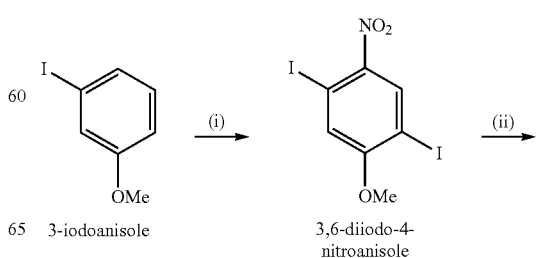

3-iodoanisole 3,6-diiodo-4-nitroanisole

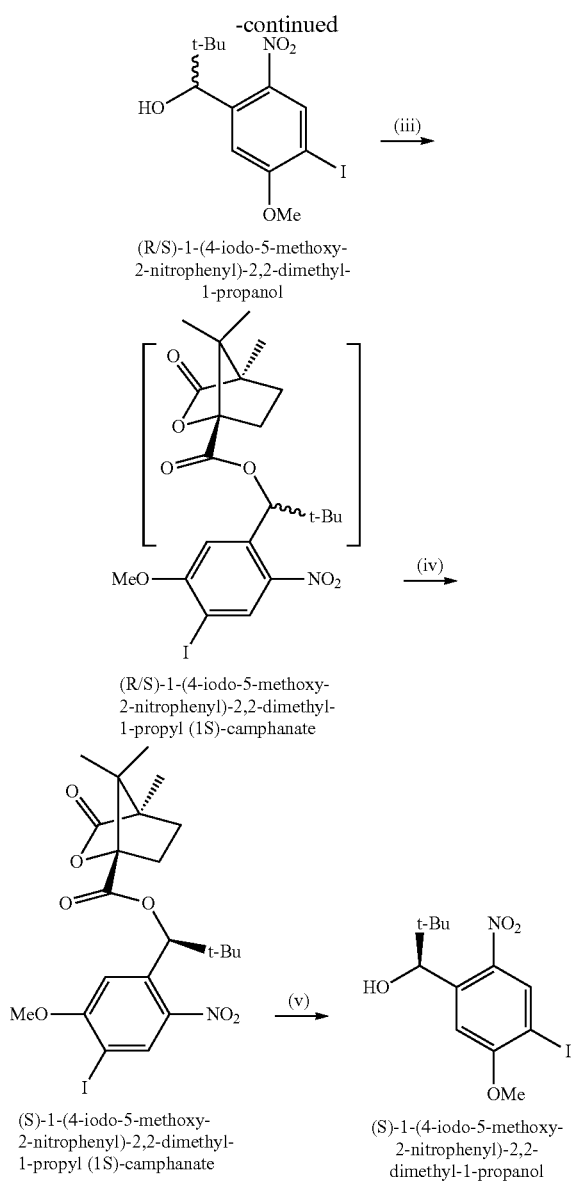

(R/S)-1-(4-iodo-5-methoxy-2-nitrophenyl)-2,2-dimethyl-1-propanol (R/S)-1-(4-iodo-5-methoxy-2-nitrophenyl)-2,2-dimethyl-1-propyl (1S)-camphanate (S)-1-(4-iodo-5-methoxy-2-nitrophenyl)-2,2-dimethyl-1-propyl (1S)-camphanate (S)-1-(4-iodo-5-methoxy-2-nitrophenyl)-2,2-dimethyl-1-propanol Synthesis of (R/S)-1-(4-iodo-5-methoxy-2-nitrophenyl)-2,2-dimethyl-1-propanol and (S)-1-(4-iodo-5-methoxy-2-nitrophenyl)-2,2-dimethyl-1-propanol. (i) NaNO₂, CH₃COOH, HNO₃, room temperature; I₂, 60° C., 25% for two steps (80% pure); (ii) PhMgCl, (CH₃)₃CCHO, THF, minus 40° C. to room temperature, 72%; (iii) (1S)-camphanic acid chloride, DMAP, CH₂Cl₂, room temperature, 80%; (iii) fractional crystallization from ethanol, 63%; (iv) K₂CO₃, MeOH, reflux, 98%.

Nitric acid (68-70%, 125 mL) was slowly mixed with glacial acetic acid (125 ml) at room temperature, followed by addition of NaNO₂ (400 mg, 5.8 mmol) and 3-iodoanisole (10 g, 42.7 mmol). After the reaction was stirred at room temperature for 24 hours, I₂ (10.8 g, 42.7 mmol) was added and the mixture was stirred at 60° C. overnight. The reaction mixture was poured into ice-water (500 ml) and extracted by CH₂Cl₂ (100 ml) three times. The combined organic phase was neutralized with saturated NaHCO₃ solution (500 ml), washed with aqueous solution of Na₂S₂O₃ (20%, 100 ml), dried over Na₂SO₄, and concentrated in vacuo. The residue was purified by silica gel column chromatography to yield crude 3,6-diiodo-4-nitroanisole (5.4 g), which is mixed with one unknown by-product (20%) and used in the next step without further purification. $^1$H NMR (400 MHz, CDCl₃): δ 8.42 (s, 1H, Ph-H), 7.33 (s, 1H, Ph-H), 3.97 (s, 3H, OCH₃).

To a solution of crude 3,6-diiodo-4-nitroanisole (770 mg, 80% purity, 1.52 mmol) in anhydrous THF (10 mL) at minus 40° C. under a nitrogen atmosphere, phenylmagnesium chloride (2 M in THF, 0.46 mL, 0.92 mmol) was added dropwise at a rate such that the temperature would not exceed minus 35° C. Upon completion of the addition, the mixture was stirred at minus 40° C. for two hours, followed by addition of trimethylacetaldehyde (0.22 mL, 1.97 mmol). The mixture was stirred at minus 30° C. for two hours and then at room temperature for another one hour. The reaction was then quenched with brine (1.0 mL), diluted with CH₂Cl₂ (100 mL), and the solution was washed with CH₃COOH (0.1 N, 50 ml) and brine (50 ml) sequentially. The organic phase was dried over Na₂SO₄, concentrated in vacuo, and the residue was purified by silica gel column chromatography to yield racemic (R/S)-1-(4-iodo-5-methoxy-2-nitrophenyl)-2,2-dimethyl-1-propanol (399 mg, 72%). $^1$H NMR (400 MHz, CDCl₃): δ 8.32 (s, 1H, Ph-H), 7.17 (s, 1H, Ph-H), 5.60 (d, 1H, J=4.0 Hz, PhCH), 3.98 (s, 3H, OCH₃), 2.12 (d, 1H, J=4.0 Hz, OH), 0.89 (s, 9H, C(CH₃)₃).

To a solution of racemic (R/S)-1-(4-iodo-5-methoxy-2-nitrophenyl)-2,2-dimethyl-1-propanol (395 mg, 1.1 mmol) and DMAP (263 mg, 2.16 mmol) in anhydrous CH₂Cl₂ (5.0 mL), (1S)-camphanic chloride (Corrie et al., 1992, which is incorporated by reference) (350 mg, 1.62 mmol) was added, and the mixture was stirred overnight at room temperature under a nitrogen atmosphere. The reaction mixture was diluted with CH₂Cl₂ (50 mL) and washed with saturated NaHCO₃ solution (50 mL). The organic phase was dried over Na₂SO₄, concentrated in vacuo, and the residue was purified by silica gel column chromatography to yield (R/S)-1-(4-iodo-5-methoxy-2-nitrophenyl)-2,2-dimethyl-1-propyl(1S)-camphanate (490 mg, 80%, 1:1 mixture of diastereomers).

(R/S)-1-(4-Iodo-5-methoxy-2-nitrophenyl)-2,2-dimethyl-1-propyl(1S)-camphanate (3.4 g) was dissolved in boiling ethanol (150 ml), the solution was kept in a warm oil bath and slowly cooled to room temperature and stood overnight. Needle crystals were formed gradually and collected by filtration to yield pure single diastereomer (R)-1-(4-iodo-5-methoxy-2-nitrophenyl)-2,2-dimethyl-1-propyl(1S)-camphanate (870 mg, 51%). The remaining mother liquor was concentrated in vacuo, and the residue was dissolved again in boiling ethanol (150 ml), and the solution was quickly cooled to room temperature and needle crystals were formed within two hours. The crystals were collected by filtration to yield pure single diastereomer (S)-1-(4-iodo-5-methoxy-2-nitrophenyl)-2,2-dimethyl-1-propyl(1S)-camphanate. The crystallization process was repeated twice to yield additional pure (S)-diastereomer (total 1.07 g, 63%). $^1$H NMR (400 MHz, CDCl₃) for (R)-1-(4-iodo-5-methoxy-2-nitrophenyl)-2,2-dimethyl-1-propyl(1S)-camphanate: δ 8.48 (s, 1H, Ph-H), 6.94 (s, 1H, Ph-H), 6.84 (s, 1H, Ph-CH), 3.93 (s, 3H, OCH₃), 2.42 (m, 1H, CH), 2.11 (m, 1H, CH), 1.92 (m, 1H, CH₂), 1.75 (m, 1H, CH₂), 1.11 (s, 3H, CH₃), 1.05 (s, 3H, CH₃), 0.97 (s, 9H, C(CH₃)₃), 0.86 (s, 3H, CH₃). $^1$H NMR (400 MHz, CDCl₃) for (S)-1-(4-iodo-5-methoxy-2-nitrophenyl)-2,2-dimethyl-1 propyl(1S)-camphanate: δ 8.48 (s, 1H, Ph-H), 6.95 (s, 1H, Ph-H), 6.80 (s, 1H, Ph-CH), 3.96 (s, 3H, OCH₃), 2.37 (m, 1H, CH), 1.92 (m, 2H, CH₂), 1.66 (m, 1H, CH), 1.14 (s, 3H, CH₃), 1.07 (s, 3H, CH₃), 1.06 (s, 3H, CH₃), 0.98 (s, 9H, C(CH₃)₃).

A mixture of (S)-1-(4-iodo-5-methoxy-2-nitrophenyl)-2,2-dimethyl-1-propyl(1S)-camphanate (1.1 g, 2.0 mmol) and K₂CO₃ (552 mg, 4.0 mmol) in methanol (50 mL) was heated to reflux for one hour, then cooled down, concentrated in vacuo, and diluted with CH₂Cl₂ (50 mL). The organic phase was washed with brine (50 mL), dried over Na₂SO₄, concentrated in vacuo, and the residue was purified by silica gel column chromatography to yield enantiopure (S)-1-(4-iodo-5-methoxy-2-nitrophenyl)-2,2-dimethyl-1-propanol (720 mg, 98%). $^1$H NMR (400 MHz, CDCl$_3$): δ 8.32 (s, 1H, Ph-H), 7.17 (s, 1H, Ph-H), 5.60 (d, 1H, J=4.0 Hz, PhCH), 3.98 (s, 3H, OCH$_3$), 2.12 (d, 1H, J=4.0 Hz, OH), 0.89 (s, 9H, C(CH$_3$)$_3$).

Synthesis of dye labeled 7-{(S)-1-[4-(3-amino-1-propynyl)-5-methoxy-2-nitrophenyl]-2,2-dimethyl-propyloxy}methyl-7-deaza-2'-deoxyadenosine-5'-triphosphate and 5'-α-thiotriphosphate Scheme S25a. Synthesis of dye labeled 7-{(S)-1-[4-3-amino-1-propynyl)-5-methoxy-2-nitrophenyl]-2,2-dimethyl-propyloxy}methyl-7-deaza-2'-deoxyadenosine-5'-triphosphate and 5'-α-thiotriphosphate.

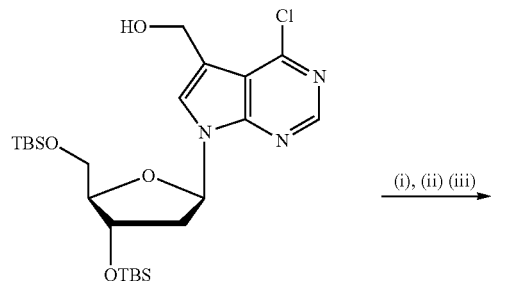

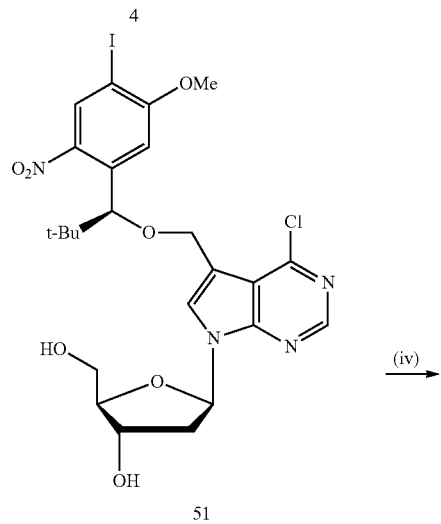

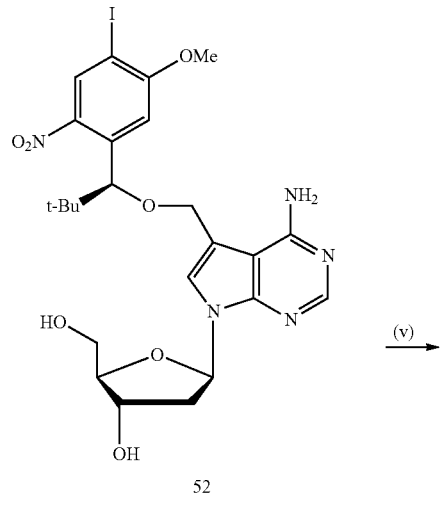

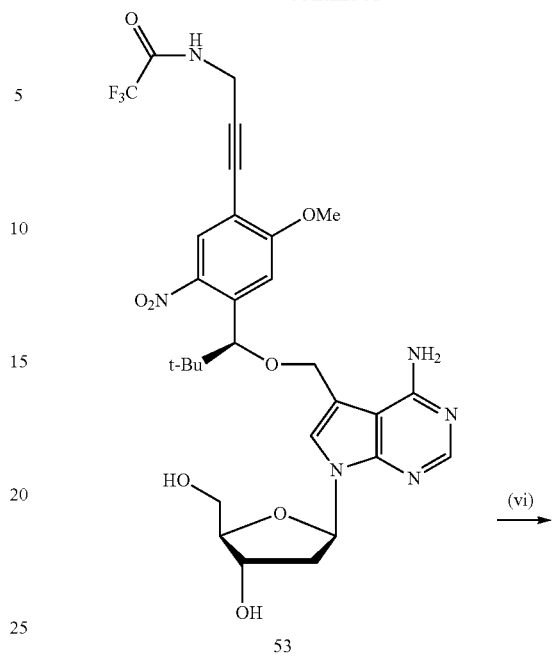

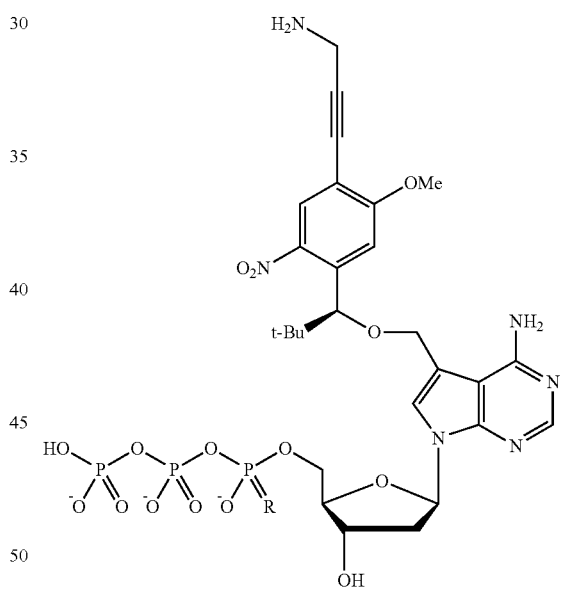

54a R = O
54b R = S

Reagents and conditions: (i) MsCl, DMAP, CH$_2$Cl$_2$, (ii) (S)-1-(4-iodo-5-methoxy-2-nitrophenyl)-2,2-dimethyl-1-propanol, 110° C.; (iii) n-Bu$_4$NF, THF, room temperature; 29% for three steps; (iv) NH$_3$, 1,4-dioxane/MeOH, 100° C., 80%; (v) N-propargyltrifluoroacetamide, Pd(PPh$_3$)$_4$(O), CuI, Et$_3$N, DMF, 98%; (vi) For 54a: POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$; NH$_4$OH. For 54b: PSCl$_3$, 2,4,6-collidine, (EtO)$_3$PO, 0° C. to room temperature; (n-Bu$_3$NH)$_2$H$_2$P$_2$O$_7$, n-Bu$_3$N, DMF; 1M HNEt$_3$HCO$_3$; NH$_4$OH.

Scheme S25b.

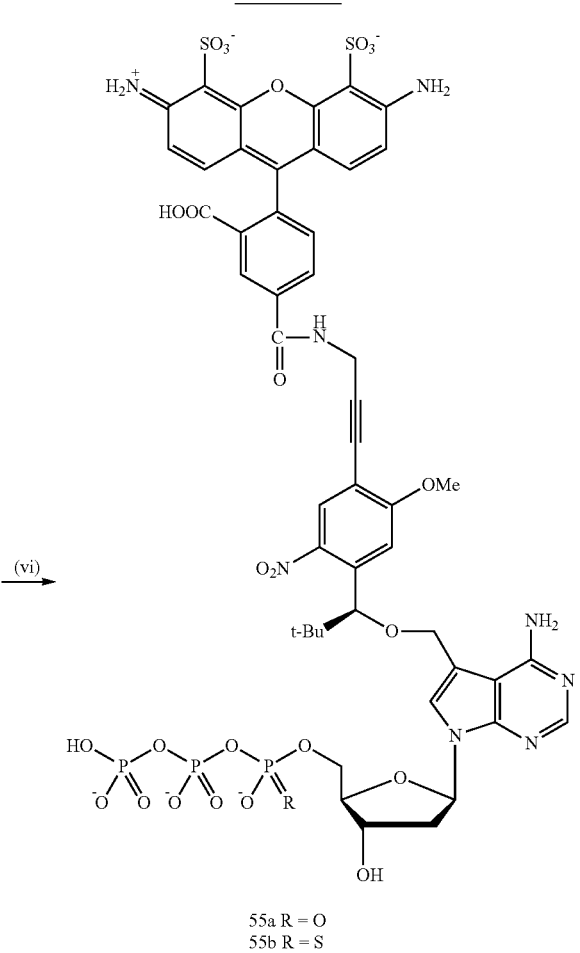

55a R = O
55b R = S (vi) Alexa Fluor 488 NHS, 0.1M Na₂CO₃/NaHCO₃ buffer (pH 9.2).

DMAP (463 mg, 3.80 mmol) and MsCl (177 µL, 2.28 mmol) were added to a solution of compound 4 (400 mg, 0.76 mmol) in anhydrous CH₂Cl₂ (5.0 mL) at 0° C. under a nitrogen atmosphere. The reaction was stirred at 0° C. for 10 mins and at room temperature for another 3 hours. The reaction was then diluted with CH₂Cl₂ (20 mL). The solution was applied on a short silica gel plug (2×3 cm) and was eluted quickly with a hexane/ethyl acetate/triethylamine solvent system (80 mL, volume ratio: 80/20/0.5). The eluent was concentrated in vacuo, and the residue was mixed with (S)-1-(4-iodo-5-methoxy-2-nitrophenyl)-2,2-dimethyl-1-propanol (500 mg, 1.37 mmol). The mixture was heated at 115° C. for 45 min under a nitrogen atmosphere, cooled to room temperature and dissolved in THF (10 mL). n-Bu₄NF (526 mg, 1.67 mmol) was added and the mixture was stirred at room temperature for 12 hours and then concentrated in vacuo. The residue was dissolved in CH₂Cl₂ (50 mL) and washed with brine (50 mL), and the aqueous phase was extracted with CH₂Cl₂ (20 mL) two times. The combined organic phase was dried over Na₂SO₄, concentrated in vacuo, and the residue was purified by silica gel chromatography to yield 6-chloro-9-(β-D-2'-deoxyribofuranosyl)-7-[(S)-1-(4-iodo-5-methoxy-2-nitrophenyl)-2,2-dimethyl-propyloxy]-methyl-7-deazapurine 51 (135 mg, 29% for three steps). ¹H NMR (400 MHz, CDCl₃): δ 8.56 (s, 1H, H-2), 8.21 (s, 1H, Ph-H), 7.34 (s, 1H, H-8), 7.02 (s, 1H, Ph-H), 6.35 (dd, 1H, J=6.0 and 8.8 Hz, H-1'), 5.20 (s, 1H, Ph-CH), 4.76 (dd, 2H, J=12.4 and 36.4 Hz, 7-CH₂), 4.74 (m, 1H, H-3'), 4.13 (m, 1H, H-4'), 3.96 (m, 1H, H-5'a), 3.92 (s, 3H, OCH₃), 3.80 (m, 1H, H-5'b), 2.85 (m, 1H, H-2'a), 2.30 (m, 1H, H-2'b), 0.83 (s, 9H, C(CH₃)₃).

Compound 51 (135 mg, 0.22 mmol) was dissolved in 1,4-dioxane (10 mL) followed by addition of NH₃ in MeOH (7 N, 20 mL). The mixture was transferred to a sealed tube and stirred at 100° C. for 24 hours, then cooled to room temperature, concentrated in vacuo, and the residue was purified by silica gel chromatography to yield 7-[(S)-1-(4-iodo-5-methoxy-2-nitrophenyl)-2,2-dimethyl-propyloxy]methyl-7-deaza-2'-deoxyadenosine 52 (110 mg, 80%). ¹H NMR (400 MHz, CDCl₃): δ 8.24 (s, 1H, H-2), 8.22 (s, 1H, Ph-H), 6.96 (s, 1H, Ph-H), 6.79 (s, 1H, H-8), 6.14 (dd, 1H, J=6.0 and 7.6 Hz, H-1'), 5.21 (s, 1H, Ph-CH), 4.74 (m, 1H, H-3'), 4.56 (dd, 2H, J=13.2 and 24.8 Hz, 7-CH₂), 4.17 (m, 1H, H-4'), 3.93 (m, 1H, H-5'a), 3.83 (s, 3H, OCH₃), 3.79 (m, 1H, H-5'b), 2.96 (m, 1H, H-2'a), 2.21 (m, 1H, H-2'b), 0.83 (s, 9H, C(CH₃)₃).

A solution of compound 52 (183 mg, 0.29 mmol), N-propargyltrifluoroacetylamide (435 mg, 2.9 mmol), tetrakis(triphenylphosphine)-palladium(0) (66 mg, 0.057 mmol), CuI (21 mg, 0.11 mmol), and Et₃N (170 µL, 1.22 mmol) in anhydrous DMF (4.0 mL) was stirred at 50° C. for 24 hours. The mixture was concentrated in vacuo and purified by silica gel column chromatography to yield 7-{(S)-1-[5-methoxy-4-(3-trifluoroacetamido-1-propynyl)-2-nitrophenyl]-2,2-dimethyl-propyloxy}methyl-7-deaza-2'-deoxyadenosine 53 (185 mg, 98%). ¹H NMR (400 MHz, MeOH-d₄): δ 8.06 (s, 1H, H-2), 7.89 (s, 1H, Ph-H), 7.17 (s, 1H, H-8), 7.15 (s, 1H, Ph-H), 6.37 (dd, 1H, J=6.0 and 7.6 Hz, H-1'), 5.23 (s, 1H, Ph-CH), 4.68 (d, 1H, J=12.8 Hz, 7-CH₂a), 4.49 (m, 1H, H-3'), 4.34 (s, 2H, CH₂), 3.97 (m, 1H, H-4'), 3.86 (s, 3H, OCH₃), 3.70 (m, 2H, H-5'), 2.59 (m, 1H, H-2'a), 2.2.8 (m, 1H, H-2'b), 0.85 (s, 9H, C(CH₃)₃).

Compound 53 (52 mg, 0.08 mmol) was phosphorylated with POCl₃ (14 µL, 0.15 mmol) and proton sponge (34 mg, 0.16 mmol) in trimethylphosphate (0.5 mL) at 0° C. for 3 hours under a nitrogen atmosphere. A solution of bis-tri-n-butylammonium pyrophosphate (237 mg, 0.5 mmol) and tri-n-butylamine (100 µL) in anhydrous DMF (1.0 mL) was added. After 10 min of stirring, triethylammonium bicarbonate solution (TEAB, 0.1 M, pH 7.5; 10 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing triphosphate were combined and lyophilized to dryness. The residue was dissolved in water (10 mL) and treated with concentrated ammonium hydroxide (10 mL, 27%) at room temperature for one hour to yield 7-{(S)-1-[4-(3-amino-1-propynyl)-5-methoxy-2-nitrophenyl]-2,2-dimethyl-propyloxy}methyl-7-deaza-2'-deoxyadenosine-5'-triphosphate 54a, which was further purified by reverse phase HPLC on a PerkinElmer Aquapore OD-300 column (7 µm, 250×4.6 mm). Mobile phase: A, 0.1 M TEAB; B, acetonitrile. HRMS (ESI): For the molecular ion C₂₇H₃₆N₆O₁₆P₃ [M–H]⁻, the calculated mass was 793.1401, and the observed mass was 793.1426.

Compound 53 (91 mg, 0.14 mmol) was thiophosphorylated with PSCl₃ (14 µL, 0.14 mmol) and 2,4,6-collidine (34 mg, 0.28 mmol) in triethylphosphate (1.0 mL) at 0° C. for 1 hour under a nitrogen atmosphere. A solution of bis-tri-n-butylammonium pyrophosphate (332 mg, 0.7 mmol) and tri-n-butylamine (140 µL) in anhydrous DMF (1.4 mL) was added. After 2 min of stirring, triethylammonium bicarbonate solution (TEAB, 1 M, pH 7.5; 20 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing thiotriphosphate were combined and lyophilized to dryness. The residue was dissolved in water (10 mL) and treated with concentrated ammonium hydroxide (10 mL, 27%) at room temperature for one hour to yield 7-{(S)-1-[4-(3-amino-1-propynyl)-5-methoxy-2-nitrophenyl]-2,2-dimethyl-propyloxy}methyl-7-deaza-2'-deoxyadenosine-5'-α-thiotriphosphate 54b, which was further purified by reverse phase HPLC on a PerkinElmer Aquapore OD-300 column (7 μm, 250×4.6 mm). Mobile phase: A, 0.1 M TEAB; B, acetonitrile. HRMS (ESI): For the molecular ion $C_{27}H_{36}N_6O_{15}P_3S$ [M−H]$^-$, the calculated mass was 809.1172, and the observed mass was 809.1155.

A solution of Alexa Fluor 488 NHS (5 mg, 7.8 μmol) in anhydrous DMSO (200 μL) was added to a solution of triphosphate Ma (1.6 μmol) in NaHCO$_3$/Na$_2$CO$_3$ buffer (0.1 M, pH 9.2, 0.4 mL). The mixture was left at room temperature in dark for one hour. The mixture was first purified by anion exchange HPLC on a Dionex DNApac PA200 column (250×4 mm). Mobile phase: A, 75% 0.1 M TEAB/25% acetonitrile; B, 75% 1.5 M TEAB/25% acetonitrile. The fractions containing dye labeled triphosphate 55a were combined and concentrated to small volume, and the product was further purified by reverse phase HPLC on a PerkinElmer Aquapore OD-300 column (7 μm, 250×4.6 mm). Mobile phase: A, 0.1 M TEAB; B, acetonitrile.

A solution of Alexa Fluor 488 NHS (5 mg, 7.8 μmol) in anhydrous DMSO (200 μL) was added to a solution of thiotriphosphate 54b (4.1 μmol) in NaHCO$_3$/Na$_2$CO$_3$ buffer (0.1 M, pH 9.2, 1.0 mL). The mixture was left at room temperature in dark for one hour. The mixture was first purified by anion exchange chromatography using a Q Sepharose FF column (2.5×10 cm). Mobile phase: A, 75% 0.1 M TEAB/25% acetonitrile; B, 75% 1.5 M TEAB/25% acetonitrile. The fractions containing dye labeled thiotriphosphate 55b were combined and lyophilized to dryness, and the product was further purified by reverse phase HPLC on a PerkinElmer Aquapore OD-300 column (7 μm, 250×4.6 mm). Mobile phase: A, 0.1 M TEAB; B, acetonitrile.

Synthesis of dye labeled 7-{(S)-1-[4-(3-amino-1-propynyl)-5-methoxy-2-nitrophenyl]-2,2-dimethyl-propyloxy}methyl-7-deaza-2'-deoxyguanosine-5'-triphosphate and 5'-α-thiotriphosphate Scheme S26a. Synthesis of dye labeld 7-{(S)-1-[4-(3-amino-1-propynyl)-5-methoxy-2-nitrophenyl]-2,2-dimethyl-propyloxy}methyl-7-deaza-2'-deoxyguanosine-5'-triphosphate and 5'-α-thiotriphosphate.

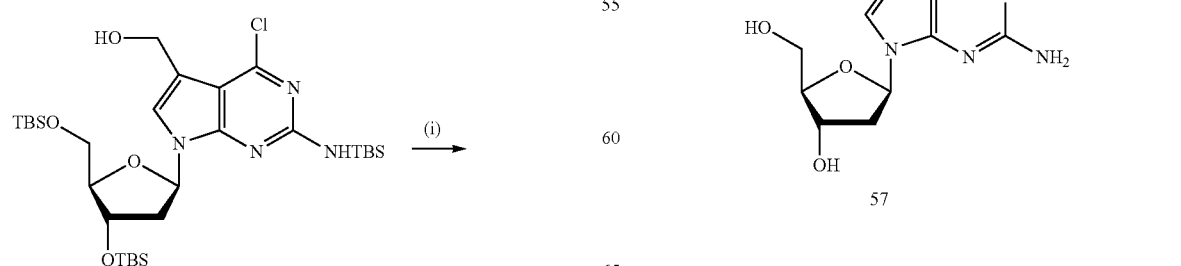

139
-continued

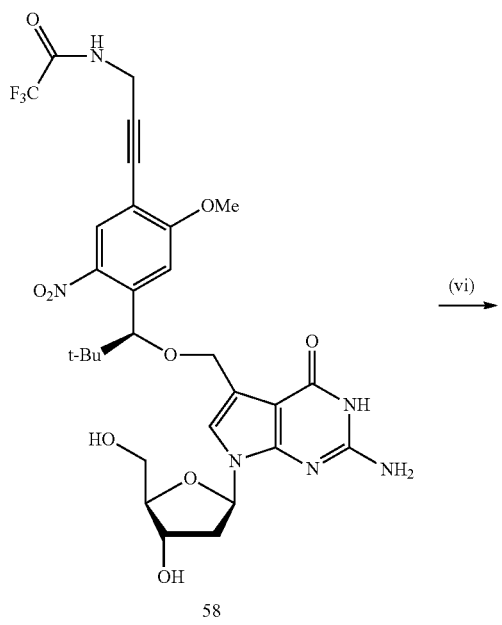

58

Scheme S26b.

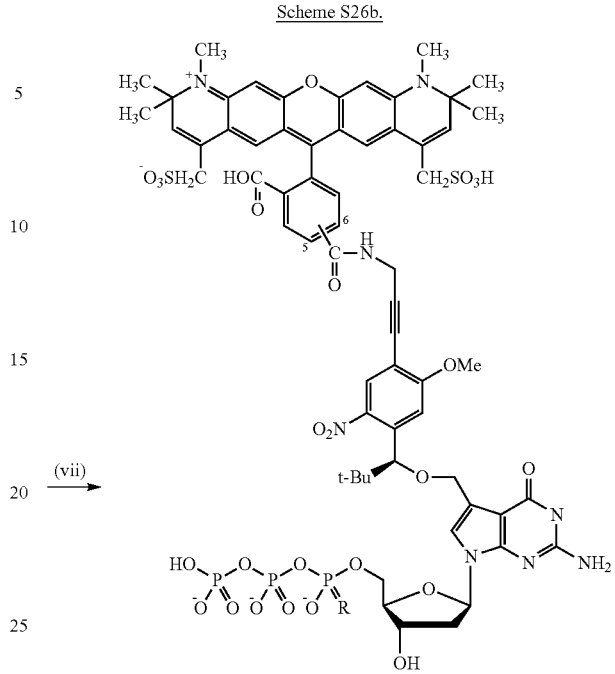

60a R = O
60b R = S (vii) Alexa Fluor 594 NHS, 0.1M Na$_2$CO$_3$/NaHCO$_3$ buffer (pH 9.2).

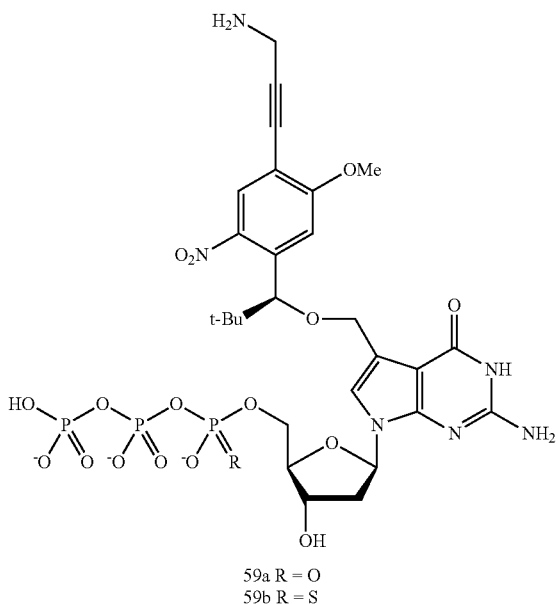

59a R = O
59b R = S

Reagents and conditions: (i) MsCl, DMAP, CH$_2$Cl$_2$, 0° C; (ii) (S)-1-(4-iodo-5-methoxy-2-nitrophenyl)-2,2-dimethyl-1-propanol, 115° C.; (iii) n-Bu$_4$NF, THF, room temperature; 18% for three steps; (iv) syn-pyridine-2-aldoxime, 1,1,3,3-tetramethyl guanidine, 1,4-dioxane/DMF, 70° C., 72%; (v) N- propargyltrifluoroacetamide, Pd(PPh$_3$)$_4$(0), CuI, Et$_3$N, DMF, 96%; (vi) For 59a: POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$; NH$_4$OH. For 59b: PSCl$_3$, 2,4,6-colidine, (EtO)$_3$PO, 0° C. to room temperature; (n-Bu$_3$NH)$_2$H$_2$P$_2$O$_7$, n-Bu$_3$N, DMF; 1M HNEt$_3$HCO$_3$; NH$_4$OH.

DMAP (502 mg, 4.1 mmol) and MsCl (238 µL, 3.1 mmol) were added to a solution of compound 18 (680 mg, 1.0 mmol) in anhydrous CH$_2$Cl$_2$ (6.0 mL) at 0° C. under a nitrogen atmosphere. The reaction was stirred at 0° C. for 10 min and then diluted with CH$_2$Cl$_2$ (20 mL). The solution was applied on a short silica gel plug (2×3 cm) and was eluted quickly with a hexane/ethyl acetate/triethylamine solvent system (80 mL, volume ratio: 80/20/0.5). The eluent was concentrated in vacuo, and the residue was mixed with (S)-1-(4-iodo-5-methoxy-2-nitrophenyl)-2,2-dimethyl-1-propanol (500 mg, 2.1 mmol). The mixture was heated at 115° C. for 45 min under a nitrogen atmosphere, cooled to room temperature and dissolved in THF (10 mL). n-Bu$_4$NF (1.07 g, 3.40 mmol) was added and the mixture was stirred at room temperature for 12 hours and then concentrated in vacuo. The residue was dissolved in CH$_2$Cl$_2$ (50 mL) and washed with brine (50 mL), and the aqueous phase was extracted with CH$_2$Cl$_2$ (20 mL) two times. The combined organic phase was dried over Na$_2$SO$_4$, concentrated in vacuo, and the residue was purified by silica gel chromatography to yield 2-amino-6-chloro-9-(β-D-2'-deoxyribofuranosyl)-7-[(S)-1-(4-iodo-5-methoxy-2-nitrophenyl)-2,2-dimethyl-propyloxy]-methyl-7-deazapurine 56 (125 mg, 18% for three steps). $^1$H NMR (400 MHz, CDCl$_3$): δ 8.24 (s, 1H, Ph-H), 7.04 (s, 1H, Ph-H), 6.91 (s, 1H, H-8), 6.17 (dd, 1H, J=6.0 and 8.4 Hz, H-1'), 5.18 (s, 1H, Ph-CH), 5.11 (br s, 2H, NH$_2$), 4.71 (m, 1H, H-3'), 4.59 (dd, 2H, J=12.4 and 24.4 Hz, 7-CH2), 4.13 (m, 1H, H-4'), 3.96 (s, 3H, OCH$_3$), 3.88 (m, 1H, H-5'a), 3.79 (m, 1H, H-5'b), 2.76 (m, 1H, H-2'a), 2.32 (m, 1H, H-2'b), 0.81 (s, 9H, (CH$_3$)$_3$).

To a solution of compound 56 (100 mg, 0.16 mmol) in 1,4-dioxane (1.5 mL) and DMF (3.0 mL), syn-pyrimidine-2-aldoxime (389 mg, 3.2 mmol) and 1,1,3,3-tetramethyl guanidine (439 µL, 3.5 mmol) were added, and the mixture was heated at 70° C. overnight under a nitrogen atmosphere. The reaction mixture was diluted with CH$_2$Cl$_2$ (20 mL) and washed sequentially with acetic acid solution (0.1 M, 50 mL), saturated NaHCO$_3$ solution (50 mL), and brine (50 mL). The organic phase was dried over Na$_2$SO$_4$, concentrated in vacuo, and the residue was purified by silica gel chromatography to yield 7-[(S)-1-(4-iodo-5-methoxy-2-nitrophenyl)-2,2-dimethyl-propyloxy]methyl-7-deaza-2'-deoxyguanosine 57 (70 mg, 72%). $^1$H NMR (400 MHz, MeOH-d$_4$): δ 8.20 (s, 1H, Ph-H), 7.17 (s, 1H, Ph-H), 6.82 (s, 1H, H-8), 6.18 (m, 1H, H-1'), 5.23 (s, 1H, Ph-CH), 4.71 (d, 1H, J=12.0 Hz, 7-CH$_2$a), 4.52 (d, 1H, J=12.0 Hz, 7-CH$_2$b), 4.43 (m, 1H, H-3'), 3.97 (s, 3H, OCH$_3$), 3.91 (m, 1H, H-4'), 3.71 (m, 2H, H-5'), 2.49 (m, 1H, H-2'a), 2.19 (m, 1H, H-2'b), 0.85 (s, 9H, (CH$_3$)$_3$).

A solution of compound 57 (50 mg, 0.08 mmol), N-propargyltrifluoroacetylamide (117 mg, 0.8 mmol), tetrakis(triphenylphosphine)-palladium(0) (18 mg, 0.02 mmol), CuI (5.9 mg, 0.03 mmol), and Et$_3$N (48 µL, 0.34 mmol) in anhydrous DMF (3.0 mL) was stirred at 50° C. for 12 hours. The mixture was concentrated in vacuo and the residue was purified by silica gel column chromatography to yield 7-{(S)-1-[5-methoxy-4-(3-trifluoroacetamido-1-propynyl)-2-nitrophenyl]-2,2-dimethyl-propyloxy}methyl-7-deaza-2'-deoxyguanosine 58 (50 mg, 96%). $^1$H NMR (400 MHz, MeOH-d$_4$): δ 7.87 (s, 1H, Ph-H), 7.26 (s, 1H, Ph-H), 6.84 (s, 1H, H-8), 6.20 (m, 1H, H-1'), 5.25 (s, 1H, Ph-CH), 4.67 (d, 1H, J=12.0 Hz, 7-CH$_2$a), 4.54 (d, 1H, J=12.0 Hz, 7-CH$_2$b), 4.43 (m, 1H, H-3'), 4.33 (s, 2H, CH$_2$), 3.95 (s, 3H, OCH$_3$), 3.89 (m, 1H, H-4'), 3.70 (m, 2H, H-5'), 2.46 (m, 1H, H-2'a), 2.18 (m, 1H, H-2'b), 0.86 (s, 9H, (CH$_3$)$_3$).

Compound 58 (52 mg, 0.08 mmol) was phosphorylated with POCl$_3$ (27 µL, 0.3 mmol) and proton sponge (33 mg, 0.16 mmol) in trimethylphosphate (0.35 mL) at 0° C. for 4 hours under a nitrogen atmosphere. A solution of bis-tri-n-butylammonium pyrophosphate (237 mg, 0.5 mmol) and tri-n-butylamine (100 µL) in anhydrous DMF (1.0 mL) was added. After 10 min of stirring, triethylammonium bicarbonate solution (TEAB, 0.1 M, pH 7.5; 10 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing triphosphate were combined and lyophilized to dryness. The residue was dissolved in water (10 mL) and treated with concentrated ammonium hydroxide (10 mL, 27%) at room temperature for one hour to yield 7-{(S)-1-[4-(3-amino-1-propynyl)-5-methoxy-2-nitrophenyl]-2,2-dimethyl-propyloxy}methyl-7-deaza-2'-deoxyguanosine-5'-triphosphate 59a, which was further purified by reverse phase HPLC on a PerkinElmer Aquapore OD-300 column (7 µm, 250×4.6 mm). Mobile phase: A, 0.1 M TEAB; B, acetonitrile. HRMS (ESI): For the molecular ion C$_{27}$H$_{36}$N$_6$O$_{17}$P$_3$ [M–H]$^-$, the calculated mass was 809.1350, and the observed mass was 809.1360.

Compound 59 (50 mg, 0.075 mmol) was thiophosphorylated with PSCl$_3$ (9 µL, 0.09 mmol) and 2,4,6-collidine (18 mg, 0.15 mmol) in triethylphosphate (0.5 mL) at room temperature for 2.5 hours under a nitrogen atmosphere. A solution of bis-tri-n-butylammonium pyrophosphate (237 mg, 0.5 mmol) and tri-n-butylamine (100 µL) in anhydrous DMF (1.0 mL) was added. After 2 min of stirring, triethylammonium bicarbonate solution (TEAB, 1 M, pH 7.5; 20 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing thiotriphosphate were combined and lyophilized to dryness. The residue was dissolved in water (10 mL) and treated with concentrated ammonium hydroxide (10 mL, 27%) at room temperature for one hour to yield 7-{(S)-1-[4-(3-amino-1-propynyl)-5-methoxy-2-nitrophenyl]-2,2-dimethyl-propyloxy}methyl-7-deaza-2'-deoxyguanosine-5'-α-thiotriphosphate 59b, which was further purified by reverse phase HPLC on a PerkinElmer Aquapore OD-300 column (7 µm, 250×4.6 mm). Mobile phase: A, 0.1 M TEAB; B, acetonitrile. HRMS (ESI): For the molecular ion C$_{27}$H$_{36}$N$_6$O$_{16}$P$_3$S [M–H]$^-$, the calculated mass was 825.1121, and the observed mass was 825.1103.

A solution of Alexa Fluor 594 NHS (4.2 mg, 5.2 µmol) in anhydrous DMSO (170 µL) was added to a solution of triphosphate 59a (2.2 µmol) in NaHCO$_3$/Na$_2$CO$_3$ buffer (0.1 M, pH 9.2, 0.5 mL). The mixture was left at room temperature in dark for one hour. The mixture was first purified by anion exchange HPLC on a Dionex DNApac PA200 column (250×4 mm). Mobile phase: A, 75% 0.1 M TEAB/25% acetonitrile; B, 75% 1.5 M TEAB/25% acetonitrile. The fractions containing dye labeled triphosphate 60a were combined and concentrated to small volume, and the product was further purified by reverse phase HPLC on a PerkinElmer Aquapore OD-300 column (7 µm, 250×4.6 mm). Mobile phase: A, 0.1 M TEAB; B, acetonitrile.

A solution of Alexa Fluor 594 NHS (5 mg, 6.2 µmol) in anhydrous DMSO (200 µL) was added to a solution of thiotriphosphate 59b (4.45 µmol) in NaHCO$_3$/Na$_2$CO$_3$ buffer (0.1 M, pH 9.2, 0.78 mL). The mixture was left at room temperature in dark for one hour. The mixture was first purified by anion exchange chromatography using a Q Sepharose FF column (2.5×10 cm). Mobile phase: A, 75% 0.1 M TEAB/25% acetonitrile; B, 75% 1.5 M TEAB/25% acetonitrile. The fractions containing dye labeled thiotriphosphate 60b were combined and concentrated to small volume, and the product was further purified by reverse phase HPLC on a PerkinElmer Aquapore OD-300 column (7 µm, 250×4.6 mm). Mobile phase: A, 0.1 M TEAB; B, acetonitrile.

Synthesis of dye labeled 5-{(S)-1-[4-(3-amino-1-propynyl)-5-methoxy-2-nitrophenyl]-2,2-dimethyl-propyloxy}methyl-2'-deoxyuridine-5'-triphosphate and 5'-α-thiotriphosphate Scheme S27a. Synthesis of dye labeled 5-{(S)-1-[4-(3-amino-1-propynyl)-5-methoxy-2-nitrophenyl]-2,2-dimethyl-propyloxy}methyl-2'-deoxyuridine-5'-triphosphate.

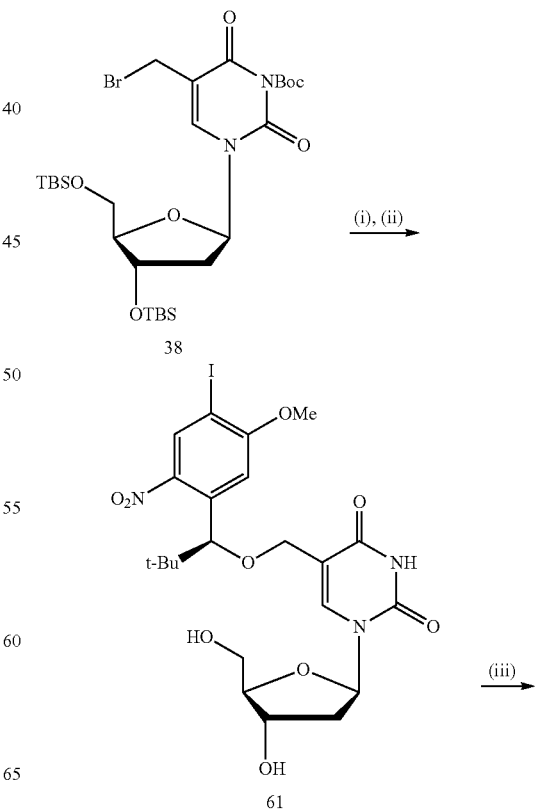

Scheme S27b.

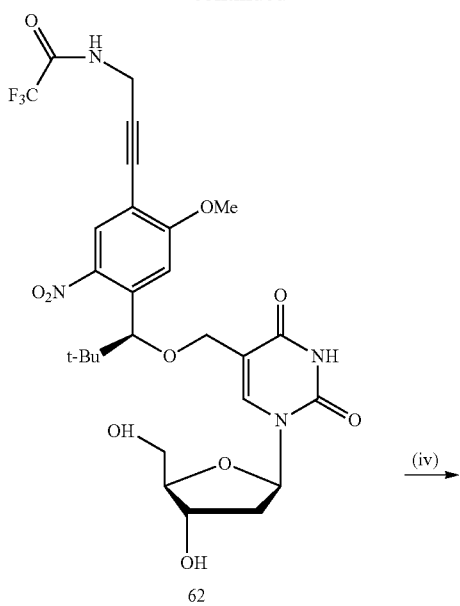

62

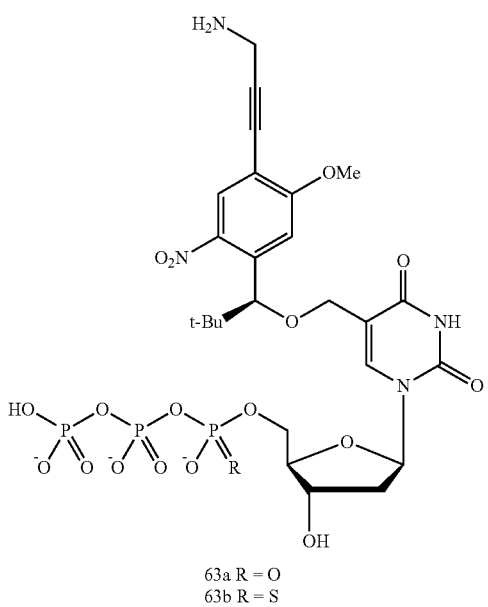

63a R = O
63b R = S

Reagents and conditions: (i) (S)-1-(4-iodo-5-methoxy-2-nitrophenyl)-2,2-dimethyl-1-propanol, 110° C.; (ii) NH$_4$F, MeOH, 50° C., 28% for two steps; (iii) N-propargyltrifluoroacetamide, Pd(PPh$_3$)$_4$(O), CuI, Et$_3$N, DMF, 90%; (iv) For 63a: POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$; NH$_4$OH. For 63b: PSCl$_3$, 2,6-lutidine, (EtO)$_3$PO, 0° C. to room temperature; (n-Bu$_3$NH)$_2$H$_2$P$_2$O$_7$, n-Bu$_3$N, DMF; 1M HNEt$_3$HCO$_3$; NH$_4$OH.

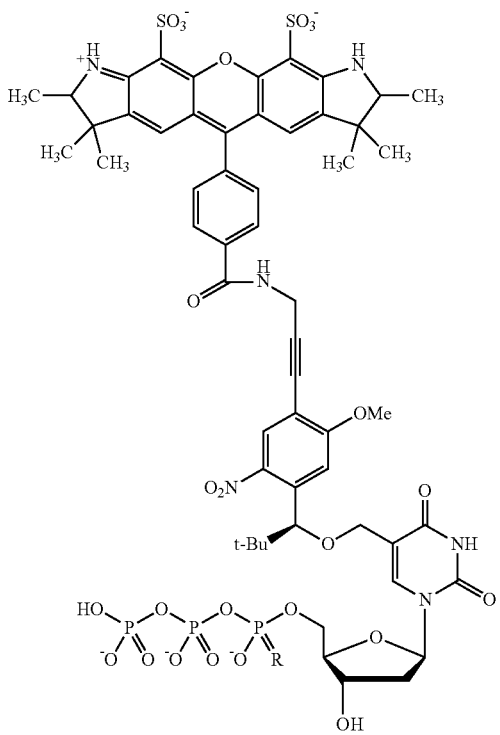

64a R = O
64b R = S (v) Alexa Fluor 532 NHS, 0.1M NaHCO$_3$/Na$_2$CO$_3$ buffer (pH 9.2).

Compound 38 (350 mg, 0.54 mmol) and (S)-1-(4-iodo-5-methoxy-2-nitrophenyl)-2,2-dimethyl-1-propanol (720 mg, 1.97 mmol) were heated at 110° C. for 45 min under a nitrogen atmosphere. The mixture was cooled down to room temperature, dissolved in MeOH (10 mL), and followed by addition of NH$_4$F (400 mg, 11.1 mmol). The mixture was stirred at 50° C. for 12 hours, concentrated in vacuo, dissolved in CH$_2$Cl$_2$ (50 mL), and washed with brine (50 mL). The organic phase was dried over Na$_2$SO$_4$, concentrated in vacuo, and the residue was purified by silica gel chromatography to yield 5-[(S)-1-(4-iodo-5-methoxy-2-nitrophenyl)-2,2-dimethyl-propyloxy]methyl-2'-deoxyuridine 61 (90 mg, 28%). $^1$H NMR (400 MHz, CDCl$_3$): δ 8.34 (s, 1H, Ph-H), 7.65 (s, 1H, H-6), 7.12 (s, 1H, Ph-H), 6.17 (t, 1H, J=6.8 Hz, H-1'), 5.18 (s, 1H, Ph-CH), 4.59 (m, 1H, H-3'), 4.27 (d, 1H, J=12.0 Hz, 5-CH$_2$a), 4.15 (d, 1H, J=12.0 Hz, 5-CH$_2$b), 4.00 (m, 1H, H-4'), 3.97 (s, 3H, OCH$_3$), 3.95 (m, 1H, H-5'a), 3.82 (m, 1H, H-5'b), 2.34 (m, 2H, H-2), 0.84 (s, 9H, C(CH$_3$)$_3$).

A solution of compound 61 (80 mg, 0.13 mmol), N-propargyltrifluoroacetylamide (196 mg, 1.30 mmol), tetrakis(triphenylphosphine)-palladium(0) (30 mg, 0.026 mmol), CuI (9.9 mg, 0.052 mmol), and Et$_3$N (80 μL) in anhydrous DMF (3.0 mL) was stirred at 50° C. for 12 hours. The mixture was concentrated in vacuo and the residue was purified by silica gel column chromatography to yield 5-{(S)-1-[5-methoxy-4-(3-trifluoroacetamido-1-propynyl)-2-nitrophenyl]-2,2-dimethyl-propyloxy}methyl-2'-deoxyuridine 62 (75 mg, 90%). $^1$H NMR (400 MHz, MeOD-d$_4$): δ 8.11 (s, 1H, H-6), 8.08 (s, 1H, Ph-H), 7.36 (s, 1H, Ph-H), 6.27 (t, 1H, J=6.4 Hz, H-1'), 5.33 (s, 1H, Ph-CH), 4.47 (m, 1H, H-3'), 4.44 (s, 2H, 5-CH$_2$), 4.32 (d, 2H, J=2.0 Hz, CH2), 4.08 (s, 3H, OCH$_3$), 3.99 (m, 1H, H-4'), 3.87 (m, 1H, H-5'a), 3.79 (m, 1H, H-5'b), 2.30 (m, 2H, H-2), 0.93 (s, 9H, C(CH$_3$)$_3$).

Compound 62 (40 mg, 0.064 mmol) was phosphorylated with POCl$_3$ (21 μL, 0.22 mmol) and proton sponge (27 mg, 0.13 mmol) in trimethylphosphate (0.35 mL) at 0° C. for 4 hours under a nitrogen atmosphere. A solution of bis-tri-n-butylammonium pyrophosphate (237 mg, 0.5 mmol) and tri-n-butylamine (100 μL) in anhydrous DMF (1.0 mL) was added. After 10 min of stirring, triethylammonium bicarbonate solution (TEAB, 0.1 M, pH 7.5; 10 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing triphosphate were combined and lyophilized to dryness. The residue was dissolved in water (10 mL) and treated with concentrated ammonium hydroxide (10 mL, 27%) at room temperature for one hour to yield 5-{(S)-1-[4-(3-amino-1-propynyl)-5-methoxy-2-nitrophenyl]-2,2-dimethyl-propyloxy}methyl-2'-deoxyuridine-5'-triphosphate 63a, which was further purified by reverse phase HPLC on a PerkinElmer Aquapore OD-300 column (7 μm, 250×4.6 mm). Mobile phase: A, 0.1 M TEAB; B, acetonitrile.

Compound 62 (130 mg, 0.21 mmol) was thiophosphorylated with PSCl$_3$ (26 μL, 0.25 mmol) and 2,6-lutidine (89 mg, 0.84 mmol) in triethylphosphate (0.6 mL) at room temperature for 1 hour under a nitrogen atmosphere. A solution of bis-tri-n-butylammonium pyrophosphate (474 mg, 1.0 mmol) and tri-n-butylamine (200 μL) in anhydrous DMF (2.0 mL) was added. After 2 min of stirring, triethylammonium bicarbonate solution (TEAB, 1 M, pH 7.5; 20 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing thiotriphosphate were combined and lyophilized to dryness. The residue was dissolved in water (10 mL) and treated with concentrated ammonium hydroxide (10 mL, 27%) at room temperature for one hour to yield 5-{(S)-1-[4-(3-amino-1-propynyl)-5-methoxy-2-nitrophenyl]-2,2-dimethyl-propyloxy}methyl-2'-deoxyuridine-5'-α-thiotriphosphate 63b, which was further purified by reverse phase HPLC on a PerkinElmer Aquapore OD-300 column (7 μm, 250×4.6 mm). Mobile phase: A, 0.1 M TEAB; B, acetonitrile. HRMS (ESI): For the molecular ion C$_{25}$H$_{34}$N$_4$O$_{17}$P$_3$S [M–H]$^-$, the calculated mass was 787.0853, and the observed mass was 787.0884.

A solution of Alexa Fluor 532 NHS (2 mg, 2.76 μmol) in anhydrous DMSO (80 μL) was added to a solution of triphosphate 62a (1.07 μmol) in NaHCO$_3$/Na$_2$CO$_3$ buffer (0.1 M, pH 9.2, 0.3 mL). The mixture was left at room temperature in dark for one hour. The mixture was first purified by anion exchange HPLC on a Dionex DNApac PA200 column (250×4 mm). Mobile phase: A, 75% 0.1 M TEAB/25% acetonitrile; B, 75% 1.5 M TEAB/25% acetonitrile. The fractions containing dye labeled triphosphate 63a were combined and concentrated to small volume, and the product was further purified by reverse phase HPLC on a PerkinElmer Aquapore OD-300 column (7 μm, 250×4.6 mm). Mobile phase: A, 0.1 M TEAB; B, acetonitrile.

A solution of Alexa Fluor 532 NHS (2.5 mg, 3.45 μmol) in anhydrous DMSO (100 μL) was added to a solution of thiotriphosphate 62b (1.03 μmol) in NaHCO$_3$/Na$_2$CO$_3$ buffer (0.1 M, pH 9.2, 0.15 mL). The mixture was left at room temperature in dark for one hour. The mixture was first purified by anion exchange chromatography using a Q Sepharose FF column (2.5×10 cm). Mobile phase: A, 75% 0.1 M TEAB/25% acetonitrile; B, 75% 1.5 M TEAB/25% acetonitrile. The fractions containing dye labeled thiotriphosphate 63b were combined and lyophilized to dryness, and the product was further purified by reverse phase HPLC on a PerkinElmer Aquapore OD-300 column (7 μm, 250×4.6 mm). Mobile phase: A, 0.1 M TEAB; B, acetonitrile.

Synthesis of dye labeled 5-{(S)-1-[4-(3-amino-1-propynyl)-5-methoxy-2-nitrophenyl]-2,2-dimethyl-propyloxy}methyl-2'-deoxycytidine-5'-triphosphate and 5'-α-thiotriphosphate Scheme S28a. Synthesis of dye labeled 5-{(S)-1-[4-(3-amino-1-propynyl)-5-methoxy-2-nitrophenyl]-2,2-dimethyl-propyloxy}methyl-2'-deoxycytidine-5'-triphosphate.

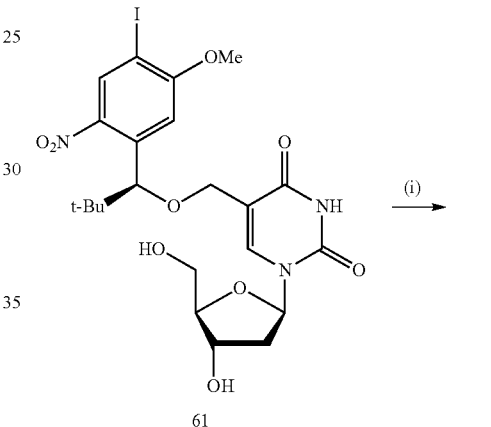

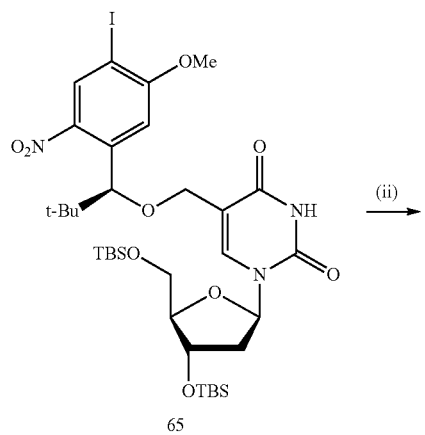

147
-continued

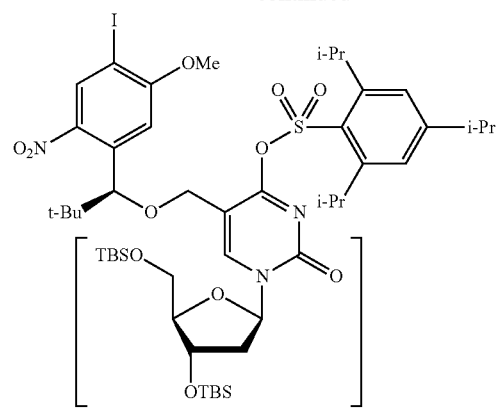

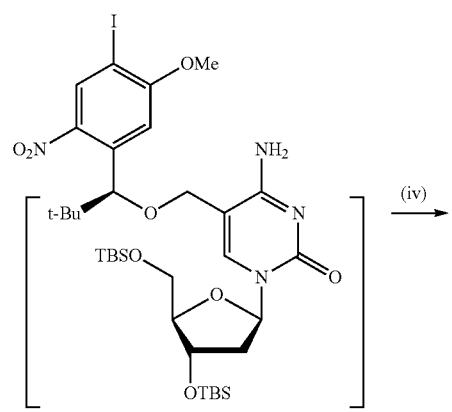

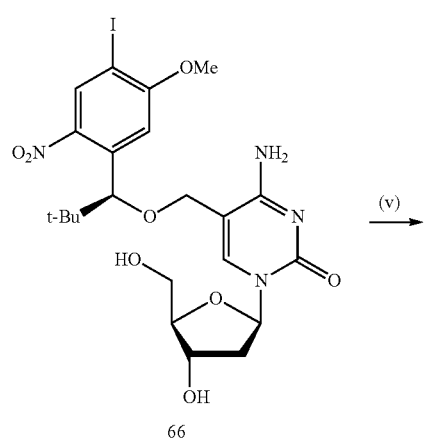

66

148
-continued

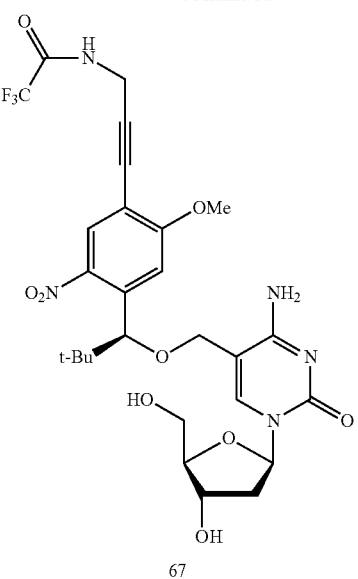

67

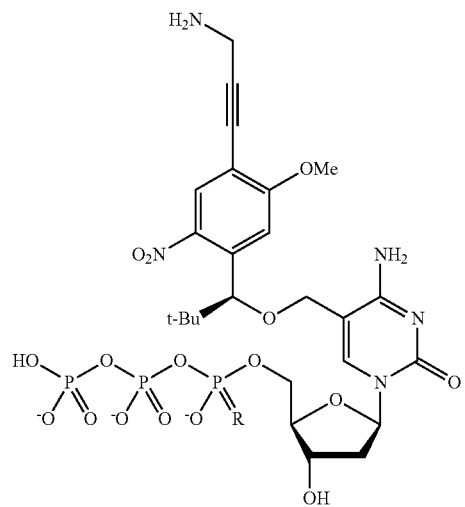

68a R = O
68b R = S

Reagents and conditions: (i) TBSCl, imidazole, DMF, room temperature, 96%; (ii) 2,4,6-triisopropylbenzenesulfonyl chloride, DMAP, Et$_3$N, CH$_2$Cl$_2$, room temperature; (iii) NH$_3$, 1,4-dioxane, 90° C.; (iv) n-Bu$_4$NF, THF, room temperature, 83% for three steps; (v) N-propargyltrifluoroacetamide, Pd(PPh$_3$)$_4$(0), CuI, Et$_3$N, DMF, 91%; (vi) For 68a: POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$; NH$_4$OH. For 68b: PSCl$_3$, 2,6-lutidine, (EtO)$_3$PO, 0° C.; (n-Bu$_3$NH)$_2$H$_2$P$_2$O$_7$, n-Bu$_3$N, DMF; 1M HNEt$_3$HCO$_3$; NH$_4$OH.

Scheme S28b.

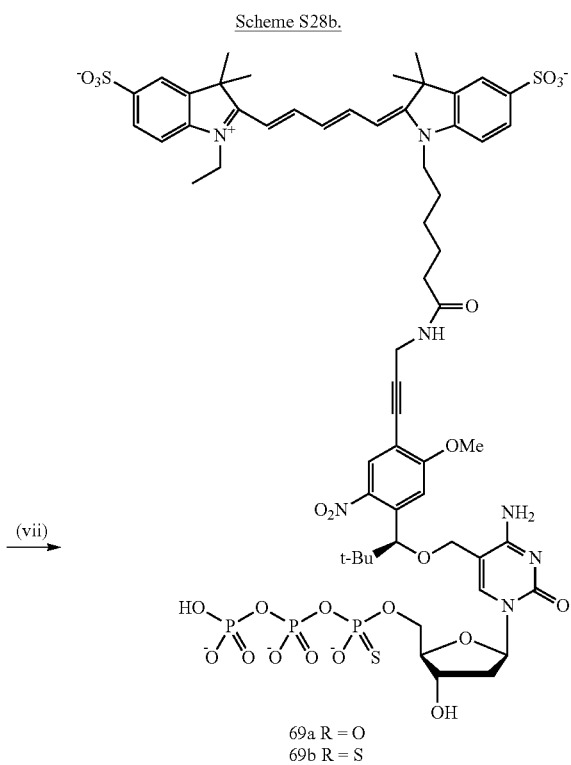

69a R = O
69b R = S (vii) Cy5 NHS, 0.1M Na$_2$CO$_3$/NaHCO$_3$ buffer (pH 9.2).

To a solution of compound 61 (295 mg, 0.49 mmol) in anhydrous DMF (5.0 mL), TBSCl (185 mg, 1.23 mmol) and imidazole (160 mg, 2.35 mmol) were added. The mixture was stirred at room temperature for 12 hours, concentrated in vacuo, and dissolved in CH$_2$Cl$_2$ (50 mL). The solution was washed with saturated NaHCO$_3$ solution (50 mL) and the aqueous phase was extracted with CH$_2$Cl$_2$ (30 mL) three times. The combined organic phase was dried with Na$_2$SO$_4$, concentrated in vacuo, and the residue was purified by silica gel chromatography to yield 3',5'-O-bis-(tert-butyldimethylsilyl)-5-[(S)-1-(4-iodo-5-methoxy-2-nitrophenyl)-2,2-dimethyl-propyloxy]methyl-2'-deoxyuridine 65 (400 mg, 96%). $^1$H NMR (400 MHz, CDCl$_3$): δ 8.32 (s, 1H, Ph-H), 7.64 (s, 1H, H-6), 7.12 (s, 1H, Ph-H), 6.12 (t, 1H, J=6.8 Hz, H-1'), 5.20 (s, 1H, Ph-CH), 4.60 (m, 1H, H-3'), 4.25 (d, 1H, J=12.0 Hz, 5-CH$_2$a), 4.14 (d, 1H, J=12.0 Hz, 5-CH$_2$b), 4.02 (m, 1H, H-4'), 3.97 (s, 3H, OCH$_3$), 3.94 (m, 1H, H-5'a), 3.83 (m, 1H, H-5'b), 2.34 (m, 2H, H-2), 0.90 and 88 (2 s, 18H, SiC(CH$_3$)$_3$), 0.84 (s, 9H, C(CH$_3$)$_3$), 0.08 (3 s, 12H, CH$_3$).

2,4,6-Triisopropyl benzenesulfonyl chloride (581 mg, 1.92 mmol) was added to a solution of compound 65 (400 mg, 0.48 mmol), DMAP (64 mg, 0.53 mmol), and triethylamine (0.60 mL, 4.32 mmol) in anhydrous CH$_2$Cl$_2$ (15 mL). The mixture was stirred at room temperature overnight under a nitrogen atmosphere, concentrated in vacuo, and the residue was dissolved in a solution of NH$_3$ in 1,4-dioxane (0.5 M, 20 mL). The mixture was transferred into a sealed tube and was heated at 90° C. overnight. The reaction was then cooled to room temperature, concentrated in vacuo, and the residue was dissolved in THF (8.0 mL) followed by addition of n-Bu$_4$NF (333 mg, 1.06 mmol). The mixture was stirred at room temperature for four hours, concentrated in vacuo, and the residue was purified by silica gel column chromatography to yield 5-[(S)-1-(4-iodo-5-methoxy-2-nitrophenyl)-2,2-dimethyl-propyloxy]methyl-2'-deoxycytidine 66 (240 mg, 83% for three steps in total). $^1$H NMR (400 MHz, MeOD-d$_4$): δ 8.33 (s, 1H, Ph-H), 7.91 (s, 1H, H-6), 7.10 (s, 1H, Ph-H), 6.16 (t, 1H, J=6.4 Hz, H-1'), 5.19 (s, 1H, Ph-CH), 4.41 (d, 1H, J=12.4 Hz, 5-CH$_2$a), 4.33 (m, 1H, H-3'), 4.26 (d, 1H, J=12.4 Hz, 5-CH$_2$b), 3.97 (s, 3H, OCH$_3$), 3.88 (m, 1H, H-4'), 3.70 (m, 2H, H-5'), 2.34 (m, 1H, H-2'a), 2.17 (m, 1H, H-2'b), 0.84 (s, 9H, C(CH$_3$)$_3$).

A solution of compound 66 (245 mg, 0.4 mmol), N-propargyltrifluoroacetylamide (603 mg, 4.0 mmol), tetrakis(triphenylphosphine)-palladium(0) (92 mg, 0.8 mmol), CuI (30 mg, 0.16 mmol), and Et$_3$N (240 µL, 1.7 mmol) in anhydrous DMF (5.0 mL) was stirred at 50° C. for 12 hours. The mixture was concentrated in vacuo and purified by silica gel column chromatography to yield 5-{(S)-1-[5-methoxy-4-(3-trifluoroacetamido-1-propynyl)-2-nitrophenyl]-2,2-dimethyl-propyloxy}methyl-2'-deoxycytidine 67 (230 mg, 91%). $^1$H NMR (400 MHz, MeOD-d$_4$): δ 7.98 (s, 1H, Ph-H), 7.92 (s, 1H, H-6), 7.19 (s, 1H, Ph-H), 6.15 (t, 1H, J=6.4 Hz, H-1'), 5.21 (s, 1H, Ph-CH), 4.41 (d, 1H, J=13.2 Hz, 5-CH$_2$a), 4.33 (m, 3H, H-3' and CH$_2$), 4.27 (d, 1H, J=13.2 Hz, 5-CH$_2$b), 3.96 (s, 3H, OCH$_3$), 3.88 (m, 1H, H-4'), 3.72 (m, 2H, H-5'), 2.30 (m, 1H, H-2'a), 2.12 (m, 1H, H-2'b), 0.84 (s, 9H, C(CH$_3$)$_3$).

Compound 67 (45 mg, 0.072 mmol) was phosphorylated with POCl$_3$ (15 µL, 0.16 mmol) and proton sponge (31 mg, 0.14 mmol) in trimethylphosphate (0.35 mL) at 0° C. for 4 hours under a nitrogen atmosphere. A solution of bis-tri-n-butylammonium pyrophosphate (237 mg, 0.5 mmol) and tri-n-butylamine (100 µL) in anhydrous DMF (1.0 mL) was added. After 10 min of stirring, triethylammonium bicarbonate solution (TEAB, 0.1 M, pH 7.5; 10 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing triphosphate were combined and lyophilized to dryness. The residue was dissolved in water (10 mL) and treated with concentrated ammonium hydroxide (10 mL, 27%) at room temperature for one hour to yield 5-{(S)-1-[4-(3-amino-1-propynyl)-5-methoxy-2-nitrophenyl]-2,2-dimethyl-propyloxy}methyl-2'-deoxycytidine-5'-triphosphate 68a, which was further purified by reverse phase HPLC on a PerkinElmer Aquapore OD-300 column (7 µm, 250×4.6 mm). Mobile phase: A, 0.1 M TEAB; B, acetonitrile. HRMS (ESI): For the molecular ion C$_{25}$H$_{35}$N$_5$O$_{17}$P$_3$ [M–H]$^-$, the calculated mass was 770.1241, and the observed mass was 770.1234.

Compound 67 (118 mg, 0.19 mmol) was thiophosphorylated with PSCl$_3$ (24 µL, 0.23 mmol) and 2,6-lutidine (80 mg, 0.75 mmol) in triethylphosphate (0.5 mL) at 0° C. for 1 hour under a nitrogen atmosphere. A solution of bis-tri-n-butylammonium pyrophosphate (474 mg, 1.0 mmol) and tri-n-butylamine (200 µL) in anhydrous DMF (2.0 mL) was added. After 2 min of stirring, triethylammonium bicarbonate solution (TEAB, 1 M, pH 7.5; 20 mL) was added. The reaction was stirred at room temperature for one hour and then concentrated in vacuo. The residue was dissolved in 75% 0.1 M TEAB/25% acetonitrile (20 mL), filtered, and purified by anion exchange chromatography using a Q Sepharose FF column (2.5×20 cm). Mobile phase: A, 75% 0.1 M TEAB/25% acetonitrile; B, 75% 1.5 M TEAB/25% acetonitrile. The fractions containing thiotriphosphate were combined and lyophilized to dryness. The residue was dissolved in water (10 mL) and treated with concentrated ammonium hydroxide (10 mL, 27%) at room temperature for one hour to yield 5-{(S)-1-[4-(3-amino-1-propynyl)-5-methoxy-2-nitrophenyl]-2,2-dimethyl-propyloxy}methyl-2'-deoxycytidine-5'-α-thiotriphosphate 68b, which was further purified by reverse phase HPLC on a PerkinElmer Aquapore OD-300 column (7 µm, 250×4.6 mm). Mobile phase: A, 0.1 M TEAB; B, acetonitrile. HRMS (ESI): For the molecular ion $C_{25}H_{35}N_5O_{16}P_3S$ [M−H]⁻, the calculated mass was 786.1012, and the observed mass was 786.0983.

A solution of Cy5 NHS (5 mg, 6.3 µmol) in anhydrous DMSO (200 µL) was added to a solution of triphosphate 68a (1.59 µmol) in NaHCO$_3$/Na$_2$CO$_3$ buffer (0.1 M, pH 9.2, 0.35 mL). The mixture was left at room temperature in dark for one hour. The dye labeled triphosphate was first purified by anion exchange HPLC on a Dionex DNApac PA200 column (250×4 mm). Mobile phase: A, 75% 0.1 M TEAB/25% acetonitrile; B, 75% 1.5 M TEAB/25% acetonitrile. The fractions containing dye labeled triphosphate 69a were combined and concentrated to small volume, and the product was further purified by reverse phase HPLC on a PerkinElmer Aquapore OD-300 column (7 µm, 250×4.6 mm). Mobile phase: A, 0.1 M TEAB; B, acetonitrile.

A solution of Cy5 NHS (5 mg, 6.3 µmol) in anhydrous DMSO (200 µL) was added to a solution of thiotriphosphate 68b (2.96 µmol) in NaHCO$_3$/Na$_2$CO$_3$ buffer (0.1 M, pH 9.2, 0.53 mL). The mixture was left at room temperature in dark for one hour. The dye labeled thiotriphosphate was first purified by anion exchange chromatography using a Q Sepharose FF column (2.5×10 cm). Mobile phase: A, 75% 0.1 M TEAB/25% acetonitrile; B, 75% 1.5 M TEAB/25% acetonitrile. The fractions containing dye labeled thiotriphosphate 69b were combined and lyophilized to dryness, and the product was further purified by reverse phase HPLC on a PerkinElmer Aquapore OD-300 column (7 µm, 250×4.6 mm). Mobile phase: A, 0.1 M TEAB; B, acetonitrile.

All of the methods disclosed and claimed herein can be made and executed without undue experimentation in light of the present disclosure. While the compositions and methods of this invention have been described in terms of certain embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 9

UV Photocleavage Studies

The rate of UV photocleavage was found to be dependent on a number of experimental factors including light intensity. See McCray et al. (1980) and McGall et al. (1997), which are both incorporated herein by reference. To compare the rates of photochemical cleavage between the nucleotide analogs described here, a protocol was developed to deliver a daily light intensity output of 0.70±0.01 W/cm² to samples, see below. A custom-designed UV deprotector used in these studies has been previously described in Wu et al. (2007), which is incorporated herein by reference, and the protocol implemented is described below.

UV Deprotector Set-Up:

The power supply was turned on for about 30 min prior to that of the lamp and recirculation bath as described by the manufacturer. The IR liquid filter was cooled to 9° C. Light intensity was determined using a model PM100 power meter (Thorlabs), a 1000 µm pinhole (Edmund Optics), a modified 0.5 mL Eppendorf tube cut in half, and a 3-axis manual translation stage (Newport), see FIG. 5. The half cut Eppendorf tube was positioned in front of the pinhole and power meter detector head to account for the geometric shape distortion of the light as it passes through a reaction solution. The translation stage was then used to align the tube/pinhole/detector device with the highest intensity from the arc beam.

Intensity Adjustment to 0.7 W/cm²:

To stabilize its output, the lamp was left on for one hour prior to intensity measurements. Thereafter, the measured power was adjusted by increasing the current from the power supply. In order to achieve intensity (I) of 0.70 W/cm², the measured power (P) was adjusted to ~5.5 mW, according to the equation:

$$I = \frac{P}{\pi \times r^2}$$

where r is the radius of pinhole. Power readings are recorded over a five minute period (in one second intervals) and were converted into intensity readings, which ranged over a six week period between 0.68±0.01 and 0.72±0.02 W/cm².

Beam Alignment with the 0.5 mL Tube Holder:

The modified Eppendorf tube, pin hole and power meter were then removed from the UV deprotector, and the rotating sample holder was installed with the height being 67.18±0.25 mm. The beam was then focused by placing an 0.5 mL Eppendorf tube into the sample holder, the tube of which was modified with an internal alignment card to provide reference lines for volume heights of 10 µL and 20 µL, see FIG. 5. The reference lines enabled the beam to be centered for a given reaction volume. Beam alignment was further verified by observing the mercury arc image of the lamp produced by the rear reflector. A second alignment card was placed into the rotating sample holder to view the image, which when properly aligned using the reflector would produce an inverted arc image on the arc gap itself. This step ensured that arc hotspots were not superimposed, which could cause overheating while maintaining a power output of ~5.5 mW. The speed of the rotating sample holder was adjusted within a range of 1,200-1,350 rpm using a Nova-Strobe DA Plus stroboscope (Monarch Instrument) by adjusting the motor's torque with an adjustment screw.

Figure 4:
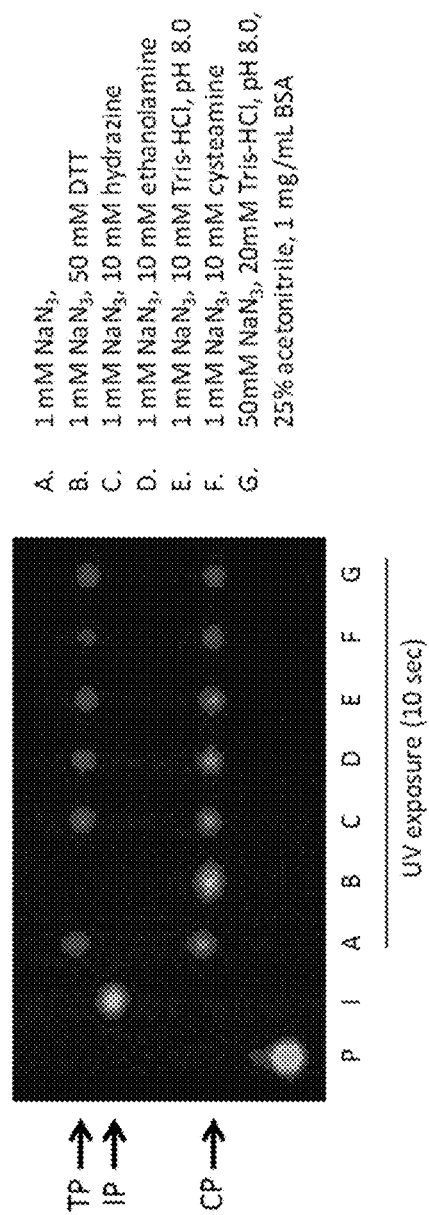
FIG. 4—DTT Eliminates the Nitroso Intermediate (TP). Fluorescent gel image of UV photochemical cleavage experiment of dU.VI incorporated by Therminator™ polymerase. Lanes: "P" (primer) contains Therminator™ bound to oligoTemplate-4 hybridized with BODIPY-FL labeled primer-1 in 1× ThermoPol buffer, "I" (incorporation) contains that found in lane "P" plus 100 nM dU.VI. Reagents A-G listed as final concentrations in the key were added, and samples were exposed to 0.70 W/cm² 365 nm light for 10 sec. "IP" denotes incorporated product, "P" denotes cleaved product, and "TP" denotes transient product.
Figure 6:
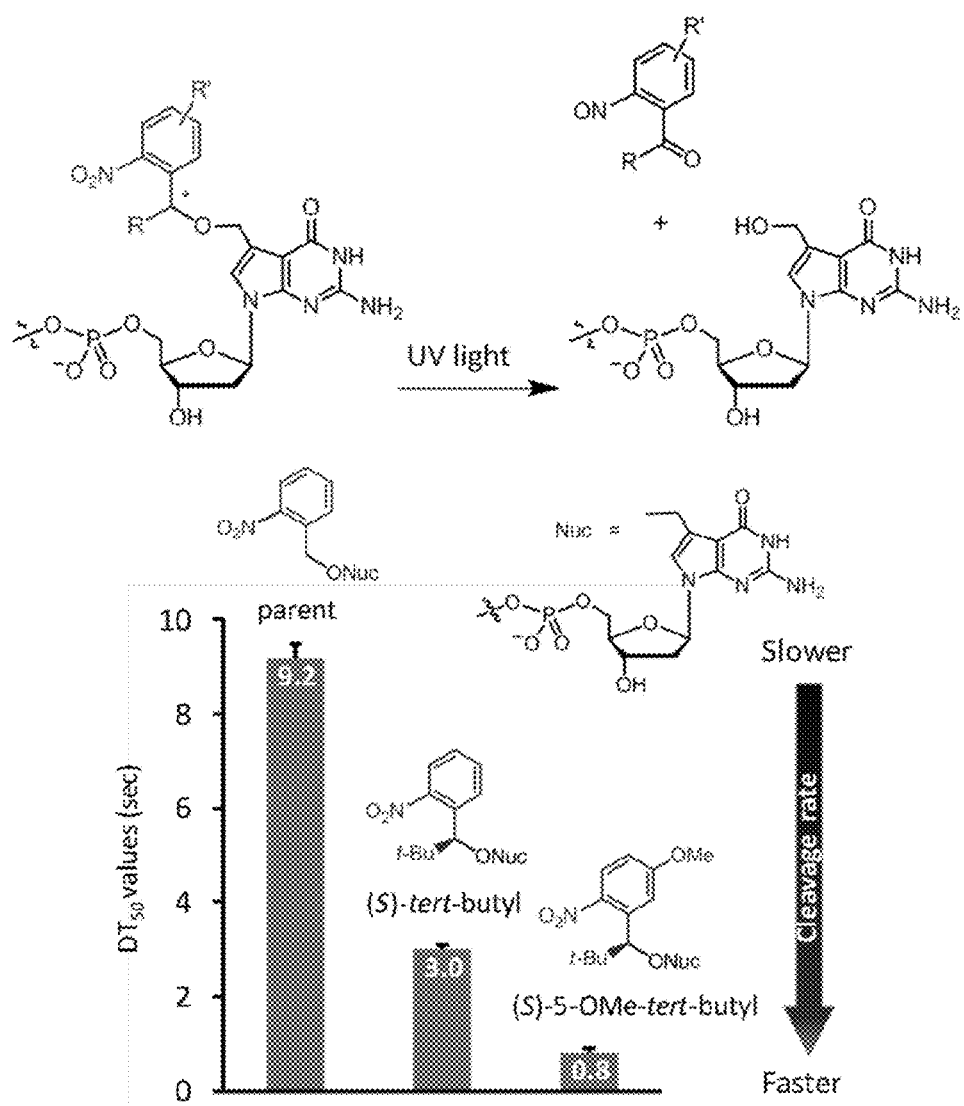
FIG. 6—Example of photochemical cleavage reaction. Upon UV-induced photochemical cleavage, the terminating 2-nitrobenzyl derivative is released to yield a natural hydroxymethyl nucleotide. The combination of a stereospecific (S)-tert-butyl group attached at the benzylic carbon coupled with a 5-OMe group modified on the 2 nitrobenzyl ring substantially increased the rate of the photochemical cleavage reaction. For the case of C$^7$-HOMedG, the rate increased by more than one order of magnitude over its corresponding parent analog.

Photochemical Cleavage Assays:

Nucleotide analogs were incorporated using 10 µL reactions, as described for the PEP assays, at a final concentration of 100 nM. See Litosh et al. (2011), which is incorporated herein by reference. OligoTemplate-2, oligoTemplate-5, and oligoTemplate-4 each hybridized with BODIPY-FL labeled primer-1 were used for $C^7$-HOMedA, $C^7$-HOMedG, and HOMedU analogs, respectively. OligoTemplate-8 hybridized with BODIPY-FL labeled primer-3 was used to assay HOMedC analogs. Incorporated reactions were quenched with either 1 mM sodium azide solution; 1 mM sodium azide, 50 mM DTT solution; or reagents C-G (see key in FIG. 4), exposed to 365 nm ultraviolet (UV) light for various time points using our UV deprotector, and then placed on ice. Ten µL of stop solution (98% deionized formamide; 10 mM Na$_2$EDTA, pH 8.0; 25 mg/mL Blue Dextran, MW 2,000,000) was added, and samples were analyzed using an AB model 377 DNA sequencer. Cleavage assays were performed in triplicate to calculate the average DT$_{50}$ value±1 SD, as described in Litosh et al. (2011), which is incorporated herein by reference.

REFERENCES

The following references, and those listed in the Appendix, to the extent that they provide exemplary procedural or other details supplementary to those set forth herein, are specifically incorporated herein by reference.

U.S. Pat. No. 3,822,996
U.S. Pat. No. 3,859,045
U.S. Pat. No. 3,917,499
U.S. Pat. No. 4,737,155
U.S. Pat. No. 4,304,568
U.S. Pat. No. 4,631,066
U.S. Pat. No. 4,737,155
U.S. Pat. No. 4,439,356
U.S. Pat. No. 5,151,507
U.S. Pat. No. 5,188,934
U.S. Pat. No. 5,302,509
U.S. Pat. No. 5,770,367
U.S. Pat. No. 6,664,079
U.S. Pat. No. 7,057,026
U.S. Pat. No. 7,345,159
U.S. Pat. No. 7,414,116
U.S. Pat. No. 7,476,734
U.S. Pat. No. 7,541,444
U.S. Pat. No. 7,556,537
U.S. Pat. No. 7,592,435
U.S. Pat. No. 7,635,578
U.S. Pat. No. 7,713,698
U.S. Pat. No. 7,771,973
U.S. Pat. No. 7,897,737
U.S. Pat. No. 7,964,352
U.S. Pat. No. 8,148,503
U.S. Patent Appl. Publication 2004/0110196
U.S. Patent Appl. Publ. 2006/0160081
U.S. Patent Appl. Publ. 2010/0041041
WO 2012/037394
Aliotta et al., *Genet Anal. Biomol Eng.*, 12:185-95, 1996.
Axelrod, *Methods Cell Biol.*, 30:245-70, 1989.
Bailey, *Ozonation in organic chemistry* Vol. 1, Academic Press, Inc., New York, 1978
Bailey, *Ozonation in organic chemistry* Vol. 2, Academic Press, Inc., New York, 1982
Barltrop et al., *Chem. Commun.*, 822-23, 1966.
Barone et al., *Nucleosides, Nucleotides, and Nucleic Acids*, 20:1141-45, 2001.
Barth et al., *J. Amer. Chem. Soc.*, 119:4149-59, 1997.
Beadling et al., *J. Mol. Diagn.*, 13:504-13, 2012.
Bentley et al., *Nature*, 456:53-59, 2008.
Berson & Brown, *J. Amer. Chem. Soc.*, 77:447-50, 1955.
Bhalla, *Toxicology Letters*, 73:91-101, 1994
Bowers et al., *Nature Methods*, 6:593-95, 2009.
Cameron and Frechet, *J. Am. Chem. Soc.*, 113:4303-13, 1991.
Canard & Sarfati, *Gene*, 148:1-6, 1994.
Carrasco & Vázquez, *Med. Res. Rev.*, 4:471-512, 1984.
Cleland, *Biochemistry*, 3:480-82, 1964.
Corrie et al., *J. Chem. Soc., Perkin Trans.* 1, 1015-19, 1992.
Corrie, in *Dynamics studies in biology*, Goeldner and Givens (Eds.), Wiley-VCH Verlag GmbH & Co. KGaA, Weinheim, pp. 1-28, 2005.
Crabtree and Kemp, *Indus. Eng. Chem.*, 38:278-296, 1946
De Mayo, in *Advances in Organic Chemistry*, Raphael et al. (Eds.), Interscience, NY, 2:367-425, 1960.
Dressman et al., *Proc. Natl. Acad. Sci. USA*, 100:8817-8822, 2003.
Eid et al., *Science*, 323:133-138, 2009.
EPA (2011) http://www.epa.gov/oar/oaqps/gooduphigh/bad.html#6. Last updated on Thursday, Jul. 21, 2011.
European Patent Appln. 87310256.0
European Patent EP 0 640 146
Fairchild et al., *Science*, 130:861-862, 1959
Fare et al., *Anal. Chem.*, 75:4672-4675, 2003.
Futreal et al., *Nature Rev. Cancer*, 4:177-83, 2004.
Gardner et al., *Nucleic Acids Res.*, 27:2545-53, 1999.
Gardner et al., *Nucleic Acids Res.*, 40:7404-15, 2012.
Gershon, *Nature Methods*, 1:263-270, 2004.
Giegrich et al., *Nucleosides Nucleotides*, 17:1987-1996, 1998.
Givens & Schowen, In *Chemiluminescence and Photochemical Reaction Detection in Chromatography*, J. W. Birks, Ed.; VCH: New York, pp 125-47, 1989.
Gommers-Ampt et al., *FASEB J.*, 9:1034-42, 1995.
Gordon and Gregory, *Organic Chemistry of Colour*, Springer-Verlag, New York, 1983
Gregory, *Encyclopedia of Chemical Technology* (Kirk, R. E., and Othmer, D. F., eds) pp. 1-66, 2009
Guo et al., *Proc. Natl. Acad. Sci. USA*, 105:9145-50, 2008.
*Handbook of Pharmaceutical Salts: Properties, and Use*, Stahl & Wermuth (Eds.), Verlag Helvetica Chimica Acta, 2002.
Hardwick et al., *Trans. Farad. Soc.*, 56:44-50, 1960.
Harris et al., *Science*, 320:106-109, 2008.
Hasan et al., *Tetrahedron*, 53:4247-64, 1997.
Hastings, *J. Mol. Evol.* 19:309-21, 1983.
Haugland, In *The handbook. A guide of fluorescent probes and labeling technologies*, Invitrogen, 2005.
Hewitt et al., *Nature*, 344:56-58, 1990
Hsia et al., *Current Opinion in Structural Biology*, 15:126-134, 2005.
Iafrate et al., *Nature Genet.*, 36:949-51, 2004.
Ito et al., *Nature*, 466:1129-33, 2010.
Ju et al., *Proc. Natl. Acad. Sci. USA*, 103:19635-40, 2006.
Kaiser et al., *J. Biol. Chem.*, 274:21387-394, 1999.
Kriaucionis & Heintz, *Science*, 324:929-30, 2009.
Lehninger, In: *Principles of Biochemistry*, 273-305, W.H. Freeman and Co., NY, 2005.
Levy et al., *PLoS Biol.*, 5:e254, 2007.
Limbach, et al., *Nucleic Acids Res.*, 22:2183-2196, 1994.
Litosh et al., *Nucleic Acid Res.*, 39:e39.
Lyamichev et al., *Nature Biotechnol.*, 17:292-296, 1999.
March's Advanced Organic Chemistry: Reactions, Mechanisms, and Structure, 2007.
Margulies et al, *Nature*, 437:376-80, 2005.
McCray et al., *Proc. Natl. Acad. Sci. USA*, 77:7237-41, 1980.
McDougall et al., *Nucleosides, Nucleotides & Nucleic Acids*, 20:501-6, 2001.
McGall et al., *J. Amer. Chem. Soc.*, 119:5081-90, 1997.
Meldrum et al. *Clin. Biochem. Rev.*, 32:177-95, 2011.
Metzker et al., *Biotechniques*, 25:446-462, 1998.
Metzker et al., *Nucleic Acids Res.*, 22:4259-67, 1994.
Metzker, *Genome Res.*, 15:1767-76, 2005.
Metzker, *Nature Rev. Genet.*, 11:31-46, 2010.
Mitra et al., *Anal. Biochem.*, 320:55-65, 2003.
Morrison, In: *The chemistry of nitro and nitroso groups*, Feuer (Ed.), Interscience publishers, NY, 165-213, 1969.
Mosher et al., *J. Chem. Phys.* 32:1888-89, 1960.
Moyer et al., *Laser Focus World*, 29(10), 1993.
Nieman, In *Chemiluminescence and Photochemical Reaction Detection in Chromatography*, J. W. Birks, Ed.; VCH: New York, pp 99-123, 1989.
Orosz et al., *Crit. Rev. Anal. Chem.*, 26:1-27. 1996.
Patchornik et al., *J. Am. Chem. Soc.*, 92:6333-35, 1970.
Patchornik, In: *Pharmacology of hormonal polypeptides and proteins* (Back et al. (Eds.), Plenum Press, NY, 11-16, 1968.

PCT Appl. PCT/US90/05565.
Ramanathan et al., *Anal. Biochem.*, 330:227-241, 2004.
Redon et al., *Nature*, 444:444-454, 2006.
Reichmanis et al., *J. Polymer Sci.*, 23:1-8, 1985.
Rockhill et al., *J. Am. Chem. Soc.*, 118:10065-68, 1997.
Ronaghi et al., *Science*, 281:363-365, 1998.
Salvin and Walker, *Textile Research Journal*, 25:571-581, 1955
Sebat et al., *Science*, 305:525-528, 2004.
Seela and Peng, In: *Current Protocols in Nucleic Acid Chemistry*, Beaucage et al. (Eds.), John Wiley & Sons, Inc., 1.10.1, 2005.
Seo et al., *Proc. Natl. Acad. Sci. USA*, 102:5926-5931, 2005.
Service, *Science*, 282:1020-1021, 1998.
Smith and Ho, *J. Org. Chem.*, 55:2543, 1990.
Soengas et al., *J. Mol. Biol.*, 253:517-29, 1995
Sousa & Weinstein, *J. Org. Chem.*, 27:3155-59, 1962.
Staudiner & Meyer, *Helv. Chim. Acta*, 2:635, 1919.
Stranger et al., *Science*, 315:848-853, 2007.
Stupi et al., *Angew. Chem. Int. Ed.*, 51:1724-1727, 2012.
Su et al., *J. Mol Diagn.*, 13:74-84, 2011.
Tahiliani et al., *Science*, 324:930-35, 2009.
Turcatti et al., *Nucleic Acids Res.*, 36:e25, 2008.
Tuzun et al., *Nature Genet.*, 37:727-32, 2005.
Walker et al., *Biochemistry*, 25:1799-1805, 1986.
Weinstein et al., *J. Org. Chem.*, 31:1983-1985, 1966.
Wettermark, *Nature*, 194:677, 1962.
Wootton & Trentham, In: *Photochemical probes in biochemistry* (*NATO Science Series C*), Nielsen (Ed)., Kluwer Academic Publishers, Ann Arbor, 272:277-296, 1989.
Wu et al., *Nature Genet.*, 44:251-253, 2012.
Wu et al., *Nucleic Acids Res.*, 35:6339-6349, 2007.
Wyatt & Cohen, *Biochem. J.*, 55:774-782, 1953.

What is claimed is:

1. A method of identifying a plurality of bases in a target nucleic acid comprising the following steps:
   (i) attaching the 5'-end of a primer to a solid surface;
   (ii) hybridizing a target nucleic acid to the primer attached to the solid surface to form a hybridized primer/target nucleic acid complex;
   (iii) obtaining a polymerase and a compound of formulas I-VII, with the proviso that compounds of different formulas I-VII have different reporters:

-continued

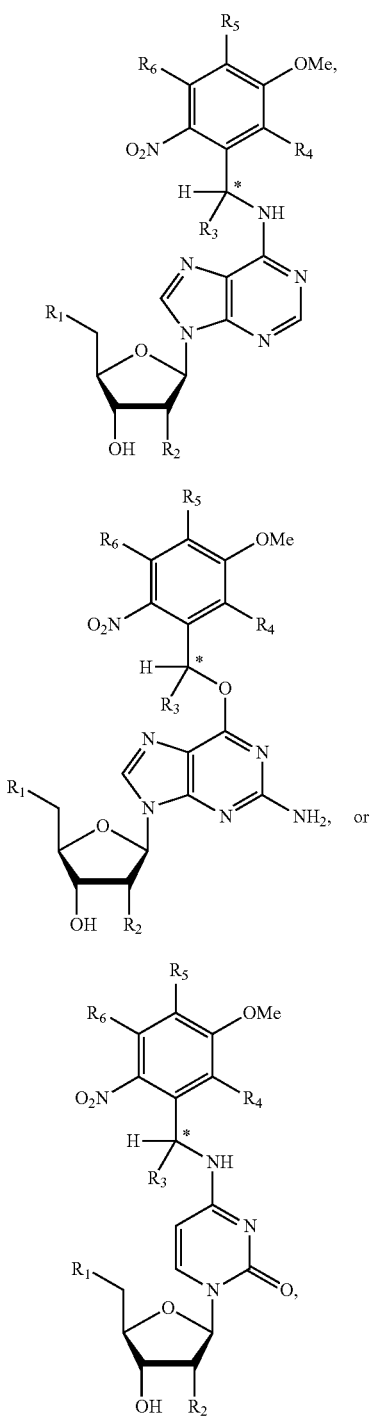

wherein:
$R_1$ is triphosphate or α-thiotriphosphate;
$R_2$ is hydrogen or hydroxy;
$R_3$ is alkyl$_{(C \leq 8)}$ or substituted alkyl$_{(C \leq 8)}$;
$R_4$ is
hydrogen, hydroxy, halo, amino, nitro, cyano, azido or mercapto;
alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;

$R_5$ is a -linker-reporter, wherein the reporter is based on a dye;
$R_6$ is:
hydrogen, hydroxy, halo, amino, nitro, cyano, azido or mercapto;
alkyl$_{(C \leq 6)}$, alkenyl$_{(C \leq 6)}$, alkynyl$_{(C \leq 6)}$, aryl$_{(C \leq 6)}$, aralkyl$_{(C \leq 8)}$, heteroaryl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;
or a salt, tautomer, or optical isomer thereof;

(iv) reacting the hybridized primer/target nucleic acid complex with a polymerase and one or more of the compounds of step (iii) to form a growing primer strand via a polymerase reaction;

(v) imaging the growing primer strand to identify the incorporated compound of step (iv) via its reporter;

(vi) exposing the solid surface with the growing primer strand to a light source to remove a photocleavable terminating moiety of the formula:

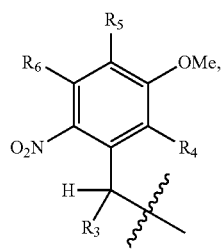

with the variables as defined by the claim referenced in step (iii); and (vii) repeating steps (iv) through (vi) one or more times to identify a plurality of bases in the target nucleic acid, where the extended primer of step (vi) of the previous cycle reacts in place of the hybridized primer/target nucleic acid complex in step (iv) of the subsequent cycle.

2. The method of claim 1, wherein step (vi) is conducted in the presence of sodium acetate.

3. The method of claim 1, wherein steps (v) or (vi) is conducted in the presence of thiourea.

4. The method of claim 1, wherein step (vi) is conducted in the presence of dithiothreitol (DTT).

5. A method of identifying a plurality of bases in a target nucleic acid comprising the following steps:
(i) attaching the 5'-end of a target nucleic acid to a solid surface;
(ii) hybridizing a primer to the nucleic acid attached to the solid surface to form a hybridized primer/target nucleic acid complex;
(iii) obtaining a polymerase and a compound of formulas I-VII, with the proviso that compounds of different formulas I-VII have different reporters:

(I)
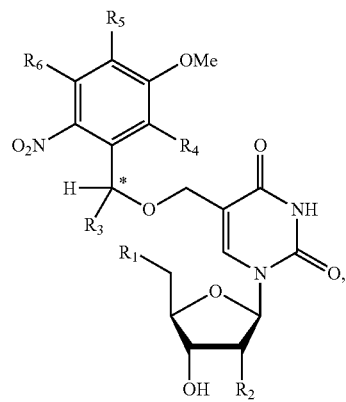
(II)
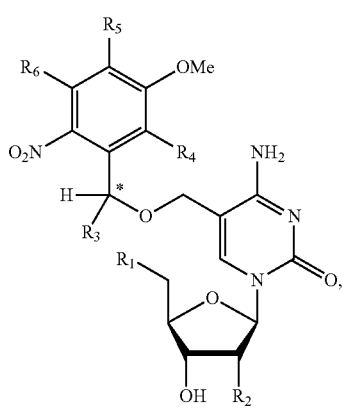
(III)
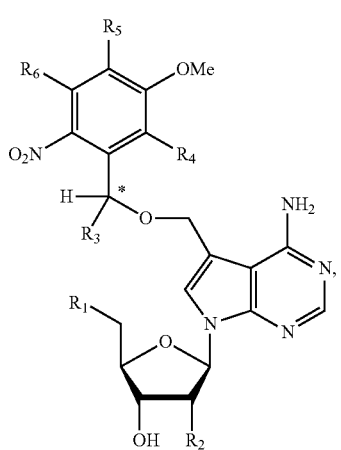
(IV)
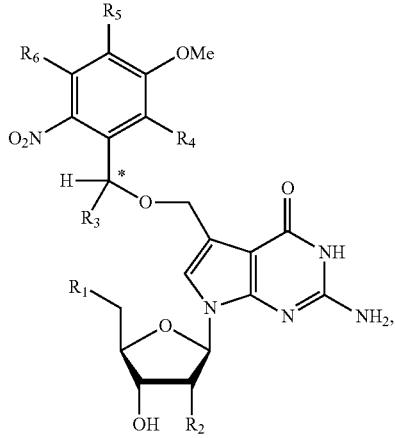
(V)
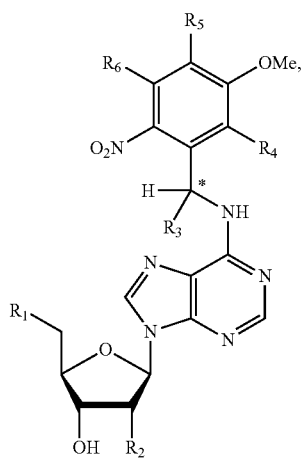
(VI)
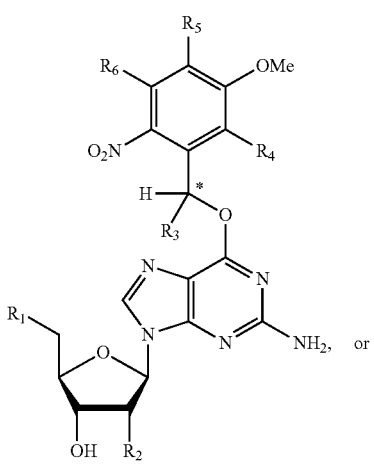
or -continued

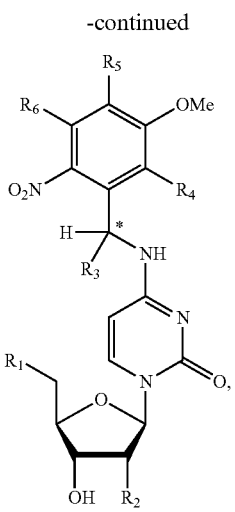

(VII)

wherein:
R₁ is triphosphate or α-thiotriphosphate;
R₂ is hydrogen or hydroxy;
R₃ is alkyl(8) or substituted alkyl(8);
R₄ is
  hydrogen, hydroxy, halo, amino, nitro, cyano, azido or mercapto;
  alkyl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
R₅ is a -linker-reporter, wherein the reporter is based on a dye;
R₆ is:
  hydrogen, hydroxy, halo, amino, nitro, cyano, azido or mercapto;
  alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
or a salt, tautomer, or optical isomer thereof;
or a salt, tautomer, or optical isomer thereof;
(iv) reacting the hybridized primer/target nucleic acid complex with a polymerase and one or more of the compounds of step (iii) to form a growing primer strand via a polymerase reaction;
(v) imaging the growing primer strand to identify the incorporated compound of step (iv) via its reporter;
(vi) exposing the solid surface with the growing primer strand to a light source to remove a photocleavable terminating moiety of the formula:

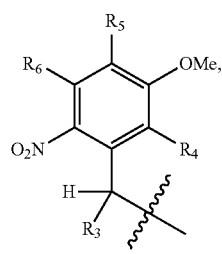

with the variables as defined by the claim referenced in step (iii); and (vii) repeating steps (iv) through (vi) one or more times to identify a plurality of bases in the target nucleic acid, where the extended primer of step (vi) of the previous cycle reacts in place of the hybridized primer/target nucleic acid complex in step (iv) of the subsequent cycle.

6. The method of claim 5, wherein step (vi) is conducted in the presence of dithiothreitol (DTT).

7. The method of claim 1, wherein the incorporation of at least one compound according to step (iv) occurs at about 70% to about 100% of the efficiency of incorporation of its natural nucleotide counterpart.

8. The method of claim 7, wherein the incorporation efficiency occurs at about 85% to about 100%.

9. The method of claim 1, wherein the polymerase is selected from the group consisting of reverse transcriptase, terminal transferase, and DNA polymerase.

10. The method of claim 1, wherein about 85% to about 100% of the photocleavable terminating moieties are removed by exposure to a light source in step (vi).

11. The method of claim 1, wherein incorporation of at least one compound according to step (iv) is followed by termination of strand growth at an efficiency of from about 90% to about 100%.

12. The method of claim 1, further comprising prior to step (iv) capping any primers or growing primer strands that did not react in step (iv).

13. The method of claim 1, further comprising sequencing multiple target nucleic acids synchronistically.

14. The method of claim 1, wherein R₁ is a triphosphate.

15. The method of claim 1, wherein R₁ is an α-thiotriphosphate.

16. The method of claim 1, wherein R₃ is alkyl$_{(C≤8)}$.

17. The method of claim 16, wherein R₃ is alkyl$_{(C3-4)}$.

18. The method of claim 17, wherein R₃ is tert-butyl.

19. The method of claim 1, wherein R₄ is hydrogen.

20. The method of claim 1, wherein the linker of the -linker-reporter is:

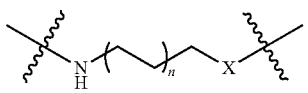

wherein
X is
  —O—, —S—, or —NH—; or
  alkanediyl$_{(C≤12)}$, alkenediyl$_{(C≤12)}$, alkynediyl$_{(C≤12)}$, arenediyl$_{(C≤12)}$, heteroarenediyl$_{(C≤12)}$, or a substituted version of any of these groups; and
n is an integer from 0-6.

21. The method of claim 20, wherein X is —C≡C—.

22. The method of claim 20, wherein n is zero.

23. The method of claim 1, wherein the dye is a zanthene, fluorescein, rhodamine, BODIPY, cyanine, coumarin, pyrene, phthalocyanine, phycobiliprotein, or a squaraine dye.

24. The method of claim 1, wherein the reporter is:
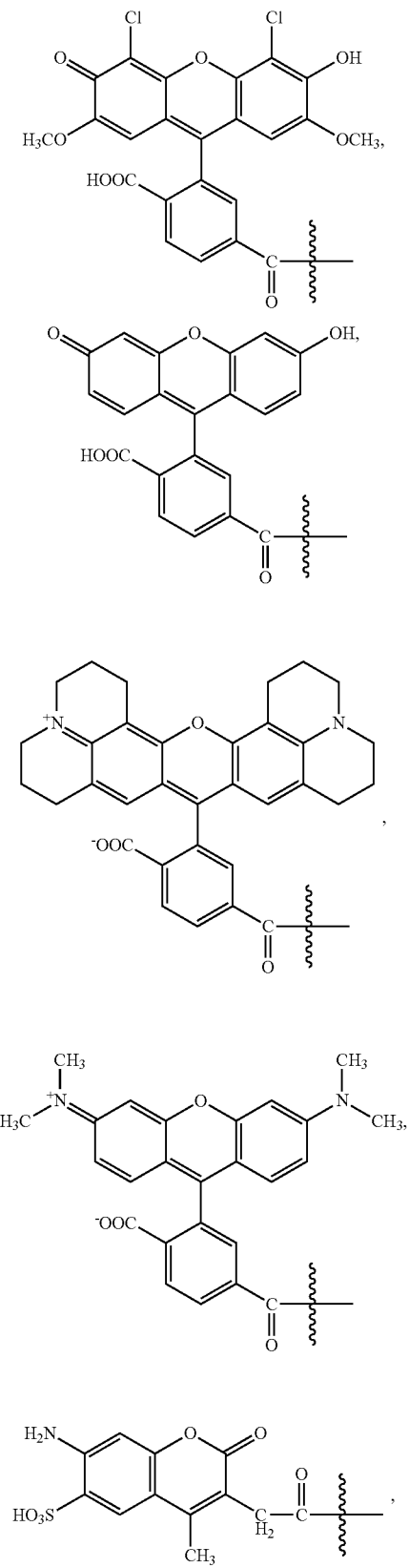
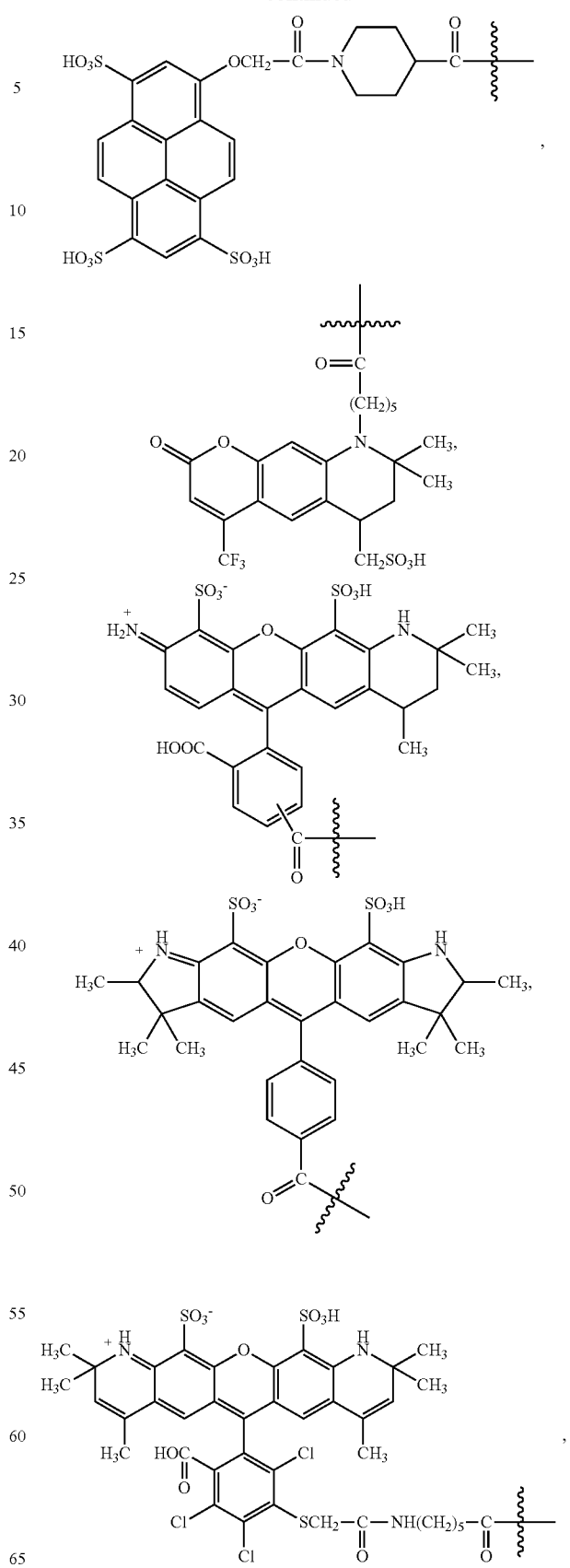
-continued -continued
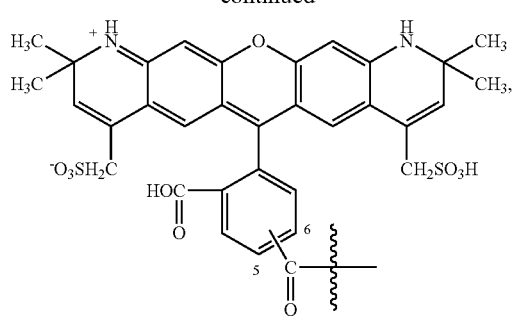
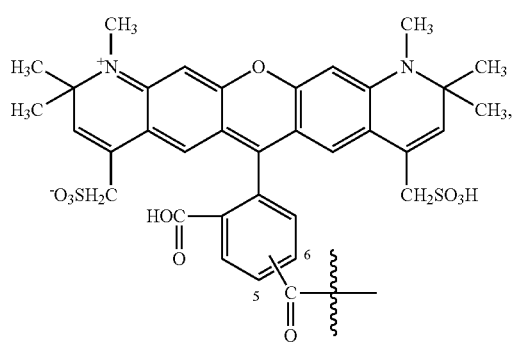
-continued
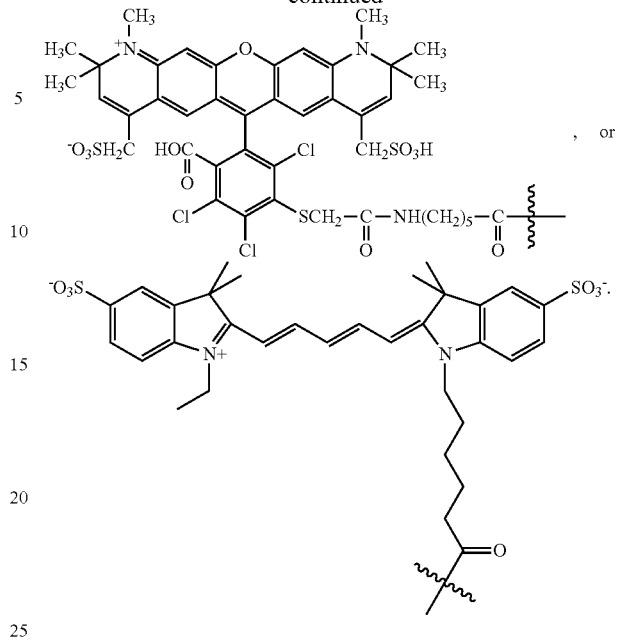
, or
25. The method of claim 1, wherein $R_6$ is hydrogen.
26. The method of claim 1, wherein the starred carbon atom is in the S configuration.
* * * * *